(12) United States Patent
Nakaya et al.

(10) Patent No.: US 9,708,314 B2
(45) Date of Patent: Jul. 18, 2017

(54) HETEROCYCLIC AMIDE COMPOUND

(71) Applicant: NISSAN CHEMICAL INDUSTRIES, LTD., Tokyo (JP)

(72) Inventors: Yoshihiko Nakaya, Funabashi (JP); Daisuke Tanima, Funabashi (JP); Masamitsu Inaba, Funabashi (JP); Yuuki Miyakado, Shiraoka (JP); Takamasa Furuhashi, Shiraoka (JP); Kazushige Maeda, Funabashi (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 0 days.

(21) Appl. No.: 14/894,817

(22) PCT Filed: May 30, 2014

(86) PCT No.: PCT/JP2014/064492
§ 371 (c)(1),
(2) Date: Nov. 30, 2015

(87) PCT Pub. No.: WO2014/192936
PCT Pub. Date: Dec. 4, 2014

(65) Prior Publication Data
US 2016/0108037 A1    Apr. 21, 2016

(30) Foreign Application Priority Data

May 31, 2013 (JP) ................ 2013-115196
Oct. 18, 2013 (JP) ................ 2013-217697
(Continued)

(51) Int. Cl.
C07D 471/04 (2006.01)
A01N 43/90 (2006.01)
(52) U.S. Cl.
CPC .......... C07D 471/04 (2013.01); A01N 43/90 (2013.01)
(58) Field of Classification Search
CPC ................ C07D 471/04; A01N 43/90
(Continued)

(56) References Cited

U.S. PATENT DOCUMENTS 4,671,818 A     6/1987 Calvino et al.
2005/0004368 A1 * 1/2005 Mio .................. A01N 43/80
                                              546/269.1
(Continued)

FOREIGN PATENT DOCUMENTS

CA      1252642 A    4/1989
EP      2562174      * 2/2013
(Continued)

OTHER PUBLICATIONS

Jul. 12, 2016 Office Action issued in Chinese Patent Application No. 201480029334.X.
(Continued)

*Primary Examiner* — Noble Jarrell
*Assistant Examiner* — Daniel Carcanague
(74) *Attorney, Agent, or Firm* — Oliff PLC

(57) ABSTRACT

The present invention provides a heterocyclic amide compound of Formula (1), and an agricultural chemical containing it, particularly a herbicide:

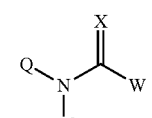

(1)

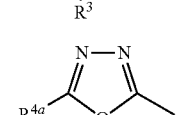

Q-1

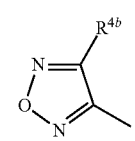

Q-2

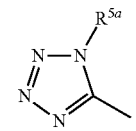

Q-3

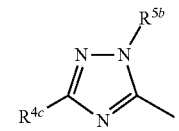

Q-4

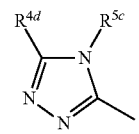

Q-5

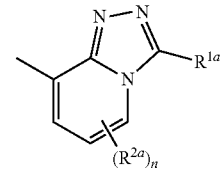

W-1

(Continued)

-continued

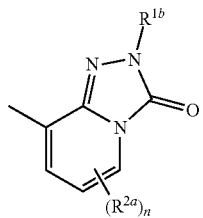

W-2

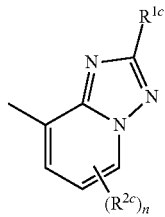

W-3 in which Q is an aromatic heterocycle of any one of Q-1 to Q-5, W is an aromatic heterocycle of W-1, W-2, or W-3, X is an oxygen atom, etc., $R^{1a}$ is a hydrogen atom, a halogen atom, or $C_{1-6}$ alkyl, etc., $R^{1b}$ is a hydrogen atom, $R^{1c}$ is $C_{1-6}$ alkyl, $R^{2a}$ is a halogen atom, or $C_{1-6}$ alkyl, etc., $R^{2c}$ is $C_{1-6}$ haloalkyl, $R^3$ is a hydrogen atom, etc., $R^{4a}$, $R^{4b}$, $R^{4c}$ and $R^{4d}$ are each independently a hydrogen atom, or $C_{1-6}$ alkyl, etc., $R^{5a}$, $R^{5b}$ and $R^{5c}$ are each independently a hydrogen atom, or $C_{1-6}$ alkyl, etc., and n is an integer of 0, 1, 2 or 3.

12 Claims, No Drawings

(30) Foreign Application Priority Data

Jan. 29, 2014 (JP) .................................. 2014-013999
Mar. 31, 2014 (JP) .................................. 2014-072736

(58) Field of Classification Search
USPC ........................................................ 546/113
See application file for complete search history.

(56) References Cited

U.S. PATENT DOCUMENTS

2005/0090521 A1 4/2005 Thota et al.
2012/0058892 A1 3/2012 Braun et al.

FOREIGN PATENT DOCUMENTS

| JP | S61-76405 | A | | 4/1986 |
| JP | 2007-506788 | A | | 3/2007 |
| JP | 2016108336 | | * | 6/2016 |
| JP | 2016117714 | | * | 6/2016 |
| WO | 2005/030774 | A1 | | 4/2005 |
| WO | 2011/035874 | A1 | | 3/2011 |
| WO | 2012/028579 | A1 | | 3/2012 |
| WO | 2012/089644 | A1 | | 7/2012 |
| WO | 2012/123409 | A1 | | 9/2012 |
| WO | 2012/123416 | A1 | | 9/2012 |
| WO | 2012/123420 | A1 | | 9/2012 |
| WO | 2012/126932 | A1 | | 9/2012 |
| WO | 2012/130684 | A1 | | 10/2012 |
| WO | 2012/130685 | A1 | | 10/2012 |
| WO | 2013/017559 | A1 | | 2/2013 |
| WO | 2013/064457 | A1 | | 5/2013 |
| WO | 2013/064458 | A1 | | 5/2013 |
| WO | 2013/064459 | A1 | | 5/2013 |
| WO | 2013/072300 | A1 | | 5/2013 |
| WO | 2013/072402 | A1 | | 5/2013 |
| WO | 2013/072450 | A1 | | 5/2013 |
| WO | 2013/072528 | A2 | | 5/2013 |
| WO | 2013/076315 | A2 | | 5/2013 |
| WO | 2013/076316 | A2 | | 5/2013 |
| WO | 2013/083859 | A2 | | 6/2013 |
| WO | 2013/087577 | A1 | | 6/2013 |
| WO | 2013/092834 | A1 | | 6/2013 |
| WO | 2013/104705 | A1 | | 7/2013 |
| WO | 2013/124228 | A1 | | 8/2013 |
| WO | 2013/124238 | A1 | | 8/2013 |
| WO | 2013/139760 | A1 | | 9/2013 |
| WO | 2013/144231 | A1 | | 10/2013 |
| WO | 2013/144234 | A1 | | 10/2013 |
| WO | 2013/164331 | A1 | | 11/2013 |
| WO | 2013/164333 | A1 | | 11/2013 |
| WO | 2013/174843 | A1 | | 11/2013 |
| WO | 2013/174845 | A1 | | 11/2013 |
| WO | 2014/037342 | A1 | | 3/2014 |
| WO | 2014/053473 | A1 | | 4/2014 |
| WO | 2014/072250 | A1 | | 5/2014 |

OTHER PUBLICATIONS

Aug. 19, 2014 International Search Report issued in International Patent Application No. PCT/JP2014/064492.
Aug. 19, 2014 Written Opinion of the International Searching Authority issued in International Patent Application No. PCT/JP2014/064492.

* cited by examiner

HETEROCYCLIC AMIDE COMPOUND

TECHNICAL FIELD

The present invention relates to a novel heterocyclic amide compound and a salt thereof, and agricultural chemicals, in particular herbicides, containing the heterocyclic amide compound and the salt thereof as an active component. The agricultural chemical in the present invention means an insecticide/acaricide, a nematicide, a herbicide, a bactericide and the like in agricultural and horticultural fields.

BACKGROUND ART

For example, a certain type of heterocyclic amide compounds has been disclosed in Patent Documents 1 to 6. The heterocyclic amide compound according to the present invention, however, has not been disclosed at all.

PRIOR ART DOCUMENTS

Patent Documents

Patent Document 1: International Publication No. 2012/028579 (WO 2012/028579)
Patent Document 2: International Publication No. 2012/123409 (WO 2012/123409)
Patent Document 3: International Publication No. 2012/123416 (WO 2012/123416)
Patent Document 4: International Publication No. 2012/126932 (WO 2012/126932)
Patent Document 5: International Publication No. 2013/017559 (WO 2013/017559)
Patent Document 6: International Publication No. 2013/064457 (WO 2013/064457)

SUMMARY OF THE INVENTION

Problem to be Solved by the Invention

An object of the present invention is to provide a chemical substance that reliably exerts effects on various weeds in a low application amount of the chemical substance, has reduced land pollution and influence on succeeding crops and has a high level of safety, and is useful as an active component of herbicides.

Means for Solving the Problem

As a result of intensive investigation for solving the problem, the inventors of the present invention have found that a novel heterocyclic amide compound of Formula (1) according to the present invention has excellent herbicidal activity as a herbicide and a high level of safety to target crops as well as almost no adverse effect on non-target creatures such as mammals, fish, and beneficial insects, and that the compound is an extremely useful compound, and thus the inventors have accomplished the present invention.

More specifically, the present invention relates to the following [1] to [115].

[1]
A heterocyclic amide compound of Formula (1):

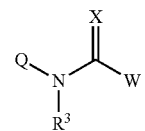
(1)

[where Q is an aromatic heterocycle of any one of Q-1 to Q-5;

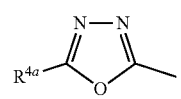
Q-1

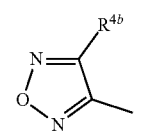
Q-2

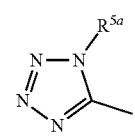
Q-3

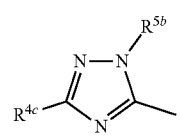
Q-4

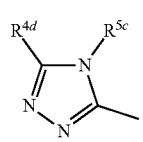
Q-5

W is an aromatic heterocycle of W-1, W-2, or W-3;

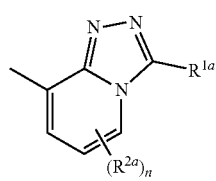
W-1

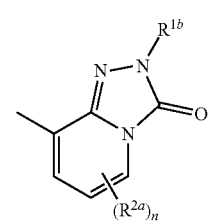
W-2

-continued

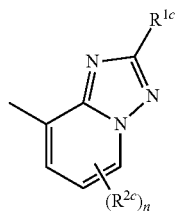
W-3

X is an oxygen atom or a sulfur atom;

$R^{1a}$ is a hydrogen atom, a halogen atom, $C_{1-6}$ alkyl, $(C_{1-6})$ alkyl optionally substituted with $R^6$, $C_{3-6}$ cycloalkyl, $(C_{3-6})$ cycloalkyl optionally substituted with $R^6$, $C_{2-6}$ alkenyl, $C_{2-6}$ alkynyl, $C_{3-6}$ cycloalkenyl, —C(O)$R^8$, —C(O)O$R^{16}$, cyano, —O$R^9$, —S(O)$_{m1}R^{10}$, —N($R^{11}$)$R^{12}$, —C(=N$R^{12b}$)$R^{8b}$, phenyl, phenyl substituted with $(R^7)_p$, naphthyl, or any one group of U-1 to U-25;

$R^{1b}$ is a hydrogen atom, $C_{1-6}$ alkyl, $(C_{1-6})$ alkyl optionally substituted with $R^6$, $C_{3-6}$ cycloalkyl, $(C_{3-6})$ cycloalkyl optionally substituted with $R^6$, $C_{2-6}$ alkenyl, $C_{2-6}$ alkynyl, phenyl, phenyl substituted with $(R^7)_p$, naphthyl, 5-6-membered heteroaryl, 5-6-membered heteroaryl (optionally substituted with $R^{28}$ and $R^{28a}$), 3-7-membered heterocyclyl, or 3-7-membered heterocyclyl (optionally substituted with $R^{28}$ and $R^{28a}$);

$R^{1c}$ is $C_{1-6}$ alkyl;

$R^{2a}$ is a halogen atom, $C_{1-6}$ alkyl, $C_{1-6}$ haloalkyl, —C(O)$R^{18}$, —C(O)O$R^{24}$, cyano, nitro, —O$R^{19}$, —S(O)$_{m3}R^{20}$, —N($R^{21}$)$R^{22}$, phenyl, or phenyl substituted with $(R^7)_p$; when n is an integer of 2 or more, $R^{2a}$ are optionally the same as or different from each other, and when two $R^{2a}$ are adjacent, the two adjacent $R^{2a}$ optionally form a 6-membered ring together with carbon atoms bonded to each $R^{2a}$ by forming —CH=CH—CH=CH—;

$R^{2c}$ is $C_{1-6}$ haloalkyl;

$R^3$ is a hydrogen atom, $C_{1-6}$ alkyl, $(C_{1-6})$ alkyl optionally substituted with $R^{27}$, $C_{3-6}$ cycloalkyl, $C_{3-6}$ halocycloalkyl, $C_{2-6}$ alkenyl, $C_{2-6}$ haloalkenyl, $C_{2-6}$ alkynyl, $C_{2-6}$ haloalkynyl, —C(O)$R^{25}$, or —C(O)O$R^{26}$;

$R^{4a}$ is a hydrogen atom, a halogen atom, $C_{1-6}$ alkyl, $(C_{1-6})$ alkyl optionally substituted with $R^{27}$, $C_{3-6}$ cycloalkyl, $(C_{3-6})$ cycloalkyl optionally substituted with $R^{27}$, $C_{2-6}$ alkenyl, $C_{2-6}$ haloalkenyl, $C_{2-6}$ alkynyl, $C_{2-6}$ haloalkynyl, $C_{3-6}$ cycloalkenyl, —NH$_2$, $C_{1-6}$ alkylamino, di($C_{1-6}$ alkyl)amino, —NHC(O)$R^8$, phenyl, phenyl substituted with $(R^{28})_r$, 5-6-membered heteroaryl, 5-6-membered heteroaryl (optionally substituted with $R^{28}$ and $R^{28a}$), 3-7-membered heterocyclyl, or 3-7-membered heterocyclyl (optionally substituted with $R^{28}$ and $R^{28a}$);

$R^{4b}$ is a hydrogen atom, a halogen atom, cyano, nitro, $C_{1-6}$ alkyl, $(C_{1-6})$ alkyl optionally substituted with $R^{27}$, $C_{3-6}$ cycloalkyl, $(C_{3-6})$ cycloalkyl optionally substituted with $R^{27}$, $C_{2-6}$ alkenyl, $C_{2-6}$ haloalkenyl, $C_{2-6}$ alkynyl, $C_{2-6}$ haloalkynyl, $C_{3-6}$ cycloalkenyl, —C(O)O$R^{16}$, —O$R^{38}$, —S(O)$_{m3}R^{20}$, —NH$_2$, $C_{1-6}$ alkylamino, di($C_{1-6}$ alkyl)amino, —NHC(O)$R^8$, phenyl, phenyl substituted with $(R^{28})_r$, 5-6-membered heteroaryl, 5-6-membered heteroaryl (optionally substituted with $R^{28}$ and $R^{28a}$), 3-7-membered heterocyclyl, or 3-7-membered heterocyclyl (optionally substituted with $R^{28}$ and $R^{28a}$);

$R^{4c}$ is a hydrogen atom, a halogen atom, $C_{1-6}$ alkyl, $(C_{1-6})$ alkyl optionally substituted with $R^{27}$, $C_{3-6}$ cycloalkyl, $(C_{3-6})$ cycloalkyl optionally substituted with $R^{27}$, phenyl, phenyl substituted with $(R^{28})_r$, 5-6-membered heteroaryl, 5-6-membered heteroaryl (optionally substituted with $R^{28}$ and $R^{28a}$), 3-7-membered heterocyclyl, or 3-7-membered heterocyclyl (optionally substituted with $R^{28}$ and $R^{28a}$);

$R^{5d}$ is a hydrogen atom, $C_{1-6}$ alkyl, or $(C_{1-6})$ alkyl optionally substituted with $R^{35}$;

U-1 to U-6, U-6a, U-7 to U-10, U-10a, U-11, U-11a, U-12, U-12a, U-13, U-13a, U-14 to U-22, U-22a, U-23, U-24, U-25, and U-26 are respective heterocycles of the following structures;

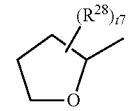
U-1

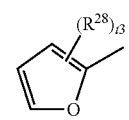
U-2

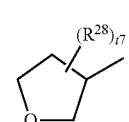
U-3

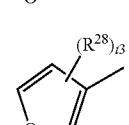
U-4

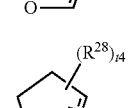
U-5

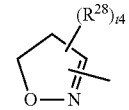
U-5a

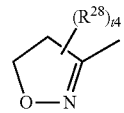
U-6

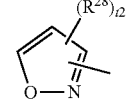
U-6a

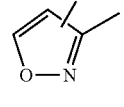
U-7

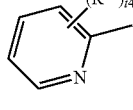
U-8

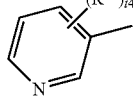
U-9

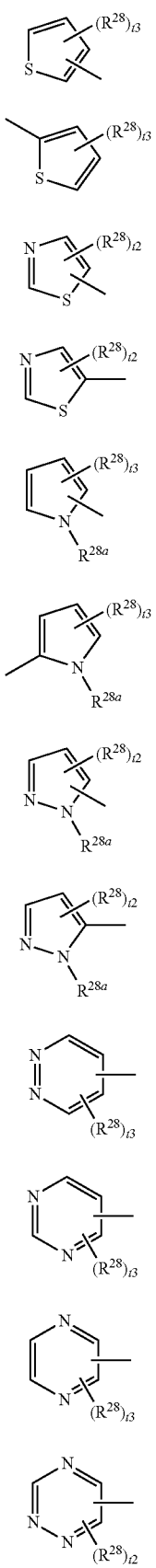

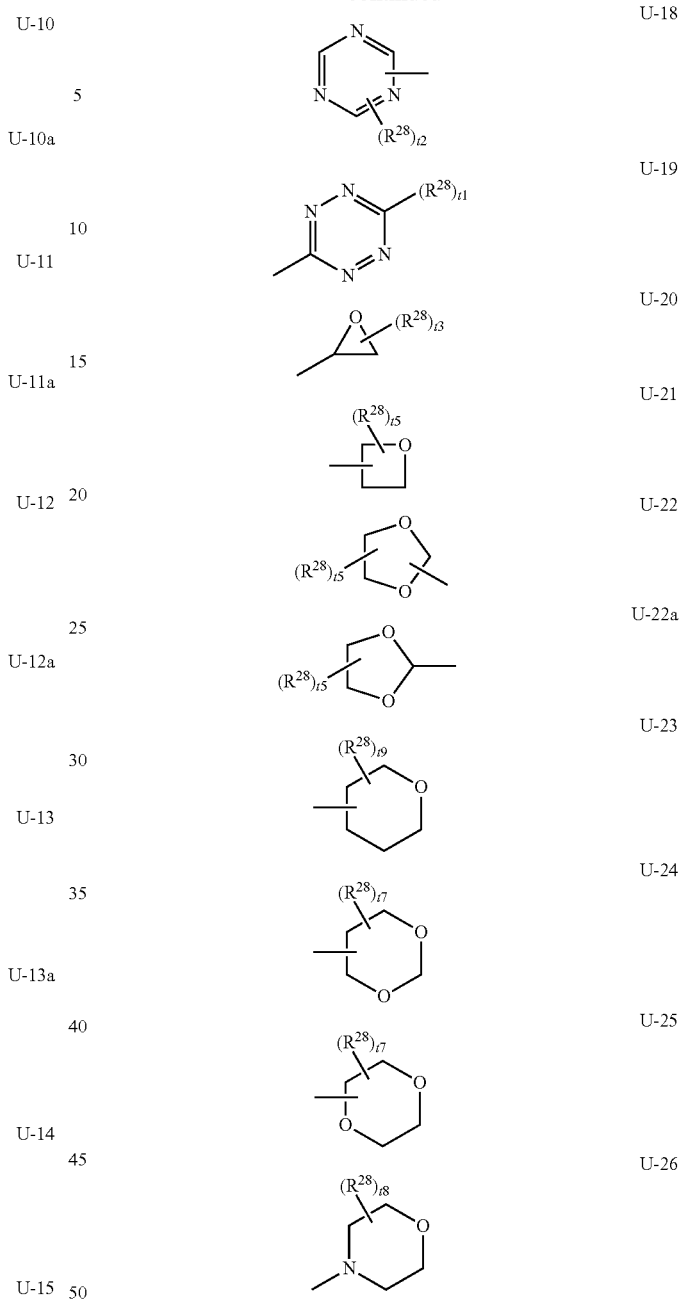

$R^{5a}$ and $R^{5b}$ are each independently a hydrogen atom, $C_{1-6}$ alkyl, $(C_{1-6})$ alkyl optionally substituted with $R^{27}$, $C_{3-6}$ cycloalkyl, $C_{3-6}$ halocycloalkyl, $C_{2-6}$ alkenyl, $C_{2-6}$ haloalkenyl, $C_{2-6}$ alkynyl, $C_{2-6}$ haloalkynyl, $C_{3-6}$ cycloalkenyl, phenyl, or phenyl substituted with $(R^{28})_r$;

$R^{5c}$ is a hydrogen atom, $C_{1-6}$ alkyl, or $(C_{1-6})$ alkyl optionally substituted with $R^{36}$, or $R^{5c}$ optionally forms a 6-membered ring together with a nitrogen atom to which $R^{5c}$ is bonded and a carbon atom to which $R^{4d}$ is bonded by forming —$(CH_2)_4$— or —CH=CH—CH=CH— with $R^{4d}$;

$R^6$ is a halogen atom, cyano, $C_{3-6}$ cycloalkyl, —C(O)$R^8$, —C(O)O$R^{16}$, —O$R^{13}$, —S(O)$_{m2}R^{14}$, phenyl, or phenyl substituted with $(R^7)_p$;

$R^7$ is a halogen atom, cyano, nitro, $C_{1-6}$ alkyl, $(C_{1-6})$ alkyl optionally substituted with $R^{27}$, $C_{3-6}$ cycloalkyl, $C_{3-6}$ halocycloalkyl, $C_{2-6}$ alkenyl, $C_{2-6}$ haloalkenyl, $C_{2-6}$ alkynyl, $C_{2-6}$ haloalkynyl, $C_{3-6}$ cycloalkenyl, $C_{1-6}$ alkylcarbonyl, $C_{3-6}$ cycloalkylcarbonyl, $C_{1-6}$ haloalkylcarbonyl, $C_{3-6}$ halocycloalkylcarbonyl, $C_{1-6}$ alkoxycarbonyl, $C_{1-6}$ halo alkoxycarbonyl, $C_{1-6}$ alkylaminocarbonyl, $C_{1-6}$ haloalkylaminocarbonyl, di($C_{1-6}$ alkylamino)carbonyl, —$OR^{15}$, —$S(O)_{m3}R^{20}$, $C_{1-6}$ alkylaminosulfonyl, di($C_{1-6}$ alkyl)aminosulfonyl, —$NH_2$, $C_{1-6}$ alkylamino, di($C_{1-6}$ alkyl)amino, 5-6-membered heteroaryl, 5-6-membered heteroaryl (optionally substituted with $R^{28}$ and $R^{28a}$), 3-7-membered heterocyclyl, or 3-7-membered heterocyclyl (optionally substituted with $R^{28}$ and $R^{28a}$);

$R^8$ is a hydrogen atom, $C_{1-6}$ alkyl, or —$N(R^{11a})R^{12a}$;

$R^{8b}$ is a hydrogen atom or $C_{1-6}$ alkyl;

$R^9$ is a hydrogen atom, $C_{1-6}$ alkyl, or phenyl;

$R^{10}$ is a hydrogen atom, $C_{1-6}$ alkyl, ($C_{1-6}$) alkyl optionally substituted with $R^{34}$, $C_{3-6}$ cycloalkyl, $C_{3-6}$ halocycloalkyl, $C_{2-6}$ alkenyl, $C_{2-6}$ haloalkenyl, $C_{2-6}$ alkynyl, or $C_{2-6}$ haloalkynyl;

$R^{11}$ and $R^{12}$ are each independently a hydrogen atom, $C_{1-6}$ alkyl, ($C_{1-6}$) alkyl optionally substituted with $R^{34}$, $C_{3-6}$ cycloalkyl, $C_{2-6}$ alkenyl, $C_{2-6}$ haloalkenyl, $C_{2-6}$ alkynyl, $C_{2-6}$ haloalkynyl, phenylsulfonyl, phenyl, phenyl substituted with $(R^7)_p$, U-7, U-8, U-9, or U-14 to U-19, or $R^{11}$ optionally forms a 3-7-membered ring together with a nitrogen atom to which $R^{11}$ and $R^{12}$ are bonded by forming a $C_{2-6}$ alkylene chain together with $R^{12}$, and in this case, the alkylene chain optionally contains one O, S, S(O), S(O)$_2$, or N($R^{33}$) and is optionally substituted with an oxo group or a thioxo group;

$R^{11a}$ and $R^{12a}$ are each independently a hydrogen atom, $C_{1-6}$ alkyl, or phenyl, or $R^{11a}$ optionally forms a 3-7-membered ring together with a nitrogen atom to which $R^{11a}$ and $R^{12a}$ are bonded by forming a $C_{2-6}$ alkylene chain together with $R^{12a}$, and in this case, the alkylene chain optionally contains one O, S, S(O), S(O)$_2$, or N($R^{33}$) and is optionally substituted with an oxo group or a thioxo group;

$R^{12b}$ is —$OR^{19b}$;

$R^{13}$ is a hydrogen atom, $C_{1-6}$ alkyl, ($C_{1-6}$) alkyl optionally substituted with $R^{34}$, $C_{2-6}$ alkenyl, $C_{2-6}$ haloalkenyl, $C_{2-6}$ alkynyl, $C_{2-6}$ haloalkynyl, —C(O)$R^8$, or phenyl;

$R^{14}$ is a hydrogen atom, $C_{1-6}$ alkyl, ($C_{1-6}$) alkyl optionally substituted with $R^{34}$, $C_{2-6}$ alkenyl, $C_{2-6}$ haloalkenyl, $C_{2-6}$ alkynyl, $C_{2-6}$ haloalkynyl, or phenyl;

$R^{15}$ is a hydrogen atom, $C_{1-6}$ alkyl, ($C_{1-6}$) alkyl optionally substituted with $R^{27}$, $C_{3-6}$ cycloalkyl, $C_{3-6}$ halocycloalkyl, $C_{2-6}$ alkenyl, $C_{2-6}$ haloalkenyl, $C_{2-6}$ alkynyl, $C_{2-6}$ haloalkynyl, or $C_{3-6}$ cycloalkenyl;

$R^{16}$ is a hydrogen atom, $C_{1-6}$ alkyl, or ($C_{1-6}$) alkyl optionally substituted with $R^{37}$;

$R^{18}$ is a hydrogen atom or $C_{1-6}$ alkyl;

$R^{19}$ is a hydrogen atom, $C_{1-6}$ alkyl, or phenyl;

$R^{19b}$ is a hydrogen atom or $C_{1-6}$ alkyl;

$R^{20}$ is $C_{1-6}$ alkyl, $C_{1-6}$ haloalkyl, $C_{3-6}$ cycloalkyl, $C_{2-6}$ alkenyl, $C_{2-6}$ haloalkenyl, $C_{2-6}$ alkynyl, $C_{2-6}$ haloalkynyl, or $C_{3-6}$ cycloalkenyl;

$R^{21}$ and $R^{22}$ are each independently a hydrogen atom, $C_{1-6}$ alkyl, or phenyl, or $R^{21}$ optionally forms a 3-7-membered ring together with a nitrogen atom to which $R^{21}$ and $R^{22}$ are bonded by forming a $C_{2-6}$ alkylene chain together with $R^{22}$, and in this case, the alkylene chain optionally contains one O, S, S(O), S(O)$_2$, or N($R^{39}$) and is optionally substituted with an oxo group or a thioxo group;

$R^{24}$ is a hydrogen atom or $C_{1-6}$ alkyl;

$R^{25}$ and $R^{26}$ are each independently a hydrogen atom, $C_{1-6}$ alkyl, $C_{1-6}$ haloalkyl, $C_{3-6}$ cycloalkyl, $C_{3-6}$ halocycloalkyl, $C_{2-6}$ alkenyl, $C_{2-6}$ haloalkenyl, $C_{2-6}$ alkynyl, $C_{2-6}$ haloalkynyl, $C_{3-6}$ cycloalkenyl, or phenyl;

$R^{27}$ is a halogen atom, cyano, nitro, phenyl, phenyl substituted with $(R^{28})_r$, —C(O)$OR^{16}$, —$OR^{29}$, —$S(O)_{m4}R^{30}$, 5-6-membered heteroaryl, 5-6-membered heteroaryl (optionally substituted with $R^{28}$ and $R^{28a}$), 3-7-membered heterocyclyl, or 3-7-membered heterocyclyl (optionally substituted with $R^{28}$ and $R^{28a}$);

$R^{28}$ is a halogen atom, cyano, nitro, $C_{1-6}$ alkyl, $C_{1-6}$ haloalkyl, $C_{3-6}$ cycloalkyl, $C_{3-6}$ halocycloalkyl, $C_{2-6}$ alkenyl, $C_{2-6}$ haloalkenyl, $C_{2-6}$ alkynyl, $C_{2-6}$ haloalkynyl, ($C_{1-6}$ alkoxy) $C_{1-6}$ alkyl, —$OR^{31}$, or —$S(O)_{m4}R^{30}$; when t2, t3, t4, t5, t7, t8, or t9 is an integer of 2 or more, $R^{28}$ are optionally the same as or different from each other; further when two $R^{28}$ are adjacent, the two adjacent $R^{28}$ optionally form a 6-membered ring together with carbon atoms to which each $R^{28}$ is bonded by forming —CH=CH—CH=CH—;

$R^{28a}$ is $C_{1-6}$ alkyl, $C_{1-6}$ haloalkyl, ($C_{1-6}$ alkoxy) $C_{1-6}$ alkyl, or ($C_{1-6}$ alkylthio) $C_{1-6}$ alkyl;

$R^{29}$, $R^{30}$, and $R^{31}$ are each independently a hydrogen atom, $C_{1-6}$ alkyl, $C_{1-6}$ haloalkyl, $C_{3-6}$ cycloalkyl, $C_{3-6}$ halocycloalkyl, $C_{2-6}$ alkenyl, $C_{2-6}$ haloalkenyl, $C_{2-6}$ alkynyl, $C_{2-6}$ haloalkynyl, $C_{3-6}$ cycloalkenyl, or phenyl;

$R^{33}$ is a hydrogen atom or $C_{1-6}$ alkyl;

$R^{34}$ is a halogen atom, cyano, $C_{3-6}$ cycloalkyl, —C(O)$R^8$, —C(O)$OR^{16}$, —$OR^{33}$, —$S(O)_{m6}R^{33}$, phenyl, phenyl substituted with $(R^7)_p$, U-1, U-3, U-7, U-8, U-9, or U-14 to U-25;

$R^{35}$ is a halogen atom or $C_{1-6}$ alkoxy;

$R^{36}$ is a halogen atom or $C_{1-6}$ alkoxy;

$R^{37}$ is $C_{1-6}$ alkoxy, $R^{38}$ is $C_{1-6}$ alkyl, ($C_{1-6}$) alkyl optionally substituted with $R^{34}$, $C_{3-6}$ cycloalkyl, $C_{3-6}$ halocycloalkyl, $C_{2-6}$ alkenyl, $C_{2-6}$ haloalkenyl, $C_{2-6}$ alkynyl, $C_{2-6}$ haloalkynyl, $C_{3-6}$ cycloalkenyl, or phenyl;

$R^{39}$ is a hydrogen atom or $C_{1-6}$ alkyl;

t1 is an integer of 0 or 1;

m1, m2, m3, m4, m6, and t2 are each independently an integer of 0, 1, or 2;

n and t3 are each independently an integer of 0, 1, 2, or 3;

p and r are each independently an integer of 1, 2, 3, 4, or 5;

t4 is an integer of 0, 1, 2, 3, or 4;

t5 is an integer of 0, 1, 2, 3, 4, or 5;

t7 is an integer of 0, 1, 2, 3, 4, 5, 6, or 7;

t8 is an integer of 0, 1, 2, 3, 4, 5, 6, 7, or 8; and t9 is an integer of 0, 1, 2, 3, 4, 5, 6, 7, 8, or 9] or a salt thereof.

[2]

The heterocyclic amide compound or the salt thereof according to [1], in which W is an aromatic heterocycle of W-1 or W-2; and $R^{2a}$ is a halogen atom, $C_{1-6}$ alkyl, $C_{1-6}$ haloalkyl, —C(O)$R^{18}$, —C(O)$OR^{24}$, cyano, nitro, —$OR^{19}$, or —$S(O)_{m3}R^{20}$, and when n is an integer of 2 or more, $R^{2a}$ are optionally the same as or different from each other.

[3]

The heterocyclic amide compound or the salt thereof according to [2], in which $R^{1b}$ is a hydrogen atom, $C_{1-6}$ alkyl, ($C_{1-6}$) alkyl optionally substituted with $R^6$, $C_{3-6}$ cycloalkyl, ($C_{3-6}$) cycloalkyl optionally substituted with $R^6$, $C_{2-6}$ alkenyl, $C_{2-6}$ alkynyl, phenyl, phenyl substituted with $(R^7)_p$, naphthyl, or any one group of U-1 to U-25;

$R^{4a}$ is a hydrogen atom, a halogen atom, $C_{1-6}$ alkyl, ($C_{1-6}$) alkyl optionally substituted with $R^{27}$, $C_{3-6}$ cycloalkyl, ($C_{3-6}$) cycloalkyl optionally substituted with $R^{27}$, $C_{2-6}$ alkenyl, $C_{2-6}$ haloalkenyl, $C_{2-6}$ alkynyl, $C_{2-6}$ haloalkynyl, $C_{3-6}$ cycloalkenyl, —NH$_2$, C$_{1-6}$ alkylamino, di(C$_{1-6}$ alkyl)amino, —NHC(O)R$^8$, phenyl, phenyl substituted with (R$^{28}$)$_r$, or any one group of U-1 to U-26;

R$^7$ is a halogen atom, cyano, nitro, C$_{1-6}$ alkyl, (C$_{1-6}$) alkyl optionally substituted with R$^{27}$, C$_{3-6}$ cycloalkyl, C$_{3-6}$ halocycloalkyl, C$_{2-6}$ alkenyl, C$_{2-6}$ haloalkenyl, C$_{2-6}$ alkynyl, C$_{2-6}$ haloalkynyl, C$_{3-6}$ cycloalkenyl, C$_{1-6}$ alkylcarbonyl, C$_{3-6}$ cycloalkylcarbonyl, C$_{1-6}$ haloalkylcarbonyl, C$_{3-6}$ halocycloalkylcarbonyl, C$_{1-6}$ alkoxycarbonyl, C$_{1-6}$ halo alkoxycarbonyl, C$_{1-6}$ alkylaminocarbonyl, C$_{1-6}$ haloalkylaminocarbonyl, di(C$_{1-6}$ alkyl amino)carbonyl, —OR$^{15}$, —S(O)$_{m3}$R$^{20}$, C$_{1-6}$ alkylaminosulfonyl, di(C$_{1-6}$ alkyl)aminosulfonyl, —NH$_2$, C$_{1-6}$ alkylamino, di(C$_{1-6}$ alkyl)amino, or any one group of U-1 to U-26; and R$^{27}$ is a halogen atom, cyano, nitro, phenyl, phenyl substituted with (R$^{28}$)$_r$, —C(O)OR$^{16}$, —OR$^{29}$, —S(O)$_{m4}$R$^{30}$, or any one group of U-1 to U-26.

[4]

The heterocyclic amide compound or the salt thereof according to [3], in which R$^{1a}$ is a hydrogen atom, a halogen atom, C$_{1-6}$ alkyl, (C$_{1-6}$) alkyl optionally substituted with R$^6$, C$_{3-6}$ cycloalkyl, (C$_{3-6}$) cycloalkyl optionally substituted with R$^6$, C$_{2-6}$ alkenyl, C$_{2-6}$ alkynyl, C$_{3-6}$ cycloalkenyl, —C(O)R$^8$, —OR$^9$, —S(O)$_{m1}$R$^{10}$, —N(R$^{11}$)R$^{12}$, —C(=NR$^{12b}$)R$^{8b}$, phenyl, phenyl substituted with (R$^7$)$_p$, U-3, U-5a, U-6a, U-7, U-8, U-10a, U-11a, U-12a, or U-13a;

R$^{1b}$ is C$_{1-6}$ alkyl or (C$_{1-6}$) alkyl optionally substituted with R$^6$;

R$^{2a}$ is a halogen atom, C$_{1-6}$ alkyl, C$_{1-6}$ haloalkyl, or —S(O)$_{m3}$R$^{20}$, and when n is an integer of 2 or more, R$^{2a}$ are optionally the same as or different from each other;

R$^3$ is a hydrogen atom or C$_{1-6}$ alkyl;

R$^{4a}$ is a hydrogen atom, C$_{1-6}$ alkyl, (C$_{1-6}$) alkyl optionally substituted with R$^{27}$, C$_{3-6}$ cycloalkyl, phenyl, phenyl substituted with (R$^{28}$), or a heterocycle of U-1, U-2, U-7, U-10a, or U-26;

R$^{4b}$ is C$_{1-6}$ alkyl;

R$^{4c}$ is a hydrogen atom;

R$^{4d}$ is C$_{1-6}$ alkyl;

R$^{5a}$ is a hydrogen atom, C$_{1-6}$ alkyl, (C$_{1-6}$) alkyl optionally substituted with R$_{27}$, C$_{2-6}$ alkenyl, or phenyl;

R$^{5b}$ is a hydrogen atom or C$_{1-6}$ alkyl;

R$^{5c}$ is C$_{1-6}$ alkyl, or R$^{5c}$ optionally forms a 6-membered ring together with a nitrogen atom to which R$^{5c}$ is bonded and a carbon atom to which R$^{4d}$ is bonded by forming —(CH$_2$)$_4$— or —CH=CH—CH=CH— with R$^{4d}$;

R$^7$ is a halogen atom, C$_{1-6}$ alkyl, (C$_{1-6}$) alkyl optionally substituted with R$^{27}$, or —OR$^{15}$;

R$^{8b}$ is a hydrogen atom;

R$^9$ is C$_{1-6}$ alkyl;

R$^{10}$ is C$_{1-6}$ alkyl, (C$_{1-6}$) alkyl optionally substituted with R$^{34}$, C$_{3-6}$ cycloalkyl, C$_{2-6}$ alkenyl, or C$_{2-6}$ alkynyl;

R$^{11}$ is C$_{1-6}$ alkyl, (C$_{1-6}$) alkyl optionally substituted with R$^{34}$, C$_{3-6}$ cycloalkyl, C$_{2-6}$ alkenyl, C$_{2-6}$ alkynyl, phenylsulfonyl, phenyl, phenyl substituted with (R$^7$)$_p$, or U-7;

R$^{12}$ is a hydrogen atom or C$_{1-6}$ alkyl;

R$^{11}$ optionally forms a 5-6-membered ring together with a nitrogen atom to which R$^{11}$ and R$^{12}$ are bonded by forming a C$_{4-5}$ alkylene chain together with R$^{12}$, and in this case, the alkylene chain optionally contains one O, S, S(O), or S(O)$_2$;

R$^{11}$ is C$_{1-6}$ alkyl;

R$^{12a}$ is a hydrogen atom;

R$^{13}$ is a hydrogen atom, C$_{1-6}$ alkyl, (C$_{1-6}$) alkyl optionally substituted with R$^{34}$, —C(O)R$^8$, or phenyl;

R$^{14}$ is C$_{1-6}$ alkyl or (C$_{1-6}$) alkyl optionally substituted with R$^{34}$;

R$^{15}$ is C$_{1-6}$ alkyl;

R$^{19b}$ is C$_{1-6}$ alkyl;

R$^{20}$ is C$_{1-6}$ alkyl;

R$^{27}$ is a halogen atom, phenyl, phenyl substituted with (R$^{28}$)$_r$, —OR$^{29}$, —C(O)OR$^{16}$, or —S(O)$_{m4}$R$^{30}$;

R$^{28}$ is a halogen atom, C$_{1-6}$ alkyl, or —OR$^{31}$; when t2, t3, t4, t5, or t7 is an integer of 2 or more, R$^{28}$ are optionally the same as or different from each other; and further when two R$^{28}$ are adjacent, the two adjacent R$^{28}$ optionally form a 6-membered ring together with carbon atoms to which each R$^{28}$ is bonded by forming —CH=CH—CH=CH—;

R$^{29}$ is C$_{1-6}$ alkyl;

R$^{30}$ is C$_{1-6}$ alkyl;

R$^{31}$ is C$_{1-6}$ alkyl;

R$^{33}$ is C$_{1-6}$ alkyl; and

R$^{34}$ is a halogen atom, cyano, C$_{3-6}$ cycloalkyl, —C(O)R$^8$, —C(O)OR$^{16}$, —OR$^{33}$, —S(O)$_{m6}$R$^{33}$, phenyl, phenyl substituted with (R$^7$)$_p$, U-1, U-8, or U-22a.

[5]

The heterocyclic amide compound or the salt thereof according to [4], in which Q is an aromatic heterocycle of Q-1; and W is an aromatic heterocycle of W-1.

[6]

The heterocyclic amide compound or the salt thereof according to [5], in which X is an oxygen atom;

R$^{1a}$ a hydrogen atom, a halogen atom, C$_{1-6}$ alkyl, (C$_{1-6}$) alkyl optionally substituted with R$^6$, C$_{3-6}$ cycloalkyl, (C$_{3-6}$) cycloalkyl optionally substituted with R$^6$, C$_{2-6}$ alkenyl, C$_{2-6}$ alkynyl, C$_{3-6}$ cycloalkenyl, —C(O)R$^8$, —OR$^9$, —S(O)$_{m1}$R$^{10}$, —N(R$^{11}$)R$^{12}$, —C(NR$^{12b}$)R$^{8b}$, phenyl, phenyl substituted with (R$^7$)$_p$, U-5a, U-6a, U-7, U-8, U-10a, U-11a, U-12a, or U-13a;

R$^{2a}$ is C$_{1-6}$ alkyl, C$_{1-6}$ haloalkyl, or —S(O)$_{m3}$R$^{20}$, and when n is an integer of 2 or more, R$^{2a}$ are optionally the same as or different from each other;

R$^6$ is a halogen atom, cyano, C$_{3-6}$ cycloalkyl, —C(O)R$^8$, —C(O)OR$^{16}$, —OR$^{13}$, —S(O)$_{m2}$R$^{14}$, or phenyl substituted with (R$^7$)$_p$; and R$^{27}$ is a halogen atom, phenyl, —OR$^{29}$, or —S(O)$_{m4}$R$^{30}$

[7]

The heterocyclic amide compound or the salt thereof according to [6], in which R$^{4a}$ is a hydrogen atom, C$_{1-6}$ alkyl, (C$_{1-6}$) alkyl optionally substituted with R$^{27}$, or C$_{3-6}$ cycloalkyl; and R$^{27}$ is a halogen atom or —OR$^{29}$.

[8]

The heterocyclic amide compound or the salt thereof according to [4], in which Q is an aromatic heterocycle of Q-3; and W is an aromatic heterocycle of W-1.

[9]

The heterocyclic amide compound or the salt thereof according to [8], in which R$^{1a}$ is a hydrogen atom, a halogen atom, C$_{1-6}$ alkyl, (C$_{1-6}$) alkyl optionally substituted with R$^6$, C$_{3-6}$ cycloalkyl, (C$_{3-6}$) cycloalkyl optionally substituted with R$^6$, C$_{2-6}$ alkenyl, C$_{2-6}$ alkynyl, —C(O)R$^8$, —S(O)$_{m1}$R$^{10}$, —N(R$^{11}$)R$^{12}$, phenyl, phenyl substituted with (R$^7$)$_p$, U-3, U-5a, U-6a, U-8, U-10a, or U-13a;

R$^{2a}$ is a halogen atom, C$_{1-6}$ alkyl, or C$_{1-6}$ haloalkyl, and when n is an integer of 2 or more, R$^{2a}$ are optionally the same as or different from each other;

R$^6$ is a halogen atom, —C(O)OR$^{16}$, —OR$^{13}$, —S(O)$_{m2}$R$^{14}$, or phenyl substituted with (R$^7$)$_p$;

R$^7$ is a halogen atom, C$_{1-6}$ alkyl, or —OR$^{15}$;

R$^8$ is a hydrogen atom or C$_{1-6}$ alkyl;

$R^{11}$ is $C_{1-6}$ alkyl, $(C_{1-6})$ alkyl optionally substituted with $R^{34}$, $C_{3-6}$ cycloalkyl, $C_{2-6}$ alkenyl, $C_{2-6}$ alkynyl, phenyl, or phenyl substituted with $(R^7)_p$;

$R^{11}$ optionally forms a 6-membered ring together with a nitrogen atom to which $R^{11}$ and $R^{12}$ are bonded by forming a $C_5$ alkylene chain together with $R^{12}$, and in this case, the alkylene chain optionally contains one O, S, S(O), or $S(O)_2$;

$R^{16}$ is a hydrogen atom or $C_{1-6}$ alkyl;

$R^{27}$ is phenyl substituted with $(R^{28})$, $-OR^{29}$, $-C(O)OR^{16}$, or $-S(O)_{m4}R^{30}$;

$R^{28}$ is a halogen atom or $C_{1-6}$ alkyl; and $R^{34}$ is a halogen atom, cyano, $C_{3-6}$ cycloalkyl, $-OR^{33}$, $-S(O)_{m6}R^{33}$, phenyl, phenyl substituted with $(R^7)_p$, U-1, or U-8.

[10]

The heterocyclic amide compound or the salt thereof according to [9], in which $R^{5a}$ is $C_{1-6}$ alkyl, $(C_{1-6})$ alkyl optionally substituted with $R^{27}$, or $C_{2-6}$ alkenyl; and $R^{27}$ is $-OR^{29}$ or $-S(O)_{m4}R^{30}$.

[11]

The heterocyclic amide compound or the salt thereof according to any one of [1] to [10], in which X is an oxygen atom.

[12]

The heterocyclic amide compound or the salt thereof according to any one of [1] to [10], in which X is a sulfur atom.

[13]

The heterocyclic amide compound or the salt thereof according to any one of [1] to [12], in which $R^3$ is a hydrogen atom.

[14]

The heterocyclic amide compound or the salt thereof according to any one of [1] to [12], in which $R^3$ is $C_{1-6}$ alkyl.

[15]

The heterocyclic amide compound or the salt thereof according to any one of [1] to [14], in which $R^{2a}$ is $C_{1-6}$ haloalkyl.

[16]

The heterocyclic amide compound or the salt thereof according to any one of [1] to [14], in which $R^{2a}$ is a halogen atom.

[17]

The heterocyclic amide compound or the salt thereof according to any one of [1] to [14], in which $R^{2a}$ is $-S(O)_{m3}R^{20}$; and $R^{20}$ is $C_{1-6}$ alkyl.

[18]

The heterocyclic amide compound or the salt thereof according to any one of [1] to [14], in which $R^{2a}$ is trifluoromethyl.

[19]

The heterocyclic amide compound or the salt thereof according to any one of [1] to [18], in which n is an integer of 1, 2, or 3.

[20]

The heterocyclic amide compound or the salt thereof according to any one of [1] to [18], in which n is an integer of 1.

[21]

The heterocyclic amide compound or the salt thereof according to any one of [1] to [20], in which Q is an aromatic heterocycle of Q-2; and W is an aromatic heterocycle of W-1.

[22]

The heterocyclic amide compound or the salt thereof according to any one of [1] to [20], in which Q is an aromatic heterocycle of Q-4; and W is an aromatic heterocycle of W-1.

[23]

The heterocyclic amide compound or the salt thereof according to any one of [1] to [20], in which Q is an aromatic heterocycle of Q-5; and W is an aromatic heterocycle of W-1.

[24]

The heterocyclic amide compound or the salt thereof according to any one of [1] to [20], in which Q is an aromatic heterocycle of Q-1; and W is an aromatic heterocycle of W-2.

[25]

The heterocyclic amide compound or the salt thereof according to any one of [1] to [20], in which Q is an aromatic heterocycle of Q-2; and W is an aromatic heterocycle of W-2.

[26]

The heterocyclic amide compound or the salt thereof according to any one of [1] to [20], in which Q is an aromatic heterocycle of Q-3; and W is an aromatic heterocycle of W-2.

[27]

The heterocyclic amide compound or the salt thereof according to any one of [1] to [20], in which Q is an aromatic heterocycle of Q-4; and W is an aromatic heterocycle of W-2.

[28]

The heterocyclic amide compound or the salt thereof according to any one of [1] to [20], in which Q is an aromatic heterocycle of Q-5; and W is an aromatic heterocycle of W-2.

[29]

The heterocyclic amide compound or the salt thereof according to any one of [1] to [20], in which Q is an aromatic heterocycle of Q-1; and W is an aromatic heterocycle of W-3.

[30]

The heterocyclic amide compound or the salt thereof according to any one of [1] to [20], in which Q is an aromatic heterocycle of Q-2; and W is an aromatic heterocycle of W-3.

[31]

The heterocyclic amide compound or the salt thereof according to any one of [1] to [20], in which Q is an aromatic heterocycle of Q-3; and W is an aromatic heterocycle of W-3.

[32]

The heterocyclic amide compound or the salt thereof according to any one of [1] to [20], in which Q is an aromatic heterocycle of Q-4; and W is an aromatic heterocycle of W-3.

[33]

The heterocyclic amide compound or the salt thereof according to any one of [1] to [20], in which Q is an aromatic heterocycle of Q-5; and W is an aromatic heterocycle of W-3.

[34]

The heterocyclic amide compound or the salt thereof according to any one of [1] to [33], in which $R^{4a}$ is a hydrogen atom.

[35]

The heterocyclic amide compound or the salt thereof according to any one of [1] to [33], in which $R^{4a}$ is a hydrogen atom or $C_{1-6}$ alkyl.

[36]
The heterocyclic amide compound or the salt thereof according to any one of [1] to [33], in which $R^{4a}$ is $C_{1-6}$ alkyl.

[37]
The heterocyclic amide compound or the salt thereof according to any one of [1] to [33], in which $R^{4a}$ is $C_{1-3}$ alkyl.

[38]
The heterocyclic amide compound or the salt thereof according to any one of [1] to [33], in which $R^{4a}$ is methyl.

[39]
The heterocyclic amide compound or the salt thereof according to any one of [1] to [33], in which $R^{4a}$ is ethyl.

[40]
The heterocyclic amide compound or the salt thereof according to any one of [1] to [33], in which $R^{4a}$ is $C_{3-6}$ cycloalkyl.

[41]
The heterocyclic amide compound or the salt thereof according to any one of [1] to [33], in which $R^{4a}$ is $C_{1-3}$ haloalkyl.

[42]
The heterocyclic amide compound or the salt thereof according to any one of [1] to [41], in which $R^{5a}$ is a hydrogen atom.

[43]
The heterocyclic amide compound or the salt thereof according to any one of [1] to [41], in which $R^{5a}$ is $C_{1-6}$ alkyl.

[44]
The heterocyclic amide compound or the salt thereof according to any one of [1] to [41], in which $R^{5a}$ is $C_{1-3}$ alkyl.

[45]
The heterocyclic amide compound or the salt thereof according to any one of [1] to [41], in which $R^{5a}$ is methyl.

[46]
The heterocyclic amide compound or the salt thereof according to any one of [1] to [41], in which $R^{5a}$ is ethyl.

[47]
The heterocyclic amide compound or the salt thereof according to any one of [1] to [41], in which $R^{5a}$ is $(C_{1-6})$ alkyl optionally substituted with $R^{27}$;
$R^{27}$ is —$OR^{29}$ or —$S(O)_{m4}R^{30}$;
$R^{29}$ is $C_{1-6}$ alkyl; and
$R^{30}$ is $C_{1-6}$ alkyl.

[48]
The heterocyclic amide compound or the salt thereof according to any one of [1] to [41], in which $R^{5a}$ is $C_{2-6}$ alkenyl.

[49]
The heterocyclic amide compound or the salt thereof according to any one of [1] to [48], in which $R^{1a}$ is $C_{1-6}$ alkyl, $(C_{1-6})$ alkyl optionally substituted with $R^6$, $C_{3-6}$ cycloalkyl, $(C_{3-6})$ cycloalkyl optionally substituted with $R^6$, $C_{2-6}$ alkenyl, —CHO, —$S(O)_{m1}R^{10}$, —$N(R^{11})R^{12}$, phenyl, phenyl substituted with $(R^7)_p$, U-3, U-5a, U-6a, U-7, U-8, U-10a, U-11a, U-12a, or U-13a;
$R^6$ is a halogen atom, cyano, $C_{3-6}$ cycloalkyl, —C(O)$OR^{16}$, —$OR^{13}$, —$S(O)_{m2}R^{14}$, phenyl, or phenyl substituted with $(R^7)_p$;
$R^8$ is $C_{1-6}$ alkyl;
$R^{10}$ is $C_{1-6}$ alkyl, $(C_{1-6})$ alkyl optionally substituted with $R^{34}$, $C_{3-6}$ cycloalkyl, or $C_{2-6}$ alkenyl;
$R^{11}$ is $C_{1-6}$ alkyl, $(C_{1-6})$ alkyl optionally substituted with $R^{34}$, $C_{3-6}$ cycloalkyl, $C_{2-6}$ alkenyl, phenyl, phenyl substituted with $(R^7)_p$, or U-7;
$R^{12}$ is a hydrogen atom or $C_{1-6}$ alkyl;
$R^{11}$ optionally forms a 5-6-membered ring together with a nitrogen atom to which $R^{11}$ and $R^{12}$ are bonded by forming a $C_{4-5}$ alkylene chain together with $R^{12}$, and in this case, the alkylene chain optionally contains one O, S, S(O), or $S(O)_2$;
$R^{13}$ is a hydrogen atom, $C_{1-6}$ alkyl, or $(C_{1-6})$ alkyl optionally substituted with $R^{34}$;
$R^{14}$ is $C_{1-6}$ alkyl or $(C_{1-6})$ alkyl optionally substituted with $R^{34}$;
$R^{16}$ is a hydrogen atom, $C_{1-6}$ alkyl, or $(C_{1-6})$ alkyl optionally substituted with $R^{37}$; and
$R^{34}$ is cyano, $C_{3-6}$ cycloalkyl, —C(O)$R^8$, —C(O)$OR^{16}$, —$OR^{33}$, —$S(O)_{m6}R^{33}$, or U-1.

[50]
The heterocyclic amide compound or the salt thereof according to any one of [1] to [48], in which $R^{1a}$ is $C_{1-6}$ alkyl, $C_{3-6}$ cycloalkyl, $C_{2-6}$ alkenyl, or —CHO.

[51]
The heterocyclic amide compound or the salt thereof according to any one of [1] to [48], in which $R^{1a}$ is $C_{1-6}$ alkyl or $C_{3-6}$ cycloalkyl.

[52]
The heterocyclic amide compound or the salt thereof according to any one of [1] to [48], in which $R^{1a}$ is $C_{1-6}$ alkyl.

[53]
The heterocyclic amide compound or the salt thereof according to any one of [1] to [48], in which $R^{1a}$ is $C_{3-6}$ cycloalkyl.

[54]
The heterocyclic amide compound or the salt thereof according to any one of [1] to [48], in which $R^{1a}$ is $(C_{1-6})$ alkyl optionally substituted with $R^6$; and
$R^6$ is a halogen atom.

[55]
The heterocyclic amide compound or the salt thereof according to any one of [1] to [48], in which $R^{1a}$ is $(C_{1-6})$ alkyl optionally substituted with $R^6$; and
$R^6$ is cyano.

[56]
The heterocyclic amide compound or the salt thereof according to any one of [1] to [48], in which $R^{1a}$ is $(C_{1-6})$ alkyl optionally substituted with $R^6$; and
$R^6$ is $C_{3-6}$ cycloalkyl.

[57]
The heterocyclic amide compound or the salt thereof according to any one of [1] to [48], in which $R^{1a}$ is $(C_{1-6})$ alkyl optionally substituted with $R^6$; and
$R^6$ is —C(O)$OR^{16}$.

[58]
The heterocyclic amide compound or the salt thereof according to any one of [1] to [48], in which $R^{1a}$ is $(C_{1-6})$ alkyl optionally substituted with $R^6$;
$R^6$ is —$OR^{13}$; and
$R^{13}$ is $C_{1-6}$ alkyl.

[59]
The heterocyclic amide compound or the salt thereof according to any one of [1] to [48], in which $R^{1a}$ is $(C_{1-6})$ alkyl optionally substituted with $R^6$;
$R^6$ is —$OR^{13}$;
$R^{13}$ is $(C_{1-6})$ alkyl optionally substituted with $R^{34}$;
$R^{34}$ is —$OR^{33}$; and
$R^{33}$ is $C_{1-6}$ alkyl.

[60]
The heterocyclic amide compound or the salt thereof according to any one of [1] to [48], in which $R^{1a}$ is $(C_{1-6})$ alkyl optionally substituted with $R^6$;
$R^6$ is $-S(O)_{m2}R^{14}$;
$R^{14}$ is $C_{1-6}$ alkyl or $(C_{1-6})$ alkyl optionally substituted with $R^{34}$;
$R^{34}$ is a halogen atom or $-OR^{33}$; and
$R^{33}$ is $C_{1-6}$ alkyl.

[61]
The heterocyclic amide compound or the salt thereof according to any one of [1] to [48], in which $R^{1a}$ is $(C_{1-6})$ alkyl optionally substituted with $R^6$;
$R^6$ is $-S(O)_{m2}R^{14}$;
$R^8$ is $C_{1-6}$ alkyl;
$R^{14}$ is $(C_{1-6})$ alkyl optionally substituted with $R^{34}$;
$R^{16}$ is $C_{1-6}$ alkyl;
$R^{34}$ is cyano, $C_{3-6}$ cycloalkyl, $-C(O)R^8$, $-C(O)OR^{16}$, $-OR^{33}$, or $-S(O)_{m6}R^{33}$; and
$R^{33}$ is $C_{1-6}$ alkyl.

[62]
The heterocyclic amide compound or the salt thereof according to any one of [1] to [48], in which $R^{1a}$ is $(C_{1-6})$ alkyl optionally substituted with $R^6$;
$R^6$ is $-S(O)_{m2}R^{14}$; and
$R^{14}$ is $C_{2-6}$ alkenyl, $C_{2-6}$ haloalkenyl, $C_{2-6}$ alkynyl, or $C_{2-6}$ haloalkynyl.

[63]
The heterocyclic amide compound or the salt thereof according to any one of [1] to [48], in which $R^{1a}$ is $(C_{3-6})$ cycloalkyl optionally substituted with $R^6$; and
$R^6$ is a halogen atom.

[64]
The heterocyclic amide compound or the salt thereof according to any one of [1] to [48], in which $R^{1a}$ is $(C_{3-6})$ cycloalkyl optionally substituted with $R_6$;
$R^6$ is $-OR^{13}$; and
$R^{13}$ is $C_{1-6}$ alkyl.

[65]
The heterocyclic amide compound or the salt thereof according to any one of [1] to [48], in which $R^{1a}$ is $-S(O)_{m1}R^{10}$.

[66]
The heterocyclic amide compound or the salt thereof according to any one of [1] to [48], in which $R^{1a}$ is $-S(O)_{m1}R^{10}$.
$R^{10}$ is $C_{1-6}$ alkyl, $(C_{1-6})$ alkyl optionally substituted with $R^{34}$, $C_{3-6}$ cycloalkyl, or $C_{2-6}$ alkenyl;
$R^{34}$ is a halogen atom, cyano, $C_{3-6}$ cycloalkyl, $-C(O)R^8$, $-C(O)OR^{16}$, or $-OR^{33}$;
$R^8$ is $C_{1-6}$ alkyl;
$R^{16}$ is $C_{1-6}$ alkyl; and
$R^{33}$ is $C_{1-6}$ alkyl.

[67]
The heterocyclic amide compound or the salt thereof according to any one of [1] to [48], in which $R^{1a}$ is $-S(O)_{m1}R^{10}$; and
$R^{10}$ is $C_{1-6}$ alkyl.

[68]
The heterocyclic amide compound or the salt thereof according to any one of [1] to [48], in which $R^{1a}$ is $-S(O)_{m1}R^{10}$; and
$R^{10}$ is 6 cycloalkyl.

[69]
The heterocyclic amide compound or the salt thereof according to any one of [1] to [48], in which $R^{1a}$ is $-S(O)_{m1}R^{10}$; and
$R^{10}$ is $C_{2-6}$ alkenyl.

[70]
The heterocyclic amide compound or the salt thereof according to any one of [1] to [48], in which $R^{1a}$ is $-S(O)_{m1}R^{10}$; and
$R^{10}$ is $C_{2-6}$ alkynyl.

[71]
The heterocyclic amide compound or the salt thereof according to any one of [1] to [48], in which $R^{1a}$ is $-S(O)_{m1}R^{10}$;
$R^{10}$ is $(C_{1-6})$ alkyl optionally substituted with $R^{34}$; and
$R^{34}$ is a halogen atom.

[72]
The heterocyclic amide compound or the salt thereof according to any one of [1] to [48], in which $R^{1a}$ is $-S(O)_{m1}R^{10}$;
$R^{10}$ is $(C_{1-6})$ alkyl optionally substituted with $R^{34a}$ and
$R^{34}$ is cyano.

[73]
The heterocyclic amide compound or the salt thereof according to any one of [1] to [48], in which $R^{1a}$ is $-S(O)_{m1}R^{10}$;
$R^{10}$ is $(C_{1-6})$ alkyl optionally substituted with $R^{34a}$ and
$R^{34}$ is $C_{3-6}$ cycloalkyl.

[74]
The heterocyclic amide compound or the salt thereof according to any one of [1] to [48], in which $R^{1a}$ is $-S(O)_{m1}R^{10}$;
$R^{10}$ is $(C_{1-6})$ alkyl optionally substituted with $R^{34}$;
$R^{34}$ is $-C(O)R^8$ and $-C(O)OR^{16}$;
$R^8$ is $C_{1-6}$ alkyl; and
$R^{16}$ is $C_{1-6}$ alkyl.

[75]
The heterocyclic amide compound or the salt thereof according to any one of [1] to [48], in which $R^{1a}$ is $-S(O)_{m1}R^{10}$;
$R^{10}$ is $(C_{1-6})$ alkyl optionally substituted with $R^{34}$;
$R^{34}$ is $-OR^{33}$; and
$R^{33}$ is $C_{1-6}$ alkyl.

[76]
The heterocyclic amide compound or the salt thereof according to any one of [1] to [48], in which $R^{1a}$ is $-S(O)_{m1}R^{10}$
$R^{10}$ is $(C_{1-6})$ alkyl optionally substituted with $R^{34}$;
$R^{34}$ is $-S(O)_{n6}R^{33}$; and
$R^{33}$ is $C_{1-6}$ alkyl.

[77]
The heterocyclic amide compound or the salt thereof according to any one of [1] to [48], in which $R_{1a}$ is $-N(R^{11})R^{12}$.

[78]
The heterocyclic amide compound or the salt thereof according to any one of [1] to [48], in which $R^{1a}$ is $-N(R^{11})R^{12}$;
$R^{11}$ is $C_{1-6}$ alkyl;
$R^{12}$ is a hydrogen atom or $C_{1-6}$ alkyl.

[79]
The heterocyclic amide compound or the salt thereof according to any one of [1] to [48], in which $R^{1a}$ is $-N(R^{11})R^{12}$;
$R^{11}$ is $(C_{1-6})$ alkyl optionally substituted with $R^{34}$, $C_{3-6}$ cycloalkyl, or $C_{2-6}$ alkenyl;
$R^{12}$ is a hydrogen atom or $C_{1-6}$ alkyl;
$R^{34}$ is a halogen atom, cyano, or $-S(O)_{m6}R^{33}$; and
$R^{33}$ is $C_{1-6}$ alkyl.

[80]
The heterocyclic amide compound or the salt thereof according to any one of [1] to [48], in which $R^{1a}$ is $—N(R^{11})R^{12}$;
$R^{11}$ is $(C_{1-6})$ alkyl optionally substituted with $R^{34}$;
$R^{12}$ is a hydrogen atom or $C_{1-6}$ alkyl;
$R^{34}$ is $—OR^{33}$; and
$R^{33}$ is $C_{1-6}$ alkyl.

[81]
The heterocyclic amide compound or the salt thereof according to any one of [1] to [48], in which $R^{1a}$ is $—N(R^{11})R^{12}$; and
$R^{11}$ optionally forms a 5-6-membered ring together with a nitrogen atom to which $R^{11}$ and $R^{12}$ are bonded by forming a $C_{4-5}$ alkylene chain together with $R^{12}$, and in this case, the alkylene chain optionally contains one O, S, S(O), or $S(O)_2$.

[82]
The heterocyclic amide compound or the salt thereof according to any one of [1] to [48], in which $R^{1a}$ is a substituent of the following structure formulae:

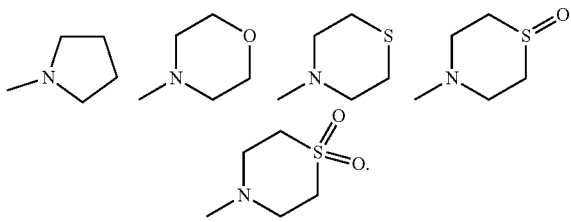

[83]
The heterocyclic amide compound or the salt thereof according to any one of [1] to [48], in which $R^{1a}$ is a substituent of the following structure formulae:

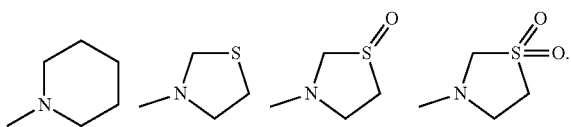

[84]
The heterocyclic amide compound or the salt thereof according to any one of [1] to [48], in which $R^{1a}$ is phenyl or phenyl substituted with $(R^7)_p$.

[85]
The heterocyclic amide compound or the salt thereof according to any one of [1] to [48], in which $R^{1a}$ is $(C_{1-6})$ alkyl optionally substituted with $R^6$; and
$R^6$ is phenyl or phenyl substituted with $(R^7)_p$.

[86]
The heterocyclic amide compound or the salt thereof according to any one of [1] to [48], in which $R^{1a}$ is $(C_{1-6})$ alkyl optionally substituted with $R^6$;
$R^6$ is $—OR^{13}$;
$R^{13}$ is $(C_{1-6})$ alkyl optionally substituted with $R^{34}$; and
$R^{34}$ is phenyl or phenyl substituted with $(R^7)_p$.

[87]
The heterocyclic amide compound or the salt thereof according to any one of [1] to [48], in which $R^{1a}$ is $(C_{1-6})$ alkyl optionally substituted with $R^6$;
$R^6$ is $—S(O)_{m2}R^{14}$;
$R^{14}$ is $(C_{1-6})$ alkyl optionally substituted with $R^{34}$; and
$R^{34}$ is phenyl or phenyl substituted with $(R^7)_p$.

[88]
The heterocyclic amide compound or the salt thereof according to any one of [1] to [48], in which $R^{1a}$ is $—S(O)_{m1}R^{10}$;
$R^{10}$ is $(C_{1-6})$ alkyl optionally substituted with $R^{34}$; and
$R^{34}$ is phenyl or phenyl substituted with $(R^7)_p$.

[89]
The heterocyclic amide compound or the salt thereof according to any one of [1] to [48], in which $R^{1a}$ is $—N(R^{11})R^{12}$;
$R^{11}$ is $(C_{1-6})$ alkyl optionally substituted with $R^{34}$;
$R^{12}$ is a hydrogen atom or $C_{1-6}$ alkyl;
$R^{34}$ is phenyl or phenyl substituted with $(R^7)_p$.

[90]
The heterocyclic amide compound or the salt thereof according to any one of [1] to [48], in which $R^{1a}$ is $—N(R^{11})R^{12}$;
$R^{11}$ is phenyl or phenyl substituted with $(R^7)_p$; and
$R^{12}$ is a hydrogen atom or $C_{1-6}$ alkyl.

[91]
The heterocyclic amide compound or the salt thereof according to any one of [84] to [90], in which $R^7$ is a halogen atom, $C_{1-6}$ alkyl, $(C_{1-6})$ alkyl optionally substituted with $R^{27}$ or $—OR^{15}$;
$R^{15}$ is $C_{1-6}$ alkyl;
$R^{27}$ is a halogen atom, $—OR^{29}$, or $—S(O)_{m4}R^{30}$; and
$R^{29}$ and $R^{30}$ are each independently $C_{1-6}$ alkyl.

[92]
The heterocyclic amide compound or the salt thereof according to any one of [84] to [90], in which $R^7$ is a halogen atom, $C_{1-6}$ alkyl, $(C_{1-6})$ alkyl optionally substituted with $R^{27}$, or $—OR^{15}$;
$R^{15}$ is $C_{1-6}$ alkyl; and
$R^{27}$ is a halogen atom.

[93]
The heterocyclic amide compound or the salt thereof according to any one of [1] to [48], in which $R^{1a}$ is any one of heterocycles of U-1 to U-25.

[94]
The heterocyclic amide compound or the salt thereof according to any one of [1] to [48], in which $R^{1a}$ is U-3, U-5a, U-6a, U-7, U-8, U-10a, U-11a, U-12a, or U-13a.

[95]
The heterocyclic amide compound or the salt thereof according to any one of [1] to [48], in which $R^{1a}$ is $—N(R^{11})R^{12}$; and
$R^{11}$ is U-7, U-8, U-9, or U-14 to U-19; and
$R^{12}$ is a hydrogen atom or $C_{1-6}$ alkyl.

[96]
The heterocyclic amide compound or the salt thereof according to any one of [1] to [48], in which $R^{1a}$ is $—N(R^{11})R^{12}$;
$R^{11}$ is U-7; and
$R^{12}$ is a hydrogen atom or $C_{1-6}$ alkyl.

[97]
The heterocyclic amide compound or the salt thereof according to any one of [1] to [48], in which $R^{1a}$ is $—S(O)_{m1}R^{10}$;
$R^{10}$ is $(C_{1-6})$ alkyl optionally substituted with $R^{34}$; and
$R^{34}$ is U-7, U-8, U-9, or U-14 to U-19.

[98]
The heterocyclic amide compound or the salt thereof according to any one of [1] to [48], in which $R^{1a}$ is $—S(O)_{m1}R^{10}$;
$R^{10}$ is $(C_{1-6})$ alkyl optionally substituted with $R^{34}$; and
$R^{34}$ is U-1, U-3, or U-20 to U-25.

[99]
The heterocyclic amide compound or the salt thereof according to any one of [1] to [48], in which $R^{1a}$ is —S(O)$_{m1}$R$^{10}$;
$R^{10}$ is (C$_{1-6}$) alkyl optionally substituted with $R^{34}$; and
$R^{34}$ is U-1, U-3, or U-22a.

[100]
The heterocyclic amide compound or the salt thereof according to any one of [1] to [48], in which $R^{1a}$ is —N(R$^{11}$)R$^{12}$;
$R^{11}$ is (C$_{1-6}$) alkyl optionally substituted with $R^{34}$;
$R^{12}$ is a hydrogen atom or C$_{1-6}$ alkyl; and
$R^{34}$ is U-7, U-8, U-9, or U-14 to U-19.

[101]
The heterocyclic amide compound or the salt thereof according to any one of [1] to [48], in which $R^{1a}$ is —N(R$^{11}$)R$^{12}$;
$R^{11}$ is (C$_{1-6}$) alkyl optionally substituted with $R^{34}$;
$R^{12}$ is a hydrogen atom or C$_{1-6}$ alkyl; and
$R^{34}$ is U-1, U-3, or U-20 to U-25.

[102]
The heterocyclic amide compound or the salt thereof according to any one of [1] to [48], in which $R^{1a}$ is —N(R$^{11}$)R$^{12}$;
$R^{11}$ is (C$_{1-6}$) alkyl optionally substituted with $R^{34}$;
$R^{12}$ is a hydrogen atom or C$_{1-6}$ alkyl; and
$R^{34}$ is U-1, U-3, or U-22a.

[103]
The heterocyclic amide compound or the salt thereof according to any one of [1] to [48], in which $R^{1a}$ is (C$_{1-6}$) alkyl optionally substituted with $R^6$;
$R^6$ is ⁻OR$^{13}$;
$R^{13}$ is (C$_{1-6}$) alkyl optionally substituted with $R^{34}$; and
$R^{34}$ is U-7, U-8, U-9, or U-14 to U-19.

[104]
The heterocyclic amide compound or the salt thereof according to any one of [1] to [48], in which $R^{1a}$ is (C$_{1-6}$) alkyl optionally substituted with $R^6$;
$R^6$ is ⁻OR$^{13}$;
$R^{13}$ is (C$_{1-6}$) alkyl optionally substituted with $R^{34}$; and
$R^{34}$ is U-1, U-3, or U-20 to U-25.

[105]
The heterocyclic amide compound or the salt thereof according to any one of [1] to [48], in which $R^{1a}$ is (C$_{1-6}$) alkyl optionally substituted with $R^6$;
$R^6$ is ⁻OR$^{13}$;
$R^{13}$ is (C$_{1-6}$) alkyl optionally substituted with $R^{34}$; and
$R^{34}$ is U-1, U-3, or U-22a.

[106]
The heterocyclic amide compound or the salt thereof according to any one of [1] to [48], in which $R^{1a}$ is (C$_{1-6}$) alkyl optionally substituted with $R^6$;
$R^6$ is ⁻S(O)$_{m2}$R$^{14}$;
$R^{14}$ is (C$_{1-6}$) alkyl optionally substituted with $R^{34}$; and
$R^{34}$ is U-7, U-8, U-9, or U-14 to U-19.

[107]
The heterocyclic amide compound or the salt thereof according to any one of [1] to [48], in which $R^{1a}$ is (C$_{1-6}$) alkyl optionally substituted with $R^6$;
$R^6$ is ⁻S(O)$_{m2}$R$^{14}$;
$R^{14}$ is (C$_{1-6}$) alkyl optionally substituted with $R^{34}$; and
$R^{34}$ is U-1, U-3, or U-20 to U-25.

[108]
The heterocyclic amide compound or the salt thereof according to any one of [1] to [48], in which $R^{1a}$ is (C$_{1-6}$) alkyl optionally substituted with $R^6$;
$R^6$ is ⁻S(O)$_{m2}$R$^{14}$;
$R^{14}$ is (C$_{1-6}$) alkyl optionally substituted with $R^{34}$; and
$R^{34}$ is U-1, U-3, or U-22a.

[109]
The heterocyclic amide compound or the salt thereof according to any one of [93] to [108], in which t1, t2, t3, t4, t5, t7, t8, and t9 are each independently an integer of 0.

[110]
The heterocyclic amide compound or the salt thereof according to any one of [93] to [108], in which $R^{28}$ is a halogen atom, cyano, C$_{1-6}$ alkyl, C$_{1-6}$ haloalkyl, C$_{3-6}$ cycloalkyl, (C$_{1-6}$ alkoxy) C$_{1-6}$ alkyl, —OR$^{31}$, or —S(O)$_{m4}$R$^{30}$.

[111]
The heterocyclic amide compound or the salt thereof according to any one of [93] to [108], in which $R^{28}$ is a halogen atom.

[112]
The heterocyclic amide compound or the salt thereof according to any one of [93] to [108], in which $R^{28}$ is C$_{1-6}$ alkyl.

[113]
The heterocyclic amide compound or the salt thereof according to any one of [93] to [108], in which $R^{28}$ is C$_{1-6}$ alkoxy.

[114]
An agricultural chemical comprising one or two or more of compounds selected from the heterocyclic amide compound and the salt thereof as described in any one of [1] to [113] as an active component.

[115]
A herbicide comprising one or two or more of compounds selected from the heterocyclic amide compound and the salt thereof as described in any one of [1] to [113] as an active component.

Effects of the Invention

The compound of the present invention has excellent herbicidal activity to various weeds and has a high level of safety to the target crops. In addition, the compound of the present invention has almost no adverse effect on non-target creatures such as mammals, fish, and beneficial insects and has light environmental burden due to low residual properties.

Accordingly, the present invention can provide a useful herbicide in the agricultural and horticultural fields such as paddy fields, dry fields, and orchards.

MODES FOR CARRYING OUT THE INVENTION

The compounds included in the present invention may include the geometric isomers of an E-form and a Z-form depending on the substituents. The present invention includes the E-form, the Z-form, and a mixture of the E-form and the Z-form in any ratios. The compounds included in the present invention include optically active isomers due to the existence of one or two or more of asymmetric carbon atoms. The present invention includes all optically active isomers or racemic forms.

The compounds included in the present invention may include tautomers depending on the substituents. The present invention includes all tautomers or a mixture of the tautomers included in any ratios. For example, in the case of the compound of Formula (1): [where W is W-1; $R^{1a}$ is hydroxy group; n, Q, $R^{2a}$, $R^3$, and X mean the same as described above], the following tautomers are included.

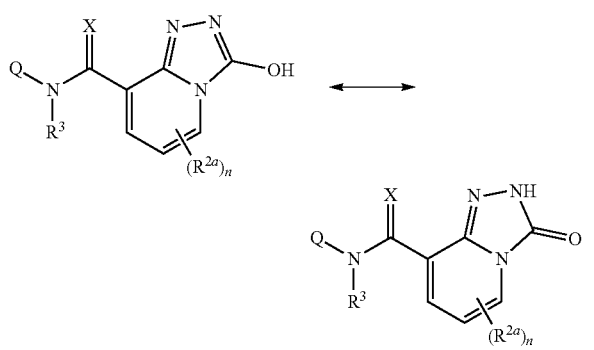

Similarly, in the case of the compound of Formula (1): [where W is W-1; $R^{1a}$ is —SH group; n, Q, $R^{2a}$, $R^3$, and X mean the same as described above], the following tautomers are included.

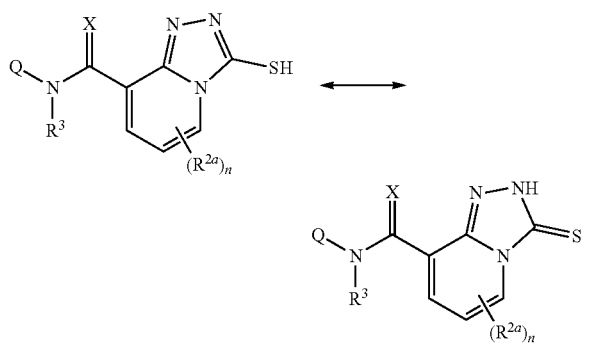

Among the compounds included in the present invention, the compounds that can form acid-added salt by a conventional method may form, for example, the salts of hydrohalic acids such as hydrofluoric acid, hydrochloric acid, hydrobromic acid, and hydroiodic acid; the salts of inorganic acids such as nitric acid, sulfuric acid, phosphoric acid, chloric acid, and perchloric acid; the salts of sulfonic acids such as methanesulfonic acid, ethanesulfonic acid, trifluoromethanesulfonic acid, benzenesulfonic acid, and p-toluenesulfonic acid; the salts of carboxylic acids such as formic acid, acetic acid, propionic acid, trifluoroacetic acid, fumaric acid, tartaric acid, oxalic acid, maleic acid, malic acid, succinic acid, benzoic acid, mandelic acid, ascorbic acid, lactic acid, gluconic acid, and citric acid; or the salts of amino acids such as glutamic acid and aspartic acid.

Among the compounds included in the present invention, the compounds that can form metal salt by a conventional method may form, for example, the salts of alkali metals such as lithium, sodium, and potassium; the salts of alkaline earth metals such as calcium, barium, and magnesium; or the salt of aluminum.

Specific examples of each substituent described in this specification will be described below. Here, n- means normal; i- means iso; s- means secondary; and tert- means tertiary and Ph means phenyl.

Examples of the halogen atom in this specification may include a fluorine atom, a chlorine atom, a bromine atom, and an iodine atom. The expression of "halo" in this specification is also these halogen atoms.

The expression of $C_{a-b}$ alkyl in this specification is a linear or a branched hydrocarbon group having a carbon atom number of a to b. Specific examples of the $C_{a-b}$ alkyl may include methyl group, ethyl group, n-propyl group, i-propyl group, n-butyl group, i-butyl group, s-butyl group, tert-butyl group, n-pentyl group, 1,1-dimethyl propyl group, n-hexyl group and the like. Each of these groups is selected in a range of the specified carbon atom number.

The expression of $C_{a-b}$ cycloalkyl in this specification is a cyclic hydrocarbon group having a carbon atom number of a to b and can form a monocyclic structure or a fused ring structure of a 3-membered ring to a 6-membered ring. Each ring may be optionally substituted with an alkyl group in a range of the specified carbon atom number. Specific example of the $C_{a-b}$ cycloalkyl may include cyclopropyl group, 1-methylcyclopropyl group, 2-methylcyclopropyl group, 2,2-dimethylcyclopropyl group, cyclobutyl group, cyclopentyl group, cyclohexyl group and the like. Each of these groups is selected in a range of the specified carbon atom number.

The expression of $C_{a-b}$ halocycloalkyl in this specification is a cyclic hydrocarbon group having a carbon atom number of a to b in which the hydrogen atom bonded to the carbon atom is optionally substituted with a halogen atom and can form a monocyclic structure or a fused ring structure of a 3-membered ring to a 10-membered ring. Each ring can be optionally substituted with an alkyl group in a range of the specified carbon atom number. The substitution position with the halogen atom may be at a ring structure part, at a side chain structure part, or at both of them. When two or more halogen atoms are used as substituents, these halogen atoms are optionally the same as or different from each other. Specific examples of the $C_{a-b}$ halocycloalkyl may include 2,2-difluorocyclopropyl group, 2,2-dichlorocyclopropyl group, 2,2-dibromocyclopropyl group, 2,2-difluoro-1-methylcyclopropyl group, 2,2-dichloro-1-methylcyclopropyl group, 2,2-dibromo-1-methylcyclopropyl group, 2,2,3,3-tetra-fluorocyclobutyl group and the like. Each of these groups is selected in a range of the specified carbon atom number.

The expression of $C_{a-b}$ alkenyl in this specification is a linear or a branched unsaturated hydrocarbon group having a carbon atom number of a to b and having one or two or more double bonds in the molecule. Specific examples of the $C_{a-b}$ alkenyl may include vinyl group, 1-propenyl group, 2-propenyl group, 1-methylethenyl group, 2-butenyl group, 2-methyl-2-propenyl group, 3-methyl-2-butenyl group, 1,1-dimethyl-2-propenyl group and the like. Each of these groups is selected in a range of the specified carbon atom number.

The expression of $C_{a-b}$ haloalkenyl in this specification is a linear or a branched unsaturated hydrocarbon group having a carbon atom number of a to b in which the hydrogen atom bonded to the carbon atom is optionally substituted with a halogen atom and having one or two or more double bonds in the molecule. In this case, when two or more halogen atoms are used as substituents, these halogen atoms are optionally the same as or different from each other. Specific examples of the $C_{a-b}$ haloalkenyl may include 2,2-dichlorovinyl group, 2-fluoro-2-propenyl group, 2-chloro-2-propenyl group, 3-chloro-2-propenyl group, 2-bromo-2-propenyl group, 3,3-difluoro-2-propenyl group, 2,3-dichloro-2-propenyl, 3,3-dichloro-2-propenyl group, 2,3,3-trifluoro-2-propenyl group, 2,3,3-trichloro-2-propenyl group, 1-(trifluoromethyl) ethenyl group, 4,4-difluoro-3-butenyl group, 3,4,4-trifluoro-3-butenyl group, 3-chloro-4,4,4-trifluoro-2-butenyl group and the like. Each of these groups is selected in a range of the specified carbon atom number.

The expression of $C_{a-b}$ cycloalkenyl in this specification is a cyclic unsaturated hydrocarbon group having a carbon atom number of a to b and having one or two or more double bonds and can form a monocyclic structure or a fused ring structure of a 3-membered ring to a 6-membered ring. Each ring can be substituted with an alkyl group in a range of the specified carbon atom number. The double bond may be either endo-form or exo-form. Specific example of the $C_{a-b}$ cycloalkenyl may include 1-cyclopentene-1-yl group, 2-cyclopentene-1-yl group, 1-cyclohexen-1-yl group, 2-cyclohexen-1-yl group and the like. Each of these groups is selected in a range of the specified carbon atom number.

The expression of $C_{a-b}$ alkynyl in this specification is a linear or a branched unsaturated hydrocarbon group having a carbon atom number of a to b and having one or two or more triple bonds in the molecule. Specific examples of the $C_{a-b}$ alkynyl may include ethynyl group, 1-propynyl group, 2-propynyl group, 1-butyryl group, 2-butyryl group, 3-butyryl group, 1,1-dimethyl-2-propynyl group and the like. Each of these groups is selected in a range of the specified carbon atom number.

The expression of $C_{a-b}$ haloalkynyl in this specification is a linear or a branched unsaturated hydrocarbon group having a carbon atom number of a to b in which the hydrogen atom bonded to the carbon atom is optionally substituted with a halogen atom and having one or two or more triple bonds in the molecule. In this case, when two or more halogen atoms are used as substituents, these halogen atoms are optionally the same as or different from each other. Specific examples of the $C_{a-b}$ haloalkynyl may include 2-chloroethynyl group, 2-bromoethynyl group, 2-iodoethynyl group, 3-chloro-2-propynyl group, 3-bromo-2-propynyl group, 3-iodo-2-propynyl group and the like. Each of these groups is selected in a range of the specified carbon atom number.

The expression of $C_{a-b}$ haloalkyl in this specification is a linear or a branched hydrocarbon group having a carbon atom number of a to b in which the hydrogen atom bonded to the carbon atom is optionally substituted with a halogen atom. When two or more halogen atoms are used as substituents, these halogen atoms are optionally the same as or different from each other. Specific examples of the $C_{a-b}$ haloalkyl may include fluoromethyl group, chloromethyl group, bromomethyl group, iodomethyl group, difluoromethyl group, dichloromethyl group, a trifluoromethyl group, chlorodifluoromethyl group, trichloromethyl group, bromodifluoromethyl group, 2-fluoroethyl group, 2-chloroethyl group, 2-bromoethyl group, 2,2-difluoroethyl group, 2,2,2-trifluoroethyl group, 2-chloro-2,2-difluoroethyl group, 2,2,2-trichloroethyl group, 1,1,2,2-tetrafluoroethyl group, 2-chloro-1,1,2-trifluoroethyl group, pentafluoroethyl group, 3,3,3-trifluoropropyl group, 2,2,3,3,3-pentafluoropropyl group, 1,1,2,3,3,3-hexafluoropropyl group, heptafluoropropyl group, 2,2,2-trifluoro-1-(trifluoromethyl)ethyl group, 1,2,2,2-tetrafluoro-1-(trifluoromethyl)ethyl group, 2,2,3,3,4,4,4-heptafluorobutyl group, nonafluorobutyl group and the like. Each of these groups is selected in a range of the specified carbon atom number.

The expression of $C_{a-b}$ alkoxy in this specification is an alkyl-O— group in which this alkyl is the above meaning alkyl group having a carbon atom number of a to b. Specific examples of the $C_{a-b}$ alkoxy may include methoxy group, ethoxy group, n-propyloxy group, i-propyloxy group, n-butyloxy group, i-butyloxy group, s-butyloxy group, tert-butyloxy group and the like. Each of these groups is selected in a range of the specified carbon atom number.

The expression of $C_{a-b}$ alkylthio in this specification is an alkyl-S— group in which this alkyl is the above meaning alkyl group having a carbon atom number of a to b. Specific examples of the $C_{a-b}$ alkylthio may include methylthio group, ethylthio group, n-propylthio group, i-propylthio group, n-butylthio group, i-butylthio group, s-butylthio group, tert-butylthio group and the like. Each of these groups is selected in a range of the specified carbon atom number.

The expression of $C_{a-b}$ alkylcarbonyl in this specification is an alkyl-C(O)— group in which this alkyl is the above meaning alkyl group having a carbon atom number of a to b. Specific examples of the $C_{a-b}$ alkylcarbonyl may include acetyl group, propionyl group, butyryl group, isobutyryl group, valeryl group, isovaleryl group, 2-methylbutanoyl group, pivaloyl group, hexanoyl group, heptanoyl group and the like. Each of these groups is selected in a range of the specified carbon atom number.

The expression of $C_{a-b}$ haloalkylcarbonyl in this specification is a haloalkyl-C(O)— group in which this haloalkyl is the above meaning haloalkyl group having a carbon atom number of a to b. Specific examples of the $C_{a-b}$ haloalkylcarbonyl may include fluoroacetyl group, chloroacetyl group, difluoroacetyl group, dichloroacetyl group, trifluoroacetyl group, chlorodifluoroacetyl group, bromodifluoroacetyl group, trichloroacetyl group, pentafluoropropionyl group, heptafluorobutanoyl group, 3-chloro-2,2-dimethylpropanoyl group and the like. Each of these groups is selected in a range of the specified carbon atom number.

The expression of $C_{a-b}$ cycloalkylcarbonyl in this specification is a cycloalkyl-C(O)— group in which this cycloalkyl is the above meaning cycloalkyl group having a carbon atom number of a to b. Specific examples of the $C_{a-b}$ cycloalkylcarbonyl may include cyclopropylcarbonyl group, 2-methylcyclopropylcarbonyl group, cyclobutylcarbonyl group and the like. Each of these groups is selected in a range of the specified carbon atom number.

The expression of $C_{a-b}$ halocycloalkylcarbonyl in this specification is a halocycloalkyl-C(O)— group in which this halocycloalkyl is the above meaning halocycloalkyl having a carbon atom number of a to b. Specific examples of the $C_{a-b}$ halocycloalkylcarbonyl may include 2,2-dichlorocyclopropylcarbonyl group, 2,2-dichloro-1-methylcyclopropylcarbonyl group and the like. Each of these groups is selected in a range of the specified carbon atom number.

The expression of $C_{a-b}$ alkoxycarbonyl in this specification is an alkyl-O—C(O)— group in which this alkyl is the above meaning alkyl having a carbon atom number of a to b. Specific examples of the $C_{a-b}$ alkoxycarbonyl may include methoxycarbonyl group, ethoxycarbonyl group, n-propyloxycarbonyl group, i-propyloxycarbonyl group, n-butoxycarbonyl group, i-butoxycarbonyl group, tert-butoxycarbonyl group and the like. Each of these groups is selected in a range of the specified carbon atom number.

The expression of $C_{a-b}$ haloalkoxycarbonyl in this specification is a haloalkyl-O—C(O)— group in which this haloalkyl is the above meaning haloalkyl group having a carbon atom number of a to b. Specific examples of the $C_{a-b}$ haloalkoxycarbonyl may include chloromethoxycarbonyl group, 2-chloroethoxycarbonyl group, 2,2-difluoroethoxycarbonyl group, 2,2,2-trifluoroethoxycarbonyl group, 2,2,2-trichloroethoxycarbonyl group and the like. Each of these groups is selected in a range of the specified carbon atom number.

The expression of $C_{a-b}$ alkylaminocarbonyl in this specification is a carbamoyl group in which one hydrogen atom is substituted with the above meaning alkyl group having a carbon atom number of a to b. Specific examples of the $C_{a-b}$ alkylaminocarbonyl may include methylcarbamoyl group, ethylcarbamoyl group, n-propylcarbamoyl group, i-propylcarbamoyl group, n-butylcarbamoyl group, i-butylcarbamoyl group, s-butylcarbamoyl group, tert-butylcarbamoyl group and the like. Each of these groups is selected in a range of the specified carbon atom number.

The expression of $C_{a-b}$ haloalkylaminocarbonyl in this specification is a carbamoyl group in which one hydrogen atom is substituted with the above meaning haloalkyl group having a carbon atom number of a to b. Specific examples of the $C_{a-b}$ haloalkylaminocarbonyl may include 2-fluoroethylcarbamoyl group, 2-chloroethylcarbamoyl group, 2,2-difluoroethylcarbamoyl group, 2,2,2-trifluoroethylcarbamoyl group and the like. Each of these groups is selected in a range of the specified carbon atom number.

The expression of di($C_{a-b}$ alkyl)aminocarbonyl in this specification is a carbamoyl group in which both hydrogen atoms are substituted with the above meaning alkyl groups, which are the same as or different from each other, having a carbon atom number of a to b. Specific examples of the di($C_{a-b}$ alkyl)aminocarbonyl may include N,N-dimethylcarbamoyl group, N-ethyl-N-methylcarbamoyl group, N,N-diethylcarbamoyl group, N,N-di(n-propyl)carbamoyl group, N,N-di(n-butyl)carbamoyl group and the like. Each of these groups is selected in a range of the specified carbon atom number.

The expression of $C_{a-b}$ alkylaminosulfonyl in this specification is a sulfamoyl group in which one hydrogen atom is substituted with the above meaning alkyl group having a carbon atom number of a to b. Specific examples of the $C_{a-b}$ alkylaminosulfonyl may include methylsulfamoyl group, ethylsulfamoyl group, n-propylsulfamoyl group, i-propylsulfamoyl group, n-butylsulfamoyl group, i-butylsulfamoyl group, s-butylsulfamoyl group, tert-butylsulfamoyl group and the like. Each of these groups is selected in a range of the specified carbon atom number.

The expression of di($C_{a-b}$ alkyl)aminosulfonyl in this specification is a sulfamoyl group in which both hydrogen atoms are substituted with the above meaning alkyl groups, which are the same as or different from each other, having a carbon atom number of a to b. Specific examples of the di($C_{a-b}$ alkyl)aminosulfonyl may include N,N-dimethylsulfamoyl group, N-ethyl-N-methylsulfamoyl group, N,N-diethylsulfamoyl group, N,N-di(n-propyl)sulfamoyl group, N,N-di(n-butyl)sulfamoyl group and the like. Each of these groups is selected in a range of the specified carbon atom number.

The expression of $C_{a-b}$ alkylamino in this specification is an amino group in which one hydrogen atom is substituted with the above meaning alkyl group having a carbon atom number of a to b. Specific examples of the $C_{a-b}$ alkylamino may include methylamino group, ethylamino group, n-propylamino group, i-propylamino group, n-butylamino group, i-butylamino group, tert-butylamino group and the like. Each of these groups is selected in a range of the specified carbon atom number.

The expression of di($C_{a-b}$ alkyl)amino in this specification is an amino group in which both hydrogen atoms are substituted with the above meaning alkyl groups, which are the same as or different from each other, having a carbon atom number of a to b. Specific examples of the di($C_{a-b}$ alkyl)amino may include dimethylamino group, ethyl(methyl)amino group, diethylamino group, n-propyl(methyl) amino group, i-propyl(methyl)amino group, di(n-propyl) amino group, di(n-butyl)amino group and the like. Each of these groups is selected in a range of the specified carbon atom number.

The expression of ($C_{a-b}$) alkyl optionally substituted with $R^6$, ($C_{a-b}$) alkyl optionally substituted with $R^{27}$, ($C_{a-b}$) alkyl optionally substituted with $R^{34}$, ($C_{a-b}$) alkyl optionally substituted with $R^{35}$, or ($C_{a-b}$) alkyl optionally substituted with $R^{36}$ in this specification is the above meaning alkyl group having a carbon atom number of a to b in which the hydrogen atoms bonded to the carbon atoms are optionally substituted with any $R^6$, $R^{27}$, $R^{34}$, $R^{35}$, or $R^{36}$. Each of these groups is selected in a range of the specified carbon atom number. In this case, when two or more of substituents $R^6$, $R^{27}$, $R^{34}$, $R^{35}$, or $R^{36}$ are contained in the ($C_{a-b}$) alkyl group, $R^6$, $R^{27}$, $R^{34}$, $R^{35}$, or $R^{36}$ are optionally the same as or different from each other.

The expression of ($C_{a-b}$) cycloalkyl optionally substituted with $R^6$ or ($C_{a-b}$) cycloalkyl optionally substituted with $R^{27}$ in this specification is the above meaning cycloalkyl group having a carbon atom number of a to b in which the hydrogen atoms bonded to the carbon atoms are optionally substituted with any $R^6$ or $R^{27}$. Each of these groups is selected in a range of the specified carbon atom number. In this case, when two or more of substituents $R^6$ or $R^{27}$ are contained in the ($C_{a-b}$) cycloalkyl group, $R^6$ or $R^{27}$ are optionally the same as or different from each other. The substituted positions may be at a ring structure part, at a side chain structure part, or at both of them.

Specific examples of the expression of "$R^{11}$ optionally forms a 3-7-membered ring together with a nitrogen atom to which $R^{11}$ and $R^{12}$ are bonded by forming a $C_{2-6}$ alkylene chain together with $R^{12}$, and in this case, the alkylene chain optionally contains one O, S, S(O), S(O)$_2$, or N($R^{33}$) and is optionally substituted with an oxo group or a thioxo group", "$R^{11a}$ optionally forms a 3-7-membered ring together with a nitrogen atom to which $R^{11a}$ and $R^{12a}$ are bonded by forming a $C_{2-6}$ alkylene chain together with $R^{12a}$, and in this case, the alkylene chain optionally contains one O, S, S(O), S(O)$_2$, or N($R^{33}$) and is optionally substituted with an oxo group or a thioxo group", and "$R^{21}$ optionally forms a 3-7-membered ring together with a nitrogen atom to which $R^{21}$ and $R^{22}$ are bonded by forming a $C_{2-6}$ alkylene chain together with $R^{22}$, in this case, the alkylene chain optionally contains one O, S, S(O), S(O)$_2$, or N($R^{39}$) and is optionally substituted with an oxo group or a thioxo group" in this specification may include aziridine, azetidine, azetidin-2-one, pyrrolidin, pyrrolidin-2-one, oxazolidine, oxazolidin-2-one, oxazolidin-2-thione, thiazolidine, thiazolidin-2-one, thiazolidin-2-thione, imidazolidine, imidazolidin-2-one, imidazolidin-2-thione, piperidine, piperidin-2-one, piperidin-2-thione, 2H-3,4,5,6-tetrahydro-1,3-oxazin-2-one, 2H-3,4,5,6-tetrahydro-1,3-oxazine-2-thione, morpholine, 2H-3,4,5,6-tetrahydro-1,3-thiazin-2-one, 2H-3,4,5,6-tetrahydro-1,3-thiazin-2-thione, thiomorpholine, thiomorpholine-1-oxide, thiomorpholine-1,1-dioxide, perhydropyrimidin-2-one, piperazine, homopiperidine, homopiperidin-2-one, heptamethyleneimine and the like. Each of these groups is selected in a range of the specified carbon atom number.

The expression of ($C_{a-b}$ alkoxy) $C_{d-e}$ alkyl, ($C_{a-b}$ alkylthio) $C_{d-e}$ alkyl, or the like in this specification is a linear or a branched hydrocarbon group having a carbon atom number of d to e in which the hydrogen atom bonded to the carbon atom is optionally substituted with the any above meaning $C_{a-b}$ alkoxy group or $C_{a-b}$ alkylthio group respectively. Each of these groups is selected in a range of the specified carbon atom number.

The "5-6-membered aromatic heterocycle" in this specification means a monocyclic aromatic heterocycle in which the number of atoms forming the ring is 5 to 6 and 1 to 5 hetero atoms (the hetero atom means a nitrogen atom, an oxygen atom, or a sulfur atom) are contained in the atoms forming the ring. Specific examples of the 5-6-membered aromatic heterocycle may include pyrrole, pyrazole, imidazole, triazole, tetrazole, pyridine, pyridazine, pyrimidine, pyrazine, triazine, furan, thiophene, thiazole, isothiazole, oxazole, isoxazole, oxadiazole, thiadiazole and the like.

When the "5-6-membered aromatic heterocycle" contains a C=N double bond, the nitrogen atom may be N-oxide.

The "5-6-membered heteroaryl" in this specification means a monovalent substituent formed by removing one hydrogen atom from any position in the above meaning "5-6-membered aromatic heterocycle". Positions to which these substituents are bonded are not particularly limited and the substituents may be bonded to desired positions.

The "3-7-membered non-aromatic heterocycle" in this specification means a monocyclic non-aromatic heterocycle having the following characteristics:

1) the number of atoms forming the ring is 3 to 7,
2) 1 to 3 hetero atoms (the hetero atom means a nitrogen atom, an oxygen atom, or a sulfur atom) are contained in the atoms forming the ring,
3) a carbonyl group, a thiocarbonyl group, a double bond, or a triple bond may be contained in the ring, and
4) when a sulfur atom is contained in the atoms forming the ring, the sulfur atom may be a sulfinyl group or a sulfonyl group.

Specific examples of the 3-7-membered non-aromatic heterocycle may include azetidine, pyrrolidine, pyrrolidinone, oxazolidine, isoxazolidine, thiazolidine, isothiazolidine, piperazine, piperazinone, piperidine, piperidinone, morpholine, thiomorpholine, azepine, diazepine, oxetane, tetrahydrofuran, 1,3-dioxolane, tetrahydropyran, 1,4-dioxane, oxepane, homomorpholine and the like.

The "3-7-membered heterocyclyl" in this specification means a monovalent substituent formed by removing one hydrogen atom from any position in the above meaning "3-7-membered non-aromatic heterocycle". Positions to which these substituents are bonded are not particularly limited and the substituents may be bonded to desired positions.

The "5-6-membered heteroaryl optionally substituted with $R^{28}$ and $R^{28a}$" in this specification is a "5-6-membered heteroaryl" in which the hydrogen atoms on the carbon atoms forming the ring of the "5-6-membered heteroaryl" are substituted on the carbon atoms with any $R^{28}$ in a range of the number of the existing hydrogen atoms. In this case, when nitrogen exists among the atoms forming the ring of the "5-6-membered heteroaryl" and the nitrogen atom potentially has a NH structure, the "5-6-membered heteroaryl optionally substituted with $R^{28}$ and $R^{28a}$" is a "5-6-membered heteroaryl" in which the hydrogen atom on the nitrogen atom is optionally substituted on the nitrogen atom with any $R^{28a}$ in a range of the number of existing hydrogen atoms. In this case, when two or more substituents $R^{28}$ on the carbon atoms forming the ring of the "5-6-membered heteroaryl" and two or more substituents $R^{28a}$ substituted with the nitrogen atom potentially having a NH structure forming the ring independently exist, two or more of each of $R^{28}$ and $R^{28a}$ are optionally the same as or different from each other, and when two $R^{28}$ are adjacent, the two adjacent $R^{28}$ optionally form a 6-membered ring together with carbon atoms to which each $R^{28}$ is bonded by forming —CH=CH—CH=CH—.

The "3-7-membered heterocyclyl optionally substituted with $R^{28}$ and $R^{28a}$" in this specification is a "3-7-membered heterocyclyl" in which the hydrogen atoms on the carbon atoms forming the ring of the "3-7-membered heterocyclyl" are substituted on the carbon atoms with any $R^{28}$ in a range of the number of the existing hydrogen atoms. In this case, when nitrogen exists among the atoms forming the ring of the "3-7-membered heterocyclyl" and the nitrogen atom potentially has a NH structure, the "3-7-membered heterocyclyl optionally substituted with $R^{28a}$" is a "3-7-membered heterocyclyl" in which the hydrogen atom on the nitrogen atom is optionally substituted on the nitrogen atom with any $R^{28a}$ in a range of the number of existing hydrogen atoms. In this case, when two or more substituents $R^{28}$ on the carbon atoms forming the ring of the "3-7-membered heterocyclyl" and two or more substituents $R^{28a}$ substituted with the nitrogen atom potentially having a NH structure forming the ring independently exist, two or more of each of $R^{28}$ and $R^{28a}$ are optionally the same as or different from each other, and when two $R^{28}$ are adjacent, the two adjacent $R^{28}$ optionally form a 6-membered ring together with carbon atoms to which each $R^{28}$ is bonded by forming —CH=CH—CH=CH—.

Next, the production method of the compound of the present invention will be described below.

Production Method A

The heterocyclic amide compound of Formula (1) can be produced by, for example, reacting the compound of Formula (2) with the compound of Formula (3a).

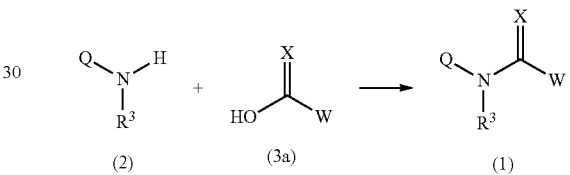

The compound of Formula (1): [where Q and $R^3$, W, and X mean the same as defined above] of the present invention can be produced by reacting the compound of Formula (2): [where Q and $R^3$ mean the same as defined above] or the salt thereof with the compound of Formula (3a): [where W and X mean the same as defined above] or the salt thereof in a solvent or without using a solvent by using a base, a condensing agent, and/or a catalyst if necessary and adding an additive if necessary.

In this reaction, the compound of Formula (3a) can be used in a range of 0.1 equivalents to 100 equivalents relative to 1 equivalent of the compound of Formula (2).

When the solvent is used, the solvent to be used may be a solvent that is inactive to the reaction. Example of the solvent may include polar solvents such as N,N-dimethylformamide, N,N-dimethylacetamide, acetonitrile, dimethylsulfoxide, and 1,3-dimethyl-2-imidazolinone; ethers such as diethyl ether, tetrahydrofuran, 1,4-dioxane, 1,2-dimethoxyethane, and diphenyl ether; aromatic hydrocarbons such as benzene, toluene, and xylene; halogenated hydrocarbons such as methylene chloride, chloroform, carbon tetrachloride, and 1,2-dichloroethane; and aliphatic hydrocarbons such as n-pentane and n-hexane. These solvents may be used singly or in combination of two or more of them.

When the base is used, examples of the base to be used may include organic bases such as triethylamine, pyridine, and 4-(dimethylamino)pyridine and inorganic bases such as potassium carbonate and sodium carbonate. These bases may be used in a range of 0.1 equivalents to 50 equivalents relative to 1 equivalent of the compound of Formula (2).

When the condensing agent is used, examples of the condensing agent to be used may include 1H-benzotriazol- 1-yloxytris(dimethylamino)phosphonium hexafluorophosphate, N,N'-dicyclohexylcarbodiimide, 1-(3-dimethylaminopropyl)-3-ethylcarbodiimide hydrochloride, and 2-chloro-1-methylpyridinium iodide. These condensing agents may be used in a range of 0.1 equivalents to 50 equivalents relative to 1 equivalent of the compound of Formula (2).

When the additive is used, examples of the additive to be used may include 3H-[1,2,3]triazolo[4,5-b]pyridine-3-ol and 1-hydroxybenzotriazole. These additives may be used in a range of 0.1 equivalents to 50 equivalents relative to 1 equivalent of the compound of Formula (2).

As the reaction temperature, any temperature from −78° C. to the reflux temperature of the reaction mixture can be set. Although the reaction time varies depending on the concentration of the reaction substrate and the reaction temperature, usually any time may be set in a range of 5 minutes to 100 hours.

Some of the compounds of Formula (2) are known compounds and some of the compounds are commercially available.

Some of the compounds of Formula (3a) are known compounds and can be synthesized in accordance with known methods described in documents. Examples of the methods known in the documents may include a method described in WO 2008/006540 Pamphlet.

Production Method B

The heterocyclic amide compound of Formula (1) can be produced by, for example, reacting the compound of Formula (2) with the compound of Formula (3b).

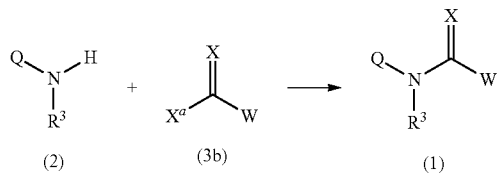

The compound of Formula (1): [where Q and $R^3$, W, and X mean the same as defined above] of the present invention can be produced by reacting the compound of Formula (2): [where Q and $R^3$ mean the same as defined above] or the salt thereof with the compound of Formula (3b): [where W and X mean the same as defined above and $X^a$ is a leaving group such as a halogen atom] or the salt thereof in a solvent or without using a solvent by using a base if necessary.

In this reaction, the compound of Formula (3b) can be used in a range of 0.1 equivalents to 100 equivalents relative to 1 equivalent of the compound of Formula (2).

When the solvent is used, the solvent to be used may be a solvent that is inactive to the reaction. Example of the solvent may include polar solvents such as N,N-dimethylformamide, N,N-dimethylacetamide, acetonitrile, dimethylsulfoxide, and 1,3-dimethyl-2-imidazolinone; ethers such as diethyl ether, tetrahydrofuran, 1,4-dioxane, 1,2-dimethoxyethane, and diphenyl ether; aromatic hydrocarbons such as benzene, toluene, and xylene; halogenated hydrocarbons such as methylene chloride, chloroform, carbon tetrachloride, and 1,2-dichloroethane; and aliphatic hydrocarbons such as n-pentane and n-hexane. These solvents may be used singly or in combination of two or more of them.

When the base is used, examples of the base to be used may include organic bases such as triethylamine, pyridine, and 4-(dimethylamino)pyridine and inorganic bases such as potassium carbonate, sodium carbonate, potassium hydrogen carbonate, sodium hydrogen carbonate, and sodium hydride. These bases may be used in a range of 0.1 equivalents to 50 equivalents relative to 1 equivalent of the compound of Formula (2). These bases may be used singly or in combination of two or more of them.

As the reaction temperature, any temperature from −78° C. to the reflux temperature of the reaction mixture can be set. Although the reaction time varies depending on the concentration of the reaction substrate and the reaction temperature, usually any time may be set in a range of 5 minutes to 100 hours.

Production Method C

The compound of Formula (1-2): [where W, Q and $R^3$ mean the same as defined above] of the present invention can be produced, for example, by reacting the compound of Formula (1-1): [where W, Q and $R^3$ mean the same as defined above] of the present invention with sulfidizing agents such as phosphorus pentasulfide, phosphorus pentasulfide-HMDO (hexamethyldisiloxane), and Lawesson's reagent (2,4-bis(4-methoxyphenyl)-1,3,2,4-dithiadiphosphetane-2,4-disulfide).

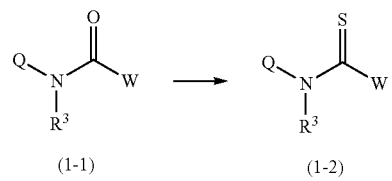

The sulfidizing agent used in this reaction can be used in a range of 0.5 equivalents to 50 equivalents relative to 1 equivalent of the compound of Formula (1-1).

Bases such as potassium carbonate, triethylamine, pyridine, and 4-(dimethylamino)pyridine can be used if necessary.

This reaction can be carried out without using a solvent. However, a solvent may be used. Examples of the solvent may include polar solvents such as N,N-dimethylformamide, N,N-dimethylacetamide, acetonitrile, dimethylsulfoxide, 1,3-dimethyl-2-imidazolinone, and water; alcohols such as methanol, ethanol, propanol, 2-propanol, and ethylene glycol; ethers such as diethyl ether, tetrahydrofuran, and diphenyl ether; aromatic hydrocarbons such as benzene, toluene, and xylene; halogenated hydrocarbons such as methylene chloride, chloroform, and carbon tetrachloride; and aliphatic hydrocarbons such as pentane and n-hexane. These solvents may be used singly or in combination of two or more of them.

As the reaction temperature, any temperature from −60° C. to the reflux temperature of the reaction mixture can be set. Although the reaction time varies depending on the concentration of the reaction substrate and the reaction temperature, usually any time may be set in a range of 5 minutes to 100 hours.

In the production method A to the production method C, usual post treatment of the reaction mixture after completion of the reaction such as direct concentration, concentration after dissolving in an organic solvent and washing with water, or concentration after pouring into ice-water and extracting with an organic solvent can give the compound of the present invention. When purification is required, the compound can be separated and purified by any purification method such as recrystallization, column chromatography, thin layer chromatography, and liquid chromatography.

Some of the compound of Formula (3b) can be synthesized in accordance with the reaction formula 1 described below.

Production Method D

The heterocyclic amide compound of Formula (1-1) can be produced by, for example, reacting the compound of Formula (1-3): [where W and Q mean the same as defined above] with the compound of Formula (4): [where $R^3$ has the same as defined above and J is a leaving group such as a halogen atom, —OH, —OSO$_2$Me, and —OSO$_2$CF$_3$].

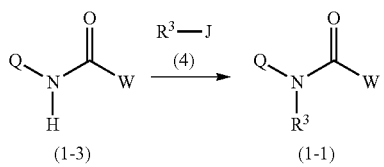

In this reaction, the compound of Formula (4) can be used in a range of 0.5 equivalents to 50 equivalents relative to 1 equivalent of the compound of Formula (1-3). Acids such as hydrochloric acid, sulfuric acid, and p-toluenesulfonic acid or bases such as potassium carbonate, triethylamine, pyridine, and 4-(dimethylamino)pyridine, sodium hydride, sodium hydroxide, and potassium hydroxide can be used if necessary. Alternatively, Mitsunobu reaction using diethyl azodicarboxylate, triphenylphosphine, and the like can be used.

This reaction can be carried out without using a solvent. However, a solvent may be used. Example of the solvent may include polar solvents such as N,N-dimethylformamide, N,N-dimethylacetamide, acetonitrile, dimethylsulfoxide, 1,3-dimethyl-2-imidazolinone, and water; alcohols such as methanol, ethanol, propanol, 2-propanol, and ethylene glycol; ethers such as diethyl ether, tetrahydrofuran, and diphenyl ether; aromatic hydrocarbons such as benzene, toluene, and xylene; halogenated hydrocarbons such as methylene chloride, chloroform, and carbon tetrachloride; and aliphatic hydrocarbons such as pentane and n-hexane. These solvents may be used singly or in combination of two or more of them.

As the reaction temperature, any temperature from −60° C. to the reflux temperature of the reaction mixture can be set. Although the reaction time varies depending on the concentration of the reaction substrate and the reaction temperature, usually any time may be set in a range of 5 minutes to 100 hours.

Some of the compounds of Formula (4) are known compounds and some of the compounds are commercially available. Compounds other than the compounds described above can be synthesized in accordance with methods described in reference documents.

Reaction Formula 1

The compound of Formula (3b) can be produced by, for example, reacting the compound of Formula (3a) with a halogenating agent.

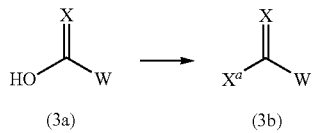

The compound of Formula (3b): [where W, X and $X^a$ mean the same as defined above] can be produced by reacting the compound of Formula (3a) [where W and X mean the same as defined above] or the salt thereof with the halogenating agent in a solvent or without using a solvent by using a base if necessary.

Examples of the halogenating agent may include thionyl chloride, oxalyl chloride, and phosphoryl chloride. The halogenating agent can be used in a range of 0.1 equivalents to 100 equivalents relative to 1 equivalent of the compound of Formula (3a).

When the solvent is used, the solvent to be used may be a solvent that is inactive to the reaction. Example of the solvent may include polar solvents such as N,N-dimethylformamide, N,N-dimethylacetamide, acetonitrile, dimethylsulfoxide, and 1,3-dimethyl-2-imidazolinone; ethers such as diethyl ether, tetrahydrofuran, 1,4-dioxane, 1,2-dimethoxyethane, and diphenyl ether; aromatic hydrocarbons such as benzene, toluene, and xylene; halogenated hydrocarbons such as methylene chloride, chloroform, carbon tetrachloride, and 1,2-dichloroethane; and aliphatic hydrocarbons such as n-pentane and n-hexane. These solvents may be used singly or in combination of two or more of them.

When the base is used, examples of the base to be used may include organic bases such as triethylamine, pyridine, and 4-(dimethylamino)pyridine and inorganic bases such as potassium carbonate, sodium carbonate, potassium hydrogen carbonate, sodium hydrogen carbonate, and sodium hydride. These bases may be used in a range of 0.1 equivalents to 50 equivalents relative to 1 equivalent of the compound of Formula (3a). These bases may be used singly or in combination of two or more of them.

As the reaction temperature, any temperature from −78° C. to the reflux temperature of the reaction mixture can be set. Although the reaction time varies depending on the concentration of the reaction substrate and the reaction temperature, usually any time may be set in a range of 5 minutes to 100 hours.

The usual post treatment for the reaction mixture after completion of the reaction can give a production intermediate serving as a starting material compound for the production method B.

The production intermediate produced by this method can be used in the following step without isolation and purification.

Specific examples of the active compound included in the present invention may include the compounds listed in First Table to Third Table. The compounds listed in First Table to Third Table, however, are compounds for exemplification, and thus the present invention is not limited to these compounds. In Tables, the substituent described as Me is methyl group. Similarly in Tables, Et is ethyl group, n-Pr and Pr-n are each normal-propyl group, i-Pr and Pr-i are each isopropyl group, c-Pr and Pr-c are each cyclopropyl group, n-Bu and Bu-n are each normal-butyl group, s-Bu and Bu-s are each secondary-butyl group, an i-Bu and Bu-i are each iso-butyl group, t-Bu and Bu-t are each tertiary-butyl group, c-Bu and Bu-c are each cyclobutyl group, n-Pen and Pen-n are each normal-pentyl group, i-Pen and Pen-i are each iso-pentyl group, s-Pen and Pen-s are each secondary-pentyl group, t-Pen and Pen-t are each tertiary-pentyl group, c-Pen and Pen-c are each cyclopentyl group, 3-Pen is —CH(Et)$_2$ group, n-Hex and Hex-n are each normal-hexyl group, c-Hex and Hex-c are each cyclohexyl, and Ph is phenyl group.

In Tables, structures of D-3, D-3a, D-4, D-4a, D-4b, D-8, D-8a, D-8b, D-8c, D-8d, D-8e, D-8f, D-8g, D-8h, D-9, D-9a, D-9b, D-9c, D-9d, D-9e, D-9f, D-9g, D-9h, D-9i, D-9j, D-9k, D-9m, D-10a, D-11, D-12, D-13a, D-14, D-15, D-16, D-16a, D-16b, D-16c, D-16d, D-16e, D-16f, D-16g, D-16h, D-16i, D-16j, D-16k, D-16m, D-16n, D-16p, D-17, D-17a, D-17b, D-18, D-19, D-21, D-24a, D-24b, D-24c, D-24d, D-24e and D-24f are the following structures.
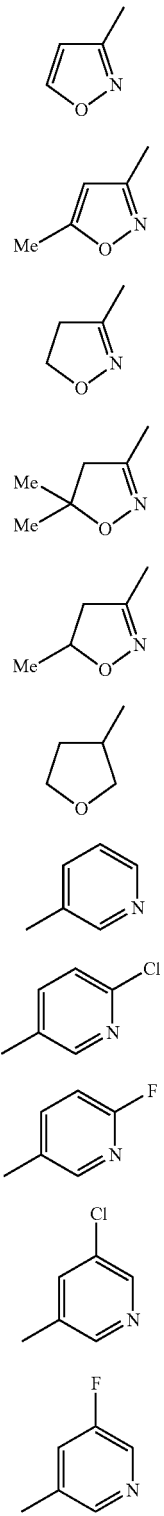
-continued
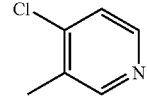
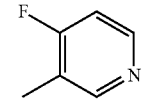
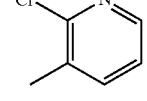
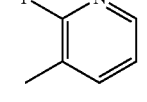
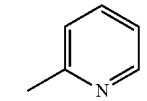
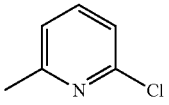
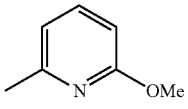
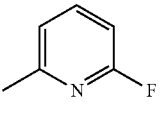
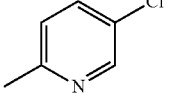
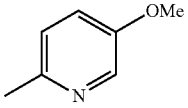
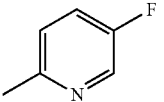
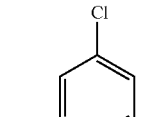
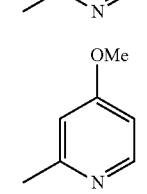

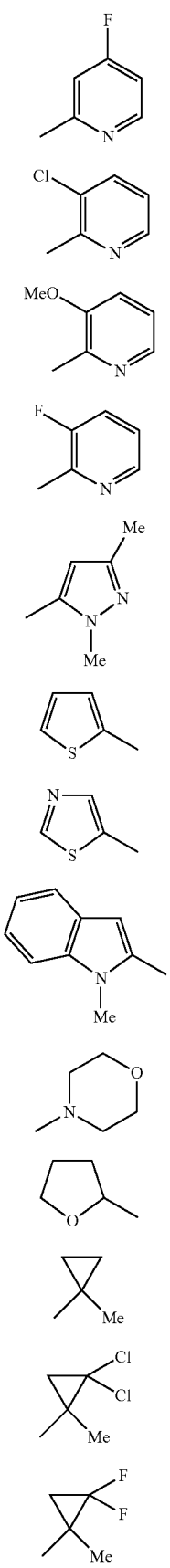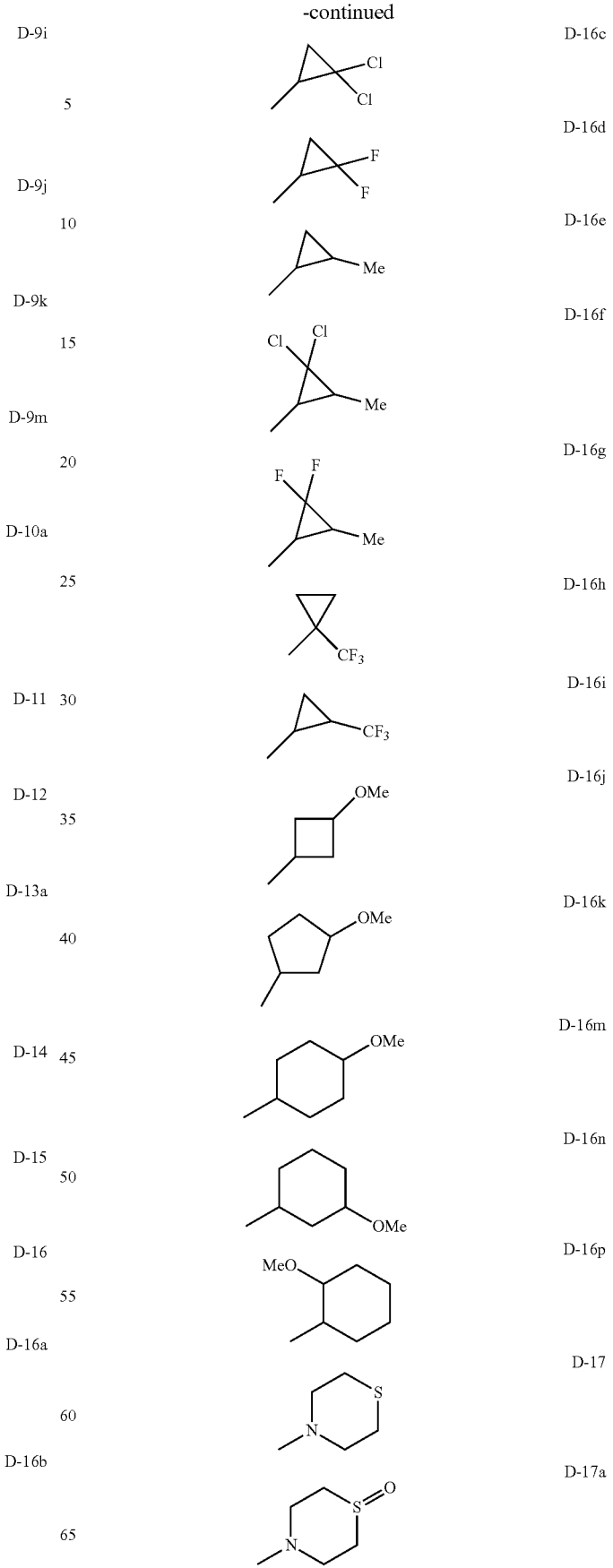

-continued
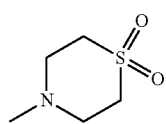
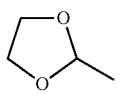
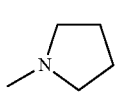
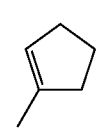
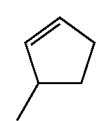
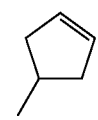
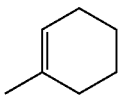
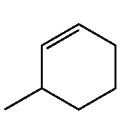
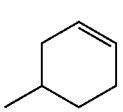
FIRST TABLE
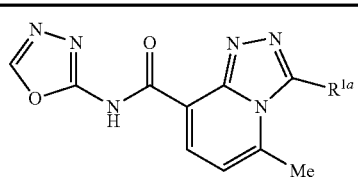
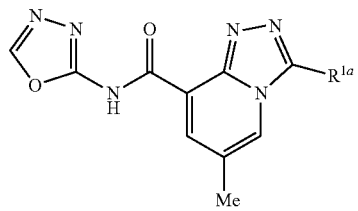
FIRST TABLE-continued
D-17b
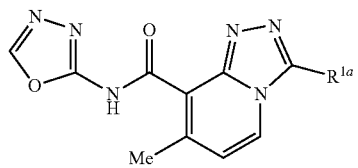
D-18
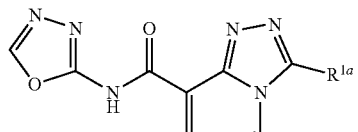
D-19
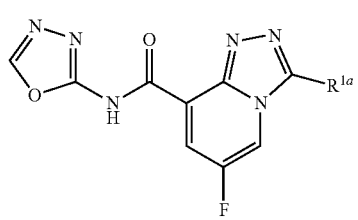
D-24a
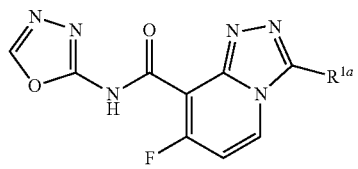
D-24b
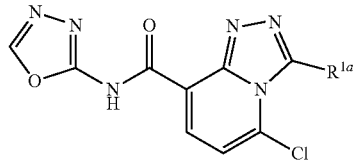
D-24c
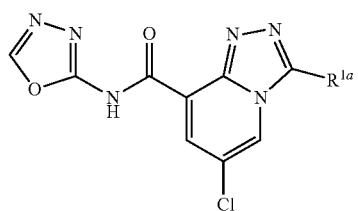
D-24d
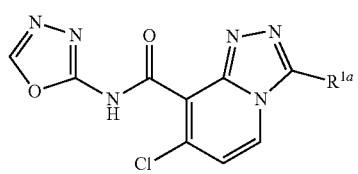
D-24e
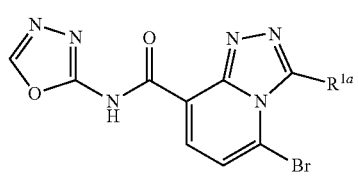
D-24f FIRST TABLE-continued
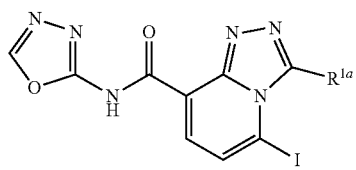
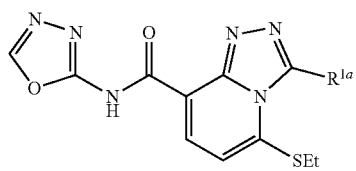
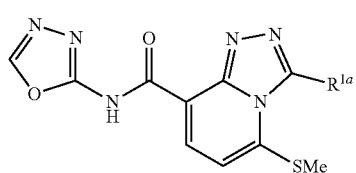
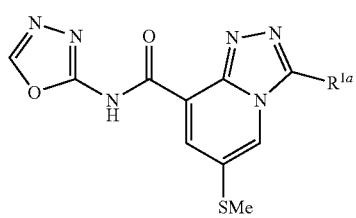
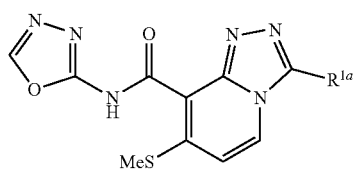
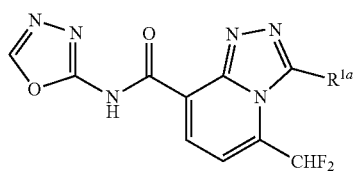
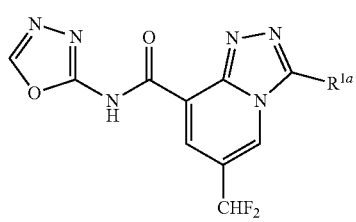
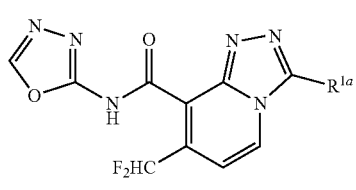
FIRST TABLE-continued
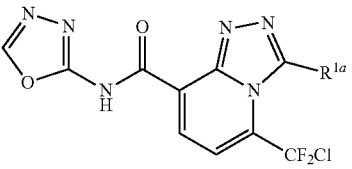
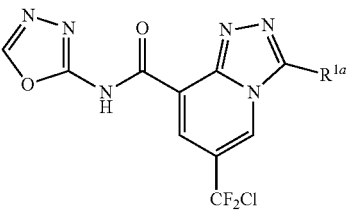
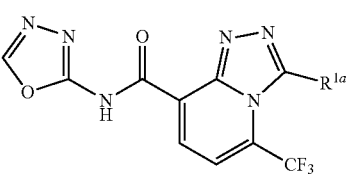
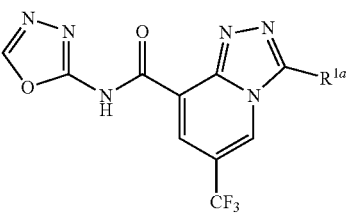
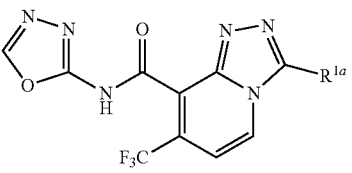
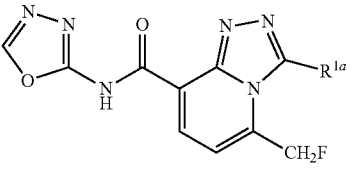
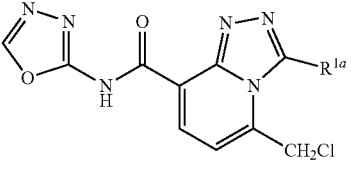

FIRST TABLE-continued
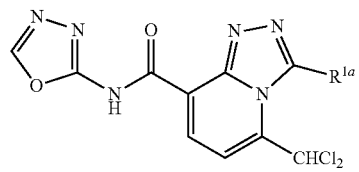
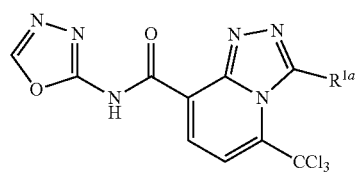
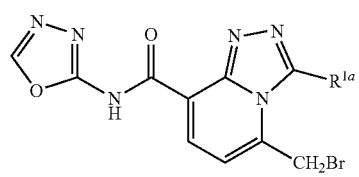
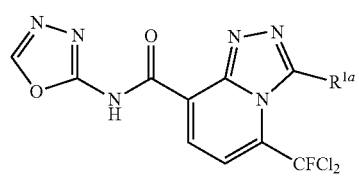
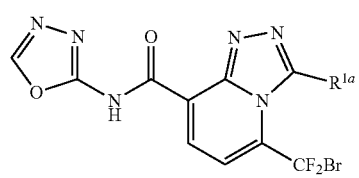
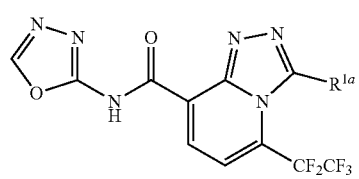
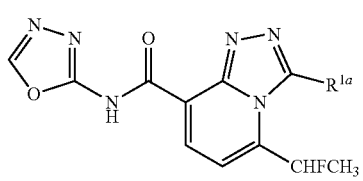
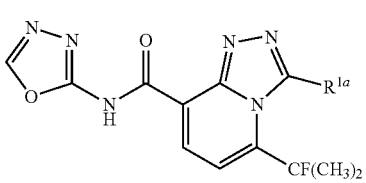
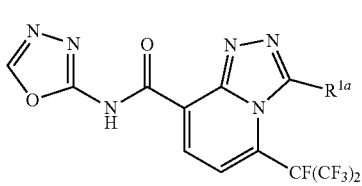
FIRST TABLE-continued
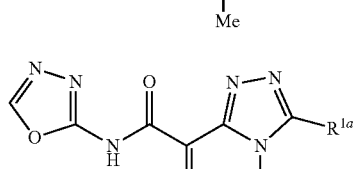
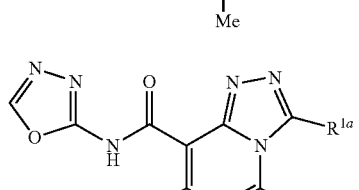
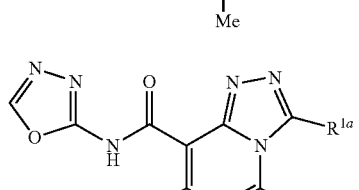
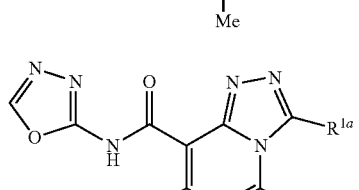
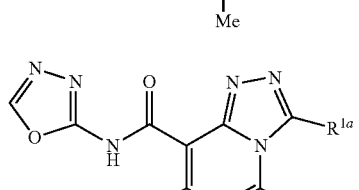
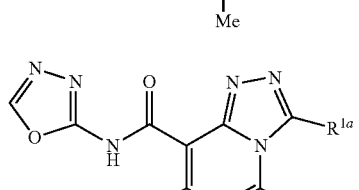
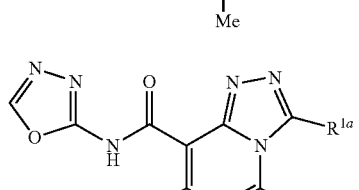
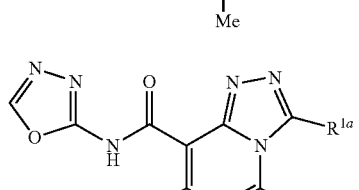

FIRST TABLE-continued
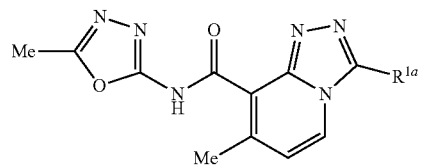
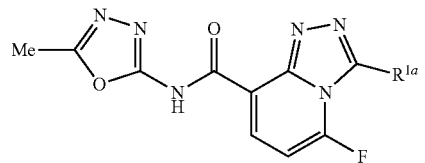
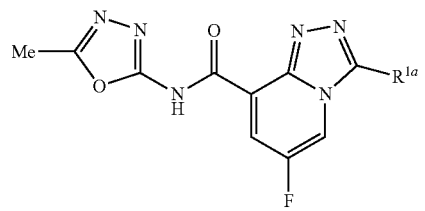
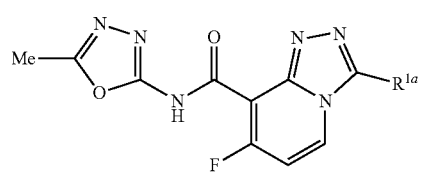
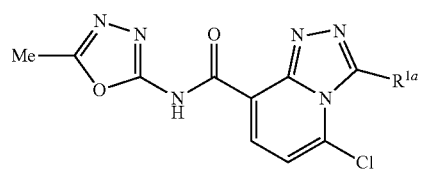
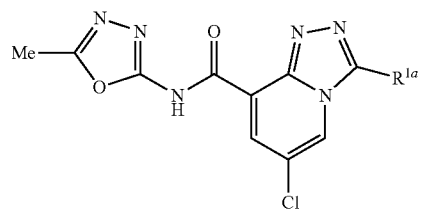
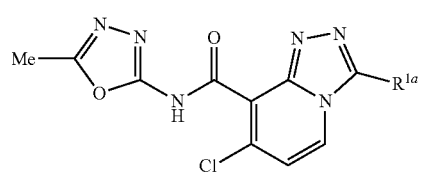
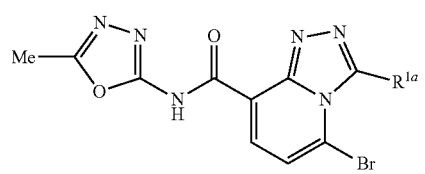
FIRST TABLE-continued
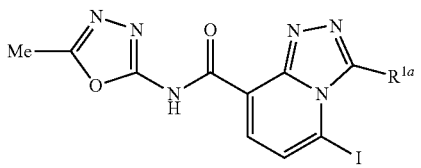
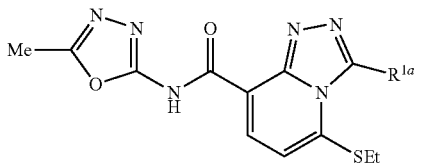
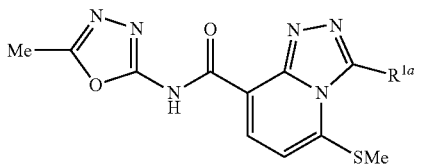
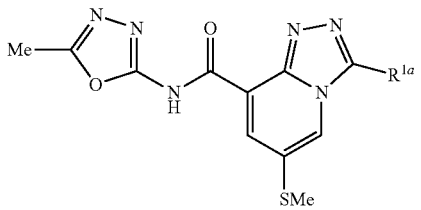
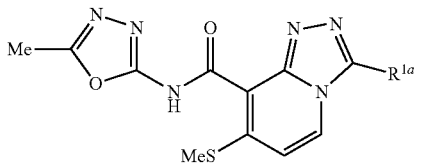
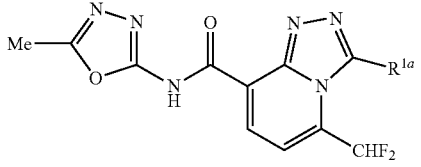
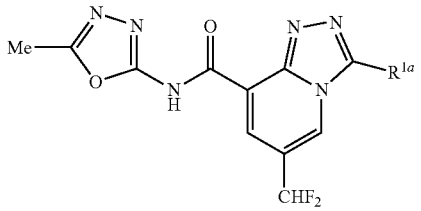
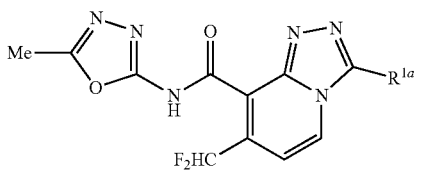

FIRST TABLE-continued
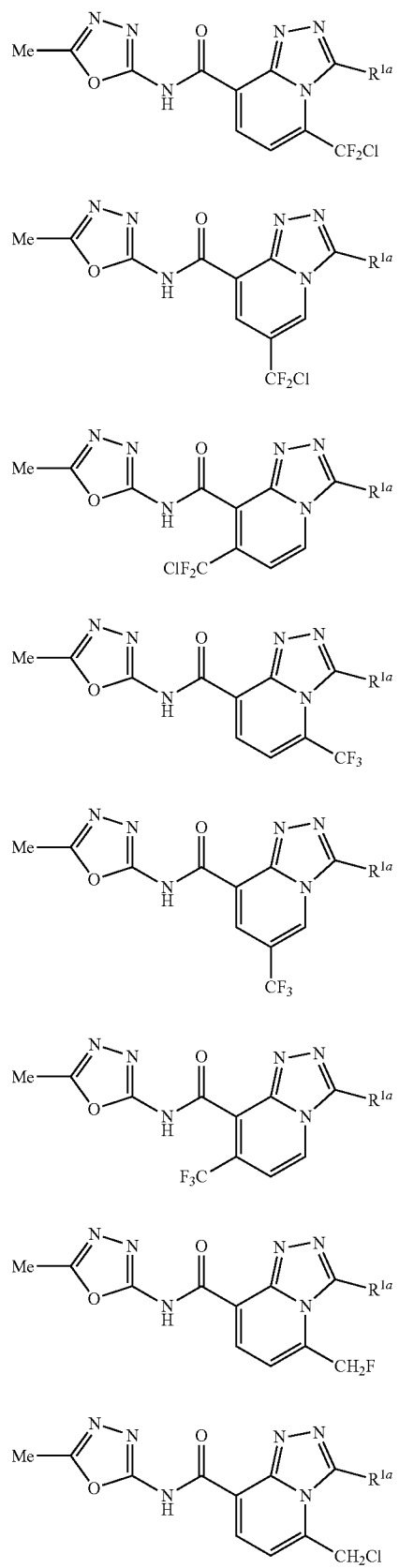
FIRST TABLE-continued
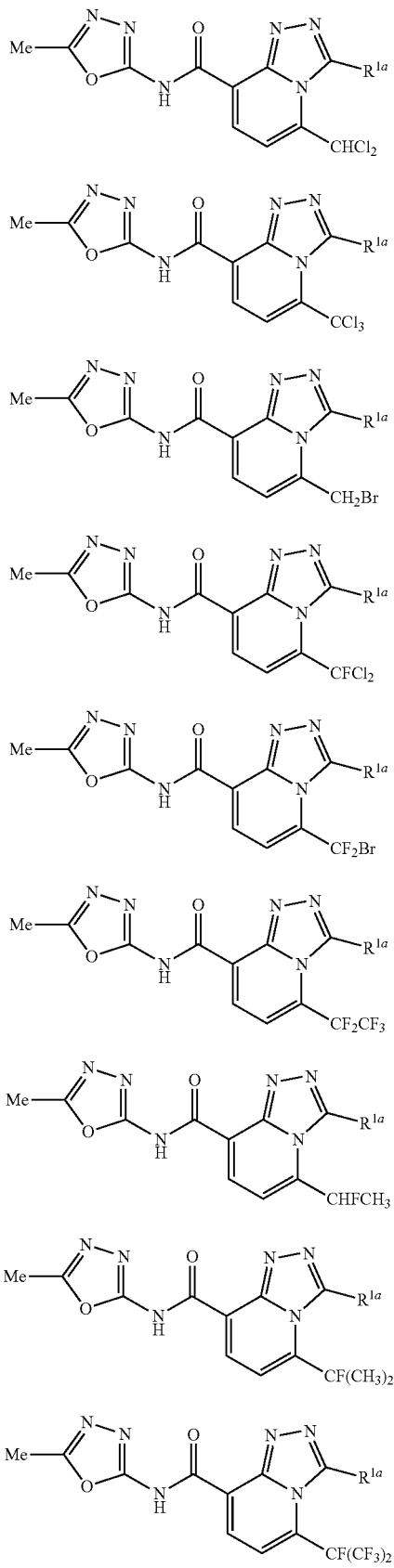

FIRST TABLE-continued
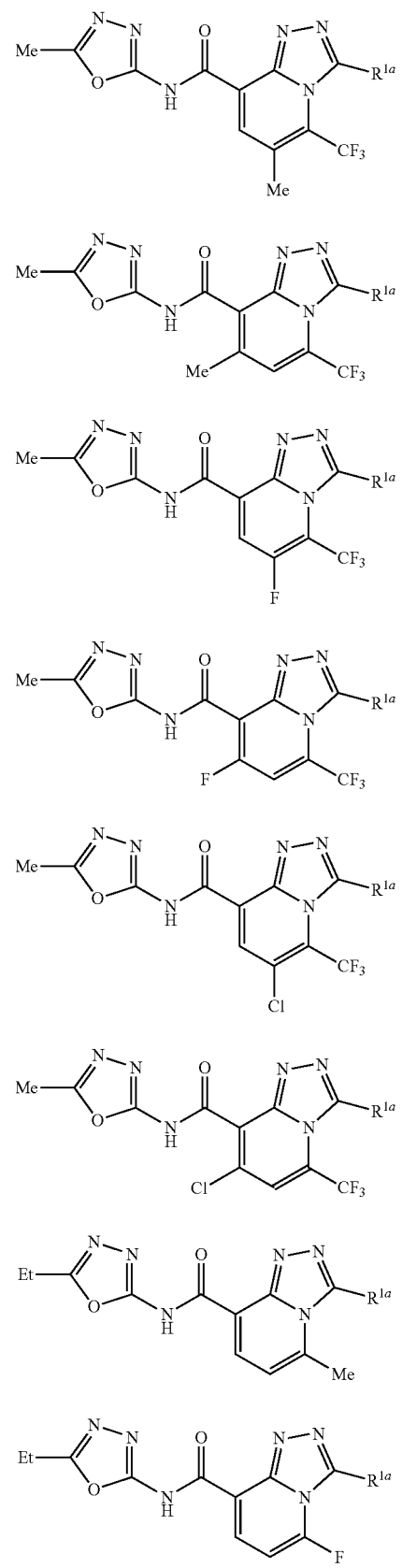
FIRST TABLE-continued
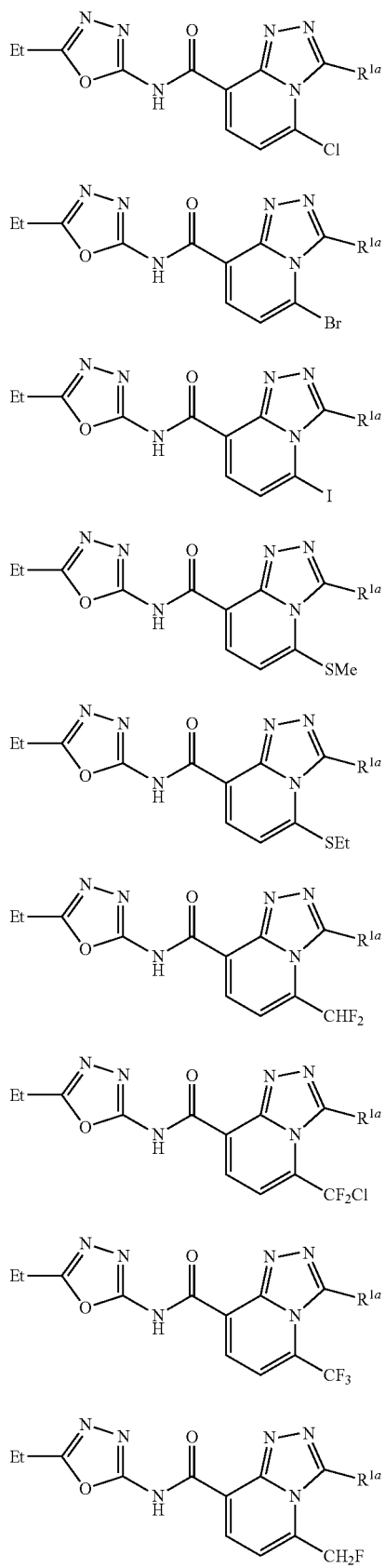

FIRST TABLE-continued
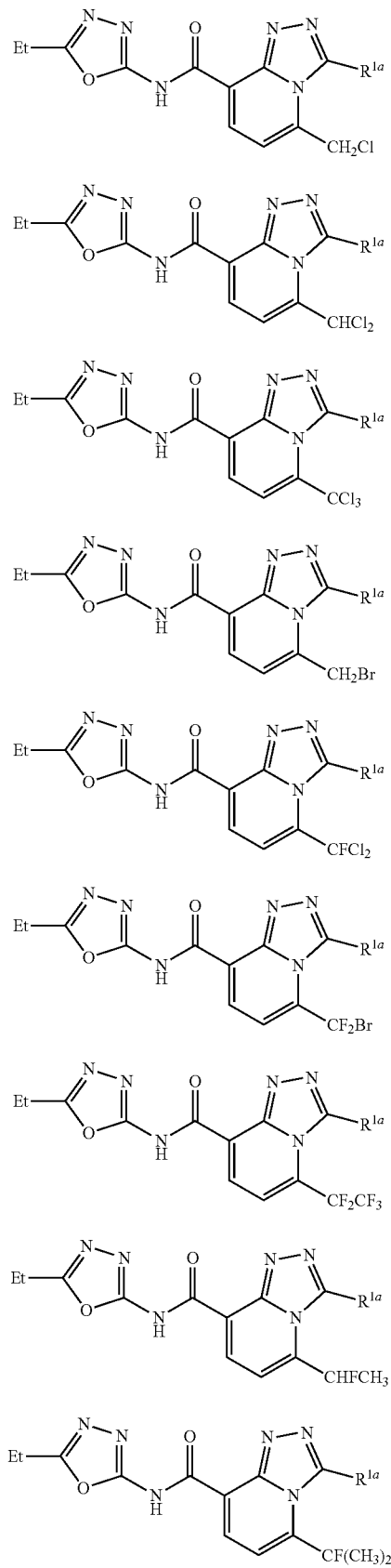
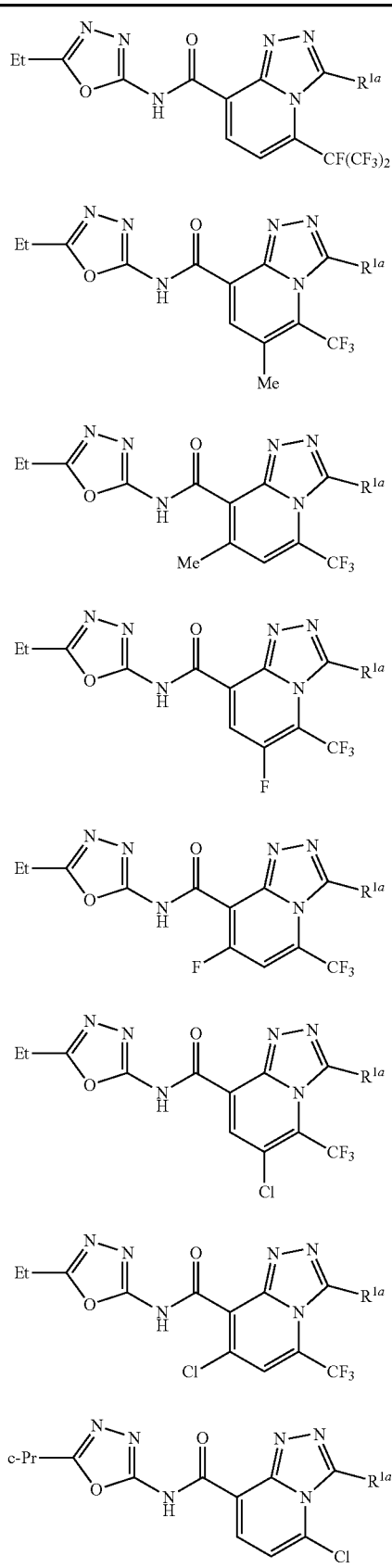

FIRST TABLE-continued
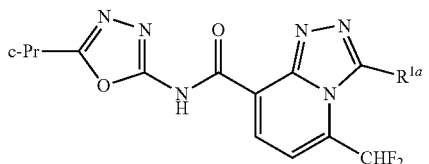
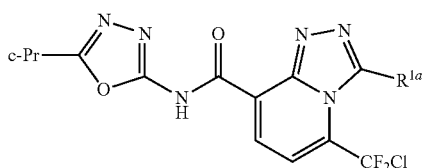
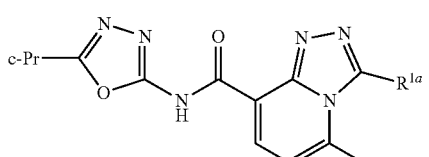
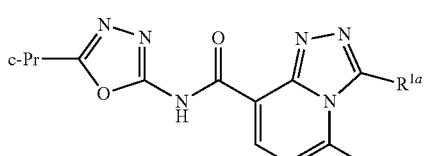
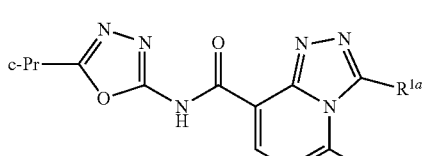
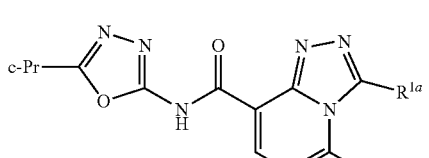
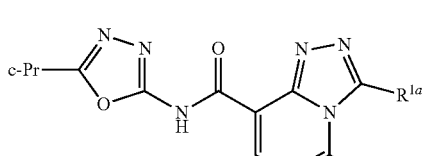
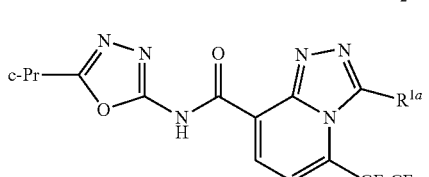
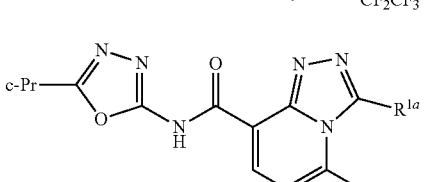
FIRST TABLE-continued
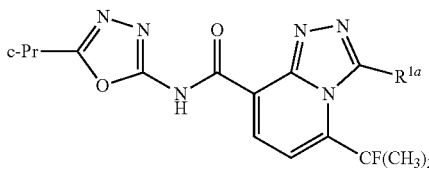
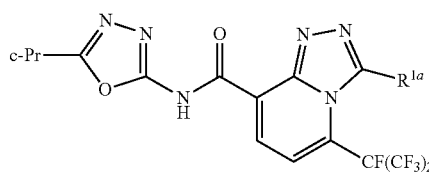
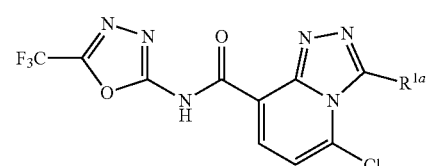
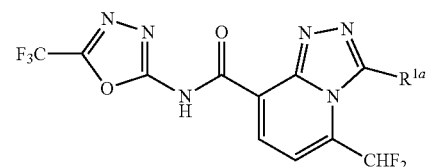
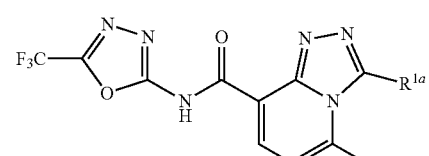
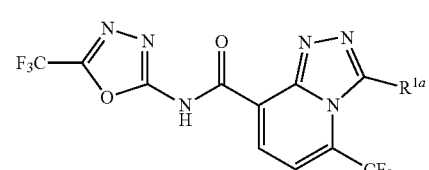
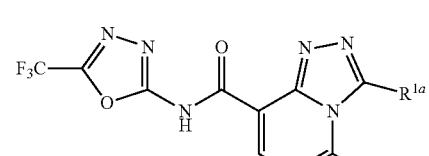
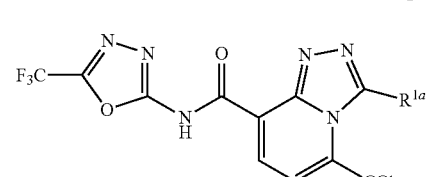
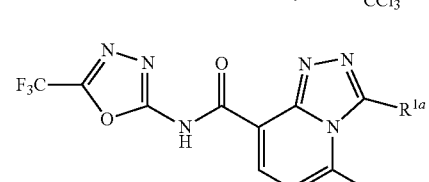

FIRST TABLE-continued
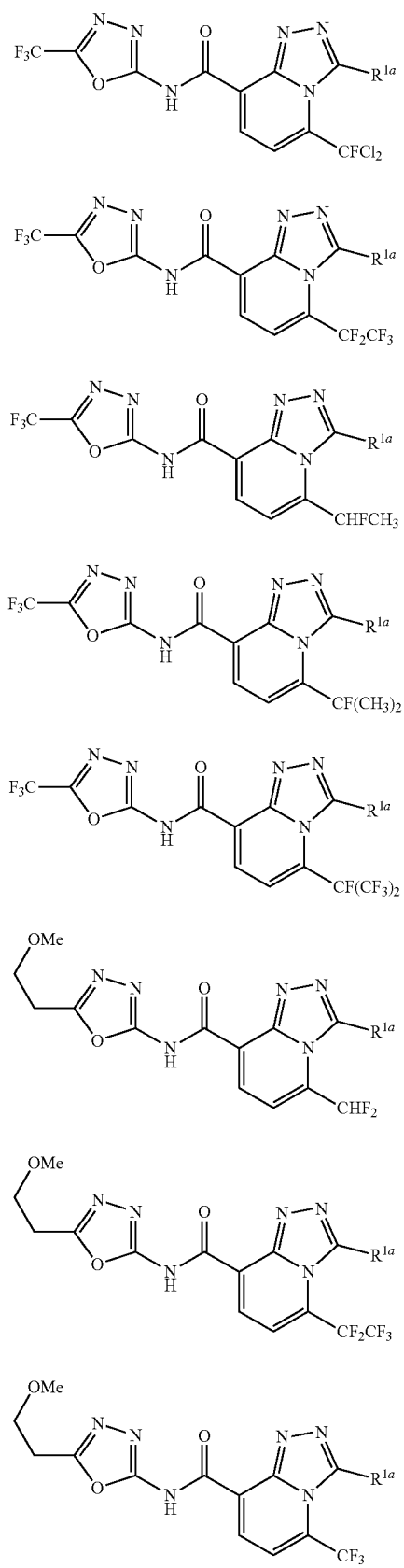
FIRST TABLE-continued
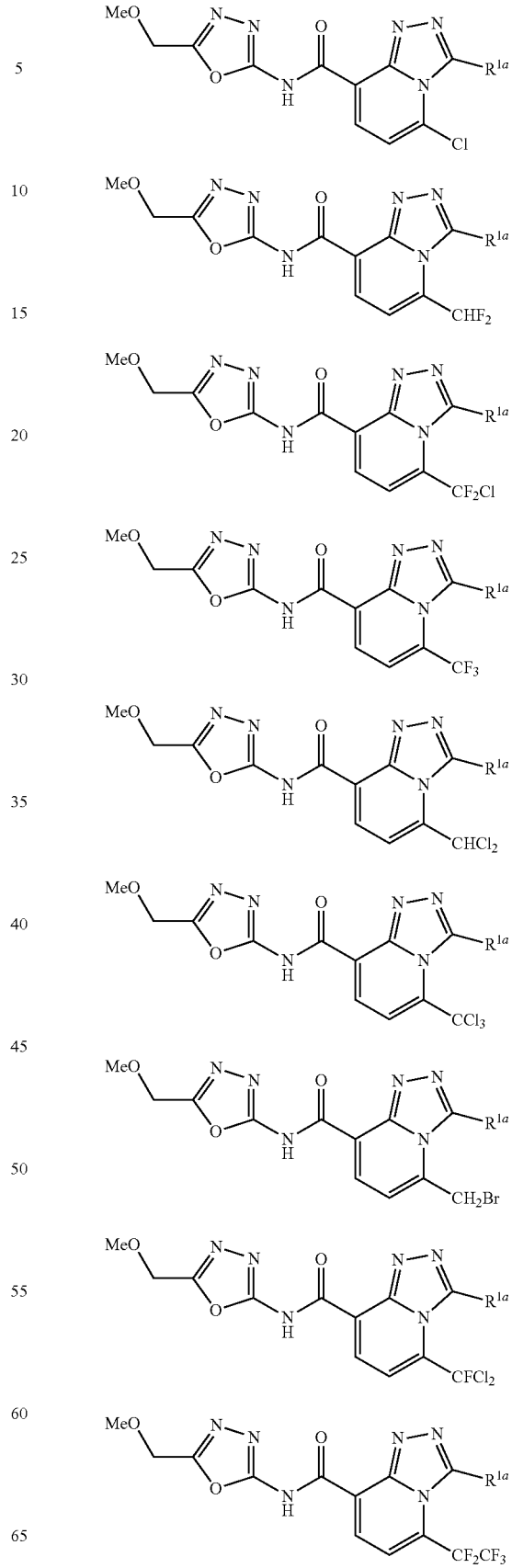

FIRST TABLE-continued
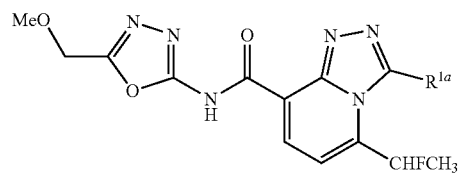
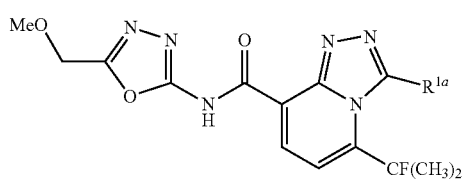
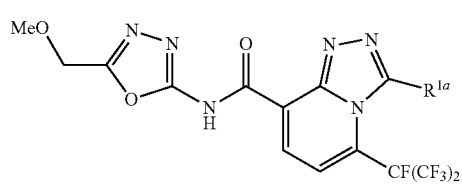
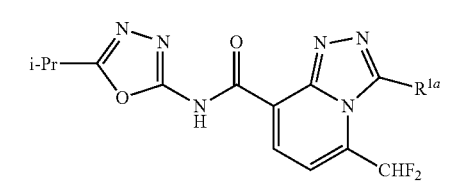
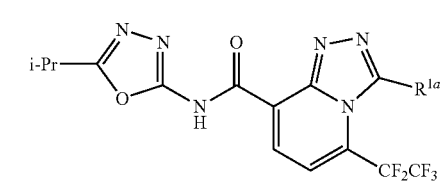
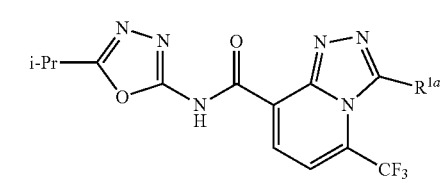
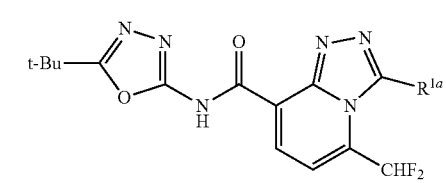
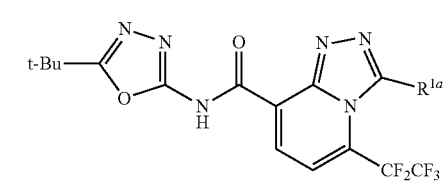
FIRST TABLE-continued
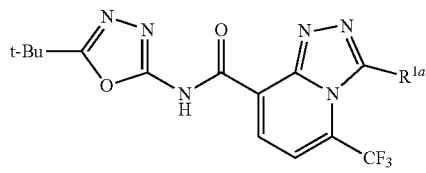
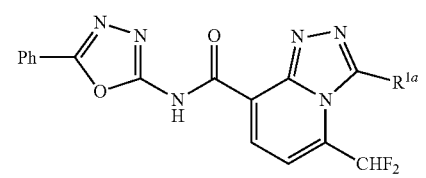
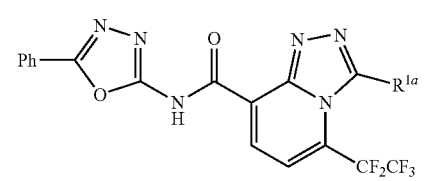
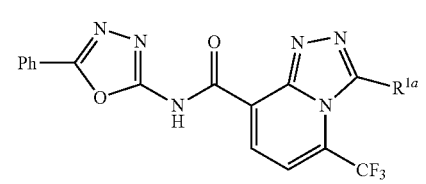
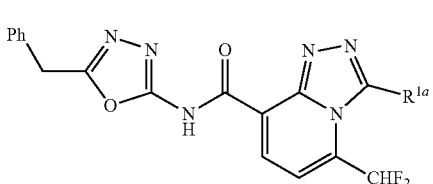
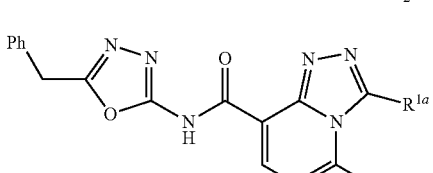
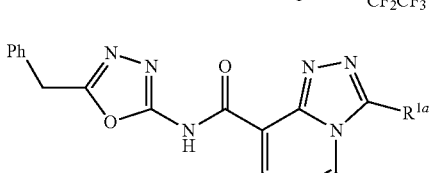
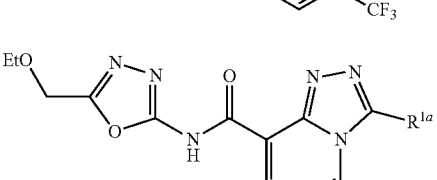
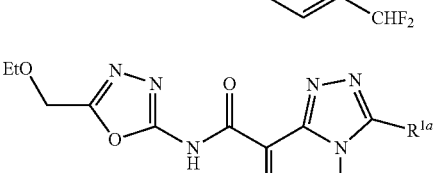
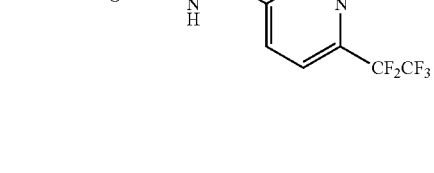

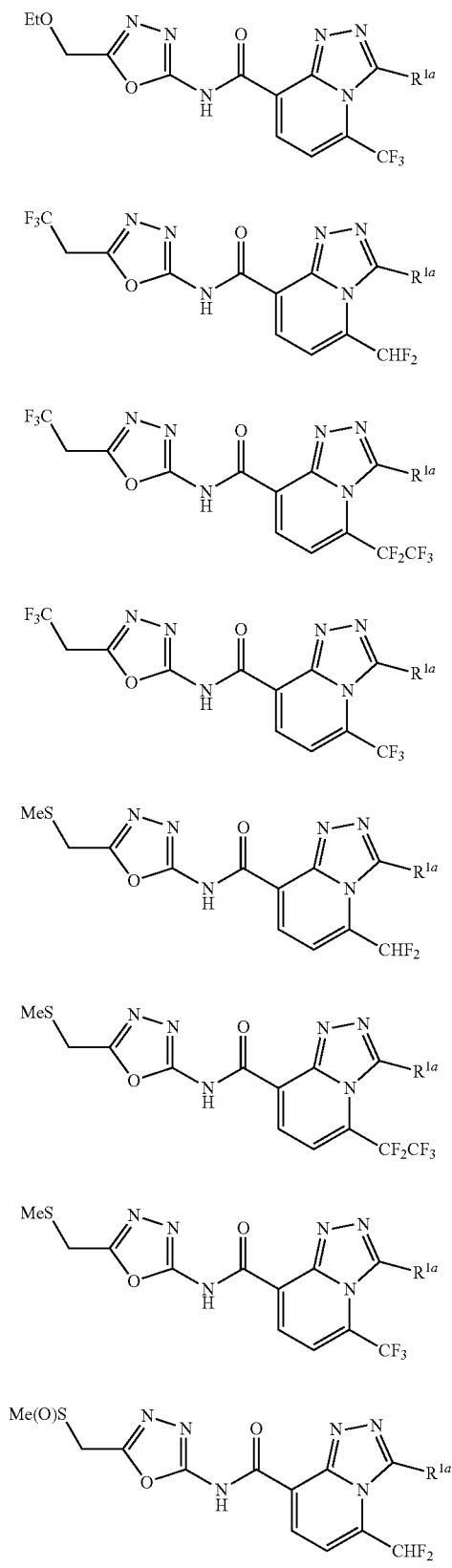
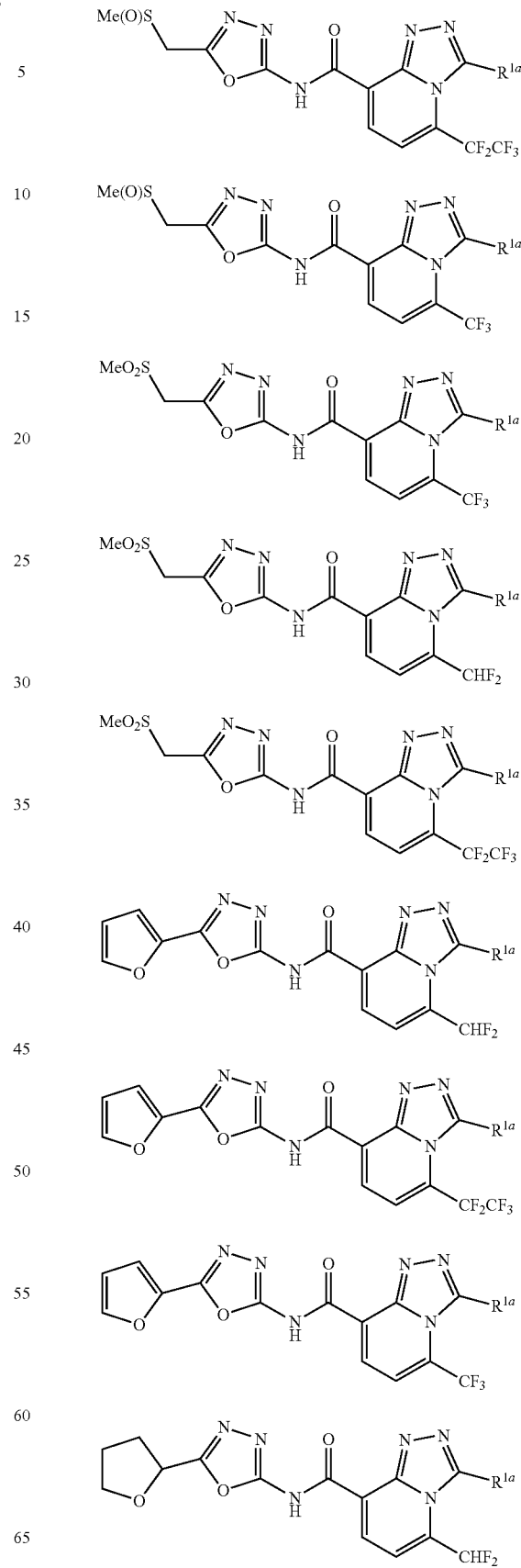

FIRST TABLE-continued
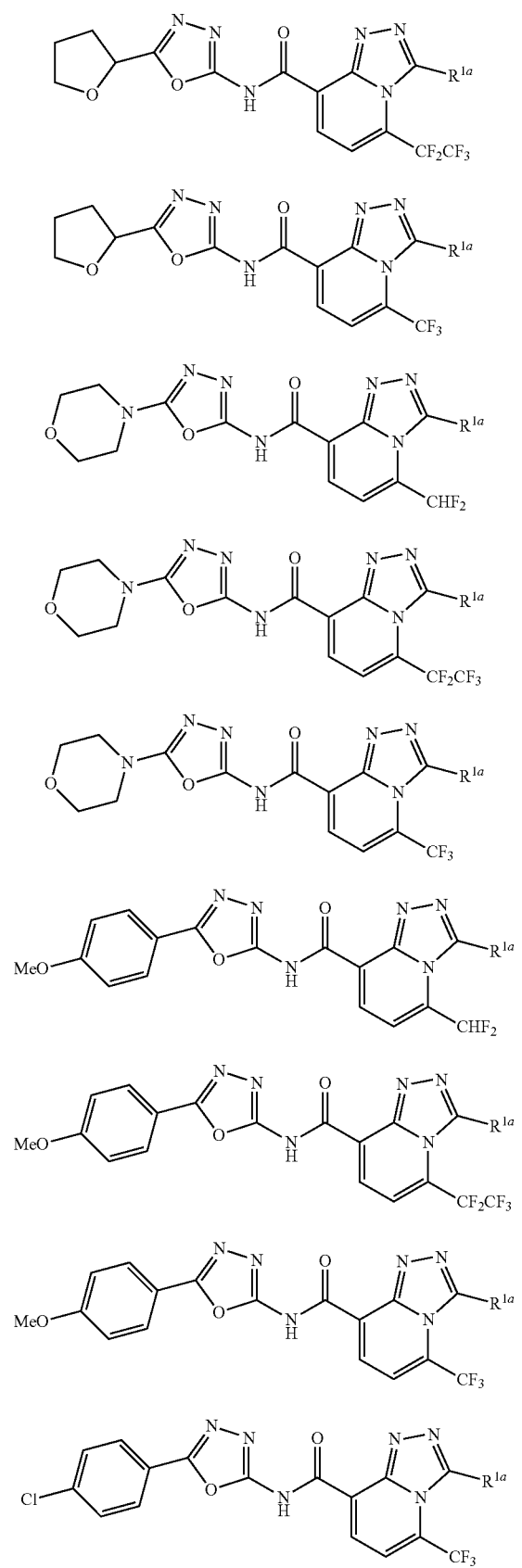
FIRST TABLE-continued
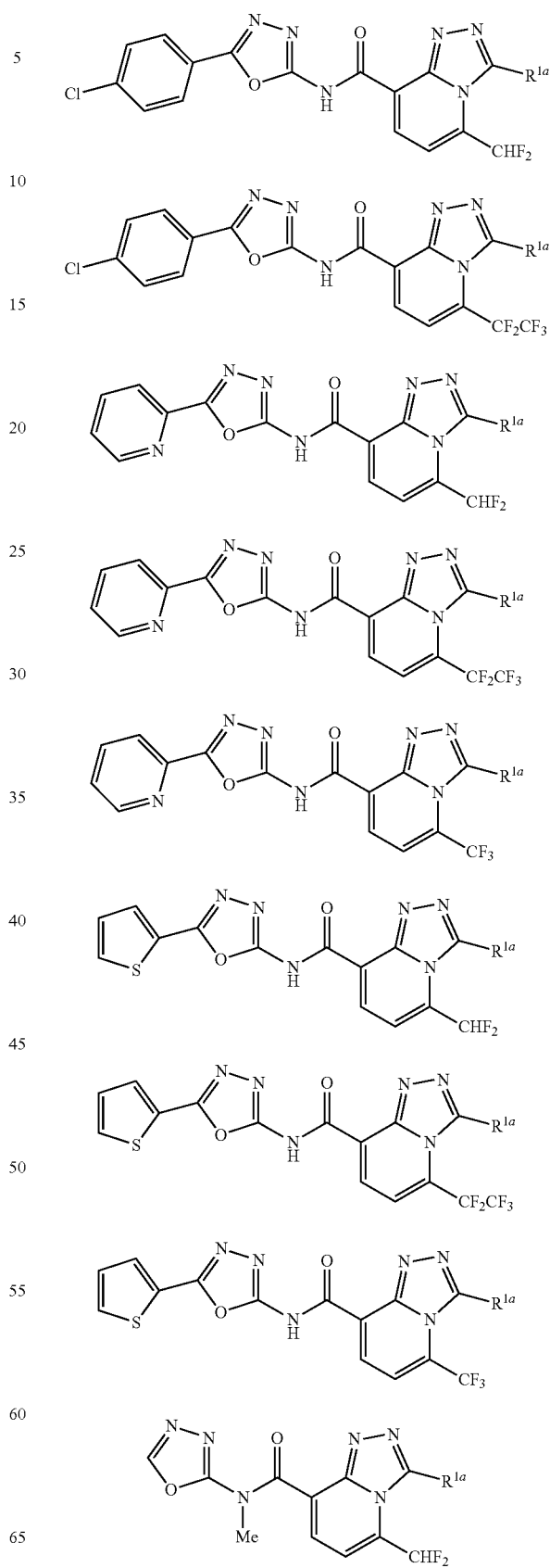

FIRST TABLE-continued
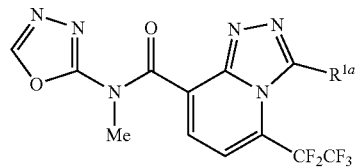
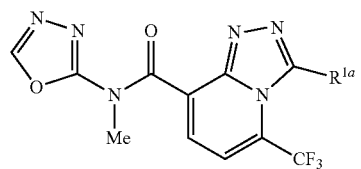
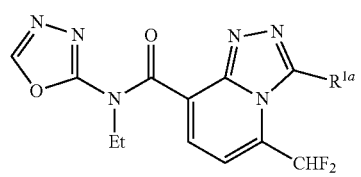
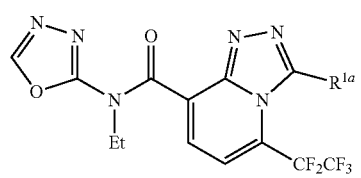
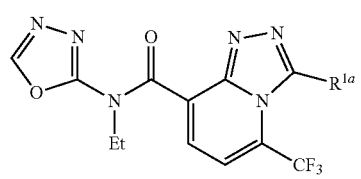
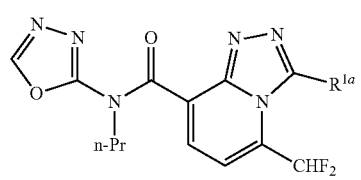
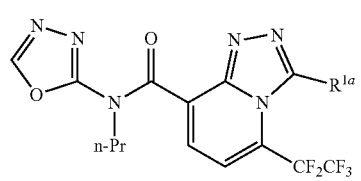
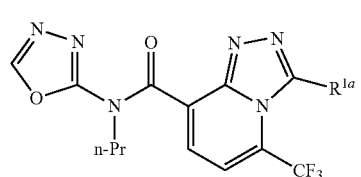
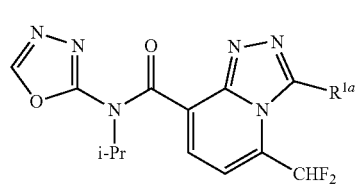
FIRST TABLE-continued
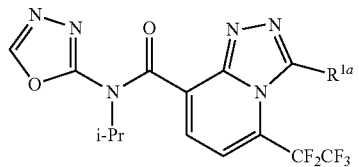
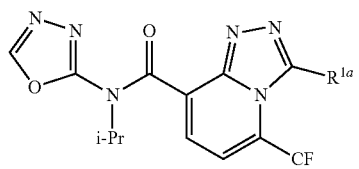
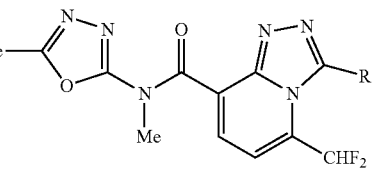
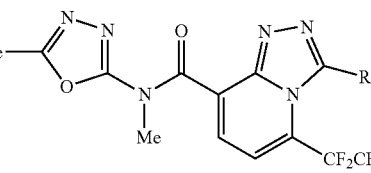
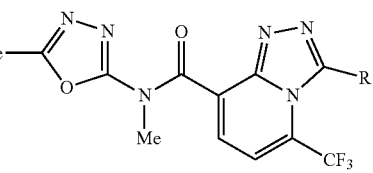
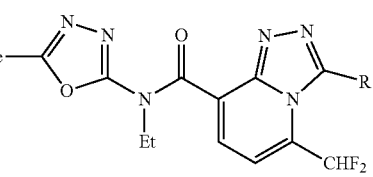
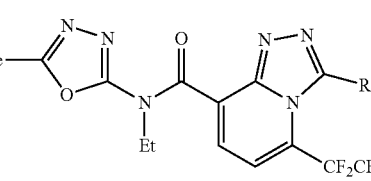
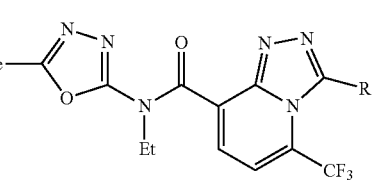
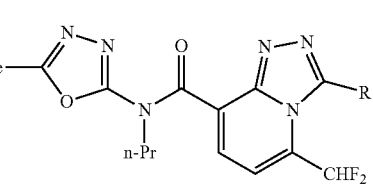

FIRST TABLE-continued

FIRST TABLE-continued
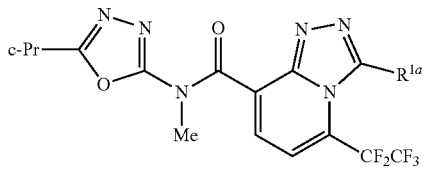
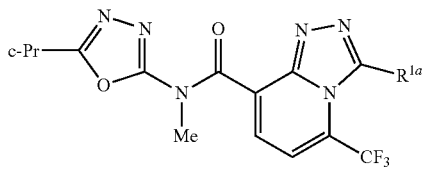
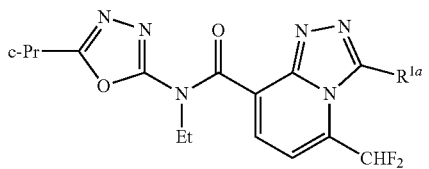
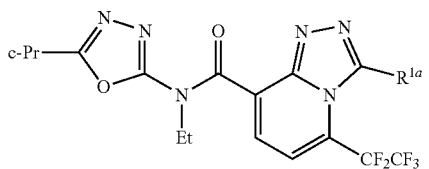
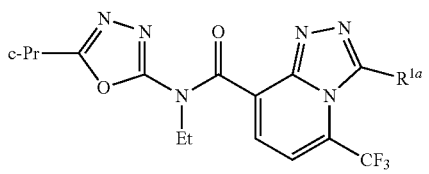
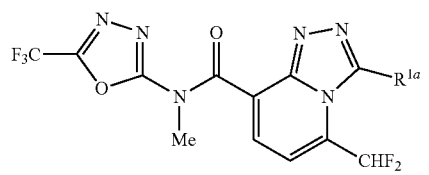
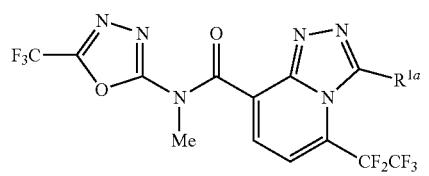
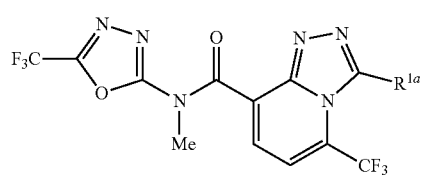
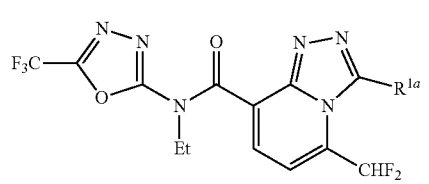
FIRST TABLE-continued
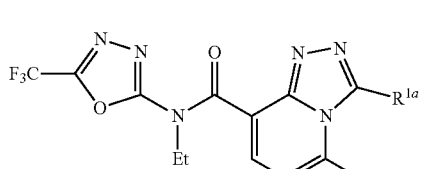
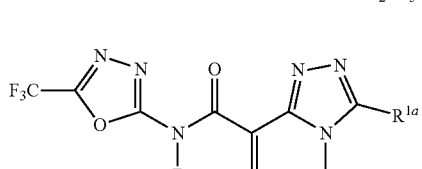
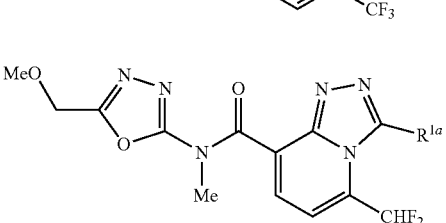
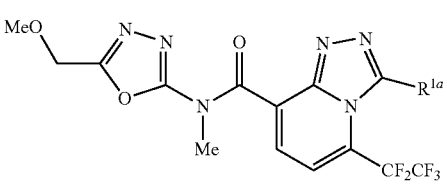
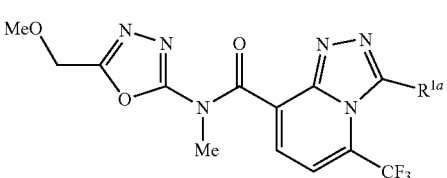
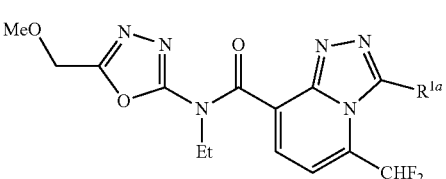
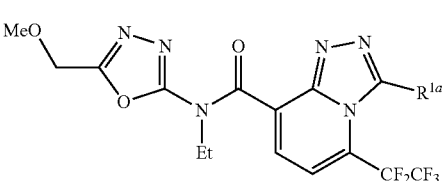
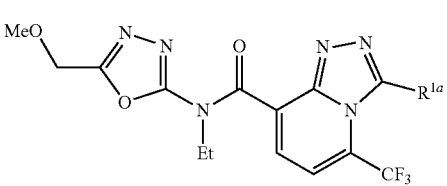

FIRST TABLE-continued
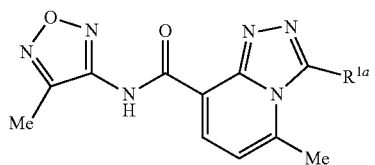
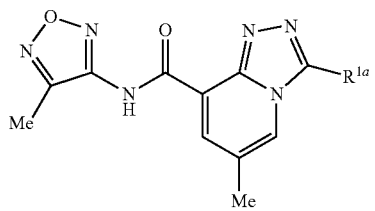
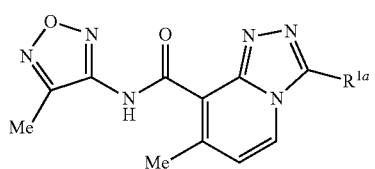
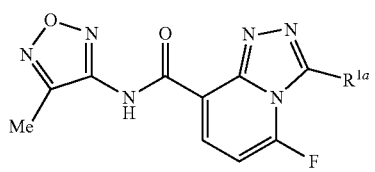
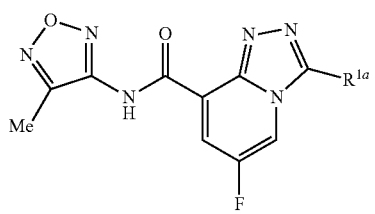
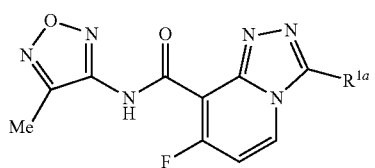
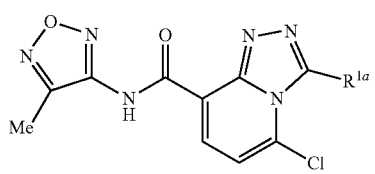
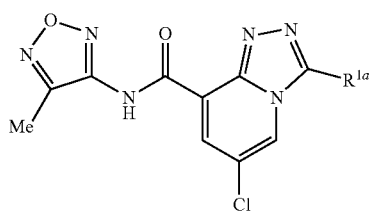
FIRST TABLE-continued
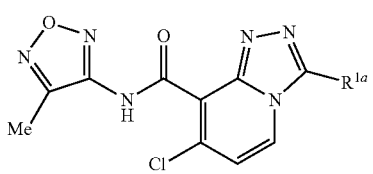
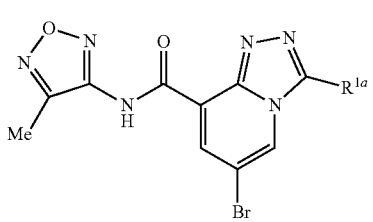
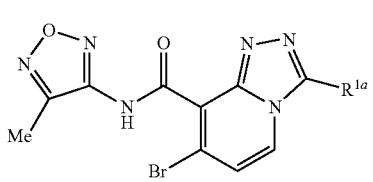
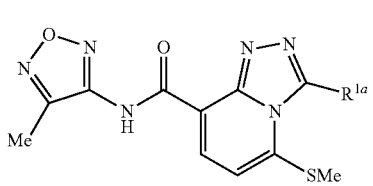
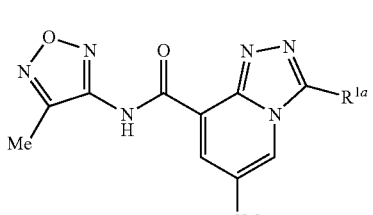
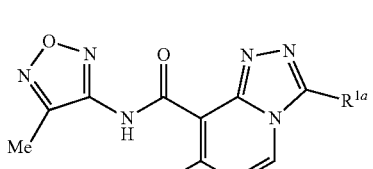
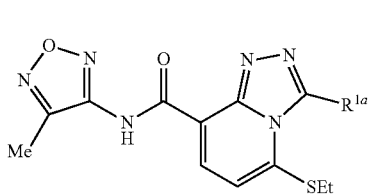

FIRST TABLE-continued
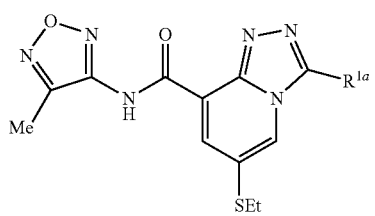
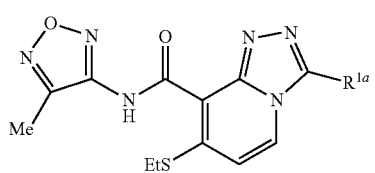
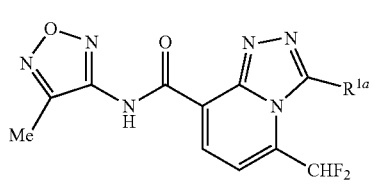
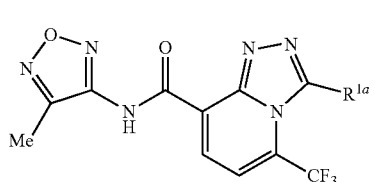
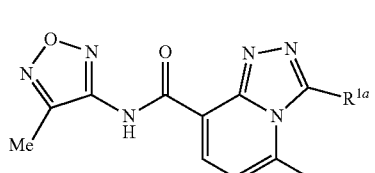
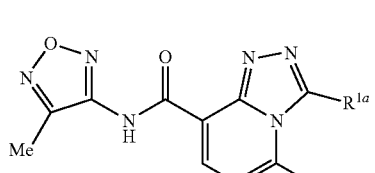
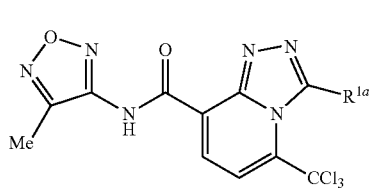
FIRST TABLE-continued
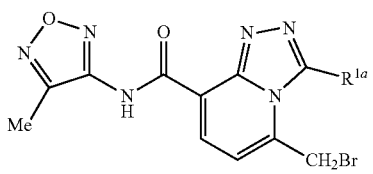
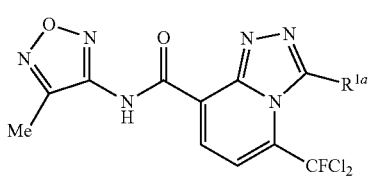
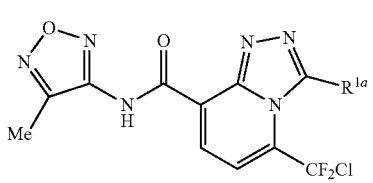
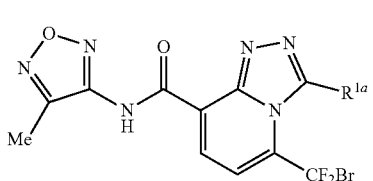
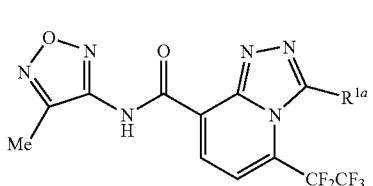
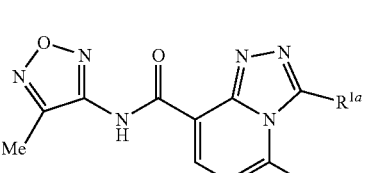
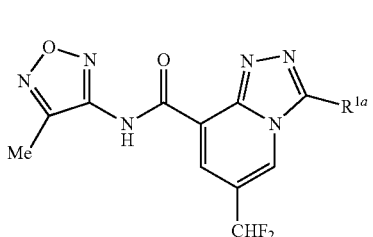
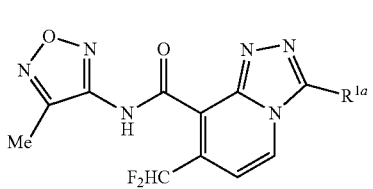

FIRST TABLE-continued
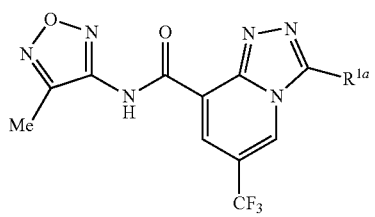
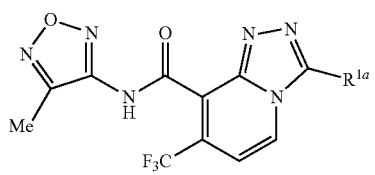
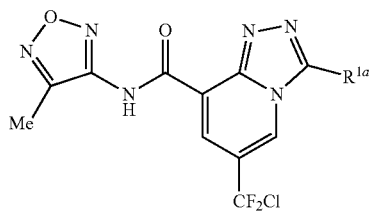
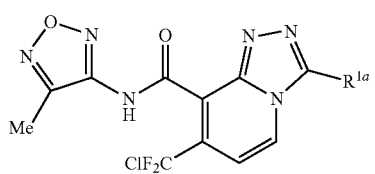
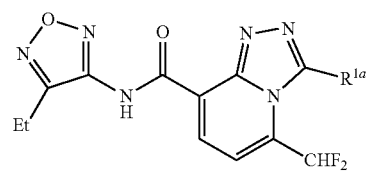
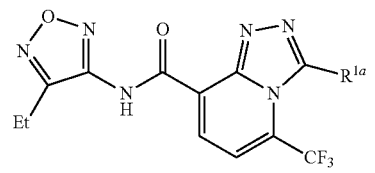
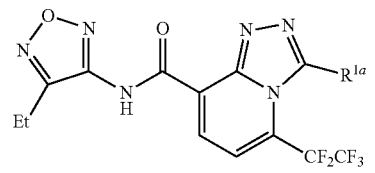
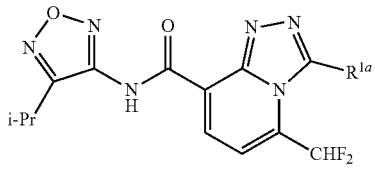
FIRST TABLE-continued
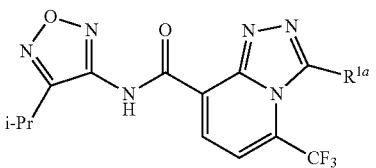
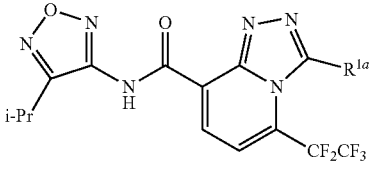
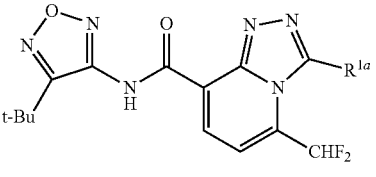
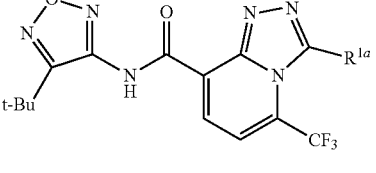
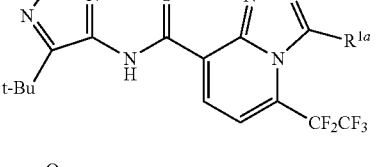
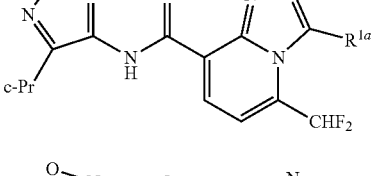
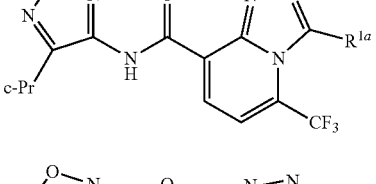
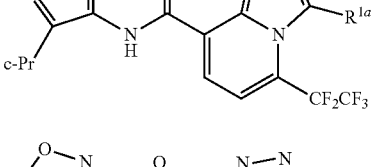
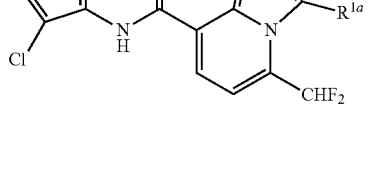

FIRST TABLE-continued
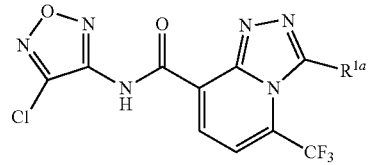
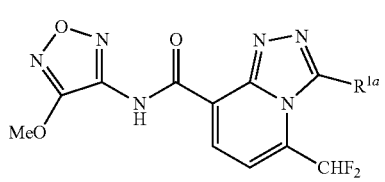
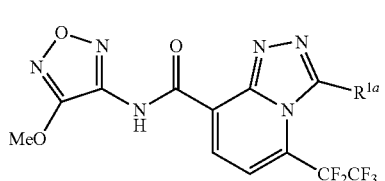
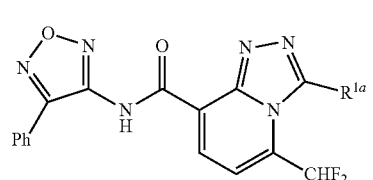
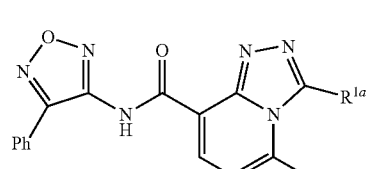
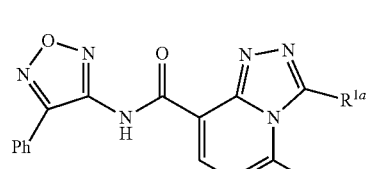
FIRST TABLE-continued
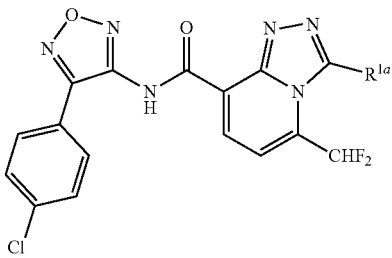
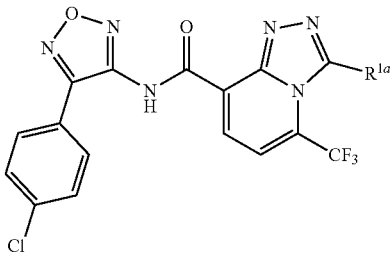
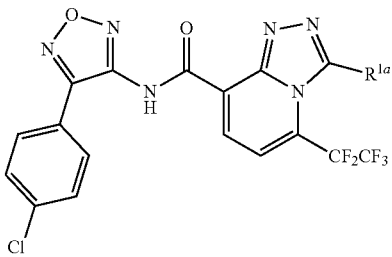
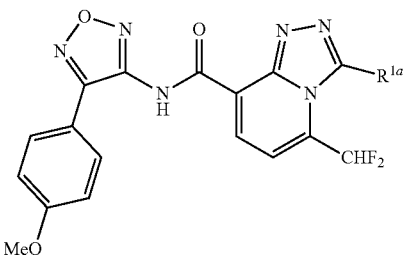
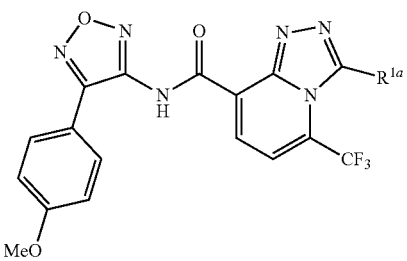
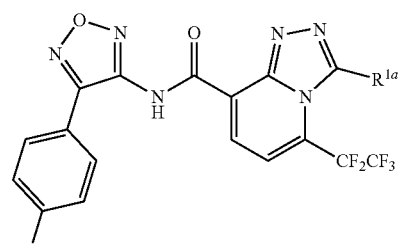

FIRST TABLE-continued
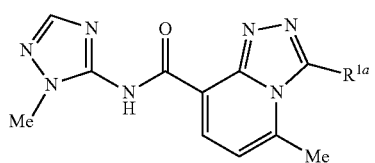
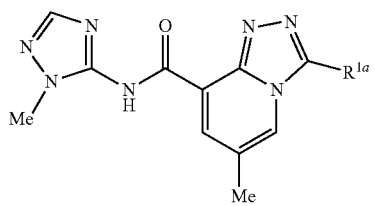
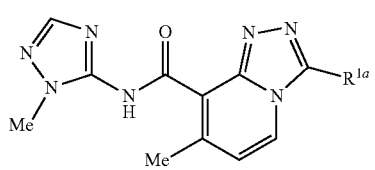
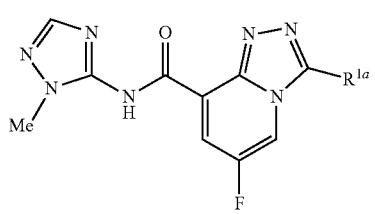
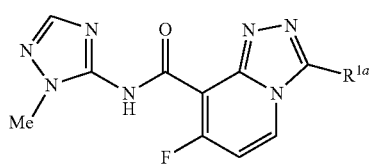
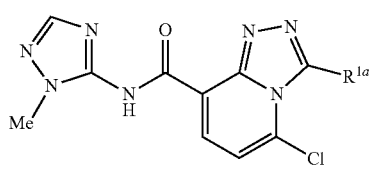
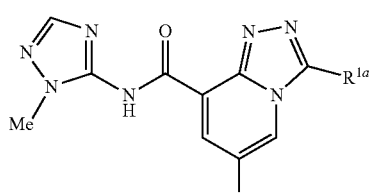
FIRST TABLE-continued
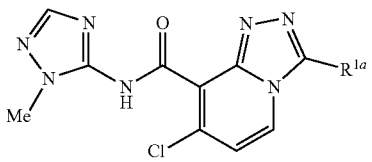
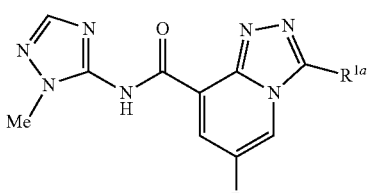
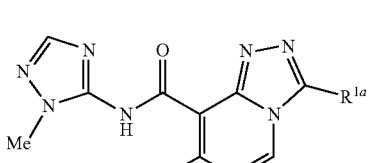
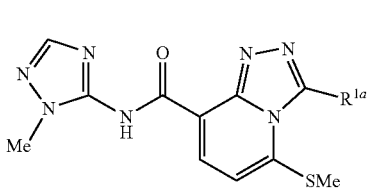
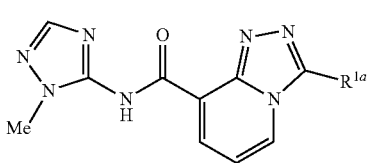
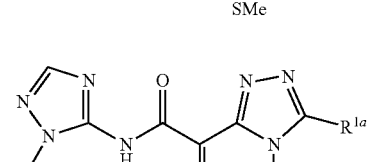
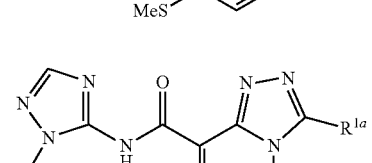

FIRST TABLE-continued
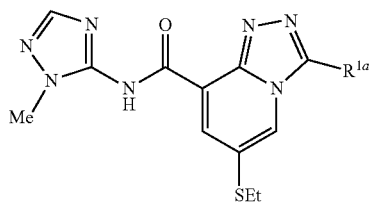
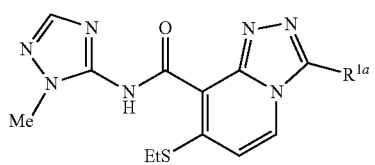
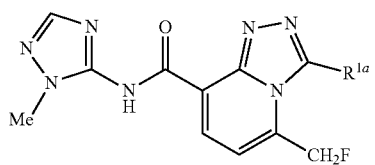
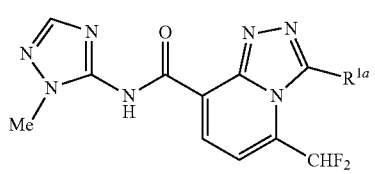
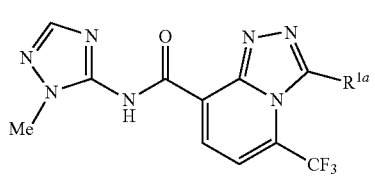
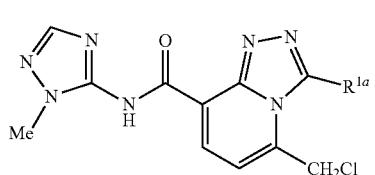
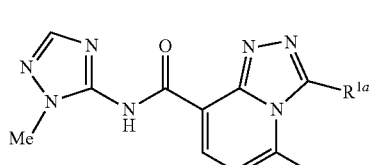
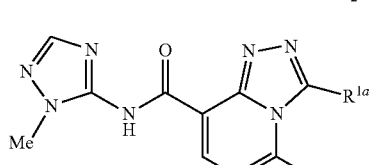
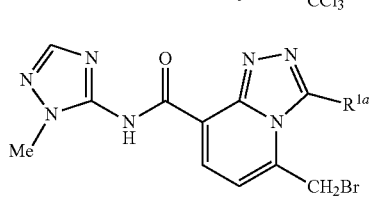
FIRST TABLE-continued
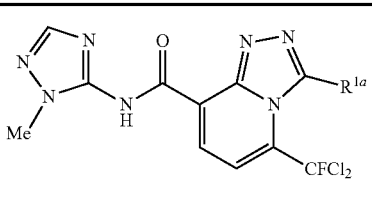
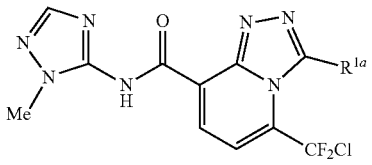
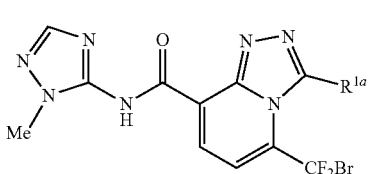
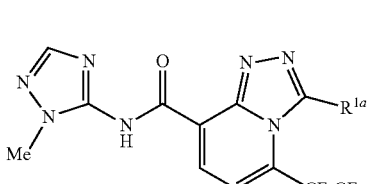
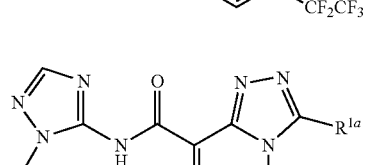
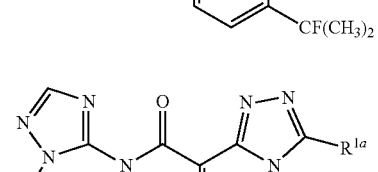
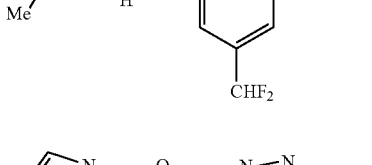
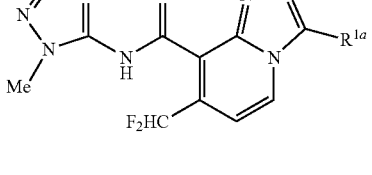

FIRST TABLE-continued
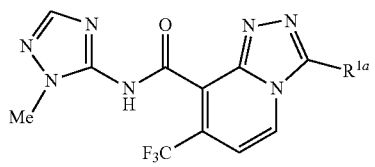
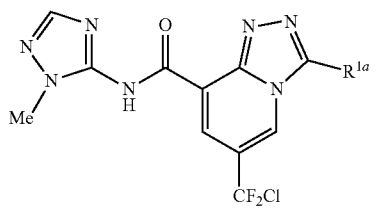
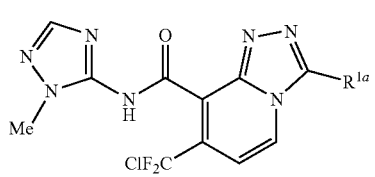
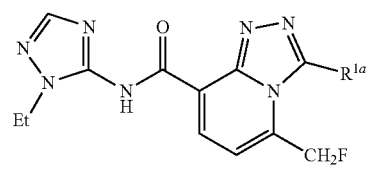
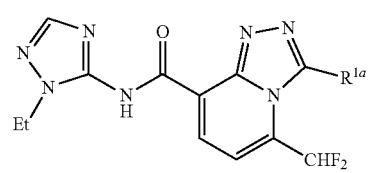
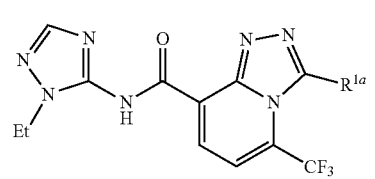
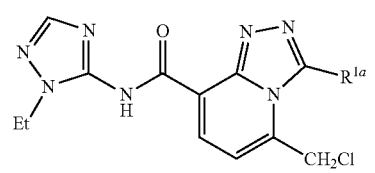
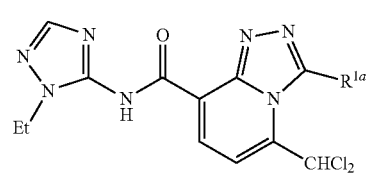
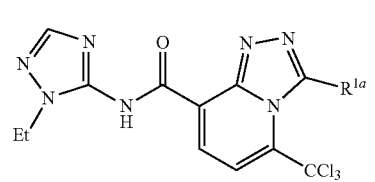
FIRST TABLE-continued
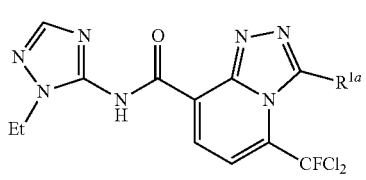
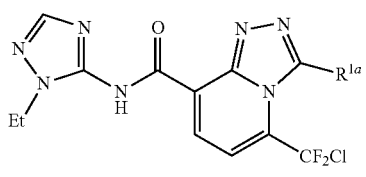
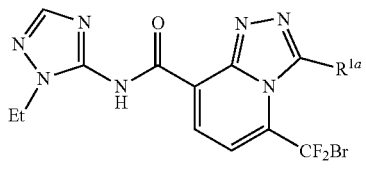
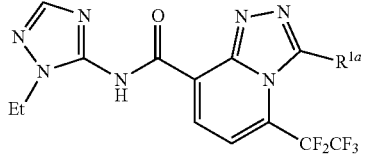
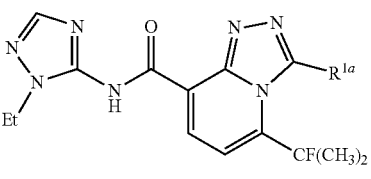
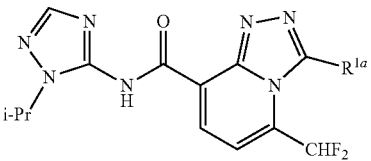
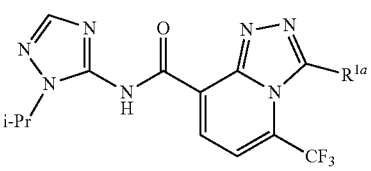
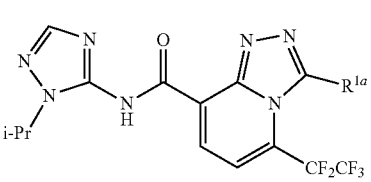

FIRST TABLE-continued
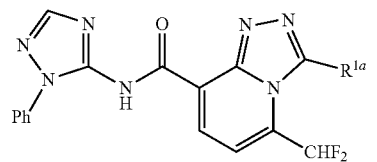
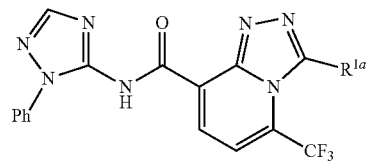
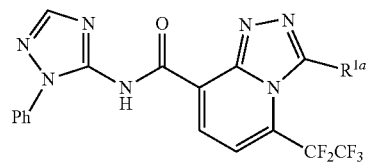
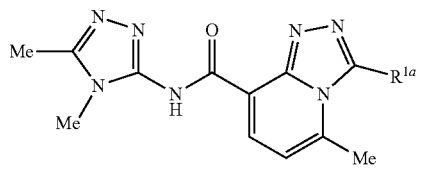
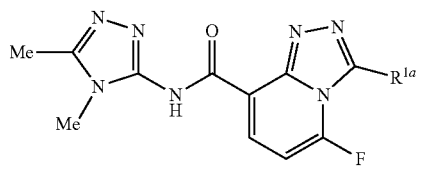
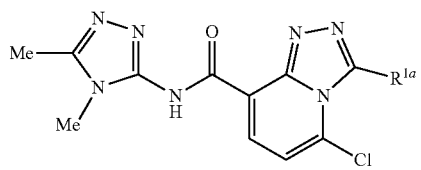
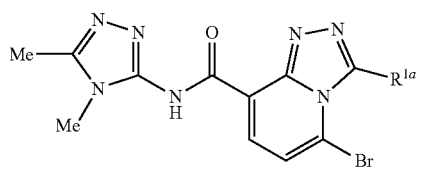
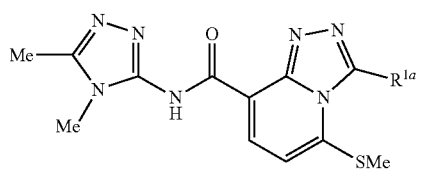
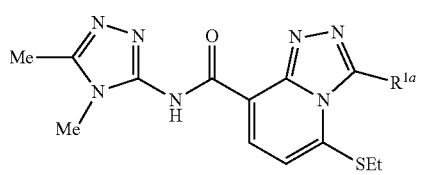
FIRST TABLE-continued
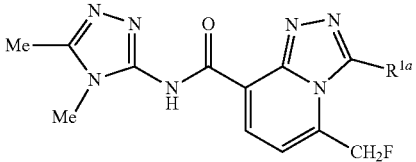
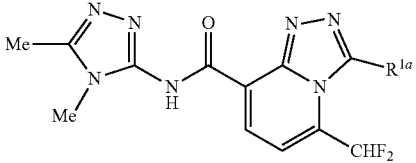
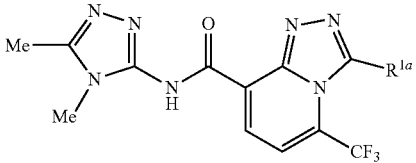
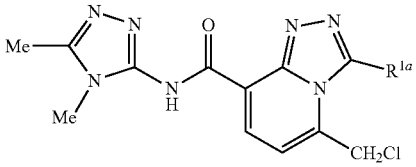
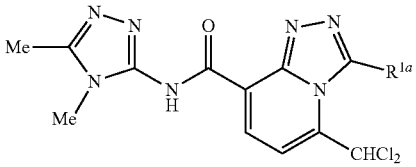
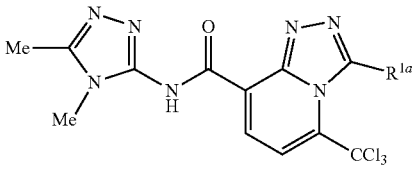
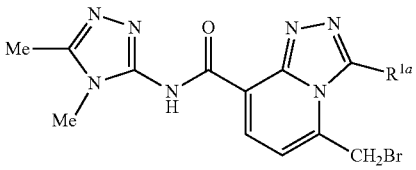
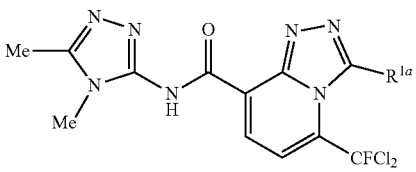
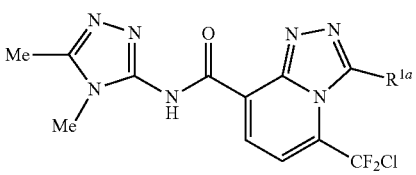

FIRST TABLE-continued

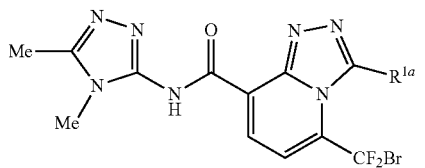
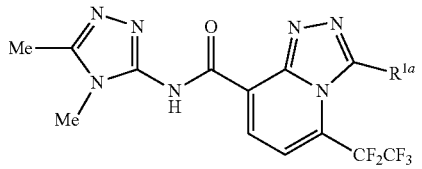
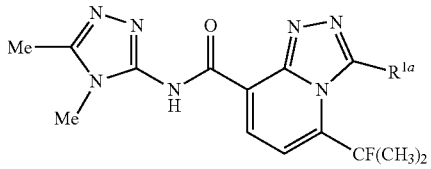
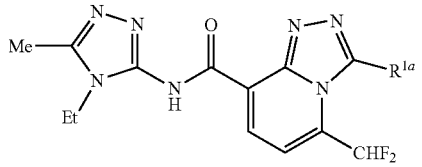
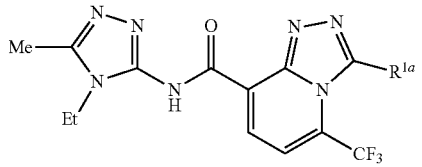
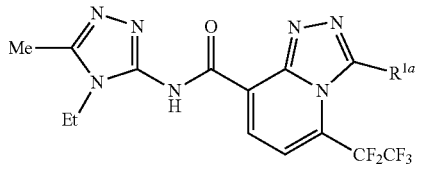
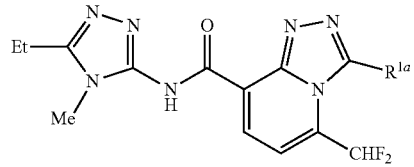
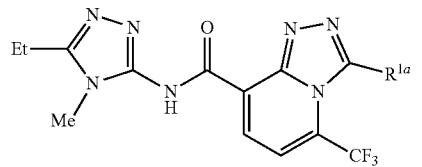
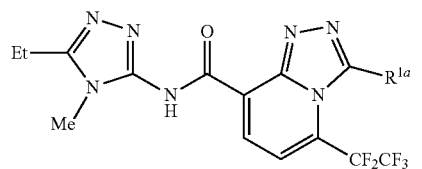

FIRST TABLE-continued

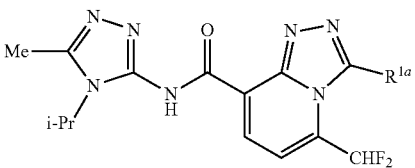
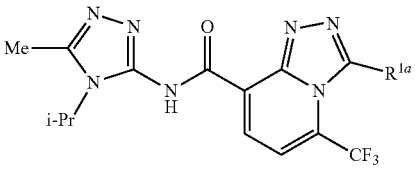
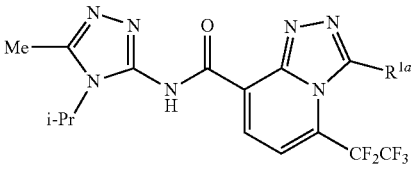

TABLE 1

| R[1a] | R[1a] | R[1a] |
|---|---|---|
| H | CH$_2$CF$_3$ | C(Me)$_2$CH$_2$CN |
| F | (CH$_2$)$_3$Cl | CH$_2$Pr-c |
| Cl | (CH$_2$)$_3$Br | CH$_2$(D-16) |
| Br | (CH$_2$)$_2$CF$_3$ | CH$_2$(D-16d) |
| I | CHFCH$_3$ | CH$_2$Bu-c |
| Me | CF$_2$CH$_3$ | CH$_2$Pen-c |
| Et | CF(CH$_3$)$_2$ | CH$_2$Hex-c |
| Pr-n | CF$_2$CF$_2$H | CH(Me)Pr-c |
| Pr-i | CF$_2$CF$_3$ | CH(Me)(D-16) |
| Pr-c | CF$_2$CF$_2$CF$_3$ | CH(Me)(D-16e) |
| Bu-n | CF(CF$_3$) | CH(Me)Bu-c |
| Bu-i | CH(Me)Cl | CH(Me)Pen-c |
| Bu-c | CH(Me)Br | CH(Me)Hex-c |
| Bu-s | CH(Et)Cl | (CH$_2$)$_2$Pr-c |
| Bu-t | CH(Et)Br | (CH$_2$)$_2$(D-16) |
| Pen-n | CH(Pr-n)Cl | (CH$_2$)$_2$(D-16e) |
| Pen-i | CH(Pr-n)Br | (CH$_2$)$_2$Bu-c |
| Pen-c | CH(Pr-i)Cl | (CH$_2$)$_2$Pen-c |
| Pen-s | CH(Pr-i)Br | (CH$_2$)$_2$Hex-c |
| Pen-t | C(Me)$_2$Cl | CH$_2$OMe |
| 3-Pen | C(Me)$_2$Br | CH$_2$OEt |
| Hex-n | CH(Me)CH$_2$Cl | CH$_2$OPr-n |
| Hex-c | CH(Me)CH$_2$Br | CH$_2$OPr-i |
| CH$_2$Cl | C(Me)$_2$CH$_2$Cl | CH$_2$OBu-n |
| CH$_2$Br | C(Me)$_2$CH$_2$Br | CH$_2$OBu-i |
| CHBr$_2$ | CH$_2$CN | CH$_2$OBu-s |
| CF$_2$H | (CH$_2$)$_2$CN | CH$_2$OBu-t |
| CF$_2$Cl | (CH$_2$)$_3$CN | CH$_2$OPen-n |
| CF$_2$Br | CH(Me)CN | CH$_2$OPen-i |
| CF$_3$ | CH(Et)CN | CH$_2$OPen-s |
| (CH$_2$)$_2$Cl | CH(Pr-n)CN | CH$_2$OPen-t |
| (CH$_2$)$_2$Br | CH(Pr-i)CN | CH$_2$OHex-n |
| CH$_2$CF$_2$H | C(Me)$_2$CN | CH(Me)OMe |
| CH$_2$CF$_2$Cl | CH(Me)CH$_2$CN | CH(Me)OEt |
| CH$_2$CF$_2$Br | CH(Et)CH$_2$CN | CH(Me)OPr-n |

TABLE 2

| R[1a] | R[1a] | R[1a] |
|---|---|---|
| CH(Me)OPr-i | C(Me)$_2$OBu-n | CH$_2$O(CH$_2$)$_2$Cl |
| CH(Me)OBu-n | C(Me)$_2$OBu-i | CH$_2$O(CH$_2$)$_2$Br |
| CH(Me)OBu-i | C(Me)$_2$OBu-s | CH(Me)OCF$_2$H |
| CH(Me)OBu-s | C(Me)$_2$OBu-t | CH(Me)OCF$_3$ |
| CH(Me)OBu-t | (CH$_2$)$_2$OMe | CH(Me)OCH$_2$CF$_2$H |

TABLE 2-continued

| R1a | R1a | R1a |
|---|---|---|
| CH(Me)OPen-n | (CH2)2OEt | CH(Me)OCH2CF3 |
| CH(Me)OPen-i | (CH2)2OPr-n | CH(Me)O(CH2)2CF3 |
| CH(Me)OPen-s | (CH2)2OPr-i | CH(Me)O(CH2)2Cl |
| CH(Me)OPen-t | (CH2)2OBu-n | CH(Me)O(CH2)2Br |
| CH(Me)OHex-n | (CH2)2OBu-i | CH(Et)OCF2H |
| CH(Et)OMe | (CH2)2OBu-s | CH(Et)OCF3 |
| CH(Et)OEt | (CH2)2OBu-t | CH(Et)OCH2CF2H |
| CH(Et)OPr-n | CH(Me)CH2OMe | CH(Et)OCH2CF3 |
| CH(Et)OPr-i | CH(Me)CH2OEt | CH(Et)O(CH2)2CF3 |
| CH(Et)OBu-n | CH(Me)CH2OPr-n | CH(Et)O(CH2)2Cl |
| CH(Et)OBu-i | CH(Me)CH2OPr-i | CH(Et)O(CH2)2Br |
| CH(Et)OBu-s | CH(Me)CH2OBu-n | C(Me)2OCF2H |
| CH(Et)OBu-t | CH(Me)CH2OBu-i | C(Me)2OCF3 |
| CH(Et)OPen-n | CH(Me)CH2OBu-s | C(Me)2OCH2CF2H |
| CH(Et)OPen-i | CH(Me)CH2OBu-t | C(Me)2OCF3 |
| CH(Et)OPen-s | CH(Et)CH2OMe | C(Me)2O(CH2)2CF3 |
| CH(Et)OPen-t | CH(Et)CH2OEt | C(Me)2O(CH2)2Cl |
| CH(Et)OHex-n | (CH2)3OMe | C(Me)2O(CH2)2Br |
| CH(Pr-n)OMe | (CH2)3OEt | (CH2)2OCF3 |
| CH(Pr-n)OEt | (CH2)3OPr-n | (CH2)2OCH2CF2H |
| CH(Pr-n)OPr-n | (CH2)3OPr-i | (CH2)2OCH2CF3 |
| CH(Pr-n)OPr-i | (CH2)3OBu-n | (CH2)2O(CH2)2Cl |
| CH(Pr-i)OMe | (CH2)3OBu-i | (CH2)2O(CH2)2Br |
| CH(Pr-i)OEt | (CH2)3OBu-s | CH2OH |
| CH(Pr-i)OPr-n | (CH2)3OBu-t | CH(Me)OH |
| CH(Pr-i)OPr-i | CH2OCF2H | CH(Et)OH |
| C(Me)2OMe | CH2OCF3 | CH(iPr)OH |
| C(Me)2OEt | CH2OCH2CF2H | C(Me)2OH |
| C(Me)2OPr-n | CH2OCH2CF3 | (CH2)2OH |
| C(Me)2OPr-i | CH2O(CH2)2CF3 | CH(Me)CH2OH |

TABLE 3

| R1a | R1a | R1a |
|---|---|---|
| (CH2)3OH | C(Me)2O(CH2)2OPr-n | CH(Me)OC(O)Pr-i |
| CH2OCH2OMe | C(Me)2O(CH2)2OPr-i | CH(Et)OC(O)Me |
| CH2OCH2OEt | (CH2)2OCH2OMe | CH(Et)OC(O)Et |
| CH2OCH2OPr-n | (CH2)2OCH2OEt | CH(Et)OC(O)Pr-i |
| CH2OCH2OPr-i | (CH2)2OCH2OPr-n | CH2OPh |
| CH2O(CH2)2OMe | (CH2)2OCH2OPr-i | CH(Me)OPh |
| CH2O(CH2)2OEt | (CH2)2O(CH2)2OMe | CH2C(O)OH |
| CH2O(CH2)2OPr-n | (CH2)2O(CH2)2OEt | CH2C(O)OMe |
| CH2O(CH2)2OPr-i | (CH2)2O(CH2)2OPr-n | CH2C(O)OEt |
| CH2OCH(Me)CH2OMe | (CH2)2O(CH2)2OPr-i | CH2C(O)OPr-n |
| CH2OCH(Me)CH2OEt | CH(Me)CH2OCH2OMe | CH2C(O)OPr-i |
| CH2OCH2CH(Me)OMe | CH(Me)CH2OCH2OEt | CH2C(O)OBu-n |
| CH2OCH2CH(Me)OEt | CH(Me)CH2O(CH2)2OMe | CH2C(O)OBu-i |
| CH2OCH(Me)OMe | CH(Me)CH2O(CH2)2OEt | CH2C(O)OBu-s |
| CH2OCH(Me)OEt | CH(Et)CH2OCH2OMe | CH2C(O)OBu-t |
| CH2O(CH2)3OMe | CH(Et)CH2OCH2OEt | CH2C(O)OPen-n |
| CH2O(CH2)3OEt | CH(Et)CH2O(CH2)2OMe | CH2C(O)OPen-i |
| CH(Me)OCH2OMe | CH(Et)CH2O(CH2)2OEt | CH2C(O)OPen-s |
| CH(Me)OCH2OEt | CH(Et)O(CH2)2OMe | CH2C(O)OPen-t |
| CH(Me)OCH2OPr-n | CH(Et)O(CH2)2OEt | CH2C(O)OHex-n |
| CH(Me)OCH2OPr-i | CH(Et)O(CH2)2OPr-n | CH2C(O)OCH2OMe |
| CH(Me)O(CH2)2OMe | CH(Et)O(CH2)2OPr-i | CH2C(O)O(CH2)2OMe |
| CH(Me)O(CH2)2OEt | CH(Pr-n)O(CH2)2OMe | CH2C(O)O(CH2)2OEt |
| CH(Me)O(CH2)2OPr-n | CH(Pr-n)O(CH2)2OEt | CH2C(O)O(CH2)2OPr-i |
| CH(Me)O(CH2)2OPr-i | CH(Pr-n)O(CH2)2OPr-n | CH2C(O)NHMe |
| CH(Me)OCH(Me)CH2OMe | CH(Pr-n)O(CH2)2OPr-i | CH2C(O)NHEt |
| CH(Me)OCH(Me)CH2OEt | CH(Pr-i)O(CH2)2OMe | CH2C(O)NHPr-n |
| CH(Me)OCH2CH(Me)OMe | CH(Pr-i)O(CH2)2OEt | CH2C(O)NHPr-i |
| CH(Me)OCH2CH(Me)OEt | CH(Pr-i)O(CH2)2OPr-n | CH(Me)C(O)OH |
| C(Me)2OCH2OMe | CH(Pr-i)O(CH2)2OPr-i | CH(Me)C(O)OMe |
| C(Me)2OCH2OEt | CH2OC(O)Me | CH(Me)C(O)OEt |
| C(Me)2OCH2OPr-n | CH2OC(O)Et | CH(Me)C(O)OPr-i |
| C(Me)2OCH2OPr-i | CH2OC(O)Pr-i | CH(Me)C(O)OCH2OMe |
| C(Me)2O(CH2)2OMe | CH(Me)OC(O)Me | CH(Me)C(O)O(CH2)2OMe |
| C(Me)2O(CH2)2OEt | CH(Me)OC(O)Et | CH(Me)C(O)O(CH2)2OEt |

TABLE 4

| R1a | R1a | R1a |
|---|---|---|
| CH(Me)C(O)O(CH2)2OPr-i | CH2S(O)2Pr-i | CH(Me)SPr-i |
| CH(Me)C(O)NHMe | CH2SBu-n | CH(Me)S(O)2Pr-i |
| CH(Me)C(O)NHEt | CH2S(O)Bu-n | CH(Me)S(O)2Pr-i |
| CH(Me)C(O)NHPr-n | CH2SBu-i | CH(Me)SBu-n |
| CH(Me)C(O)NHPr-i | CH2S(O)Bu-i | CH(Me)S(O)Bu-n |
| CH(Et)C(O)OH | CH2S(O)2Bu-n | CH(Me)S(O)2Bu-n |
| CH(Et)C(O)OMe | CH2S(O)2Bu-i | CH(Me)SBu-i |
| CH(Et)C(O)OEt | CH2SBu-s | CH(Me)S(O)Bu-i |
| CH(Et)C(O)OPr-i | CH2S(O)Bu-s | CH(Me)S(O)2Bu-i |
| CH(Et)C(O)OCH2OMe | CH2S(O)2Bu-s | CH(Me)SBu-s |
| CH(Et)C(O)O(CH2)2OMe | CH2SBu-t | CH(Me)S(O)Bu-s |
| CH(Et)C(O)O(CH2)2OEt | CH2S(O)Bu-t | CH(Me)S(O)2Bu-s |
| CH(Et)C(O)O(CH2)2OPr-i | CH2S(O)2Bu-t | CH(Me)SBu-t |
| CH(Et)C(O)NHMe | CH2SPen-n | CH(Me)S(O)Bu-t |
| CH(Et)C(O)NHEt | CH2S(O)Pen-n | CH(Me)SPen-n |
| (CH2)2C(O)OH | CH2S(O)2Pen-n | CH(Me)S(O)Pen-n |
| (CH2)2C(O)OMe | CH2SPen-i | CH(Me)S(O)2Pen-n |
| (CH2)2C(O)OEt | CH2S(O)Pen-i | CH(Me)SPen-i |
| (CH2)2C(O)O(CH2)2OMe | CH2S(O)2Pen-i | CH(Me)S(O)Pen-i |
| (CH2)2C(O)O(CH2)2OEt | CH2SPen-s | CH(Me)S(O)2Pen-i |
| (CH2)2C(O)NHMe | CH2S(O)Pen-s | CH(Me)SPen-s |
| (CH2)2C(O)NHEt | CH2S(O)2Pen-s | CH(Me)S(O)Pen-s |
| (CH2)2C(O)NHPr-n | CH2SPen-t | CH(Me)S(O)2Pen-s |
| (CH2)2C(O)NHPr-i | CH2S(O)Pen-t | CH(Me)SPen-t |
| CH2SMe | CH2S(O)2Pen-t | CH(Me)S(O)Pen-t |
| CH2S(O)Me | CH2SHex-n | CH(Me)S(O)2Pen-t |
| CH2S(O)2Me | CH2SMe | CH(Me)SHex-n |
| CH2SEt | CH(Me)SMe | C(Me)2SMe |
| CH2S(O)Et | CH(Me)S(O)Me | C(Me)2S(O)Me |
| CH2S(O)2Et | CH(Me)S(O)2Me | C(Me)2S(O)2Me |
| CH2SPr-n | CH(Me)SEt | |
| | CH(Me)S(O)Et | |

TABLE 4-continued

| $R^{1a}$ | $R^{1a}$ | $R^{1a}$ |
|---|---|---|
| CH$_2$S(O)Pr-n | CH(Me)S(O)$_2$Et | C(Me)$_2$SEt |
| CH$_2$S(O)$_2$Pr-n | CH(Me)SPr-n | C(Me)$_2$S(O)Et |
| CH$_2$SPr-i | CH(Me)S(O)Pr-n | C(Me)$_2$S(O)$_2$Et |
| CH$_2$S(O)Pr-i | CH(Me)S(O)$_2$Pr-n | C(Me)$_2$SPr-n |

TABLE 5

| $R^{1a}$ | $R^{1a}$ | $R^{1a}$ |
|---|---|---|
| C(Me)$_2$S(O)Pr-n | (CH$_2$)$_2$SPr-n | C(Me)$_2$CH$_2$S(O)$_2$Et |
| C(Me)$_2$S(O)$_2$Pr-n | (CH$_2$)$_2$S(O)Pr-n | C(Me)$_2$CH$_2$SPr-n |
| C(Me)$_2$SPr-i | (CH$_2$)$_2$S(O)$_2$Pr-n | C(Me)$_2$CH$_2$S(O)Pr-n |
| C(Me)$_2$S(O)Pr-i | (CH$_2$)$_2$SPr-i | C(Me)$_2$CH$_2$S(O)$_2$Pr-n |
| C(Me)$_2$S(O)$_2$Pr-i | (CH$_2$)$_2$S(O)Pr-i | C(Me)$_2$CH$_2$SPr-i |
| C(Me)$_2$SBu-n | (CH$_2$)$_2$S(O)$_2$Pr-i | C(Me)$_2$CH$_2$S(O)Pr-i |
| C(Me)$_2$S(O)Bu-n | (CH$_2$)$_3$SMe | C(Me)$_2$CH$_2$S(O)$_2$Pr-i |
| C(Me)$_2$S(O)$_2$Bu-n | (CH$_2$)$_3$(O)Me | CH(Et)SMe |
| C(Me)$_2$SBu-i | (CH$_2$)$_3$S(O)$_2$Me | CH(Et)S(O)Me |
| C(Me)$_2$S(O)Bu-i | (CH$_2$)$_3$SEt | CH(Et)S(O)$_2$Me |
| C(Me)$_2$S(O)$_2$Bu-i | (CH$_2$)$_3$S(O)Et | CH(Et)SEt |
| C(Me)$_2$SBu-s | (CH$_2$)$_3$S(O)$_2$Et | CH(Et)S(O)Et |
| C(Me)$_2$S(O)Bu-s | CH(Me)CH$_2$SMe | CH(Et)S(O)$_2$Et |

TABLE 5-continued

| $R^{1a}$ | $R^{1a}$ | $R^{1a}$ |
|---|---|---|
| C(Me)$_2$S(O)$_2$Bu-s | CH(Me)CH$_2$S(O)Me | CH(Et)SPr-n |
| C(Me)$_2$SBu-t | CH(Me)CH$_2$S(O)$_2$Me | CH(Et)S(O)Pr-n |
| C(Me)$_2$S(O)Bu-t | CH(Me)CH$_2$SEt | CH(Et)S(O)$_2$Pr-n |
| C(Me)$_2$S(O)$_2$Bu-t | CH(Me)CH$_2$S(O)Et | CH(Et)SPr-i |
| C(Me)$_2$SPen-n | CH(Me)CH$_2$S(O)$_2$Et | CH(Et)S(O)Pr-i |
| C(Me)$_2$S(O)Pen-n | CH(Me)CH$_2$SPr-n | CH(Et)S(O)$_2$Pr-i |
| C(Me)$_2$S(O)$_2$Pen-n | CH(Me)CH$_2$S(O)Pr-n | CH(Pr-n)SMe |
| C(Me)$_2$SPen-i | CH(Me)CH$_2$S(O)$_2$Pr-n | CH(Pr-n)S(O)Me |
| C(Me)$_2$S(O)Pen-i | CH(Me)CH$_2$SPr-i | CH(Pr-n)S(O)$_2$Me |
| C(Me)$_2$S(O)$_2$Pen-i | CH(Me)CH$_2$S(O)Pr-i | CH(Pr-n)SEt |
| C(Me)$_2$SPen-s | CH(Me)CH$_2$S(O)$_2$Pr-i | CH(Pr-n)S(O)Et |
| C(Me)$_2$S(O)Pen-s | CH(Et)CH$_2$SMe | CH(Pr-n)S(O)$_2$Et |
| C(Me)$_2$S(O)$_2$Pen-s | CH(Et)CH$_2$S(O)Me | CH(Pr-n)SPr-n |
| C(Me)$_2$SPen-t | CH(Et)CH$_2$S(O)$_2$Me | CH(Pr-n)S(O)Pr-n |
| C(Me)$_2$S(O)Pen-t | CH(Et)CH$_2$SEt | CH(Pr-n)S(O)$_2$Pr-n |
| C(Me)$_2$S(O)$_2$Pen-t | CH(Et)CH$_2$S(O)Et | CH(Pr-n)SPr-i |
| (CH$_2$)$_2$SMe | CH(Et)CH$_2$S(O)$_2$Et | CH(Pr-n)S(O)Pr-i |
| (CH$_2$)$_2$S(O)Me | C(Me)$_2$CH$_2$SMe | CH(Pr-n)S(O)$_2$Pr-i |
| (CH$_2$)$_2$S(O)$_2$Me | C(Me)$_2$CH$_2$S(O)Me | CH(Pr-i)SMe |
| (CH$_2$)$_2$SEt | C(Me)$_2$CH$_2$S(O)$_2$Me | CH(Pr-i)S(O)Me |
| (CH$_2$)$_2$S(O)Et | C(Me)$_2$CH$_2$SEt | CH(Pr-i)S(O)$_2$Me |
| (CH$_2$)$_2$S(O)$_2$Et | C(Me)$_2$CH$_2$S(O)Et | CH(Pr-i)SEt |

TABLE 6

| $R^{1a}$ | $R^{1a}$ | $R^{1a}$ |
|---|---|---|
| CH(Pr-i)S(O)Et | CH$_2$SCF(CF$_3$)$_2$ | C(Me)$_2$S(O)(CH$_2$)$_2$CF$_3$ |
| CH(Pr-i)S(O)$_2$Et | CH(Me)SCF$_2$H | C(Me)$_2$S(O)$_2$(CH$_2$)$_2$CF$_3$ |
| CH(Pr-i)SPr-n | CH(Me)S(O)CF$_2$H | C(Me)$_2$S(CH$_2$)$_2$Cl |
| CH(Pr-i)S(O)Pr-n | CH(Me)S(O)$_2$CF$_2$H | C(Me)$_2$S(O)(CH$_2$)$_2$Cl |
| CH(Pr-i)S(O)$_2$Pr-n | CH(Me)SCF$_3$ | C(Me)$_2$S(O)$_2$(CH$_2$)$_2$Cl |
| CH(Pr-i)SPr-i | CH(Me)S(O)CF$_3$ | C(Me)$_2$S(CH$_2$)$_2$Br |
| CH(Pr-i)S(O)Pr-i | CH(Me)S(O)$_2$CF$_3$ | C(Me)$_2$S(O)(CH$_2$)$_2$Br |
| CH(Pr-i)S(O)$_2$Pr-i | CH(Me)SCH$_2$CF$_2$H | C(Me)$_2$S(O)$_2$(CH$_2$)$_2$Br |
| CH$_2$SCF$_2$H | CH(Me)S(O)CH$_2$CF$_2$H | (CH$_2$)$_2$SCF$_3$ |
| CH$_2$S(O)CF$_2$H | CH(Me)S(O)$_2$CH$_2$CF$_2$H | (CH$_2$)$_2$S(O)CF$_3$ |
| CH$_2$S(O)$_2$CF$_2$H | CH(Me)SCH$_2$CF$_3$ | (CH$_2$)$_2$S(O)$_2$CF$_3$ |
| CH$_2$SCF$_3$ | CH(Me)S(O)CH$_2$CF$_3$ | (CH$_2$)$_2$SCH$_2$CF$_2$H |
| CH$_2$S(O)CF$_3$ | CH(Me)S(O)$_2$CH$_2$CF$_3$ | (CH$_2$)$_2$S(O)CH$_2$CF$_2$H |
| CH$_2$S(O)$_2$CF$_3$ | CH(Me)S(CH$_2$)$_2$CF$_3$ | (CH$_2$)$_2$S(O)$_2$CH$_2$CF$_2$H |
| CH$_2$SCH$_2$CF$_2$H | CH(Me)S(O)(CH$_2$)$_2$CF$_3$ | (CH$_2$)$_2$SCH$_2$CF$_3$ |
| CH$_2$S(O)CH$_2$CF$_2$H | CH(Me)S(O)$_2$(CH$_2$)$_2$CF$_3$ | (CH$_2$)$_2$S(O)CH$_2$CF$_3$ |
| CH$_2$S(O)$_2$CH$_2$CF$_2$H | CH(Me)S(CH$_2$)$_2$Cl | (CH$_2$)$_2$S(O)$_2$CH$_2$CF$_3$ |
| CH$_2$SCH$_2$CF$_3$ | CH(Me)S(O)(CH$_2$)$_2$Cl | (CH$_2$)$_2$S(CH$_2$)$_2$Cl |
| CH$_2$S(O)CH$_2$CF$_3$ | CH(Me)S(O)$_2$(CH$_2$)$_2$Cl | (CH$_2$)$_2$S(O)(CH$_2$)$_2$Cl |
| CH$_2$S(O)$_2$CH$_2$CF$_3$ | CH(Me)S(CH$_2$)$_2$Br | (CH$_2$)$_2$S(O)$_2$(CH$_2$)$_2$Cl |
| CH$_2$S(CH$_2$)$_2$CF$_3$ | CH(Me)S(O)(CH$_2$)$_2$Br | (CH$_2$)$_2$S(CH$_2$)$_2$Br |
| CH$_2$S(O)(CH$_2$)$_2$CF$_3$ | CH(Me)S(O)$_2$(CH$_2$)$_2$Br | (CH$_2$)$_2$S(O)(CH$_2$)$_2$Br |
| CH$_2$S(O)$_2$(CH$_2$)$_2$CF$_3$ | C(Me)$_2$SCF$_2$H | (CH$_2$)$_2$S(O)$_2$(CH$_2$)$_2$Br |
| CH$_2$S(CH$_2$)$_2$Cl | C(Me)$_2$S(O)CF$_2$H | CH=CH$_2$ |
| CH$_2$S(O)(CH$_2$)$_2$Cl | C(Me)$_2$S(O)$_2$CF$_2$H | CH=CHMe |
| CH$_2$S(O)$_2$(CH$_2$)$_2$Cl | C(Me)$_2$SCF$_3$ | CH=CMe$_2$ |
| CH$_2$S(CH$_2$)$_2$Br | C(Me)$_2$S(O)CF$_3$ | CH$_2$CH=CH$_2$ |
| CH$_2$S(O)(CH$_2$)$_2$Br | C(Me)$_2$S(O)$_2$CF$_3$ | CH$_2$CH=CHMe |
| CH$_2$S(O)$_2$(CH$_2$)$_2$Br | C(Me)$_2$SCH$_2$CF$_2$H | CH$_2$C(Me)=CH$_2$ |
| CH$_2$SCHFCH$_3$ | C(Me)$_2$S(O)CH$_2$CF$_2$H | (CH$_2$)$_2$CH=CMe$_2$ |
| CH$_2$SCF$_2$CH$_3$ | C(Me)$_2$S(O)$_2$CH$_2$CF$_2$H | C(Me)=CH$_2$ |
| CH$_2$SCF(CH$_3$)$_2$ | C(Me)$_2$SCH$_2$CF$_3$ | C(Me)=CHMe |
| CH$_2$SCF$_2$CF$_2$H | C(Me)$_2$S(O)CH$_2$CF$_3$ | C(Me)=CMe$_2$ |
| CH$_2$SCF$_2$CF$_3$ | C(Me)$_2$S(O)$_2$CH$_2$CF$_3$ | CH(Me)CH=CH$_2$ |
| CH$_2$SCF$_2$CF$_2$CF$_3$ | C(Me)$_2$S(CH$_2$)$_2$CF$_3$ | C(Et)=CH$_2$ |

TABLE 7

| $R^{1a}$ | $R^{1a}$ | $R^{1a}$ |
|---|---|---|
| C(Et)=CHMe | 2,4-(Cl)$_2$—Ph | 3-F-4-Cl—Ph |
| C(Et)=CMe$_2$ | 2,5-(Cl)$_2$—Ph | 3-F-5-Cl—Ph |
| CH(Et)CH=CH$_2$ | 2,6-(Cl)$_2$—Ph | 2-Me-3-F—Ph |
| C≡CH | 3,4-(Cl)$_2$—Ph | 2-Me-4-F—Ph |
| C≡CMe | 3,5-(Cl)$_2$—Ph | 2-Me-5-F—Ph |
| CH$_2$C≡CH | 2,3-(Me)$_2$—Ph | 3-Me-4-F—Ph |
| CH$_2$C≡CMe | 2,4-(Me)$_2$—Ph | 3-Me-5-F—Ph |
| CH(Me)C≡CH | 2,5-(Me)$_2$—Ph | 2-Cl-3-MeO—Ph |
| CH(Me)C≡CMe | 2,6-(Me)$_2$—Ph | 2-Cl-4-MeO—Ph |
| Ph | 3,4-(Me)$_2$—Ph | 2-Cl-5-MeO—Ph |
| 2-F—Ph | 3,5-(Me)$_2$—Ph | 2-Cl-6-MeO—Ph |
| 3-F—Ph | 2,3-(MeO)$_2$—Ph | 3-Cl-4-MeO—Ph |
| 4-F—Ph | 2,4-(MeO)$_2$—Ph | 3-Cl-5-MeO—Ph |
| 2-Cl—Ph | 2,5-(MeO)$_2$—Ph | 2-F-3-MeO—Ph |
| 3-Cl—Ph | 2,6-(MeO)$_2$—Ph | 2-F-4-MeO—Ph |
| 4-Cl—Ph | 3,4-(MeO)$_2$—Ph | 2-F-5-MeO—Ph |
| 2-Br—Ph | 3,5-(MeO)$_2$—Ph | 2-F-6-MeO—Ph |
| 3-Br—Ph | 2-Cl-3-Me—Ph | 3-F-4-MeO—Ph |
| 4-Br—Ph | 2-Cl-4-Me—Ph | 3-F-5-MeO—Ph |
| 2-Me—Ph | 2-Cl-5-Me—Ph | 2-MeO-3-F—Ph |
| 3-Me—Ph | 3-Cl-4-Me—Ph | 2-MeO-4-F—Ph |
| 4-Me—Ph | 3-Cl-5-Me—Ph | 2-MeO-5-F—Ph |
| 2-CF$_3$—Ph | 2-Cl-3-F—Ph | 2-MeO-6-F—Ph |
| 3-CF$_3$—Ph | 2-Cl-4-F—Ph | 3-MeO-4-F—Ph |
| 4-CF$_3$—Ph | 2-Cl-5-F—Ph | 3-MeO-5-F—Ph |
| 2-MeO—Ph | 3-Cl-4-F—Ph | 2-MeO-3-Cl—Ph |
| 3-MeO—Ph | 3-Cl-5-F—Ph | 2-MeO-4-Cl—Ph |
| 4-MeO—Ph | 2-F-3-Me—Ph | 2-MeO-5-Cl—Ph |
| 2,3-(F)$_2$—Ph | 2-F-4-Me—Ph | 2-MeO-6-Cl—Ph |
| 2,4-(F)$_2$—Ph | 2-F-5-Me—Ph | 3-MeO-4-Cl—Ph |
| 2,5-(F)$_2$—Ph | 3-F-4-Me—Ph | 3-MeO-5-Cl—Ph |
| 2,6-(F)$_2$—Ph | 3-F-5-Me—Ph | 2-Me-3-MeO—Ph |
| 3,4-(F)$_2$—Ph | 2-F-3-Cl—Ph | 2-Me-4-MeO—Ph |
| 3,5-(F)$_2$—Ph | 2-F-4-Cl—Ph | 2-Me-5-MeO—Ph |
| 2,3-(Cl)$_2$—Ph | 2-F-5-Cl—Ph | 2-Me-6-MeO—Ph |

TABLE 8

| $R^{1a}$ | $R^{1a}$ | $R^{1a}$ |
|---|---|---|
| 3-Me-4-MeO—Ph | D-11 | CH$_2$(2,5-(MeO)$_2$—Ph) |
| 3-Me-5-MeO—Ph | D-12 | CH$_2$(2,6-(MeO)$_2$—Ph) |
| 2-MeO-3-Me—Ph | D-13a | CH$_2$(3,4-(MeO)$_2$—Ph) |
| 2-MeO-4-Me—Ph | D-14 | CH$_2$(3,5-(MeO)$_2$—Ph) |
| 2-MeO-5-Me—Ph | D-16 | CH(Me)(2-MeO—Ph) |
| 2-MeO-6-Me—Ph | D-16a | CH(Me)(3-MeO—Ph) |
| 3-MeO-4-Me—Ph | D-16b | CH(Me)(4-MeO—Ph) |
| 3-MeO-5-Me—Ph | D-16c | CH(Me)(2,3-(MeO)$_2$—Ph) |
| 3,5-(F)$_2$-4-Me—Ph | D-16d | CH(Me)(2,4-(MeO)$_2$—Ph) |
| 3,5-(F)$_2$-4-MeO—Ph | D-16e | CH(Me)(2,5-(MeO)$_2$—Ph) |
| 3,4,5-(MeO)$_3$—Ph | D-16f | CH(Me)(2,6-(MeO)$_2$—Ph) |
| D-3 | D-16g | CH(Me)(3,4-(MeO)$_2$—Ph) |
| D-3a | D-16h | CH(Me)(3,5-(MeO)$_2$—Ph) |
| D-4 | D-16i | CH(Et)(2-MeO—Ph) |
| D-4a | D-16j | CH(Et)(3-MeO—Ph) |
| D-4b | D-16k | CH(Et)(4-MeO—Ph) |
| D-8 | D-16m | (CH$_2$)$_2$(2-MeO—Ph) |
| D-8a | D-16n | (CH$_2$)$_2$(3-MeO—Ph) |
| D-8b | D-16p | (CH$_2$)$_2$(4-MeO—Ph) |
| D-8c | D-17 | CHO |
| D-8d | D-17a | CH=NOMe |
| D-8e | D-17b | OMe |
| D-8f | D-19 | OEt |
| D-8g | D-24a | OPr-n |
| D-8h | D-24b | OPr-i |
| D-9 | D-24c | OBu-n |
| D-9a | D-24d | OBu-i |
| D-9c | D-24e | OBu-s |
| D-9d | D-24f | OBu-t |
| D-9f | CH$_2$Ph | OPen-n |
| D-9g | CH$_2$(2-MeO—Ph) | OPen-i |
| D-9i | CH$_2$(3-MeO—Ph) | OPen-s |
| D-9j | CH$_2$(4-MeO—Ph) | OPen-t |
| D-9m | CH$_2$(2,3-(MeO)$_2$—Ph) | OHex-n |
| D-10a | CH$_2$(2,4-(MeO)$_2$—Ph) | SMe |

TABLE 9

| $R^{1a}$ | $R^{1a}$ | $R^{1a}$ |
|---|---|---|
| S(O)Me | SPen-n | S(CH₂)₂Cl |
| S(O)₂Me | S(O)Pen-n | S(O)(CH₂)₂Cl |
| SEt | S(O)₂Pen-n | S(O)₂(CH₂)₂Cl |
| S(O)Et | SPen-i | SCH(Me)CH₂Cl |
| S(O)₂Et | S(O)Pen-i | SCH₂CH(Me)Cl |
| SPr-n | S(O)₂Pen-i | S(CH₂)₃Cl |
| S(O)Pr-n | SPen-c | SCF₃ |
| S(O)₂Pr-n | S(O)Pen-c | SCH₂CF₃ |
| SPr-i | S(O)₂Pen-c | S(O)CH₂CF₃ |
| S(O)Pr-i | SPen-s | S(O)₂CH₂CF₃ |
| S(O)₂Pr-i | S(O)Pen-s | SCH(Me)CF₃ |
| SPr-c | S(O)₂Pen-s | S(CH₂)₂CF₃ |
| S(O)Pr-c | SPen-t | S(CH₂)₃CF₃ |
| S(O)₂Pr-c | S(O)Pen-t | SCHFCH₃ |
| S(D-16) | S(O)₂Pen-t | SCF₂CH₃ |
| S(O)(D-16) | SHex-n | SCF(CH₃)₂ |
| S(O)₂(D-16) | SHex-c | SCF₂CF₂H |
| S(D-16e) | SCH₂CH=CH₂ | SCF₂CF₃ |
| S(O)(D-16e) | S(O)CH₂CH=CH₂ | SCF₂CF₂CF₃ |
| S(O)₂(D-16e) | S(O)₂CH₂CH=CH₂ | SCF(CF₃) |
| SBu-n | SCH(Me)CH=CH₂ | SCH₂OMe |
| S(O)Bu-n | SC(Me)₂CH=CH₂ | S(CH₂)₂OMe |
| S(O)₂Bu-n | SCH₂CH=CHMe | S(O)(CH₂)₂OMe |
| SBu-i | SCH₂C(Me)=CH₂ | S(O)₂(CH₂)₂OMe |
| S(O)Bu-i | S(CH₂)₂CH=CMe₂ | SCH(Me)CH₂OMe |
| S(O)₂Bu-i | SC(Me)=CH₂ | S(O)CH(Me)CH₂OMe |
| SBu-c | SC(Me)=CH(Me) | S(O)₂CH(Me)CH₂OMe |
| S(O)Bu-c | SCH₂C≡CH | SCH₂CH(Me)OMe |
| S(O)₂Bu-c | S(O)CH₂C≡CH | S(O)CH₂CH(Me)OMe |
| SBu-s | S(O)₂CH₂C≡CH | S(O)₂CH₂CH(Me)OMe |
| S(O)Bu-s | SCH(Me)C≡CH | SC(Me)₂CH₂OMe |
| S(O)₂Bu-s | SC(Me)₂C≡CH | S(CH₂)₃OMe |
| SBu-t | SCH₂C≡CMe | SCH₂OEt |
| S(O)Bu-t | SCH₂Cl | S(CH₂)₂OEt |
| S(O)₂Bu-t | SCH(Me)Cl | S(O)(CH₂)₂OEt |

TABLE 10

| $R^{1a}$ | $R^{1a}$ | $R^{1a}$ |
|---|---|---|
| S(O)₂(CH₂)₂OEt | S(O)₂CH₂CN | SCH(Me)C(O)Me |
| SCH(Me)CH₂OEt | SCH(Me)CN | S(CH₂)₂C(O)Me |
| SCH₂OPr-i | S(O)CH(Me)CN | SCH₂C(O)OMe |
| S(CH₂)₂OPr-i | S(O)₂CH(Me)CN | SCH(Me)C(O)OMe |
| S(O)(CH₂)₂OPr-i | SC(Me)₂CN | S(CH₂)₂C(O)OMe |
| S(O)₂(CH₂)₂OPr-i | S(O)C(Me)₂CN | SCH₂C(O)OEt |
| SCH(Me)CH₂OPr-i | S(O)₂C(Me)₂CN | SCH(Me)C(O)OEt |
| SCH₂Pr-c | S(CH₂)₂CN | S(CH₂)₂C(O)OEt |
| S(O)CH₂Pr-c | S(O)(CH₂)₂CN | SCH₂(D-8a) |
| S(O)₂CH₂Pr-c | S(O)₂(CH₂)₂CN | S(O)CH₂(D-8a) |
| SCH(Me)Pr-c | SCH₂Ph | S(O)₂CH₂(D-8a) |
| S(O)CH(Me)Pr-c | S(O)CH₂Ph | SCH₂(D-8b) |
| S(O)₂CH(Me)Pr-c | S(O)₂CH₂Ph | S(O)CH₂(D-8b) |
| S(CH₂)₂Pr-c | SCH(Me)Ph | S(O)₂CH₂(D-8b) |
| SCH₂(D-16) | S(O)CH(Me)Ph | SCH₂(D-8c) |
| S(O)CH₂(D-16) | S(O)₂CH(Me)Ph | S(O)CH₂(D-8c) |
| S(O)₂CH₂(D-16) | SCH₂(2-MeO—Ph) | S(O)₂CH₂(D-8c) |
| SCH₂(D-16e) | S(O)CH₂(2-MeO—Ph) | SCH₂(D-8d) |
| S(O)CH₂(D-16e) | S(O)₂CH₂(2-MeO—Ph) | S(O)CH₂(D-8d) |
| S(O)₂CH₂(D-16e) | SCH(Me)(2-MeO—Ph) | S(O)₂CH₂(D-8d) |
| SCH₂Bu-c | S(O)CH(Me)(2-MeO—Ph) | SCH₂(D-8e) |
| S(O)CH₂Bu-c | S(O)₂CH(Me)(2-MeO—Ph) | S(O)CH₂(D-8e) |
| S(O)₂CH₂Bu-c | SCH₂(3-MeO—Ph) | S(O)₂CH₂(D-8e) |
| SCH(Me)Bu-c | S(O)CH₂(3-MeO—Ph) | SCH₂(D-8f) |
| S(CH₂)₂Bu-c | S(O)₂CH₂(3-MeO—Ph) | S(O)CH₂(D-8f) |
| SCH₂Pen-c | SCH(Me)(3-MeO—Ph) | S(O)₂CH₂(D-8f) |
| S(O)CH₂Pen-c | S(O)CH(Me)(3-MeO—Ph) | SCH₂(D-8g) |
| S(O)₂CH₂Pen-c | S(O)₂CH(Me)(3-MeO—Ph) | S(O)CH₂(D-8g) |
| SCH(Me)Pen-c | SCH₂(4-MeO—Ph) | SCH₂(D-8h) |
| S(CH₂)₂Pen-c | S(O)CH₂(4-MeO—Ph) | S(O)CH₂(D-8h) |
| SCH₂Hex-c | S(O)₂CH₂(4-MeO—Ph) | S(O)₂CH₂(D-8h) |
| SCH(Me)Hex-c | SCH(Me)(4-MeO—Ph) | SCH₂(D-15) |
| S(CH₂)₂Hex-c | S(O)CH(Me)(4-MeO—Ph) | S(O)CH₂(D-15) |
| SCH₂CN | S(O)₂CH(Me)(4-MeO—Ph) | S(O)CH(Me)(D-15) |

TABLE 10-continued

| $R^{1a}$ | $R^{1a}$ | $R^{1a}$ |
|---|---|---|
| SCH₂CN | S(O)₂CH(Me)(4-MeO—Ph) | S(O)₂CH(Me)(D-15) |
| S(O)CH₂CN | SCH₂C(O)Me | S(CH₂)₂(D-15) |

TABLE 11

| $R^{1a}$ | $R^{1a}$ | $R^{1a}$ |
|---|---|---|
| S(O)(CH₂)₂(D-15) | N(Me)Pr-c | N(Pr-i)Pr-i |
| S(O)₂(CH₂)₂(D-15) | N(Me)(D-16) | N(Pr-i)Pr-c |
| SCH₂(D-18) | N(Me)(D-16e) | N(Pr-i)(D-16) |
| S(O)CH₂(D-18) | N(Me)Bu-n | N(Pr-i)(D-16e) |
| S(O)₂CH₂(D-18) | N(Me)Bu-i | N(Pr-i)Bu-n |
| SCH(Me)(D-18) | N(Me)Bu-c | N(Pr-i)Bu-i |
| S(O)CH(Me)(D-18) | N(Me)Bu-s | N(Pr-i)Bu-c |
| S(O)₂CH(Me)(D-18) | N(Me)Bu-t | N(Pr-i)Bu-s |
| S(CH₂)₂(D-18) | N(Me)Pen-n | NHCH₂OMe |
| S(O)(CH₂)₂(D-18) | N(Me)Pen-i | NHCH₂OEt |
| S(O)₂(CH₂)₂(D-18) | N(Me)Pen-c | NHCH(Me)OMe |
| NHMe | N(Me)Pen-s | NHCH(Me)OEt |
| NHEt | N(Me)Pen-t | NHC(Me)₂OMe |
| NHPr-n | N(Me)(3-Pen) | NHC(Me)₂OEt |
| NHPr-i | N(Me)Hex-n | NH(CH₂)₂OMe |
| NHPr-c | N(Me)Hex-c | NH(CH₂)₂OEt |
| NH(D-16) | N(Et)Et | NH(CH₂)₂OPr-i |
| NH(D-16e) | N(Et)Pr-n | NH(CH₂)₂OPr-i |
| NHBu-n | N(Et)Pr-i | N(Me)CH₂OMe |
| NHBu-i | N(Et)Pr-c | N(Me)CH₂OEt |
| NHBu-c | N(Et)(D-16) | N(Me)CH(Me)OMe |
| NHBu-s | N(Et)(D-16e) | N(Me)CH(Me)OEt |
| NHBu-t | N(Et)Bu-n | N(Me)C(Me)₂OMe |
| NHPen-n | N(Et)Bu-i | N(Me)C(Me)₂OEt |
| NHPen-i | N(Et)Bu-c | N(Me)(CH₂)₂OMe |
| NHPen-c | N(Et)Bu-s | N(Me)(CH₂)₂OEt |
| NHPen-s | N(Pr-n)Pr-n | N(Me)(CH₂)₂OPr-n |
| NHPen-t | N(Pr-n)Pr-i | N(Me)(CH₂)₂OPr-i |
| NH(3-Pen) | N(Pr-n)Pr-c | N(Et)C(Me)₂OMe |
| NHHex-n | N(Pr-n)(D-16) | N(Et)C(Me)₂OEt |
| NHHex-c | N(Pr-n)(D-16e) | N(Et)(CH₂)₂OMe |
| N(Me)Me | N(Pr-n)Bu-n | N(Et)(CH₂)₂OEt |
| N(Me)Et | N(Pr-n)Bu-i | N(Et)(CH₂)₂OPr-n |
| N(Me)Pr-n | N(Pr-n)Bu-c | N(Et)(CH₂)₂OPr-i |
| N(Me)Pr-i | N(Pr-n)Bu-s | N(Pr-n)(CH₂)₂OMe |

TABLE 12

| $R^{1a}$ | $R^{1a}$ | $R^{1a}$ |
|---|---|---|
| N(Pr-n)(CH₂)₂OEt | N(Me)(CH₂)₂S(O)Pr-i | NH(2,6-(MeO)₂—Ph) |
| N(Pr-n)(CH₂)₂OPr-n | N(Me)(CH₂)₂S(O)₂Pr-i | NH(3,4-(MeO)₂—Ph) |
| N(Pr-n)(CH₂)₂OPr-i | N(Pr-i)(CH₂)₂OMe | NH(3,5-(MeO)₂—Ph) |
| N(Pr-i)(CH₂)₂OMe | NHCF₃ | N(Me)Ph |
| N(Pr-i)(CH₂)₂OEt | NHCF₂CF₂H | N(Me)(2-MeO—Ph) |
| N(Pr-i)(CH₂)₂OPr-n | NHCH₂CF₃ | N(Me)(3-MeO—Ph) |
| N(Pr-i)(CH₂)₂OPr-i | NH(CH₂)₂CF₃ | N(Me)(4-MeO—Ph) |
| NHCH₂SMe | NH(CH₂)₂Cl | N(Me)(2,3-(MeO)₂—Ph) |
| NHCH₂SEt | NH(CH₂)₃Cl | N(Me)(2,4-(MeO)₂—Ph) |
| NHCH(Me)SMe | N(Me)CF₂H | N(Me)(2,5-(MeO)₂—Ph) |
| NHCH(Me)SEt | N(Me)CF₃ | N(Me)(2,6-(MeO)₂—Ph) |
| NHC(Me)₂SMe | N(Me)CH₂CF₂H | N(Me)(3,4-(MeO)₂—Ph) |
| NHC(Me)₂SEt | N(Me)CH₂CF₃ | N(Me)(3,5-(MeO)₂—Ph) |
| NH(CH₂)₂SMe | N(Me)(CH₂)₂CF₃ | NHCH₂Ph |
| NH(CH₂)₂S(O)Me | N(Me)(CH₂)₂Cl | NHCH₂(2-MeO—Ph) |
| NH(CH₂)₂S(O)₂Me | N(Me)(CH₂)₃Cl | NHCH₂(3-MeO—Ph) |
| NH(CH₂)₂SEt | NHCH=CH₂ | NHCH₂(4-MeO—Ph) |
| NH(CH₂)₂S(O)Et | N(Me)CH=CH₂ | N(Me)CH₂Ph |
| NH(CH₂)₂S(O)₂Et | NHCH₂C≡CH | N(Me)CH₂(2-MeO—Ph) |
| NH(CH₂)₂SPr-i | NHCH₂C≡CMe | N(Me)CH₂(3-MeO—Ph) |
| NH(CH₂)₂S(O)Pr-i | N(Me)CH₂C≡CH | N(Me)CH₂(4-MeO—Ph) |
| NH(CH₂)₂S(O)₂Pr-i | N(Me)CH₂C≡CMe | NH(D-9b) |
| N(Me)CH₂SMe | NHCH₂CN | NH(D-9e) |
| N(Me)CH₂SEt | NH(CH₂)₂CN | NH(D-9h) |
| N(Me)CH(Me)SMe | NH(CH₂)₃CN | NH(D-9k) |
| N(Me)CH(Me)SEt | N(Me)CH₂CN | N(Me)(D-9b) |

TABLE 12-continued
| R$^{1a}$ | R$^{1a}$ | R$^{1a}$ |
|---|---|---|
| N(Me)C(Me)$_2$SMe | N(Me)(CH$_2$)$_2$CN | N(Me)(D-9e) |
| N(Me)C(Me)$_2$SEt | N(Me)(CH$_2$)$_3$CN | N(Me)(D-9h) |
| N(Me)(CH$_2$)$_2$SMe | NHPh | N(Me)(D-9k) |
| N(Me)(CH$_2$)$_2$S(O)Me | NH(2-MeO—Ph) | NHSO$_2$Ph |
| N(Me)(CH$_2$)$_2$S(O)$_2$Me | NH(3-MeO—Ph) | N(Me)SO$_2$Ph |
| N(Me)(CH$_2$)$_2$SEt | NH(4-MeO—Ph) | |
| N(Me)(CH$_2$)$_2$S(O)Et | NH(2,3-(MeO)$_2$—Ph) | |
| N(Me)(CH$_2$)$_2$S(O)$_2$Et | NH(2,4-(MeO)$_2$—Ph) | |
| N(Me)(CH$_2$)$_2$SPr-i | NH(2,5-(MeO)$_2$—Ph) | |
SECOND TABLE
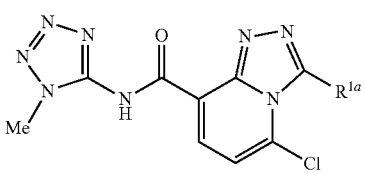
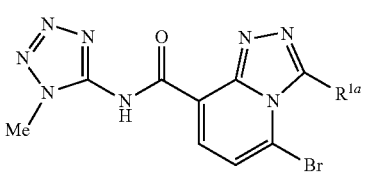
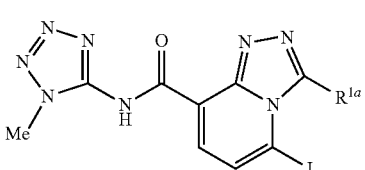
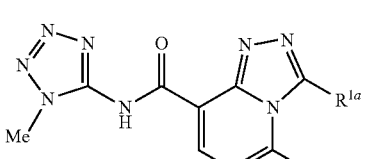
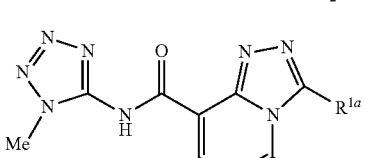
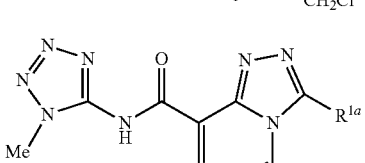
SECOND TABLE-continued
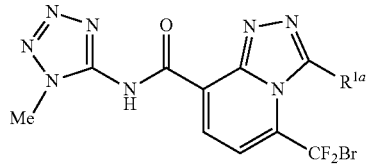
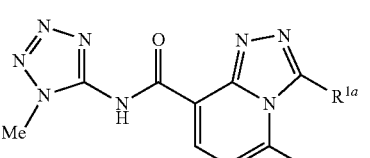
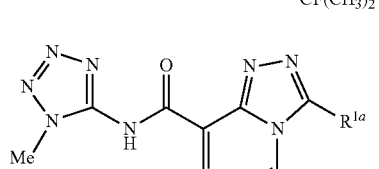
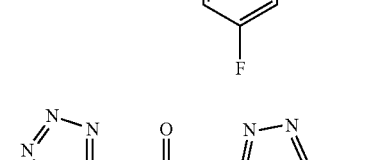
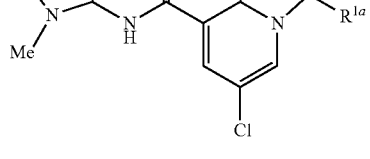
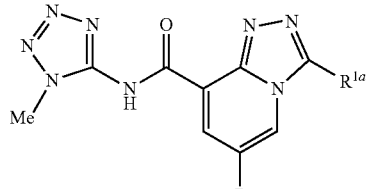

SECOND TABLE-continued
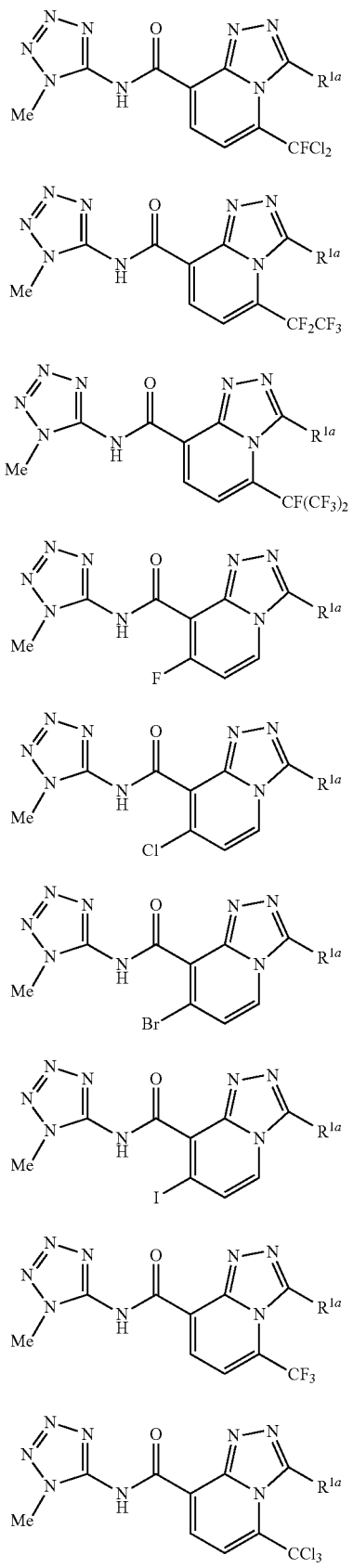
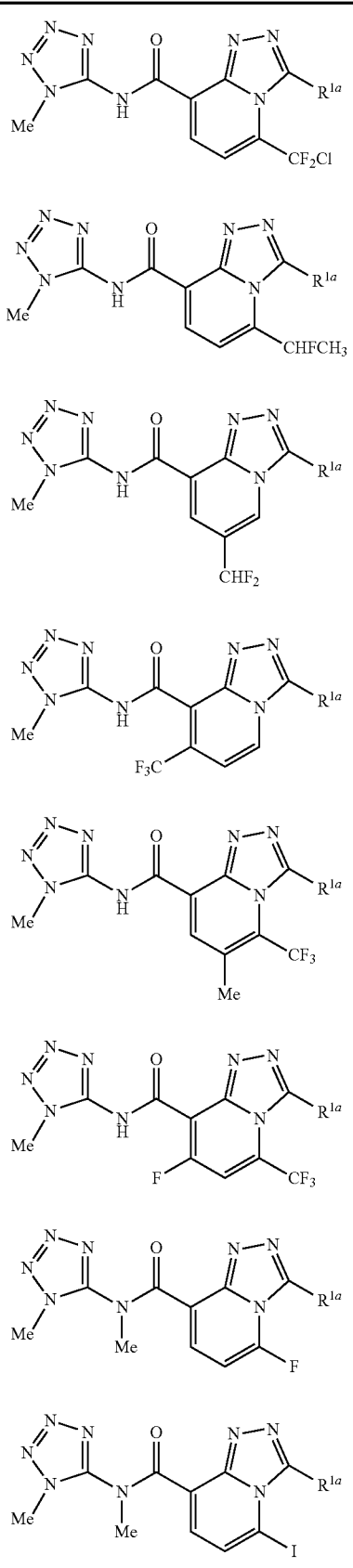

SECOND TABLE-continued
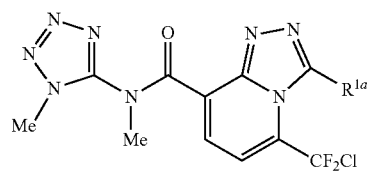
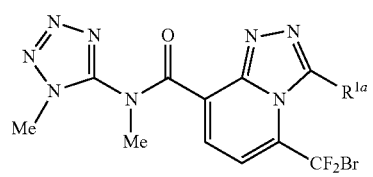
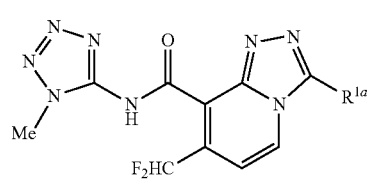
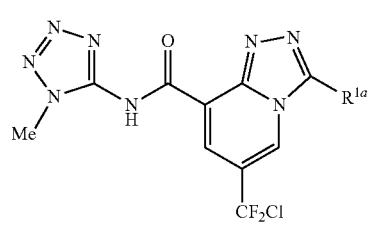
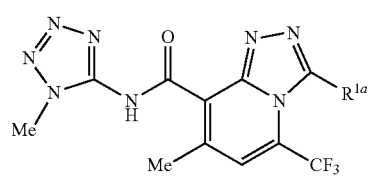
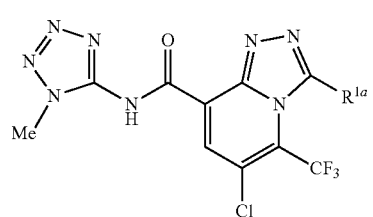
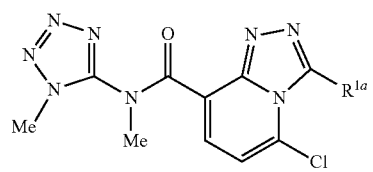
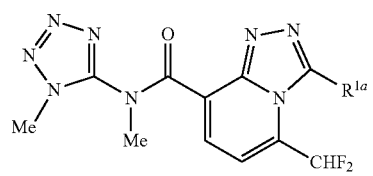
SECOND TABLE-continued
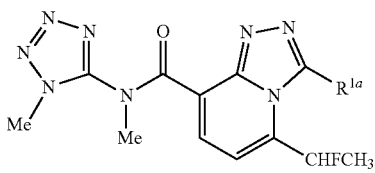
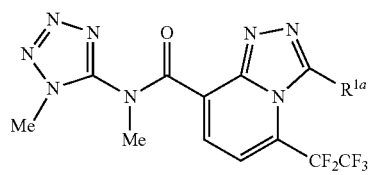
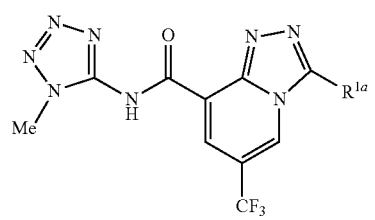
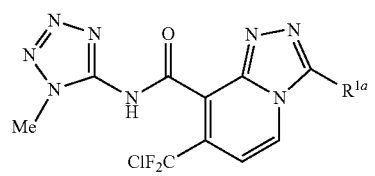
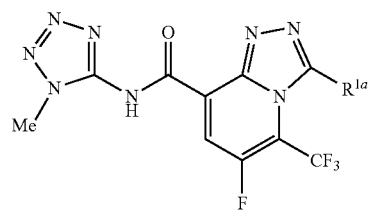
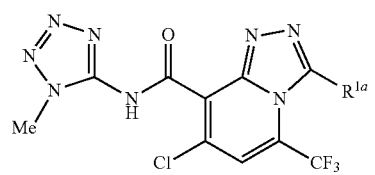
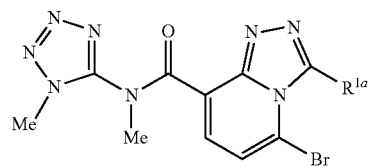
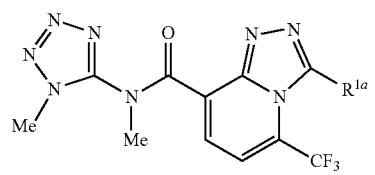

SECOND TABLE-continued
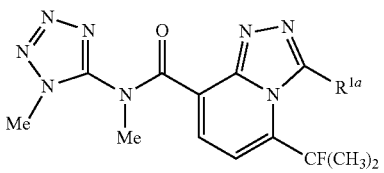
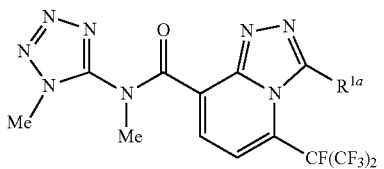
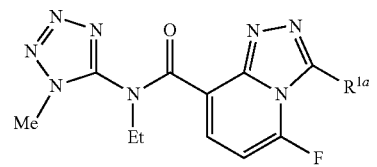
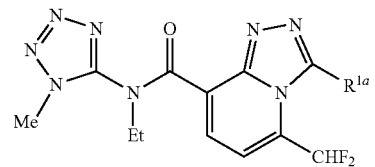
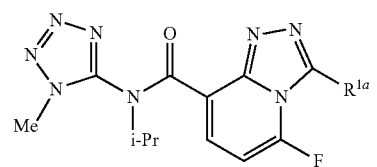
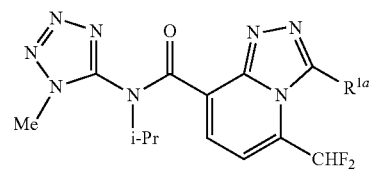
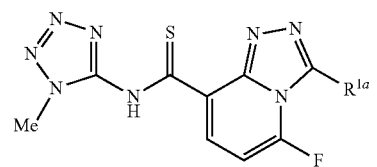
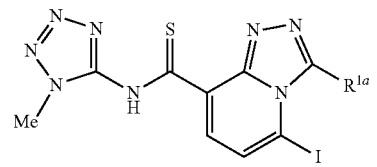
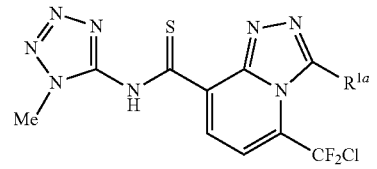
SECOND TABLE-continued
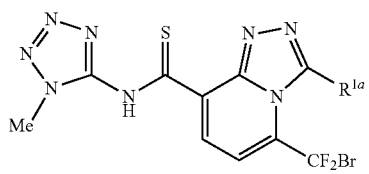
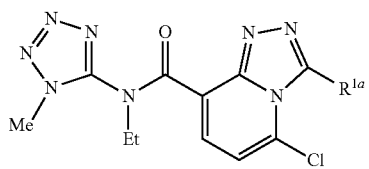
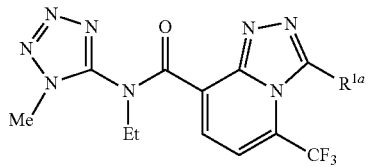
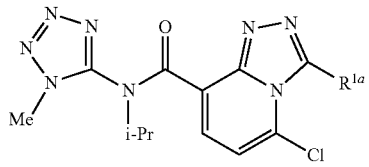
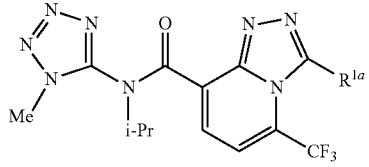
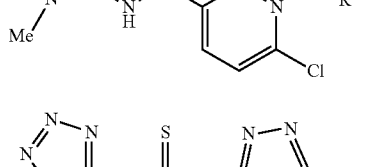
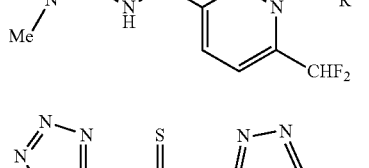
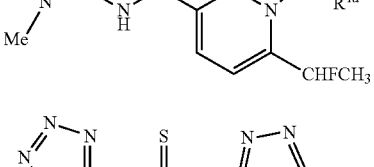
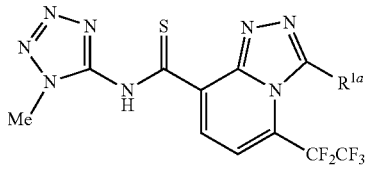

| 101 | 102 |
|---|---|
| SECOND TABLE-continued | SECOND TABLE-continued |
| 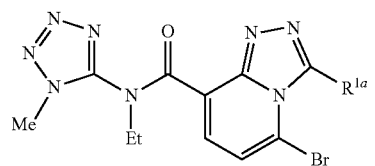 | 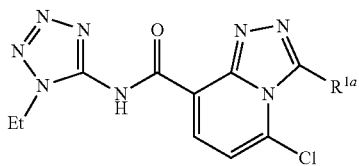 |
| 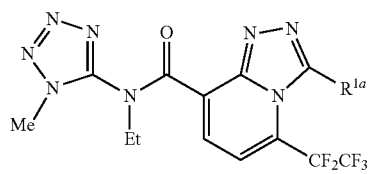 | 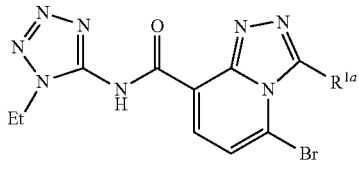 |
| 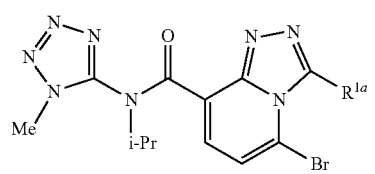 | 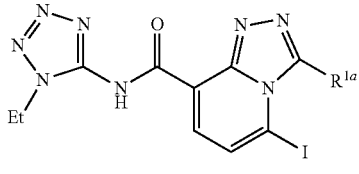 |
| 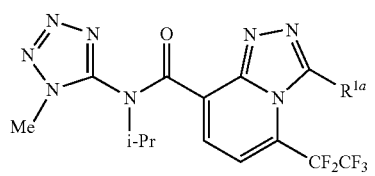 | 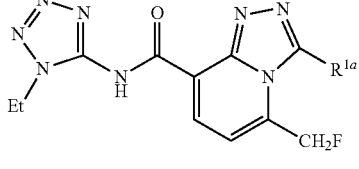 |
|  | 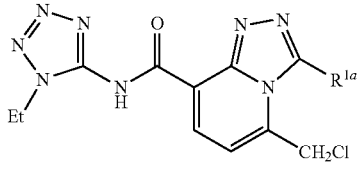 |
|  | 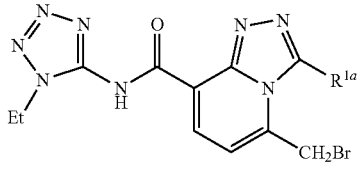 |
| 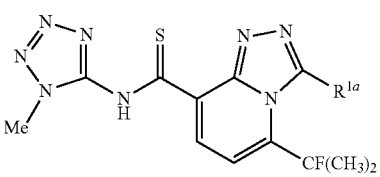 | 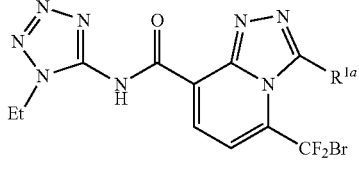 |
| 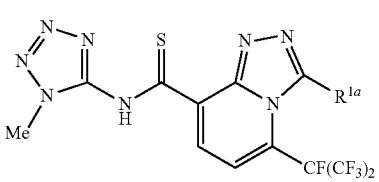 | 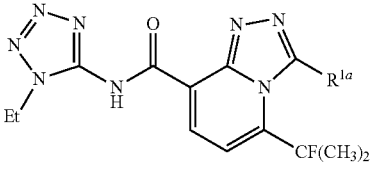 |
| 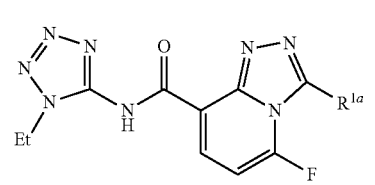 | 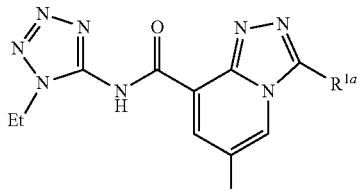 |

SECOND TABLE-continued
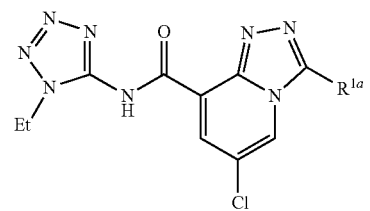
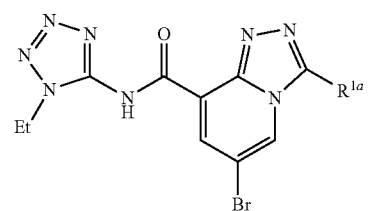
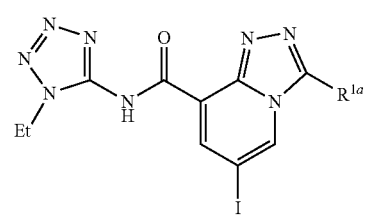
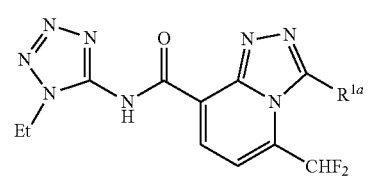
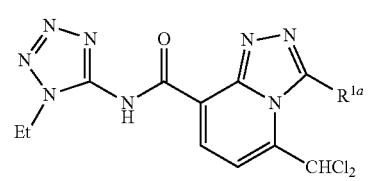
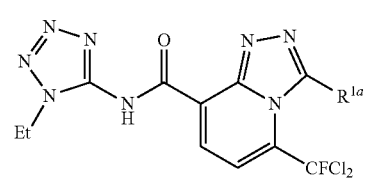
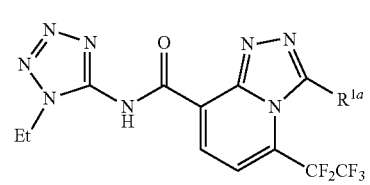
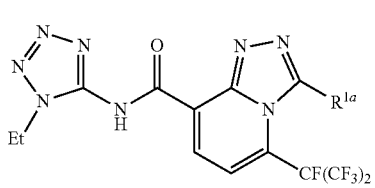
SECOND TABLE-continued
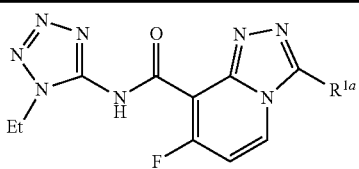
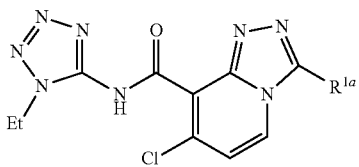
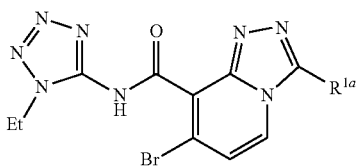
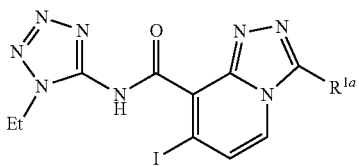
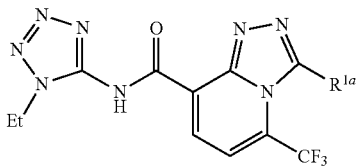
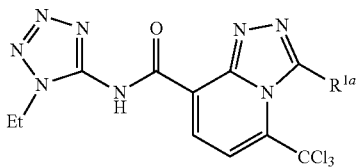
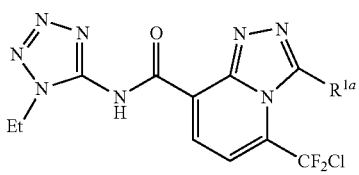
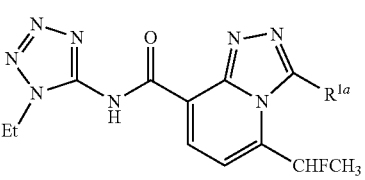
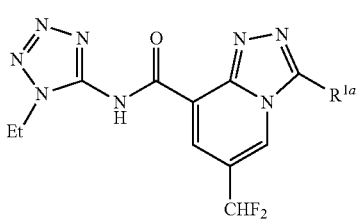

SECOND TABLE-continued
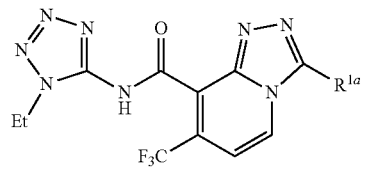
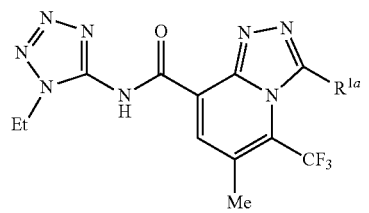
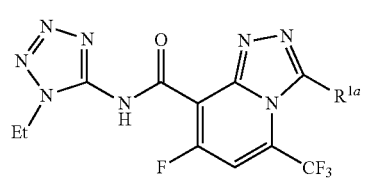
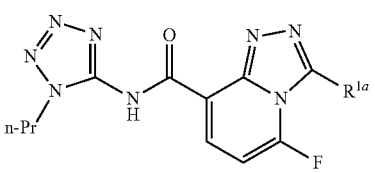
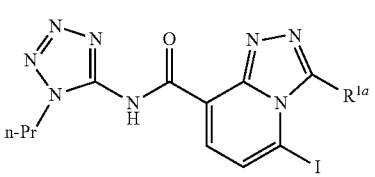
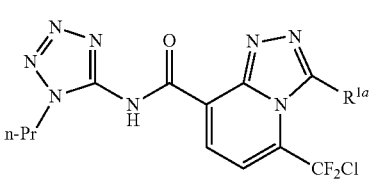
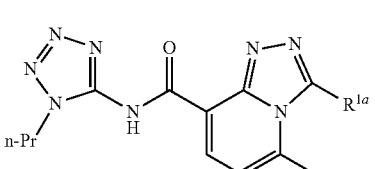
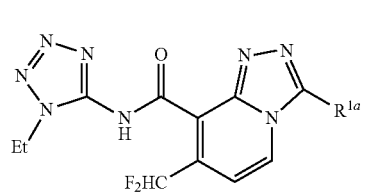
SECOND TABLE-continued
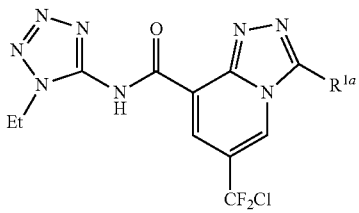
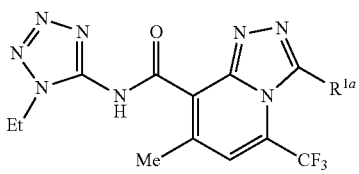
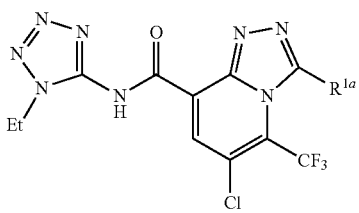
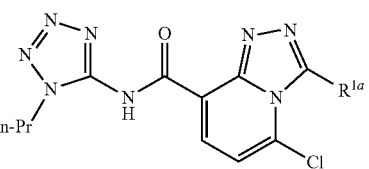
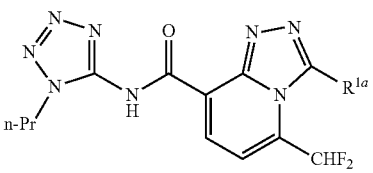
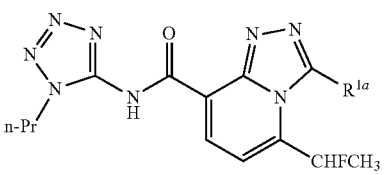
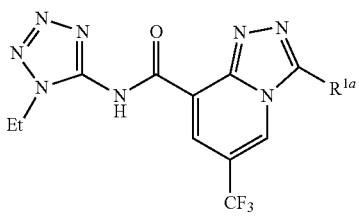

SECOND TABLE-continued
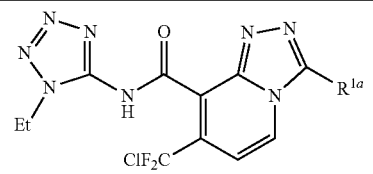
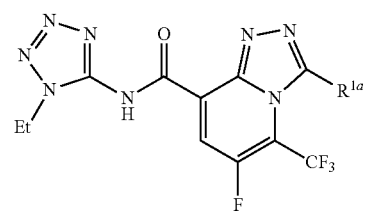
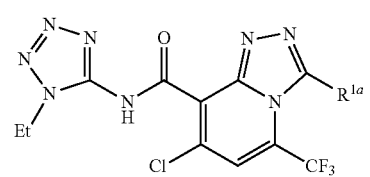
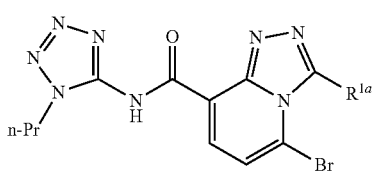
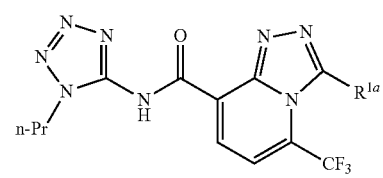
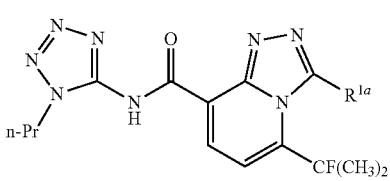
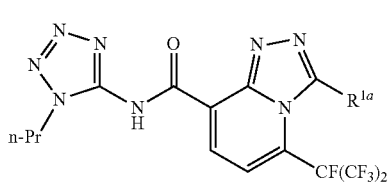
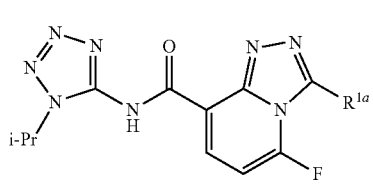
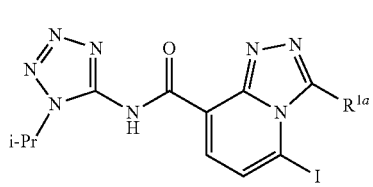
SECOND TABLE-continued
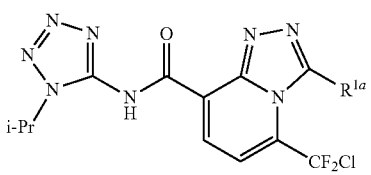
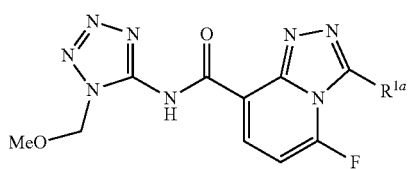
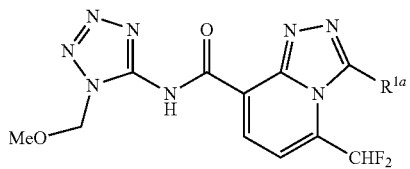
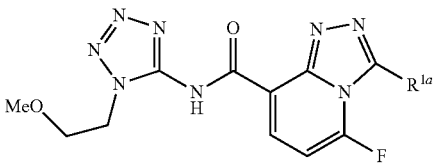
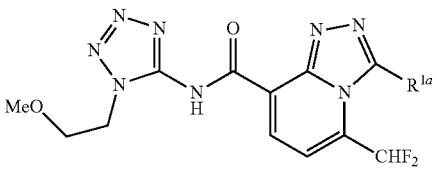
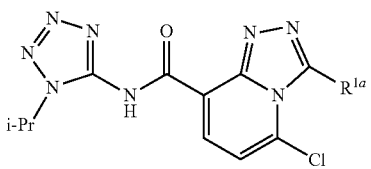
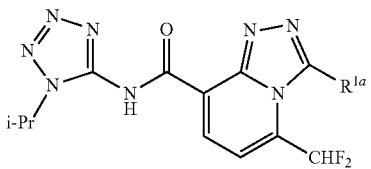
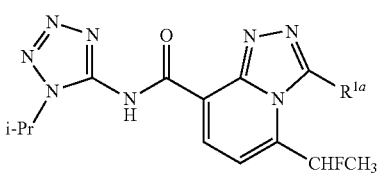

SECOND TABLE-continued
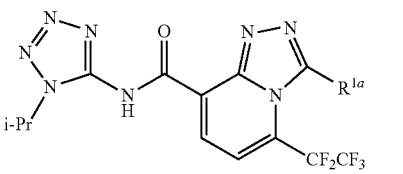
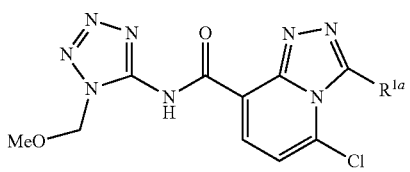
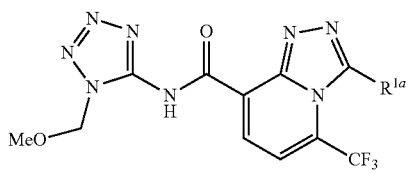
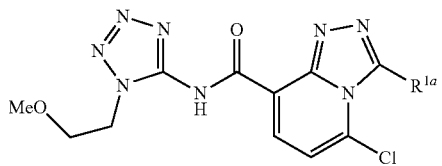
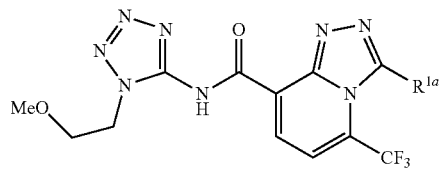
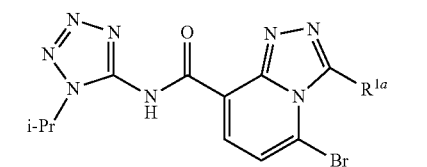
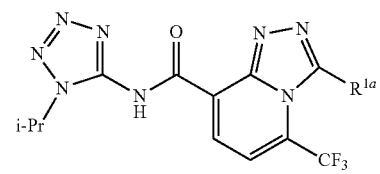
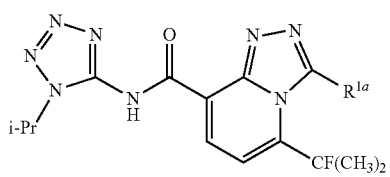
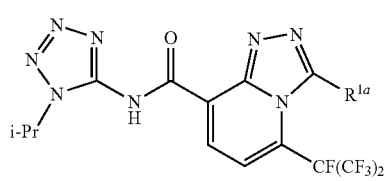
SECOND TABLE-continued
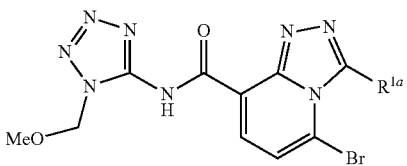
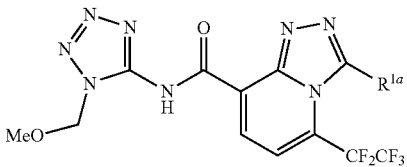
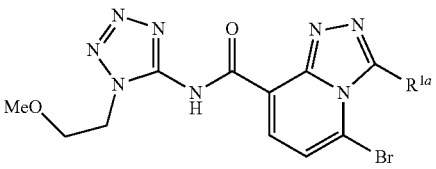
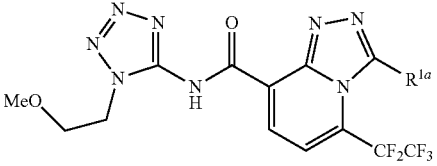
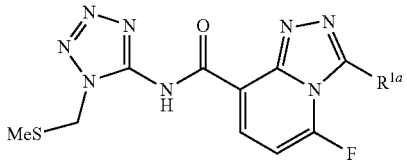
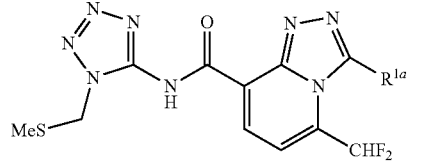
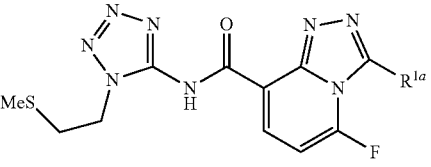
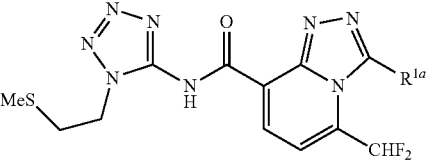
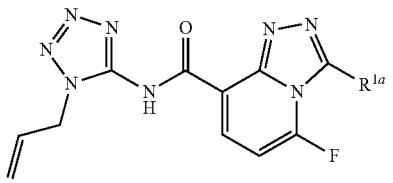

SECOND TABLE-continued
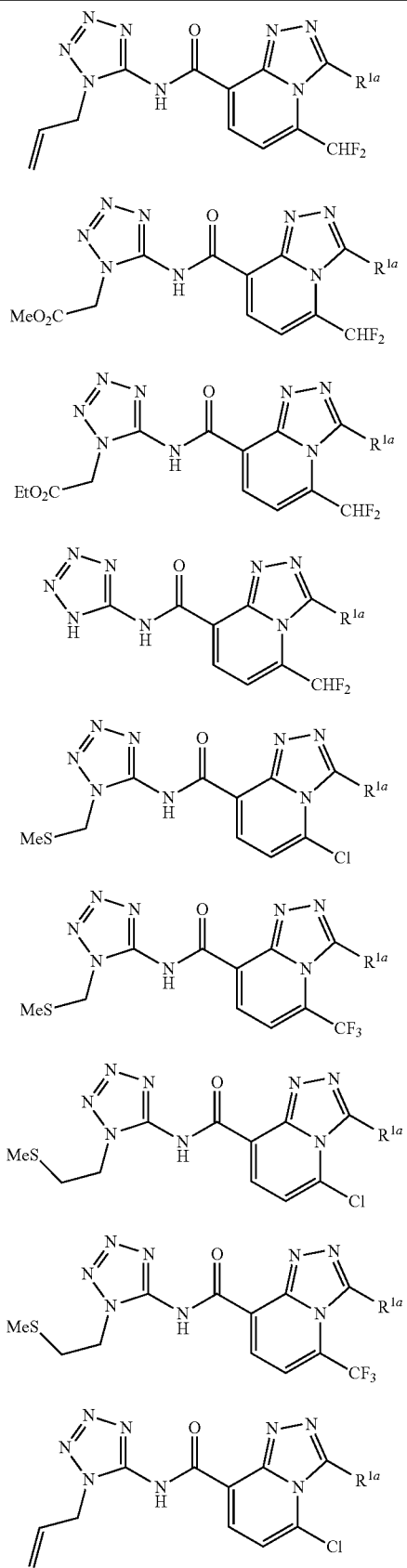
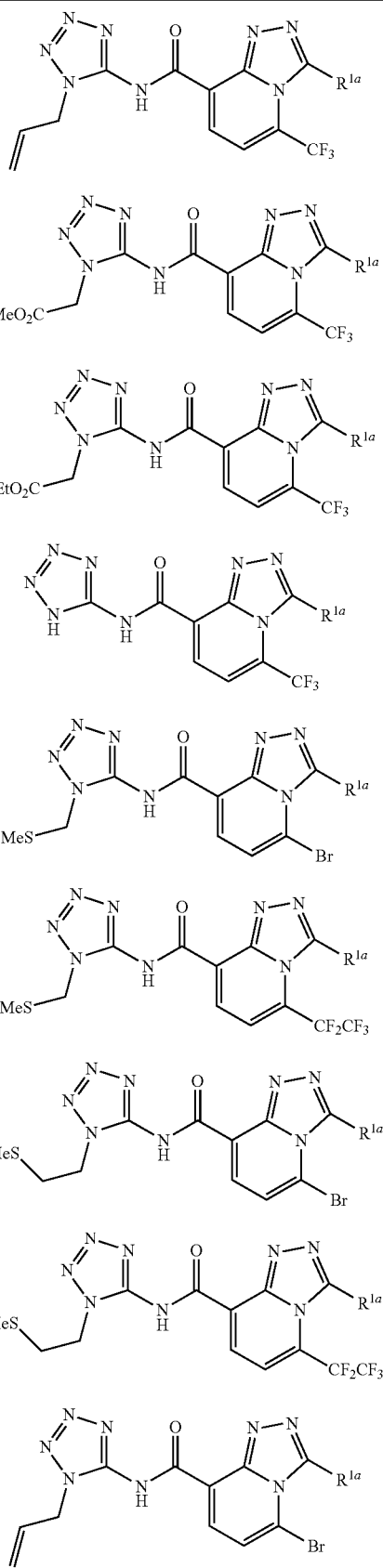

SECOND TABLE-continued
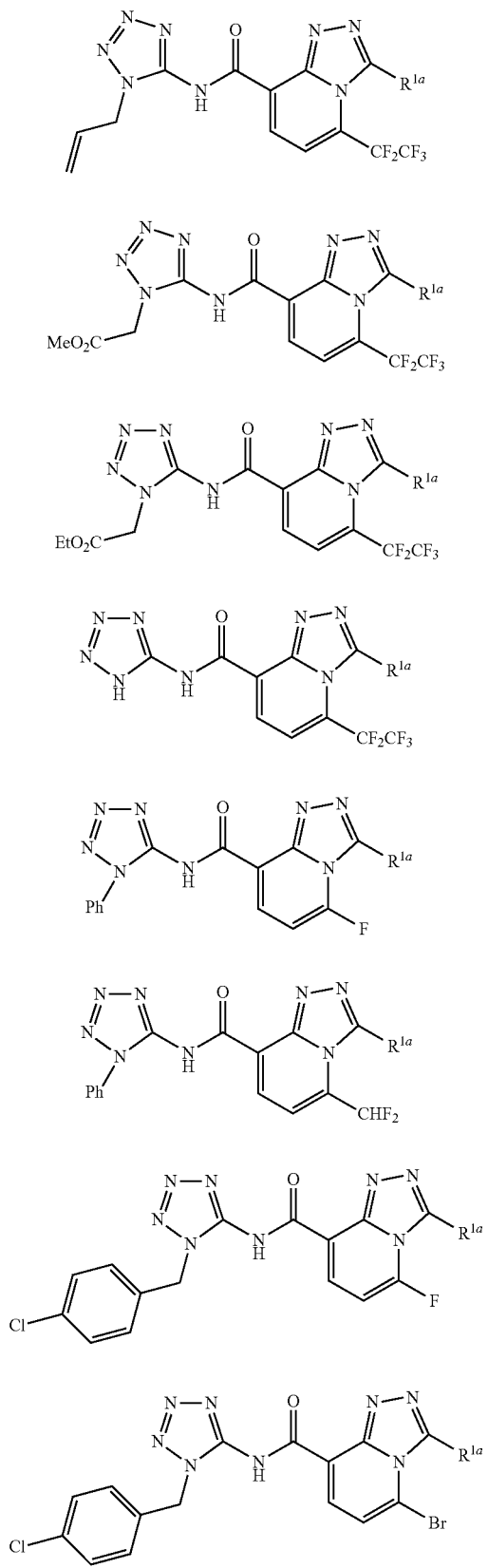
SECOND TABLE-continued
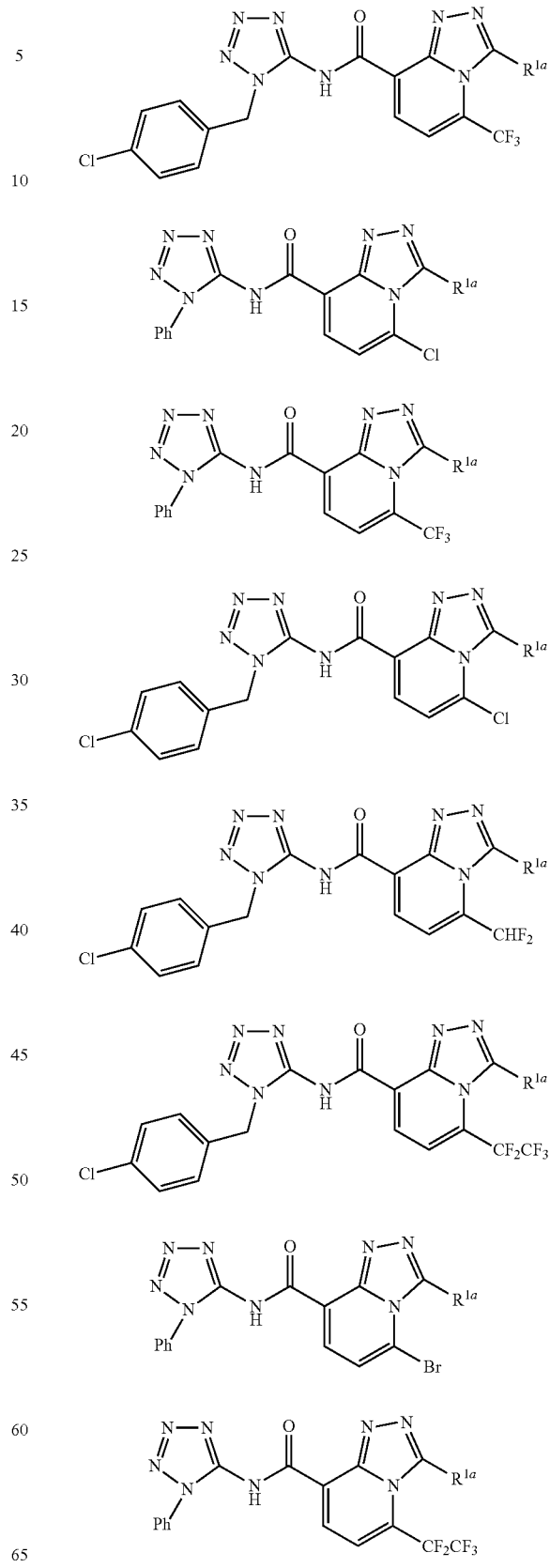

TABLE 13

| $R^{1a}$ | $R^{1a}$ | $R^{1a}$ |
| --- | --- | --- |
| H | CH$_2$OHex-n | C(Me)$_2$OMe |
| F | CH(Me)OMe | C(Me)$_2$OEt |
| Cl | CH(Me)OEt | C(Me)$_2$OPr-n |
| Br | CH(Me)OPr-n | C(Me)$_2$OPr-i |
| I | CH(Me)OPr-i | C(Me)$_2$OBu-n |
| Me | CH(Me)OBu-n | C(Me)$_2$OBu-i |
| Et | CH(Me)OBu-i | C(Me)$_2$OBu-s |
| Pr-n | CH(Me)OBu-s | C(Me)$_2$OBu-t |
| Pr-i | CH(Me)OBu-t | (CH$_2$)$_2$OMe |
| Pr-c | CH(Me)OPen-n | (CH$_2$)$_2$OEt |
| Bu-n | CH(Me)OPen-i | (CH$_2$)$_2$OPr-n |
| Bu-i | CH(Me)OPen-s | (CH$_2$)$_2$OPr-i |
| Bu-c | CH(Me)OPen-t | (CH$_2$)$_2$OBu-n |
| Bu-s | CH(Me)OHex-n | (CH$_2$)$_2$OBu-i |
| Bu-t | CH(Et)OMe | (CH$_2$)$_2$OBu-s |
| Pen-n | CH(Et)OEt | (CH$_2$)$_2$OBu-t |
| Pen-i | CH(Et)OPr-n | CH(Me)CH$_2$OMe |
| Pen-c | CH(Et)OPr-i | CH(Me)CH$_2$OEt |
| Pen-s | CH(Et)OBu-n | CH(Me)CH$_2$OPr-n |
| Pen-t | CH(Et)OBu-i | CH(Me)CH$_2$OPr-i |
| 3-Pen | CH(Et)OBu-s | CH(Me)CH$_2$OBu-n |
| Hex-n | CH(Et)OBu-t | CH(Me)CH$_2$OBu-i |
| Hex-c | CH(Et)OPen-n | CH(Me)CH$_2$OBu-s |
| CH$_2$OMe | CH(Et)OPen-i | CH(Me)CH$_2$OBu-t |
| CH$_2$OEt | CH(Et)OPen-s | CH(Et)CH$_2$OMe |
| CH$_2$OPr-n | CH(Et)OPen-t | CH(Et)CH$_2$OEt |
| CH$_2$OPr-i | CH(Et)OHex-n | (CH$_2$)$_3$OMe |
| CH$_2$OBu-n | CH(Pr-n)OMe | (CH$_2$)$_3$OEt |
| CH$_2$OBu-i | CH(Pr-n)OEt | (CH$_2$)$_3$OPr-n |
| CH$_2$OBu-s | CH(Pr-n)OPr-n | (CH$_2$)$_3$OPr-i |
| CH$_2$OBu-t | CH(Pr-n)OPr-i | (CH$_2$)$_3$OBu-n |
| CH$_2$OPen-n | CH(Pr-i)OMe | (CH$_2$)$_3$OBu-i |
| CH$_2$OPen-i | CH(Pr-i)OEt | (CH$_2$)$_3$OBu-s |
| CH$_2$OPen-s | CH(Pr-i)OPr-n | (CH$_2$)$_3$OBu-t |
| CH$_2$OPen-t | CH(Pr-i)OPr-i | CH$_2$OCF$_2$H |

TABLE 14

| $R^{1a}$ | $R^{1a}$ | $R^{1a}$ |
| --- | --- | --- |
| CH$_2$OCF$_3$ | CH(iPr)OH | C(Me)$_2$OCH$_2$OPr-n |
| CH$_2$OCH$_2$CF$_2$H | C(Me)$_2$OH | C(Me)$_2$OCH$_2$OPr-i |
| CH$_2$OCH$_2$CF$_3$ | (CH$_2$)$_2$OH | C(Me)$_2$O(CH$_2$)$_2$OMe |
| CH$_2$O(CH$_2$)$_2$CF$_3$ | CH(Me)CH$_2$OH | C(Me)$_2$O(CH$_2$)$_2$OEt |
| CH$_2$O(CH$_2$)$_2$Cl | (CH$_2$)$_3$OH | C(Me)$_2$O(CH$_2$)$_2$OPr-n |
| CH$_2$O(CH$_2$)$_2$Br | CH$_2$OCH$_2$OMe | C(Me)$_2$O(CH$_2$)$_2$OPr-i |
| CH(Me)OCF$_2$H | CH$_2$OCH$_2$OEt | (CH$_2$)$_2$OCH$_2$OMe |
| CH(Me)OCF$_3$ | CH$_2$OCH$_2$OPr-n | (CH$_2$)$_2$OCH$_2$OEt |
| CH(Me)OCH$_2$CF$_2$H | CH$_2$OCH$_2$OPr-i | (CH$_2$)$_2$OCH$_2$OPr-n |
| CH(Me)OCH$_2$CF$_3$ | CH$_2$O(CH$_2$)$_2$OMe | (CH$_2$)$_2$OCH$_2$OPr-i |
| CH(Me)O(CH$_2$)$_2$CF$_3$ | CH$_2$O(CH$_2$)$_2$OEt | (CH$_2$)$_2$O(CH$_2$)$_2$OMe |
| CH(Me)O(CH$_2$)$_2$Cl | CH$_2$O(CH$_2$)$_2$OPr-n | (CH$_2$)$_2$O(CH$_2$)$_2$OEt |
| CH(Me)O(CH$_2$)$_2$Br | CH$_2$O(CH$_2$)$_2$OPr-i | (CH$_2$)$_2$O(CH$_2$)$_2$OPr-n |
| CH(Et)OCF$_2$H | CH$_2$OCH(Me)CH$_2$OMe | (CH$_2$)$_2$O(CH$_2$)$_2$OPr-i |
| CH(Et)OCF$_3$ | CH$_2$OCH(Me)CH$_2$OEt | CH(Me)CH$_2$OCH$_2$OMe |
| CH(Et)OCH$_2$CF$_2$H | CH$_2$OCH$_2$CH(Me)OMe | CH(Me)CH$_2$OCH$_2$OEt |
| CH(Et)OCH$_2$CF$_3$ | CH$_2$OCH$_2$CH(Me)OEt | CH(Me)CH$_2$O(CH$_2$)$_2$OMe |
| CH(Et)O(CH$_2$)$_2$CF$_3$ | CH$_2$OCH(Me)OMe | CH(Me)CH$_2$O(CH$_2$)$_2$OEt |
| CH(Et)O(CH$_2$)$_2$Cl | CH$_2$OCH(Me)OEt | CH(Et)CH$_2$OCH$_2$OMe |
| CH(Et)O(CH$_2$)$_2$Br | CH$_2$O(CH$_2$)$_3$OMe | CH(Et)CH$_2$OCH$_2$OEt |
| C(Me)$_2$OCF$_2$H | CH$_2$O(CH$_2$)$_3$OEt | CH(Et)CH$_2$O(CH$_2$)$_2$OMe |
| C(Me)$_2$OCF$_3$ | CH(Me)OCH$_2$OMe | CH(Et)CH$_2$O(CH$_2$)$_2$OEt |
| C(Me)$_2$OCH$_2$CF$_2$H | CH(Me)OCH$_2$OEt | CH(Et)O(CH$_2$)$_2$OMe |
| C(Me)$_2$OCH$_2$CF$_3$ | CH(Me)OCH$_2$OPr-n | CH(Et)O(CH$_2$)$_2$OEt |
| C(Me)$_2$O(CH$_2$)$_2$CF$_3$ | CH(Me)OCH$_2$OPr-i | CH(Et)O(CH$_2$)$_2$OPr-i |
| C(Me)$_2$O(CH$_2$)$_2$Cl | CH(Me)O(CH$_2$)$_2$OMe | CH(Pr-n)O(CH$_2$)$_2$OMe |
| C(Me)$_2$O(CH$_2$)$_2$Br | CH(Me)O(CH$_2$)$_2$OEt | CH(Pr-n)O(CH$_2$)$_2$OEt |
| (CH$_2$)$_2$OCF$_3$ | CH(Me)O(CH$_2$)$_2$OPr-n | CH(Pr-n)O(CH$_2$)$_2$OPr-n |
| (CH$_2$)$_2$OCH$_2$CF$_2$H | CH(Me)O(CH$_2$)$_2$OPr-i | CH(Pr-n)O(CH$_2$)$_2$OPr-i |
| (CH$_2$)$_2$OCH$_2$CF$_3$ | CH(Me)OCH(Me)CH$_2$OMe | CH(Pr-i)O(CH$_2$)$_2$OMe |
| (CH$_2$)$_2$O(CH$_2$)$_2$Cl | CH(Me)OCH(Me)CH$_2$OEt | CH(Pr-i)O(CH$_2$)$_2$OEt |
| (CH$_2$)$_2$O(CH$_2$)$_2$Br | CH(Me)OCH$_2$CH(Me)OMe | CH(Pr-i)O(CH$_2$)$_2$OPr-n |
| CH$_2$OH | CH(Me)OCH$_2$CH(Me)OEt | CH(Pr-i)O(CH$_2$)$_2$OPr-i |
| CH(Me)OH | C(Me)$_2$OCH$_2$OMe | CH$_2$OC(O)Me |
| CH(Et)OH | C(Me)$_2$OCH$_2$OEt | |

TABLE 15

| $R^{1a}$ | $R^{1a}$ | $R^{1a}$ |
| --- | --- | --- |
| CH$_2$OC(O)Et | CH(Et)C(O)OEt | CH$_2$S(O)Pen-n |
| CH$_2$OC(O)Pr-i | CH(Et)C(O)OPr-i | CH$_2$S(O)$_2$Pen-n |
| CH(Me)OC(O)Me | CH(Et)C(O)OCH$_2$OMe | CH$_2$SPen-i |
| CH(Me)OC(O)Et | CH(Et)C(O)O(CH$_2$)$_2$OMe | CH$_2$S(O)Pen-i |
| CH(Me)OC(O)Pr-i | CH(Et)C(O)O(CH$_2$)$_2$OEt | CH$_2$S(O)$_2$Pen-i |
| CH(Et)OC(O)Me | CH(Et)C(O)O(CH$_2$)$_2$OPr-i | CH$_2$SPen-s |
| CH(Et)OC(O)Et | (CH$_2$)$_2$C(O)OMe | CH$_2$S(O)Pen-s |
| CH(Et)OC(O)Pr-i | (CH$_2$)$_2$C(O)OEt | CH$_2$S(O)$_2$Pen-s |
| CH$_2$OPh | (CH$_2$)$_2$C(O)O(CH$_2$)$_2$OMe | CH$_2$SPen-t |

TABLE 15-continued

| R$^{1a}$ | R$^{1a}$ | R$^{1a}$ |
|---|---|---|
| CH(Me)OPh | (CH$_2$)$_2$C(O)O(CH$_2$)$_2$OEt | CH$_2$S(O)Pen-t |
| CH$_2$C(O)OMe | CH$_2$SMe | CH$_2$S(O)$_2$Pen-t |
| CH$_2$C(O)OEt | CH$_2$S(O)Me | CH$_2$SHex-n |
| CH$_2$C(O)OPr-n | CH$_2$S(O)$_2$Me | CH(Me)SMe |
| CH$_2$C(O)OPr-i | CH$_2$SEt | CH(Me)S(O)Me |
| CH$_2$C(O)OBu-n | CH$_2$S(O)Et | CH(Me)S(O)$_2$Me |
| CH$_2$C(O)OBu-i | CH$_2$S(O)$_2$Et | CH(Me)SEt |
| CH$_2$C(O)OBu-s | CH$_2$SPr-n | CH(Me)S(O)Et |
| CH$_2$C(O)OBu-t | CH$_2$S(O)Pr-n | CH(Me)S(O)$_2$Et |
| CH$_2$C(O)OPen-n | CH$_2$S(O)$_2$Pr-n | CH(Me)SPr-n |
| CH$_2$C(O)OPen-i | CH$_2$SPr-i | CH(Me)S(O)Pr-n |
| CH$_2$C(O)OPen-s | CH$_2$S(O)Pr-i | CH(Me)S(O)$_2$Pr-n |
| CH$_2$C(O)OPen-t | CH$_2$S(O)$_2$Pr-i | CH(Me)SPr-i |
| CH$_2$C(O)OHex-n | CH$_2$SBu-n | CH(Me)S(O)Pr-i |
| CH$_2$C(O)OCH$_2$OMe | CH$_2$S(O)Bu-n | CH(Me)S(O)$_2$Pr-i |
| CH$_2$C(O)O(CH$_2$)$_2$OMe | CH$_2$S(O)$_2$Bu-n | CH(Me)SBu-n |
| CH$_2$C(O)O(CH$_2$)$_2$OEt | CH$_2$SBu-i | CH(Me)S(O)Bu-n |
| CH$_2$C(O)O(CH$_2$)$_2$OPr-i | CH$_2$S(O)Bu-i | CH(Me)S(O)$_2$Bu-n |
| CH(Me)C(O)OMe | CH$_2$S(O)$_2$Bu-i | CH(Me)SBu-i |
| CH(Me)C(O)OEt | CH$_2$SBu-s | CH(Me)S(O)Bu-i |
| CH(Me)C(O)OPr-i | CH$_2$S(O)Bu-s | CH(Me)S(O)$_2$Bu-i |
| CH(Me)C(O)OCH$_2$OMe | CH$_2$S(O)$_2$Bu-s | CH(Me)SBu-s |
| CH(Me)C(O)O(CH$_2$)$_2$OMe | CH$_2$SBu-t | CH(Me)S(O)Bu-s |
| CH(Me)C(O)O(CH$_2$)$_2$OEt | CH$_2$S(O)Bu-t | CH(Me)S(O)$_2$Bu-s |
| CH(Me)C(O)O(CH$_2$)$_2$OPr-i | CH$_2$S(O)$_2$Bu-t | CH(Me)SBu-t |
| CH(Et)C(O)OMe | CH$_2$SPen-n | CH(Me)S(O)Bu-t |

TABLE 16

| R$^{1a}$ | R$^{1a}$ | R$^{1a}$ |
|---|---|---|
| CH(Me)S(O)$_2$Bu-t | C(Me)$_2$SBu-t | CH(Me)CH$_2$S(O)$_2$Me |
| CH(Me)SPen-n | C(Me)$_2$S(O)Bu-t | CH(Me)CH$_2$SEt |
| CH(Me)S(O)Pen-n | C(Me)$_2$S(O)$_2$Bu-t | CH(Me)CH$_2$S(O)Et |
| CH(Me)S(O)$_2$Pen-n | C(Me)$_2$SPen-n | CH(Me)CH$_2$S(O)$_2$Et |
| CH(Me)SPen-i | C(Me)$_2$S(O)Pen-n | CH(Me)CH$_2$SPr-n |
| CH(Me)S(O)Pen-i | C(Me)$_2$S(O)$_2$Pen-n | CH(Me)CH$_2$S(O)Pr-n |
| CH(Me)S(O)$_2$Pen-i | C(Me)$_2$SPen-i | CH(Me)CH$_2$S(O)$_2$Pr-n |
| CH(Me)SPen-s | C(Me)$_2$S(O)Pen-i | CH(Me)CH$_2$SPr-i |
| CH(Me)S(O)Pen-s | C(Me)$_2$S(O)$_2$Pen-i | CH(Me)CH$_2$S(O)Pr-i |
| CH(Me)S(O)$_2$Pen-s | C(Me)$_2$SPen-s | CH(Me)CH$_2$S(O)$_2$Pr-i |
| CH(Me)SPen-t | C(Me)$_2$S(O)Pen-s | CH(Et)CH$_2$SMe |
| CH(Me)S(O)Pen-t | C(Me)$_2$S(O)$_2$Pen-s | CH(Et)CH$_2$S(O)Me |
| CH(Me)S(O)$_2$Pen-t | C(Me)$_2$SPen-t | CH(Et)CH$_2$S(O)$_2$Me |
| CH(Me)SHex-n | C(Me)$_2$S(O)Pen-t | CH(Et)CH$_2$SEt |
| C(Me)$_2$SMe | C(Me)$_2$S(O)$_2$Pen-t | CH(Et)CH$_2$S(O)Et |
| C(Me)$_2$S(O)Me | (CH$_2$)$_2$SMe | CH(Et)CH$_2$S(O)$_2$Et |
| C(Me)$_2$S(O)$_2$Me | (CH$_2$)$_2$S(O)Me | C(Me)$_2$CH$_2$SMe |
| C(Me)$_2$SEt | (CH$_2$)$_2$S(O)$_2$Me | C(Me)$_2$CH$_2$S(O)Me |
| C(Me)$_2$S(O)Et | (CH$_2$)$_2$SEt | C(Me)$_2$CH$_2$S(O)$_2$Me |
| C(Me)$_2$S(O)$_2$Et | (CH$_2$)$_2$S(O)Et | C(Me)$_2$CH$_2$SEt |
| C(Me)$_2$SPr-n | (CH$_2$)$_2$S(O)$_2$Et | C(Me)$_2$CH$_2$S(O)Et |
| C(Me)$_2$S(O)Pr-n | (CH$_2$)$_2$SPr-n | C(Me)$_2$CH$_2$S(O)$_2$Et |
| C(Me)$_2$S(O)$_2$Pr-n | (CH$_2$)$_2$S(O)Pr-n | C(Me)$_2$CH$_2$SPr-n |
| C(Me)$_2$SPr-i | (CH$_2$)$_2$S(O)$_2$Pr-n | C(Me)$_2$CH$_2$S(O)Pr-n |
| C(Me)$_2$S(O)Pr-i | (CH$_2$)$_2$SPr-i | C(Me)$_2$CH$_2$S(O)$_2$Pr-n |
| C(Me)$_2$S(O)$_2$Pr-i | (CH$_2$)$_2$S(O)Pr-i | C(Me)$_2$CH$_2$SPr-i |
| C(Me)$_2$SBu-n | (CH$_2$)$_2$S(O)$_2$Pr-i | C(Me)$_2$CH$_2$S(O)Pr-i |
| C(Me)$_2$S(O)Bu-n | (CH$_2$)$_3$SMe | C(Me)$_2$CH$_2$S(O)$_2$Pr-i |
| C(Me)$_2$S(O)$_2$Bu-n | (CH$_2$)$_3$S(O)Me | CH(Et)SMe |
| C(Me)$_2$SBu-i | (CH$_2$)$_3$S(O)$_2$Me | CH(Et)S(O)Me |
| C(Me)$_2$S(O)Bu-i | (CH$_2$)$_3$SEt | CH(Et)S(O)$_2$Me |
| C(Me)$_2$S(O)$_2$Bu-i | (CH$_2$)$_3$S(O)Et | CH(Et)SEt |
| C(Me)$_2$SBu-s | (CH$_2$)$_3$S(O)$_2$Et | CH(Et)S(O)Et |
| C(Me)$_2$S(O)Bu-s | CH(Me)CH$_2$SMe | CH(Et)S(O)$_2$Et |
| C(Me)$_2$S(O)$_2$Bu-s | CH(Me)CH$_2$S(O)Me | CH(Et)SPr-n |

TABLE 17

| R$^{1a}$ | R$^{1a}$ | R$^{1a}$ |
|---|---|---|
| CH(Et)S(O)Pr-n | CH$_2$SCH$_2$CF$_2$H | CH(Me)S(O)(CH$_2$)$_2$CF$_3$ |
| CH(Et)S(O)$_2$Pr-n | CH$_2$S(O)CH$_2$CF$_2$H | CH(Me)S(O)$_2$(CH$_2$)$_2$CF$_3$ |

TABLE 17-continued

| R$^{1a}$ | R$^{1a}$ | R$^{1a}$ |
|---|---|---|
| CH(Et)SPr-i | CH$_2$S(O)$_2$CH$_2$CF$_2$H | CH(Me)S(CH$_2$)$_2$Cl |
| CH(Et)S(O)Pr-i | CH$_2$SCH$_2$CF$_3$ | CH(Me)S(O)(CH$_2$)$_2$Cl |
| CH(Et)S(O)$_2$Pr-i | CH$_2$S(O)CH$_2$CF$_3$ | CH(Me)S(O)$_2$(CH$_2$)$_2$Cl |
| CH(Pr-n)SMe | CH$_2$S(O)$_2$CH$_2$CF$_3$ | CH(Me)S(CH$_2$)$_2$Br |
| CH(Pr-n)S(O)Me | CH$_2$S(CH$_2$)$_2$CF$_3$ | CH(Me)S(O)(CH$_2$)$_2$Br |
| CH(Pr-n)S(O)$_2$Me | CH$_2$S(O)(CH$_2$)$_2$CF$_3$ | CH(Me)S(O)$_2$(CH$_2$)$_2$Br |
| CH(Pr-n)SEt | CH$_2$S(O)$_2$(CH$_2$)$_2$CF$_3$ | C(Me)$_2$SCF$_2$H |
| CH(Pr-n)S(O)Et | CH$_2$S(CH$_2$)$_2$Cl | C(Me)$_2$S(O)CF$_2$H |
| CH(Pr-n)S(O)$_2$Et | CH$_2$S(O)(CH$_2$)$_2$Cl | C(Me)$_2$S(O)$_2$CF$_2$H |
| CH(Pr-n)SPr-n | CH$_2$S(O)$_2$(CH$_2$)$_2$Cl | C(Me)$_2$SCF$_3$ |
| CH(Pr-n)S(O)Pr-n | CH$_2$S(CH$_2$)$_2$Br | C(Me)$_2$S(O)CF$_3$ |
| CH(Pr-n)S(O)$_2$Pr-n | CH$_2$S(O)(CH$_2$)$_2$Br | C(Me)$_2$S(O)$_2$CF$_3$ |
| CH(Pr-n)SPr-i | CH$_2$S(O)$_2$(CH$_2$)$_2$Br | C(Me)$_2$SCF$_2$H |
| CH(Pr-n)S(O)Pr-i | CH$_2$SCHFCH$_3$ | C(Me)$_2$S(O)CH$_2$CF$_2$H |
| CH(Pr-n)S(O)$_2$Pr-i | CH$_2$SCF$_2$CH$_3$ | C(Me)$_2$S(O)$_2$CH$_2$CF$_2$H |
| CH(Pr-i)SMe | CH$_2$SCF(CH$_3$)$_2$ | C(Me)$_2$SCH$_2$CF$_3$ |
| CH(Pr-i)S(O)Me | CH$_2$SCF$_2$CF$_2$H | C(Me)$_2$SCH$_2$CF$_3$ |
| CH(Pr-i)S(O)$_2$Me | CH$_2$SCF$_2$CF$_3$ | C(Me)$_2$S(O)CH$_2$CF$_3$ |
| CH(Pr-i)SEt | CH$_2$SCF$_2$CF$_2$CF$_3$ | C(Me)$_2$S(O)$_2$CH$_2$CF$_3$ |
| CH(Pr-i)S(O)Et | CH$_2$SCF(CF$_3$)$_2$ | C(Me)$_2$S(CH$_2$)$_2$CF$_3$ |
| CH(Pr-i)S(O)$_2$Et | CH(Me)SCF$_2$H | C(Me)$_2$S(O)(CH$_2$)$_2$CF$_3$ |
| CH(Pr-i)SPr-n | CH(Me)S(O)CF$_2$H | C(Me)$_2$S(O)$_2$(CH$_2$)$_2$CF$_3$ |
| CH(Pr-i)S(O)Pr-n | CH(Me)S(O)$_2$CF$_2$H | C(Me)$_2$S(CH$_2$)$_2$Cl |
| CH(Pr-i)S(O)$_2$Pr-n | CH(Me)SCF$_3$ | C(Me)$_2$S(O)(CH$_2$)$_2$Cl |
| CH(Pr-i)SPr-i | CH(Me)S(O)CF$_3$ | C(Me)$_2$S(O)$_2$(CH$_2$)$_2$Cl |
| CH(Pr-i)S(O)Pr-i | CH(Me)S(O)$_2$CF$_3$ | C(Me)$_2$S(CH$_2$)$_2$Br |
| CH(Pr-i)S(O)$_2$Pr-i | CH(Me)SCH$_2$CF$_2$H | C(Me)$_2$S(O)(CH$_2$)$_2$Br |
| CH$_2$SCF$_2$H | CH(Me)S(O)CH$_2$CF$_2$H | C(Me)$_2$S(O)$_2$(CH$_2$)$_2$Br |
| CH$_2$S(O)CF$_2$H | CH(Me)S(O)$_2$CH$_2$CF$_2$H | (CH$_2$)$_2$SCF$_3$ |
| CH$_2$S(O)$_2$CF$_2$H | CH(Me)SCH$_2$CF$_3$ | (CH$_2$)$_2$S(O)CF$_3$ |
| CH$_2$SCF$_3$ | CH(Me)S(O)CH$_2$CF$_3$ | (CH$_2$)$_2$S(O)$_2$CF$_3$ |
| CH$_2$S(O)CF$_3$ | CH(Me)S(O)$_2$CH$_2$CF$_3$ | (CH$_2$)$_2$SCH$_2$CF$_2$H |
| CH$_2$S(O)$_2$CF$_3$ | CH(Me)S(CH$_2$)$_2$CF$_3$ | (CH$_2$)$_2$S(O)CH$_2$CF$_2$H |
|  |  | (CH$_2$)$_2$S(O)$_2$CH$_2$CF$_2$H |

TABLE 18

| R$^{1a}$ | R$^{1a}$ | R$^{1a}$ |
|---|---|---|
| (CH$_2$)$_2$SCH$_2$CF$_3$ | 3-Cl—Ph | 2-Cl-3-Me—Ph |
| (CH$_2$)$_2$S(O)CH$_2$CF$_3$ | 4-Cl—Ph | 2-Cl-4-Me—Ph |
| (CH$_2$)$_2$S(O)$_2$CH$_2$CF$_3$ | 2-Br—Ph | 2-Cl-5-Me—Ph |
| (CH$_2$)$_2$S(CH$_2$)$_2$Cl | 3-Br—Ph | 3-Cl-4-Me—Ph |

TABLE 18-continued

| $R^{1a}$ | $R^{1a}$ | $R^{1a}$ |
|---|---|---|
| (CH$_2$)$_2$S(O)(CH$_2$)$_2$Cl | 4-Br—Ph | 3-Cl-5-Me—Ph |
| (CH$_2$)$_2$S(O)$_2$(CH$_2$)$_2$Cl | 2-Me—Ph | 2-Cl-3-F—Ph |
| (CH$_2$)$_2$S(CH$_2$)$_2$Br | 3-Me—Ph | 2-Cl-4-F—Ph |
| (CH$_2$)$_2$S(O)(CH$_2$)$_2$Br | 4-Me—Ph | 2-Cl-5-F—Ph |
| (CH$_2$)$_2$S(O)$_2$(CH$_2$)$_2$Br | 2-MeO—Ph | 3-Cl-4-F—Ph |
| CH═CH$_2$ | 3-MeO—Ph | 3-Cl-5-F—Ph |
| CH═CHMe | 4-MeO—Ph | 2-F-3-Me—Ph |
| CH═CMe$_2$ | 2,3-(F)$_2$—Ph | 2-F-4-Me—Ph |
| CH$_2$CH═CH$_2$ | 2,4-(F)$_2$—Ph | 2-F-5-Me—Ph |
| CH$_2$CH═CHMe | 2,5-(F)$_2$—Ph | 3-F-4-Me—Ph |
| CH$_2$C(Me)═CH$_2$ | 2,6-(F)$_2$—Ph | 3-F-5-Me—Ph |
| (CH$_2$)$_2$CH═CMe$_2$ | 3,4-(F)$_2$—Ph | 2-F-3-Cl—Ph |
| C(Me)═CH$_2$ | 3,5-(F)$_2$—Ph | 2-F-4-Cl—Ph |
| C(Me)═CHMe | 2,3-(Cl)$_2$—Ph | 2-F-5-Cl—Ph |
| C(Me)═CMe$_2$ | 2,4-(Cl)$_2$—Ph | 3-F-4-Cl—Ph |
| CH(Me)CH═CH$_2$ | 2,5-(Cl)$_2$—Ph | 3-F-5-Cl—Ph |
| C(Et)═CH$_2$ | 2,6-(Cl)$_2$—Ph | 2-Me-3-F—Ph |
| C(Et)═CHMe | 3,4-(Cl)$_2$—Ph | 2-Me-4-F—Ph |
| C(Et)═CMe$_2$ | 3,5-(Cl)$_2$—Ph | 2-Me-5-F—Ph |
| CH(Et)CH═CH$_2$ | 2,3-(Me)$_2$—Ph | 3-Me-4-F—Ph |
| C≡CH | 2,4-(Me)$_2$—Ph | 3-Me-5-F—Ph |
| C≡CMe | 2,5-(Me)$_2$—Ph | 2-Cl-3-MeO—Ph |
| CH$_2$C≡CH | 2,6-(Me)$_2$—Ph | 2-Cl-4-MeO—Ph |
| CH$_2$C≡CMe | 3,4-(Me)$_2$—Ph | 2-Cl-5-MeO—Ph |
| CH(Me)C≡CH | 3,5-(Me)$_2$—Ph | 2-Cl-6-MeO—Ph |
| CH(Me)C≡CMe | 2,3-(MeO)$_2$—Ph | 3-Cl-4-MeO—Ph |
| Ph | 2,4-(MeO)$_2$—Ph | 3-Cl-5-MeO—Ph |
| 2-F—Ph | 2,5-(MeO)$_2$—Ph | 2-F-3-MeO—Ph |
| 3-F—Ph | 2,6-(MeO)$_2$—Ph | 2-F-4-MeO—Ph |
| 4-F—Ph | 3,4-(MeO)$_2$—Ph | 2-F-5-MeO—Ph |
| 2-Cl—Ph | 3,5-(MeO)$_2$—Ph | 2-F-6-MeO—Ph |

TABLE 19

| $R^{1a}$ | $R^{1a}$ | $R^{1a}$ |
|---|---|---|
| 3-F-4-MeO—Ph | D-8 | CH$_2$(2,4-(MeO)$_2$—Ph) |
| 3-F-5-MeO—Ph | D-8a | CH$_2$(2,5-(MeO)$_2$—Ph) |
| 2-MeO-3-F—Ph | D-8b | CH$_2$(2,6-(MeO)$_2$—Ph) |
| 2-MeO-4-F—Ph | D-8c | CH$_2$(3,4-(MeO)$_2$—Ph) |
| 2-MeO-5-F—Ph | D-8d | CH$_2$(3,5-(MeO)$_2$—Ph) |
| 2-MeO-6-F—Ph | D-8e | CH(Me)(2-MeO—Ph) |
| 3-MeO-4-F—Ph | D-8f | CH(Me)(3-MeO—Ph) |
| 3-MeO-5-F—Ph | D-8g | CH(Me)(4-MeO—Ph) |
| 2-MeO-3-Cl—Ph | D-8h | CH(Me)(2,3-(MeO)$_2$—Ph) |
| 2-MeO-4-Cl—Ph | D-10a | CH(Me)(2,4-(MeO)$_2$—Ph) |
| 2-MeO-5-Cl—Ph | D-11 | CH(Me)(2,5-(MeO)$_2$—Ph) |
| 2-MeO-6-Cl—Ph | D-14 | CH(Me)(2,6-(MeO)$_2$—Ph) |
| 3-MeO-4-Cl—Ph | D-16 | CH(Me)(3,4-(MeO)$_2$—Ph) |
| 3-MeO-5-Cl—Ph | D-16a | CH(Me)(3,5-(MeO)$_2$—Ph) |
| 2-Me-3-MeO—Ph | D-16b | CH(Et)(2-MeO—Ph) |
| 2-Me-4-MeO—Ph | D-16c | CH(Et)(3-MeO—Ph) |
| 2-Me-5-MeO—Ph | D-16d | CH(Et)(4-MeO—Ph) |
| 2-Me-6-MeO—Ph | D-16e | (CH$_2$)$_2$(2-MeO—Ph) |
| 3-Me-4-MeO—Ph | D-16f | (CH$_2$)$_2$(3-MeO—Ph) |
| 3-Me-5-MeO—Ph | D-16g | (CH$_2$)$_2$(4-MeO—Ph) |
| 2-MeO-3-Me—Ph | D-16h | CHO |
| 2-MeO-4-Me—Ph | D-16i | SMe |
| 2-MeO-5-Me—Ph | D-16j | S(O)Me |
| 2-MeO-6-Me—Ph | D-16k | S(O)$_2$Me |
| 3-MeO-4-Me—Ph | D-16m | SEt |
| 3-MeO-5-Me—Ph | D-16n | S(O)Et |
| 3,5-(F)$_2$-4-Me—Ph | D-16p | S(O)$_2$Et |
| 3,5-(F)$_2$-4-MeO—Ph | D-17 | SPr-n |
| 3,4,5-(MeO)$_3$—Ph | D-17a | S(O)Pr-n |
| D-3 | D-17b | S(O)$_2$Pr-n |
| D-3a | CH$_2$Ph | SPr-i |
| D-4 | CH$_2$(2-MeO—Ph) | S(O)Pr-i |
| D-4a | CH$_2$(3-MeO—Ph) | S(O)$_2$Pr-i |
| D-4b | CH$_2$(4-MeO—Ph) | SPr-c |
| D-5 | CH$_2$(2,3-(MeO)$_2$—Ph) | S(O)Pr-c |

TABLE 20

| $R^{1a}$ | $R^{1a}$ | $R^{1a}$ |
|---|---|---|
| S(O)$_2$Pr-c | S(O)Pen-t | SCHFCH$_3$ |
| S(D-16) | S(O)$_2$Pen-t | SCF$_2$CH$_3$ |
| S(O)(D-16) | SHex-n | SCF(CH$_3$)$_2$ |
| S(O)$_2$(D-16) | SHex-c | SCF$_2$CF$_2$H |
| S(D-16e) | SCH$_2$CH═CH$_2$ | SCF$_2$CF$_3$ |
| S(O)(D-16e) | S(O)CH$_2$CH═CH$_2$ | SCF$_2$CF$_2$CF$_3$ |
| S(O)$_2$(D-16e) | S(O)$_2$CH$_2$CH═CH$_2$ | SCF(CF$_3$)$_2$ |
| SBu-n | SCH(Me)CH═CH$_2$ | SCH$_2$OMe |
| S(O)Bu-n | SC(Me)$_2$CH═CH$_2$ | S(CH$_2$)$_2$OMe |
| S(O)$_2$Bu-n | SCH$_2$CH═CHMe | S(O)(CH$_2$)$_2$OMe |
| SBu-i | SCH$_2$C(Me)═CH$_2$ | S(O)$_2$(CH$_2$)$_2$OMe |
| S(O)Bu-i | S(CH$_2$)$_2$CH═CMe$_2$ | SCH(Me)CH$_2$OMe |
| S(O)$_2$Bu-i | SC(Me)═CH$_2$ | S(O)CH(Me)CH$_2$OMe |
| SBu-c | SC(Me)═CH(Me) | S(O)$_2$CH(Me)CH$_2$OMe |
| S(O)Bu-c | SCH$_2$C≡CH | SCH$_2$CH(Me)OMe |
| S(O)$_2$Bu-c | S(O)$_2$CH$_2$C≡CH | S(O)CH$_2$CH(Me)OMe |
| SBu-s | SCH(Me)C≡CH | S(O)$_2$CH$_2$CH(Me)OMe |
| S(O)Bu-s | SC(Me)$_2$C≡CH | SC(Me)$_2$CH$_2$OMe |
| SBu-t | SCH$_2$C≡CMe | S(CH$_2$)$_3$OMe |
| S(O)Bu-t | SCH$_2$Cl | SCH$_2$OEt |
| S(O)$_2$Bu-t | SCH(Me)Cl | S(CH$_2$)$_2$OEt |
| SPen-n | S(CH$_2$)$_2$Cl | S(O)(CH$_2$)$_2$OEt |
| S(O)Pen-n | S(O)(CH$_2$)$_2$Cl | S(O)$_2$(CH$_2$)$_2$OEt |
| S(O)$_2$Pen-n | S(O)$_2$(CH$_2$)$_2$Cl | SCH(Me)CH$_2$OEt |
| SPen-i | SCH(Me)CH$_2$Cl | SCH$_2$OPr-i |
| S(O)Pen-i | SCH$_2$CH(Me)Cl | S(CH$_2$)$_2$OPr-i |
| S(O)$_2$Pen-i | S(CH$_2$)$_3$Cl | S(O)(CH$_2$)$_2$OPr-i |
| SPen-c | SCF$_3$ | S(O)$_2$(CH$_2$)$_2$OPr-i |
| S(O)Pen-c | SCH$_2$CF$_3$ | SCH(Me)CH$_2$OPr-i |
| S(O)$_2$Pen-c | S(O)CH$_2$CF$_3$ | SCH$_2$Pr-c |
| SPen-s | S(O)$_2$CH$_2$CF$_3$ | S(O)CH$_2$Pr-c |
| | | S(O)$_2$CH$_2$Pr-c |

TABLE 20-continued

| R$^{1a}$ | R$^{1a}$ | R$^{1a}$ |
| --- | --- | --- |
| S(O)Pen-s | SCH(Me)CF$_3$ | SCH(Me)Pr-c |
| S(O)$_2$Pen-s | S(CH$_2$)$_2$CF$_3$ | S(O)CH(Me)Pr-c |
| SPen-t | S(CH$_2$)$_3$CF$_3$ | S(O)$_2$CH(Me)Pr-c |

TABLE 21

| R$^{1a}$ | R$^{1a}$ | R$^{1a}$ |
| --- | --- | --- |
| S(CH$_2$)$_2$Pr-c | SCH(Me)Ph | SCH$_2$(D-8f) |
| SCH$_2$(D-16) | S(O)CH(Me)Ph | S(O)$_2$CH$_2$(D-8f) |
| S(O)CH$_2$(D-16) | S(O)$_2$CH(Me)Ph | SCH$_2$(D-8g) |
| S(O)$_2$CH$_2$(D-16) | SCH$_2$(2-MeO—Ph) | S(O)$_2$CH$_2$(D-8g) |
| SCH$_2$(D-16e) | S(O)CH$_2$(2-MeO—Ph) | SCH$_2$(D-8h) |
| S(O)CH$_2$(D-16e) | S(O)$_2$CH$_2$(2-MeO—Ph) | S(O)$_2$CH$_2$(D-8h) |
| S(O)$_2$CH$_2$(D-16e) | SCH(Me)(2-MeO—Ph) | SCH$_2$(D-15) |
| SCH$_2$Bu-c | S(O)CH(Me)(2-MeO—Ph) | S(O)CH$_2$(D-15) |
| S(O)CH$_2$Bu-c | S(O)$_2$CH(Me)(2-MeO—Ph) | S(O)$_2$CH$_2$(D-15) |
| S(O)$_2$CH$_2$Bu-c | SCH$_2$(3-MeO—Ph) | SCH(Me)(D-15) |
| SCH(Me)Bu-c | S(O)CH$_2$(3-MeO—Ph) | S(O)CH(Me)(D-15) |
| S(CH$_2$)$_2$Bu-c | S(O)$_2$CH$_2$(3-MeO—Ph) | S(O)$_2$CH(Me)(D-15) |
| SCH$_2$Pen-c | SCH(Me)(3-MeO—Ph) | S(CH$_2$)$_2$(D-15) |
| S(O)CH$_2$Pen-c | S(O)CH(Me)(3-MeO—Ph) | S(O)(CH$_2$)$_2$(D-15) |
| S(O)$_2$CH$_2$Pen-c | S(O)$_2$CH(Me)(3-MeO—Ph) | S(O)$_2$(CH$_2$)$_2$(D-15) |
| SCH(Me)Pen-c | SCH$_2$(4-MeO—Ph) | NHMe |
| S(CH$_2$)$_2$Pen-c | S(O)CH$_2$(4-MeO—Ph) | NHEt |
| SCH$_2$Hex-c | S(O)$_2$CH$_2$(4-MeO—Ph) | NHPr-n |
| SCH(Me)Hex-c | SCH(Me)(4-MeO—Ph) | NHPr-i |
| S(CH$_2$)$_2$Hex-c | S(O)CH(Me)(4-MeO—Ph) | NHPr-c |
| SCH$_2$CN | S(O)$_2$CH(Me)(4-MeO—Ph) | NH(D-16) |
| S(O)CH$_2$CN | SCH$_2$(D-8a) | NH(D-16e) |
| S(O)$_2$CH$_2$CN | S(O)CH$_2$(D-8a) | NHBu-n |
| SCH(Me)CN | S(O)$_2$CH$_2$(D-8a) | NHBu-i |
| S(O)CH(Me)CN | SCH$_2$(D-8b) | NHBu-c |
| S(O)$_2$CH(Me)CN | S(O)CH$_2$(D-8b) | NHBu-s |
| SC(Me)$_2$CN | S(O)$_2$CH$_2$(D-8b) | NHBu-t |
| S(O)C(Me)$_2$CN | SCH$_2$(D-8c) | NHPen-n |
| S(O)$_2$C(Me)$_2$CN | S(O)CH$_2$(D-8c) | NHPen-i |
| S(CH$_2$)$_2$CN | S(O)$_2$CH$_2$(D-8c) | NHPen-c |
| S(O)(CH$_2$)$_2$CN | SCH$_2$(D-8d) | NHPen-s |
| S(O)$_2$(CH$_2$)$_2$CN | S(O)CH$_2$(D-8d) | NHPen-t |
| SCH$_2$Ph | S(O)$_2$CH$_2$(D-8d) | NH(3-Pen) |
| S(O)CH$_2$Ph | SCH$_2$(D-8e) | NHHex-n |
| S(O)$_2$CH$_2$Ph | S(O)$_2$CH$_2$(D-8e) | NHHex-c |

TABLE 22

| R$^{1a}$ | R$^{1a}$ | R$^{1a}$ |
| --- | --- | --- |
| N(Me)Me | N(Pr-n)Bu-n | N(Et)(CH$_2$)$_2$OEt |
| N(Me)Et | N(Pr-n)Bu-i | N(Et)(CH$_2$)$_2$OPr-n |
| N(Me)Pr-n | N(Pr-n)Bu-c | N(Et)(CH$_2$)$_2$OPr-i |
| N(Me)Pr-i | N(Pr-n)Bu-s | N(Pr-n)(CH$_2$)$_2$OMe |
| N(Me)Pr-c | N(Pr-i)Pr-i | N(Pr-n)(CH$_2$)$_2$OEt |
| N(Me)(D-16) | N(Pr-i)Pr-c | N(Pr-n)(CH$_2$)$_2$OPr-n |
| N(Me)(D-16e) | N(Pr-i)(D-16) | N(Pr-n)(CH$_2$)$_2$OPr-i |
| N(Me)Bu-n | N(Pr-i)(D-16e) | N(Pr-i)(CH$_2$)$_2$OMe |
| N(Me)Bu-i | N(Pr-i)Bu-n | N(Pr-i)(CH$_2$)$_2$OEt |
| N(Me)Bu-c | N(Pr-i)Bu-i | N(Pr-i)(CH$_2$)$_2$OPr-n |
| N(Me)Bu-s | N(Pr-i)Bu-c | N(Pr-i)(CH$_2$)$_2$OPr-i |
| N(Me)Bu-t | N(Pr-i)Bu-s | NHCH$_2$SMe |
| N(Me)Pen-n | NHCH$_2$OMe | NHCH$_2$SEt |
| N(Me)Pen-i | NHCH$_2$OEt | NHCH(Me)SMe |
| N(Me)Pen-c | NHCH(Me)OMe | NHCH(Me)SEt |
| N(Me)Pen-s | NHCH(Me)OEt | NHC(Me)$_2$SMe |
| N(Me)Pen-t | NHC(Me)$_2$OMe | NHC(Me)$_2$SEt |
| N(Me)(3-Pen) | NHC(Me)$_2$OEt | NH(CH$_2$)$_2$SMe |
| N(Me)Hex-n | NH(CH$_2$)$_2$OMe | NH(CH$_2$)$_2$S(O)Me |
| N(Me)Hex-c | NH(CH$_2$)$_2$OEt | NH(CH$_2$)$_2$S(O)$_2$Me |
| N(Et)Et | NH(CH$_2$)$_2$OPr-n | NH(CH$_2$)$_2$SEt |
| N(Et)Pr-n | NH(CH$_2$)$_2$OPr-i | NH(CH$_2$)$_2$S(O)Et |
| N(Et)Pr-i | N(Me)CH$_2$OMe | NH(CH$_2$)$_2$S(O)$_2$Et |
| N(Et)Pr-c | N(Me)CH$_2$OEt | NH(CH$_2$)$_2$SPr-i |
| N(Et)(D-16) | N(Me)CH(Me)OMe | NH(CH$_2$)$_2$S(O)Pr-i |

TABLE 22-continued

| R$^{1a}$ | R$^{1a}$ | R$^{1a}$ |
| --- | --- | --- |
| N(Et)(D-16e) | N(Me)CH(Me)OEt | NH(CH$_2$)$_2$S(O)$_2$Pr-i |
| N(Et)Bu-n | N(Me)C(Me)$_2$OMe | N(Me)CH$_2$SMe |
| N(Et)Bu-i | N(Me)C(Me)$_2$OEt | N(Me)CH$_2$SEt |
| N(Et)Bu-c | N(Me)(CH$_2$)$_2$OMe | N(Me)CH(Me)SMe |
| N(Et)Bu-s | N(Me)(CH$_2$)$_2$OEt | N(Me)CH(Me)SEt |
| N(Pr-n)Pr-n | N(Me)(CH$_2$)$_2$OPr-n | N(Me)C(Me)$_2$SMe |
| N(Pr-n)Pr-i | N(Me)(CH$_2$)$_2$OPr-i | N(Me)C(Me)$_2$SEt |
| N(Pr-n)Pr-c | N(Et)C(Me)$_2$OMe | N(Me)(CH$_2$)$_2$SMe |
| N(Pr-n)(D-16) | N(Et)C(Me)$_2$OEt | N(Me)(CH$_2$)$_2$S(O)Me |
| N(Pr-n)(D-16e) | N(Et)(CH$_2$)$_2$OMe | N(Me)(CH$_2$)$_2$S(O)$_2$Me |

TABLE 23

| R$^{1a}$ | R$^{1a}$ |
| --- | --- |
| N(Me)(CH$_2$)$_2$SEt | NH(4-MeO—Ph) |
| N(Me)(CH$_2$)$_2$S(O)Et | NH(2,3-(MeO)$_2$—Ph) |
| N(Me)(CH$_2$)$_2$S(O)$_2$Et | NH(2,4-(MeO)$_2$—Ph) |
| N(Me)(CH$_2$)$_2$SPr-i | NH(2,5-(MeO)$_2$—Ph) |
| N(Me)(CH$_2$)$_2$S(O)Pr-i | NH(2,6-(MeO)$_2$—Ph) |
| N(Me)(CH$_2$)$_2$S(O)$_2$Pr-i | NH(3,4-(MeO)$_2$—Ph) |
| NHCF$_2$H | NH(3,5-(MeO)$_2$—Ph) |
| NHCF$_3$ | N(Me)Ph |
| NHCH$_2$CF$_2$H | N(Me)(2-MeO—Ph) |
| NHCH$_2$CF$_3$ | N(Me)(3-MeO—Ph) |
| NH(CH$_2$)$_2$CF$_3$ | N(Me)(4-MeO—Ph) |
| NH(CH$_2$)$_2$Cl | N(Me)(2,3-(MeO)$_2$—Ph) |
| NH(CH$_2$)$_3$Cl | N(Me)(2,4-(MeO)$_2$—Ph) |
| N(Me)CF$_2$H | N(Me)(2,5-(MeO)$_2$—Ph) |
| N(Me)CF$_3$ | N(Me)(2,6-(MeO)$_2$—Ph) |
| N(Me)CH$_2$CF$_2$H | N(Me)(3,4-(MeO)$_2$—Ph) |
| N(Me)CH$_2$CF$_3$ | N(Me)(3,5-(MeO)$_2$—Ph) |
| N(Me)(CH$_2$)$_2$CF$_3$ | |
| N(Me)(CH$_2$)$_2$Cl | |
| N(Me)(CH$_2$)$_3$Cl | |
| NHCH$_2$CH=CH$_2$ | |
| N(Me)CH$_2$CH=CH$_2$ | |
| NHCH$_2$C≡CH | |
| NHCH$_2$C≡CMe | |
| N(Me)CH$_2$C≡CH | |
| N(Me)CH$_2$C≡CMe | |
| NHCH$_2$CN | |
| NH(CH$_2$)$_2$CN | |
| NH(CH$_2$)$_3$CN | |
| N(Me)CH$_2$CN | |
| N(Me)(CH$_2$)$_2$CN | |
| N(Me)(CH$_2$)$_3$CN | |
| NHPh | |
| NH(2-MeO—Ph) | |
| NH(3-MeO—Ph) | |

THIRD TABLE

THIRD TABLE-continued
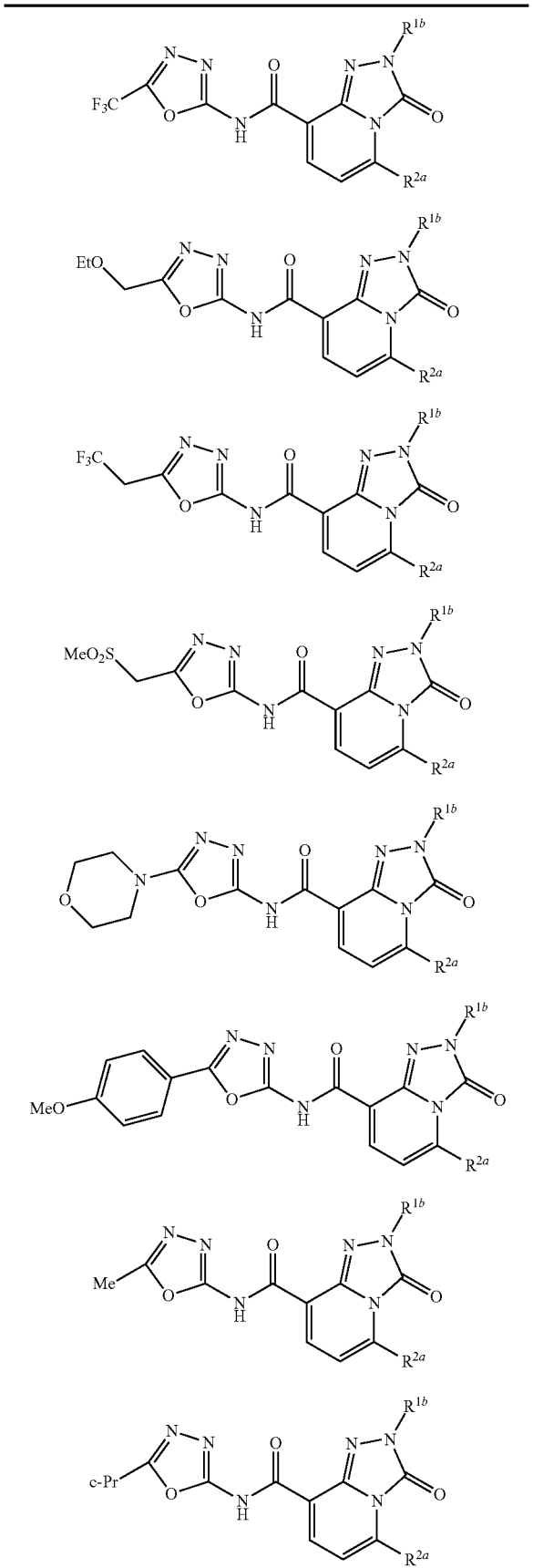
THIRD TABLE-continued
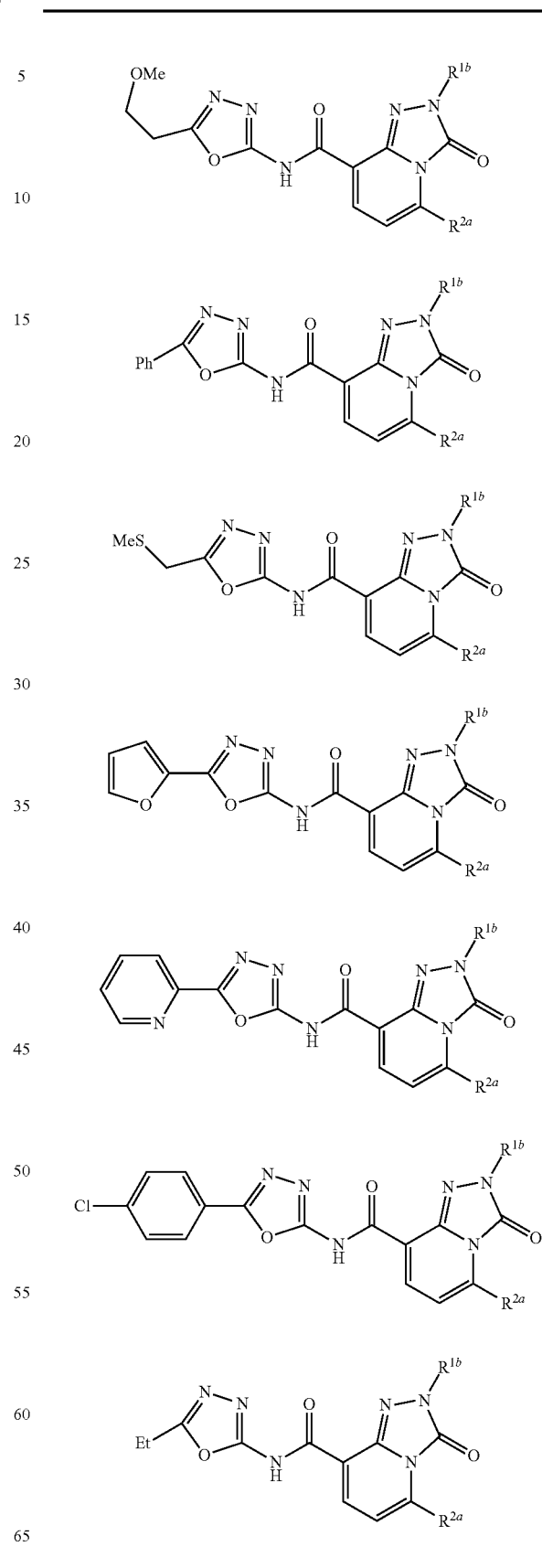

THIRD TABLE-continued
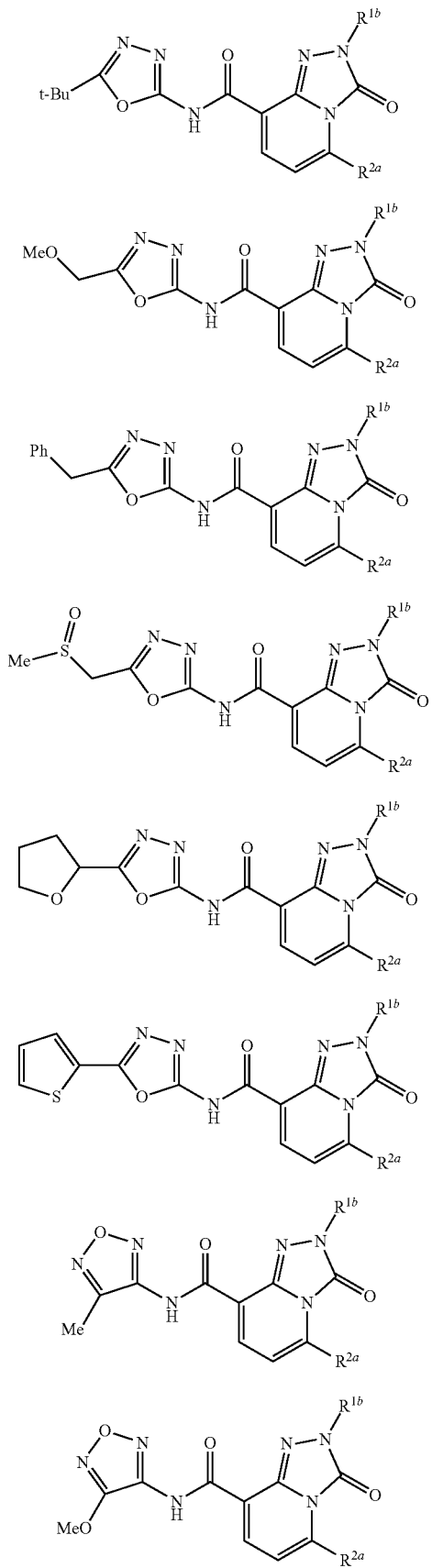
THIRD TABLE-continued
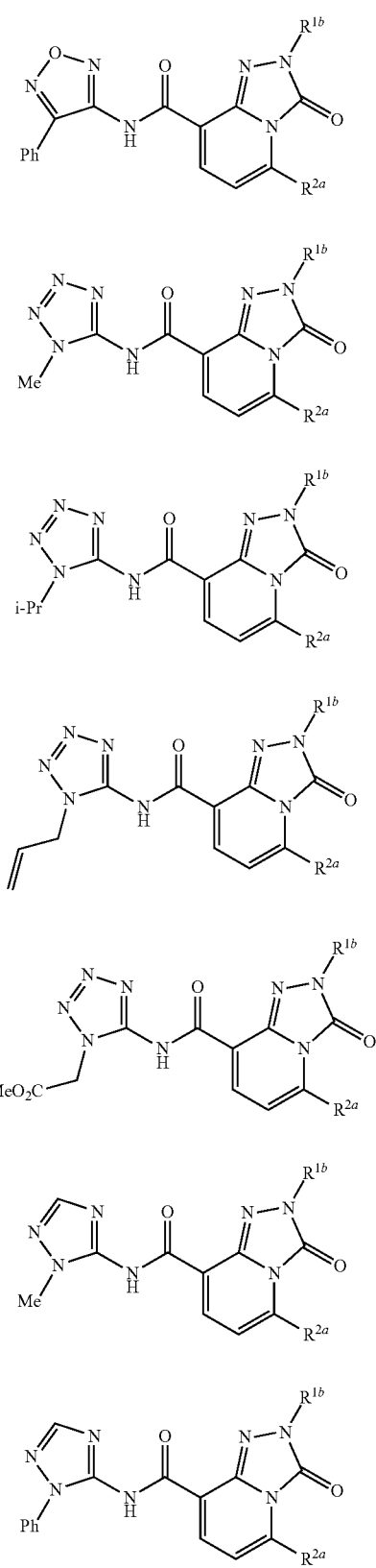

THIRD TABLE-continued
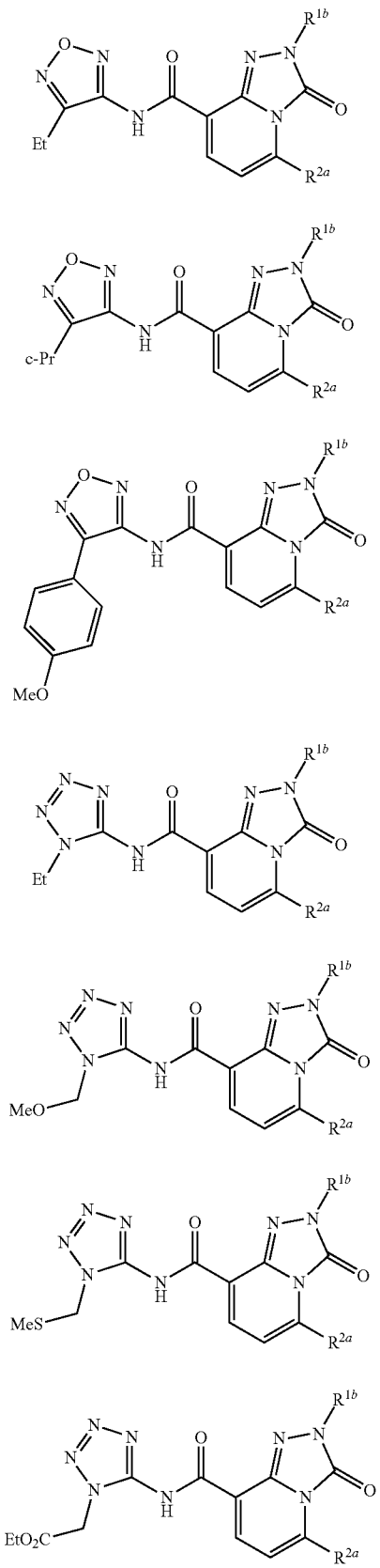
THIRD TABLE-continued
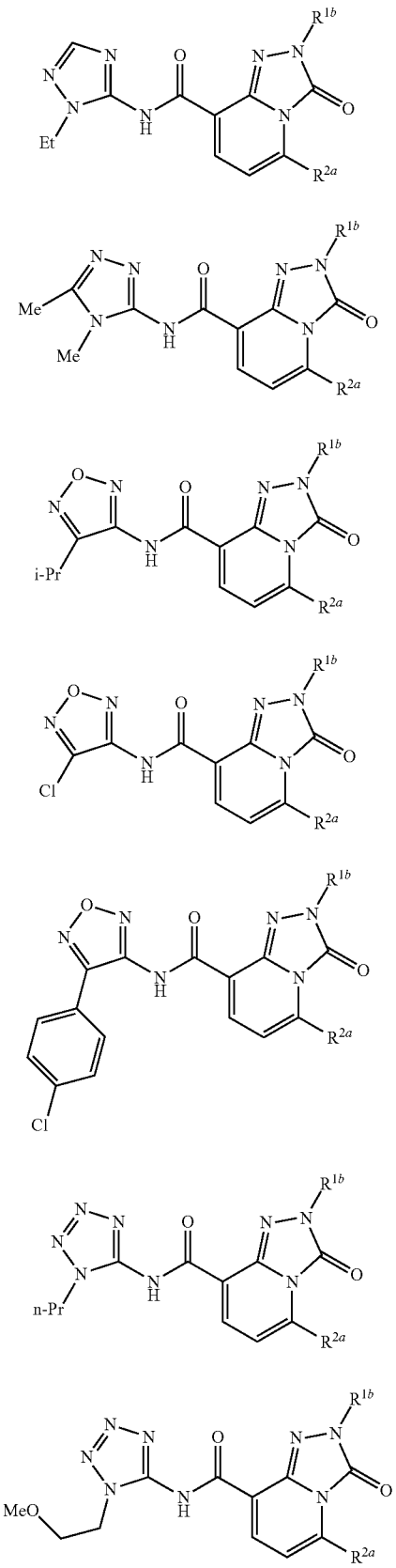

THIRD TABLE-continued

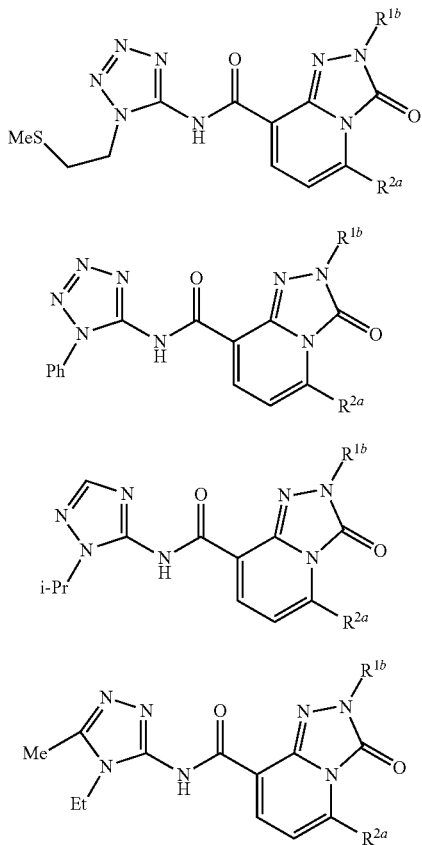

TABLE 24

| R$^{2a}$ | R$^{1b}$ |
|---|---|
| CF$_2$H | Me |
| CF$_2$H | Et |
| CF$_2$H | Pr-n |
| CF$_2$H | Pr-i |
| CF$_2$H | Pr-c |
| CF$_2$H | Bu-n |
| CF$_2$H | Bu-i |
| CF$_2$H | Bu-c |
| CF$_2$H | Bu-s |
| CF$_2$H | Bu-t |
| CF$_2$H | Pen-n |
| CF$_2$H | Pen-i |
| CF$_2$H | Pen-c |
| CF$_2$H | Pen-s |
| CF$_2$H | Pen-t |
| CF$_2$H | 3-Pen |
| CF$_2$H | Hex-n |
| CF$_2$H | Hex-c |
| CF$_2$H | CH$_2$Ph |
| CF$_2$H | CH(Me)Ph |
| CF$_2$H | (CH$_2$)$_2$Ph |
| CF$_2$H | (CH$_2$)$_3$Ph |
| CF$_2$Cl | Me |
| CF$_2$Cl | Et |
| CF$_2$Cl | Pr-n |
| CF$_2$Cl | Pr-i |
| CF$_2$Cl | Pr-c |
| CF$_2$Cl | Bu-n |
| CF$_2$Cl | Bu-i |
| CF$_2$Cl | Bu-c |
| CF$_2$Cl | Bu-s |
| CF$_2$Cl | Bu-t |
| CF$_2$Cl | Pen-n |

TABLE 24-continued

| R$^{2a}$ | R$^{1b}$ |
|---|---|
| CF$_2$Cl | Pen-i |
| CF$_2$Cl | Pen-c |
| CF$_2$Cl | Pen-s |
| CF$_2$Cl | Pen-t |
| CF$_2$Cl | 3-Pen |
| CF$_2$Cl | Hex-n |
| CF$_2$Cl | Hex-c |
| CF$_2$Cl | CH$_2$Ph |
| CF$_2$Cl | CH(Me)Ph |
| CF$_2$Cl | (CH$_2$)$_2$Ph |
| CF$_2$Cl | (CH$_2$)$_3$Ph |
| CF$_2$Br | Me |
| CF$_2$Br | Et |
| CF$_2$Br | Pr-n |
| CF$_2$Br | Pr-i |
| CF$_2$Br | Pr-c |
| CF$_2$Br | Bu-n |
| CF$_2$Br | Bu-i |
| CF$_2$Br | Bu-c |
| CF$_2$Br | Bu-s |
| CF$_2$Br | Bu-t |
| CF$_2$Br | CH$_2$Ph |
| CF$_2$Br | CH(Me)Ph |
| CF$_3$ | Me |
| CF$_3$ | Et |
| CF$_3$ | Pr-n |
| CF$_3$ | Pr-i |
| CF$_3$ | Pr-c |
| CF$_3$ | Bu-n |
| CF$_3$ | Bu-i |
| CF$_3$ | Bu-c |
| CF$_3$ | Bu-s |
| CF$_3$ | Bu-t |
| CF$_3$ | Pen-n |
| CF$_3$ | Pen-i |

TABLE 25

| R$^{2a}$ | R$^{1b}$ |
|---|---|
| CF$_3$ | Pen-c |
| CF$_3$ | Pen-s |
| CF$_3$ | Pen-t |
| CF$_3$ | 3-Pen |
| CF$_3$ | Hex-n |
| CF$_3$ | Hex-c |
| CF$_3$ | CH$_2$Ph |
| CF$_3$ | CH(Me)Ph |
| CF$_3$ | (CH$_2$)$_2$Ph |
| CF$_3$ | (CH$_2$)$_3$Ph |
| CH$_2$CF$_2$H | Me |
| CH$_2$CF$_2$H | Et |
| CH$_2$CF$_2$H | Pr-n |
| CH$_2$CF$_2$H | Pr-i |
| CH$_2$CF$_2$H | Pr-c |
| CH$_2$CF$_2$H | Bu-n |
| CH$_2$CF$_2$H | Bu-i |
| CH$_2$CF$_2$H | Bu-c |
| CH$_2$CF$_2$H | Bu-s |
| CH$_2$CF$_2$H | Bu-t |
| CH$_2$CF$_2$H | CH$_2$Ph |
| CH$_2$CF$_2$H | CH(Me)Ph |
| CH$_2$CF$_3$ | Me |
| CH$_2$CF$_3$ | Et |
| CH$_2$CF$_3$ | Pr-n |
| CH$_2$CF$_3$ | Pr-i |
| CH$_2$CF$_3$ | Pr-c |
| CH$_2$CF$_3$ | Bu-n |
| CH$_2$CF$_3$ | Bu-i |
| CH$_2$CF$_3$ | Bu-c |
| CH$_2$CF$_3$ | Bu-s |
| CH$_2$CF$_3$ | Bu-t |
| CH$_2$CF$_3$ | CH$_2$Ph |
| CH$_2$CF$_3$ | CH(Me)Ph |
| CHFCH$_3$ | Me |

TABLE 25-continued

| $R^{2a}$ | $R^{1b}$ |
|---|---|
| CHFCH$_3$ | Et |
| CHFCH$_3$ | Pr-n |
| CHFCH$_3$ | Pr-i |
| CHFCH$_3$ | Pr-c |
| CHFCH$_3$ | Bu-n |
| CHFCH$_3$ | Bu-i |
| CHFCH$_3$ | Bu-c |
| CHFCH$_3$ | Bu-s |
| CHFCH$_3$ | Bu-t |
| CHFCH$_3$ | CH$_2$Ph |
| CHFCH$_3$ | CH(Me)Ph |
| CF$_2$CH$_3$ | Me |
| CF$_2$CH$_3$ | Et |
| CF$_2$CH$_3$ | Pr-n |
| CF$_2$CH$_3$ | Pr-i |
| CF$_2$CH$_3$ | Pr-c |
| CF$_2$CH$_3$ | Bu-n |
| CF$_2$CH$_3$ | Bu-i |
| CF$_2$CH$_3$ | Bu-c |
| CF$_2$CH$_3$ | Bu-s |
| CF$_2$CH$_3$ | Bu-t |
| CF$_2$CH$_3$ | CH$_2$Ph |
| CF$_2$CH$_3$ | CH(Me)Ph |
| CF(CH$_3$)$_2$ | Me |
| CF(CH$_3$)$_2$ | Et |
| CF(CH$_3$)$_2$ | Pr-n |
| CF(CH$_3$)$_2$ | Pr-i |
| CF(CH$_3$)$_2$ | Pr-c |
| CF(CH$_3$)$_2$ | Bu-n |
| CF(CH$_3$)$_2$ | Bu-i |
| CF(CH$_3$)$_2$ | Bu-c |
| CF(CH$_3$)$_2$ | Bu-s |
| CF(CH$_3$)$_2$ | Bu-t |

TABLE 26

| $R^{2a}$ | $R^{1b}$ |
|---|---|
| CF(CH$_3$)$_2$ | CH$_2$Ph |
| CF(CH$_3$)$_2$ | CH(Me)Ph |
| CF$_2$CF$_2$H | Me |
| CF$_2$CF$_2$H | Et |
| CF$_2$CF$_2$H | Pr-n |
| CF$_2$CF$_2$H | Pr-i |
| CF$_2$CF$_2$H | Pr-c |
| CF$_2$CF$_2$H | Bu-n |
| CF$_2$CF$_2$H | Bu-i |
| CF$_2$CF$_2$H | Bu-c |
| CF$_2$CF$_2$H | Bu-s |
| CF$_2$CF$_2$H | Bu-t |
| CF$_2$CF$_2$H | Pen-n |
| CF$_2$CF$_2$H | Pen-i |
| CF$_2$CF$_2$H | Pen-c |
| CF$_2$CF$_2$H | Pen-s |
| CF$_2$CF$_2$H | Pen-t |
| CF$_2$CF$_2$H | 3-Pen |
| CF$_2$CF$_2$H | Hex-n |
| CF$_2$CF$_2$H | Hex-c |
| CF$_2$CF$_2$H | CH$_2$Ph |
| CF$_2$CF$_2$H | CH(Me)Ph |
| CF$_2$CF$_2$H | (CH$_2$)$_2$Ph |
| CF$_2$CF$_2$H | (CH$_2$)$_3$Ph |
| CF$_2$CF$_3$ | Me |
| CF$_2$CF$_3$ | Et |
| CF$_2$CF$_3$ | Pr-n |
| CF$_2$CF$_3$ | Pr-i |
| CF$_2$CF$_3$ | Pr-c |
| CF$_2$CF$_3$ | Bu-n |
| CF$_2$CF$_3$ | Bu-i |
| CF$_2$CF$_3$ | Bu-c |
| CF$_2$CF$_3$ | Bu-s |
| CF$_2$CF$_3$ | Bu-t |
| CF$_2$CF$_3$ | Pen-n |
| CF$_2$CF$_3$ | Pen-i |
| CF$_2$CF$_3$ | Pen-c |

TABLE 26-continued

| $R^{2a}$ | $R^{1b}$ |
|---|---|
| CF$_2$CF$_3$ | Pen-s |
| CF$_2$CF$_3$ | Pen-t |
| CF$_2$CF$_3$ | 3-Pen |
| CF$_2$CF$_3$ | Hex-n |
| CF$_2$CF$_3$ | Hex-c |
| CF$_2$CF$_3$ | CH$_2$Ph |
| CF$_2$CF$_3$ | CH(Me)Ph |
| CF$_2$CF$_3$ | (CH$_2$)$_2$Ph |
| CF$_2$CF$_3$ | (CH$_2$)$_3$Ph |
| CF$_2$CF$_2$CF$_3$ | Me |
| CF$_2$CF$_2$CF$_3$ | Et |
| CF$_2$CF$_2$CF$_3$ | Pr-n |
| CF$_2$CF$_2$CF$_3$ | Pr-i |
| CF$_2$CF$_2$CF$_3$ | Pr-c |
| CF$_2$CF$_2$CF$_3$ | Bu-n |
| CF$_2$CF$_2$CF$_3$ | Bu-i |
| CF$_2$CF$_2$CF$_3$ | Bu-s |
| CF$_2$CF$_2$CF$_3$ | Bu-t |
| CF(CF$_3$)$_2$ | Me |
| CF(CF$_3$)$_2$ | Et |
| CF(CF$_3$)$_2$ | Pr-n |
| CF(CF$_3$)$_2$ | Pr-i |
| CF(CF$_3$)$_2$ | Pr-c |
| CF(CF$_3$)$_2$ | Bu-n |
| CF(CF$_3$)$_2$ | Bu-i |
| CF(CF$_3$)$_2$ | Bu-s |
| CF(CF$_3$)$_2$ | Bu-t |

The compound of the present invention can be used in both treatment methods of soil application and foliage application under flooding as a herbicide for paddy fields. Examples of paddy field weeds may include Potamogetonaceae weeds represented by *Potamogeton distinctus*; Alismataceae weeds represented by *Alisma canaliculatum, Sagittaria pygmaea*, and *Sagittaria trifolia*; Gramineae weeds represented by *Leptochloa chinensis, Echinochloa crusgalli, Echinochloa oryzicola, Homalocenchrus japonocus*, and *Paspalum distichum*; Cyperaceae weeds represented by *Eleocharis kuroguwai, Scirpus juncoides, Scirpus nipponicus, Cyperus serotinus, Cyperus difformis*, and *Cyperus hakonensis*; Lemnaceae weeds represented by *Spirodela polyrhiza* and *Lemna paucicostata*; Commelinaceae weeds represented by *Murdannia keisak*; Pontederiaceae weeds represented by *Monochoria korsakowii* and *Monochoria vaginalis*; Elatinaceae weeds represented by *Elatine triandra*; Lythraceae weeds represented by *Ammannia multiflora* and *Rotala indica*; Oenotheraceae weeds represented by *Lidwigia epilobioides*; Scrophulariaceae weeds represented by *Dopatrium junceum, Gratiola japonica, Limnophila sessilifolia, Lindernia pyxidaria*, and *Lindernia dubia*; Leguminosae weeds such as *Aeschynomene indica*, and Compositae weeds represented by, *Bidens frondosa* and *Bidens tripartita* and the like.

The compound of the present invention can be used in any treatment methods of soil treatment, soil incorporation treatment, and foliage treatment as a herbicide for dry fields and orchards. Examples of the dry field weeds may include broad-leaved weeds such as Solanaceae weeds represented by *Solanum nigrum* and *Datura stramonium*; Geraniaceae weeds represented by *Granium carolinianum*; Malvaceae weeds represented by *Abutilon theophrasti* and *Sida spinosa*; Convolvulaceae weeds represented by *Ipomoea* spps. such as *Ipomoea purpurea* and *Calystegia* spps.; Amaranthaceae weeds represented by *Amaranthus lividus* and *Amaranthus retroexus*; Compositae weeds represented by *Xanthium pensylvanicum, Ambrosia artemisiaefolia, Helianthus annuus, Galinsoga ciliata, Cirsium arvense, Senecio vulgaris*, and *Erigeron annuus*; Cruciferae weeds represented by *Rorippa indica, Sinapis arvensis*, and *Capsella Bursapastoris*; Polygonaceae weeds represented by *Polygonum Blumei* and *Polygonum convolvulus*; Portulacaceae weeds represented by *Portulaca oleracea*; Chenopodiaceae weeds represented by *Chenopodium album, Chenopodium ficifolium*, and *Kochia scoparia*; Caryophyllaceae weeds represented by *Stellaria media*; Scrophulariaceae weeds represented by *Veronica persica*; Commelinaceae weeds represented by *Commelina communis*; Labiatae weeds represented by *Lamium amplexicaule* and *Lamium purpureum*; Euphorbiaceae weeds represented by *Euphorbia supina* and *Euphorbia maculate*; Rubiaceae weeds represented by *Galium spurium* and *Rubia akane*; Violaceae weeds represented by *Viola mandshurica*; Leguminosae weeds represented by *Sesbania exaltata* and *Cassia obtusifolia*; and Oxsaldaseae represented by *Oxsalis courniculata*; Graminaceous weeds represented by *Sorgham bicolor, Panicum dichotomiflorum, Sorghum halepense, Echinochloa crus-galli* var. *crus-galli, Echinochloa crus-galli* var. *praticola, Echinochloa utilis, Digitaria ciliaris, Avena fatua, Alopecurus myosuroides, Eleusine indica, Setaria viridis, Setaria faberi*, and *Alopecurus aegualis*; and Cyperaceous weeds represented by *Cyperus rotundus* and *Cyperus esculentus* and the like.

The compound of the present invention can be used in any treatment methods of soil treatment, soil incorporation treatment, and foliage treatment in non-agricultural lands such as turfs, play grounds, open grounds, road verges, and railway verges other than the agricultural and horticultural fields such as paddy fields, dry fields, and orchards. As weeds in these non-agricultural lands, the following examples of the weeds are exemplified in addition to those described as weeds in dry fields and orchards. Examples of the weed may include *Poa annua, Taraxacum officinale, Conyza sumatrensis, Cardamine flexuosa, Trifolium repens, Hydrocotyle sibthorpioides, Plantago asiatica, Cyperus brevifolius, Kyllinga brevifolia*, and *Equisetum arvense* and the like.

When the compound of the present invention is applied as the herbicide, the compound is usually mixed with an appropriate solid carrier or liquid carrier, and surfactants, penetrating agents, spreading agents, thickeners, antifreeze agents, binders, anti-caking agents, disintegrating agents stabilizing agents and the like are added, if desired. The herbicide can be applied to practical uses by any herbicide formulation of the herbicide form such as water-dispersible agents, emulsion agents, flowable agents, dry-flowable agents, liquid agents, powder agents, granule agents, or gel agents. From the viewpoint of labor saving and improvement in safety, any of the herbicide formulation of the herbicide form can be applied in an encapsulated state in a water-soluble package.

Examples of the solid carriers may include natural minerals such as quartz, kaolinite, pyrophyllite, sericite, talc, bentonite, acid clay, attapulgite, zeolite, and diatomaceous earth; inorganic salts such as calcium carbonate, ammonium sulfate, sodium sulfate and potassium chloride; and synthetic silicic acid and synthetic silicates.

Examples of the liquid carriers may include alcohols such as ethylene glycol, propylene glycol, and isopropanol; aromatic hydrocarbons such as xylene, alkylbenzene, and alkylnaphthalene; ethers such as butylcellosolve; ketones such as cyclohexanone; esters such as γ-butyrolactone; acid amides such as N-methylpyrrolidone and N-octylpyrrolidone; vegetable oils such as soybean oil, rapeseed oil, cotton seed oil, and castor oil; and water.

These solid carriers and liquid carriers may be used singly or in combination of two or more of them.

Examples of the surfactant may include nonionic surfactants such as polyoxyethylene alkyl ethers, polyoxyethylene alkylaryl ethers, polyoxyethylene styrylphenyl ethers, polyoxyethylene-polyoxypropylene block copolymers, polyoxyethylene fatty acid esters, sorbitan fatty acid esters, and polyoxyethylene sorbitan fatty acid esters; anionic surfactants such as alkyl sulfates, alkylbenzene sulfonates, lignin sulfonates, alkyl sulfosuccinates, naphthalene sulfonate, alkylnaphthalene sulfonates, salts of formalin condensate of naphthalene sulfonic acid, salts of formalin condensate of alkylnaphthalene sulfonic acid, polyoxyethylene alkylaryl ether sulfates and phosphates, polyoxyethylene styrylphenyl ether sulfates and phosphates, polycarboxylates, and polystyrene sulfonates; cationic surfactants such as alkylamine salts and alkyl quaternary ammonium salts; and amphoteric surfactants such as amino acid-type surfactants and betaine-type surfactants.

The content of the surfactants is not particularly limited. Usually, the content is preferably in a range of 0.05 parts by weight to 20 parts by weight relative to 100 parts by weight of the herbicide formulation of the present invention. These surfactants may be used singly or in combination of two or more of them.

The compound of the present invention may be applied in a mixed state with another herbicide, various insecticides, a bactericide, a plant growth regulator, a synergist, or the like at the time of herbicide formulation or application.

In particular, by applying the herbicide in a mixed state with another herbicide, reduction in cost by reduction in an application amount, expansion in herbicidal spectrum by synergistic action of mixed herbicides, and a higher herbicidal effect can be expected. At this time, a combination of a plurality of known herbicides at the same time is also possible.

Examples of the preferable herbicide used in a mixture with the compound of the present invention may include acetochlor/general name, acifluorfen/general name, aclonifen/general name, alachlor/general name, alloxydim/general name, alloxydim-sodium/general name, ametryn/general name, amicarbazone/general name, amidosulfuron/general name, aminocyclopirachlor/general name, aminocyclopirachlor-salts and esters, aminopyralid/general name, aminopyralid-salts and esters, amiprophos-methyl/general name, amitrol/general name, anilofos/general name, asulam/general name, atrazine/general name, azafenidin/general name, azimsulfuron/general name, beflubutamid/general name, benazolin-ethyl/general name, bencarbazone/general name, benfluralin (benefin)/general name, benfuresate/general name, bensulfuron-methyl/general name, bensulide/general name, bentazone/general name, bentazone-sodium/general name, bentazone-salts, benthiocarb/general name, benzfendizone/general name, benzobicyclon/general name, benzofenap/general name, bialaphos/general name, bialaphos-sodium/general name, bicyclopyrone/general name, bifenox/general name, bispyribac/general name, bispyribac-sodium/general name, bromacil/general name, bromobutide/general name, bromofenoxim/general name, bromoxynil/general name, bromoxynil-salts and esters, butachlor/general name, butafenacil/general name, butamifos/general name, butenachlor/general name, butralin/general name, butroxydim/general name, butylate/general name, cafenstrole/general name, carbetamide/general name, carfentrazone-ethyl, chlomethoxyfen/general name, chlomethoxynil/general name, chloramben/general name, chloramben-salts and esters, chloransulam-methyl/general name, chlorflurenol-methyl/general name, chloridazon/general name, chlorimuron-ethyl/general name, chlorobromuron/general name, chlorotoluron/general name, chloroxuron/general name, chlorphtalim/general name, chlorpropham/general name, chlorpropham/general name, chlorsulfuron/general name, chlorthal-dimethyl/general name, chlorthiamid/general name, cinidon-ethyl/general name, cinmethylin/general name, cinosulfuron/general name, clethodim/general name, clodinafop/general name, clodinafop-propargyl/general name, clomazone/general name, clomeprop/general name, clopyralid/general name, clopyralid-salts and esters, CNP/general name, cumyluron/general name, cyanazin/general name, cycloate/general name, cyclopyrimorate/general name (SW-065/test name), cyclosulfamuron/general name, cycloxydim/general name, cyhalofop-butyl/general name, DAH-500/test name, dalapon/general name, dazomet/general name, desmedipham/general name, desmetryn/general name, dicamba/general name, dicamba-salts and esters, dichlobenil/general name, diclofop/general name, diclofop-methyl/general name, dichlorprop/general name, dichlorprop-salts and esters, dichlorprop-P/general name, dichlorprop-P-salts and esters, diclosulam/general name, difenzoquat/general name, diflufenican/general name, diflufenzopyr/general name, diflufenzopyr-sodium/general name, dimepiperate/general name, dimethametryn/general name, dimethachlor/general name, dimethenamid/general name, dimethenamid-p/general name, dimethipin/general name, dinitramine/general name, dinoseb/general name, dinoterb/general name, DNOC/general name, diphenamid/general name, diquqt/general name, dithiopyl/general name, diuron/general name, DSMA/general name, dymron/general name, endothal/general name, EPTC/general name, esprocarb/general name, ethalfluralin/general name, ethametsulfuron-methyl/general name, ethofumesate/general name, etobenzanid/general name, ethoxysulfuron/general name, flazasulfuron/general name, fenoxaprop/general name, fenoxaprop-ethyl/general name, fenoxasulfone/general name, fenquionotrion/general name, fentrazamide/general name, flamprop/general name, flazasulfuron/general name, florasulam/general name, fluazifop/general name, fluazifop-butyl/general name, fluazolate/general name, flucarbazone-sodium/general name, flucetosulfuron/general name, flucloralin/general name, flufenacet/general name, flufenpyl-ethyl/general name, flumetsulam/general name, flumiclorac-pentyl/general name, flumioxazin/general name, fluometuron general name, fluoroglycofen-ethyl/general name, flupyrsulfuron/general name, flupoxam/general name, flurenol/general name, fluridone/general name, flurochloridone/general name, fluroxypyr/general name, fluroxypyr-esters, flurprimidol/general name, flurtamone/general name, fluthiacet-methyl/general name, fomesafen/general name, foramsulfuron/general name, fosamine/general name, glufosinate/general name, glufosinate-ammonium/general name, glyphosate/general name, glyphosate-ammonium/general name, glyphosate-iso-propylammonium/general name, glyphosate-potassium/general name, glyphosate-sodium/general name, glyphosate-trimesium/general name, halauxifen/general name, halauxifen-salts and esters, halosafen/general name, halosulfuron/general name, halosulfuron-methyl general name, haloxyfop/general name, haloxyfop-methyl/general name, hexazinone general name, imazamethabenz-methyl/general name, imazamox/general name, imazapic/general name, imazapyr/general name, imazethapyr/general name, imazaquin/general name, imazosulfuron/general name, indanofan/general name, indaziflam/general name, iodosulfuron-methyl-sodium/general name, ioxynil octanoate/general name, ioxynil-salts and esters, ipfencarbazone/general name, isoproturon general name, isouron/general name, isoxaben/general name, isox-
aflutole/general name, karbutilate/general name, lactofen/general name, lenacil/general name, linuron/general name, maleic hydrazide/general name, MCPA/general name, MCPA-salts and esters, MCPB/general name, MCPB-salts and esters, mecoprop (MCPP)/general name, mecoprop-salts and esters, mecoprop-P (MCPP-P)/general name, mecoprop-P-salts and esters, mefenacet/general name, mefluidide/general name, mesosulfuron-methyl general name, mesotrione/general name, metam/general name, metamifop/general name, metamitron/general name, metazachlor/general name, methabenzthiazuron general name, metazosulfuron/general name, methiozolin/general name, methyl azide general name, methyl bromide/general name, methyl dymron/general name, methyl iodide/general name, metobenzuron/general name, metolachlor/general name, metolachlor-S/general name, metosulam/general name, metribuzin/general name, metsulfuron-methyl/general name, metoxuron/general name, molinate/general name, monolinuron/general name, monosulfuron/general name, monosulfuron-methyl general name, MSMA/general name, naproanilide/general name, napropamide general name, naptalam/general name, naptalam-sodium/general name, neburon general name, nicosulfuron/general name, norflurazon/general name, OK-701/test name, oleic acid/general name, orbencarb/general name, orthosulfamuron/general name, oryzalin/general name, oxadiargyl/general name, oxadiazon/general name, oxasulfuron/general name, oxaziclomefone/general name, oxyfluorfen/general name, paraquat/general name, pelargonicacid/general name, pendimethalin/general name, penoxsulam/general name, pentanochlor/general name, pentoxazone/general name, pethoxamid/general name, phenmedipham-ethyl/general name, picloram/general name, picloram-salts and esters, picolinafen/general name, pinoxaden/general name, piperophos/general name, pretilachlor/general name, primisulfuron-methyl/general name, prodiamine/general name, profluazol/general name, profoxydim/general name, prometon/general name, prometryn/general name, propachlor/general name, propanil/general name, propaquizafop/general name, propazin/general name, propham general name, propisochlor/general name, propoxycarbazone-sodium/general name, propyrisulfuron/general name, propyzamide/general name, prosulfocarb/general name, prosulfuron/general name, pyraclonil/general name, pyraflufen-ethyl/general name, pyrasulfotole/general name, pyrazolynate/general name, pyrazosulfuron/general name, pyrazosulfuron-ethyl/general name, pyrazoxyfen/general name, pyribenzoxim/general name, pyributicarb/general name, pyridafol/general name, pyridate/general name, pyriftalid/general name, pyriminobac-methyl/general name, pyrimisulfan/general name, pyrithiobac-sodium/general name, pyroxasulfone/general name, pyroxsulam general name, quinclorac/general name, quinmerac/general name, quinoclamine general name, quizalofop/general name, quizalofop-ethyl/general name, quizalofop-tefuryl/general name, quizalofop-P/general name, quizalofop-P-ethyl general name, quizalofop-P-tefuryl/general name, rimsulfuron/general name, saflufenacil/general name, sethoxydim/general name, siduron/general name, simazine/general name, simetryn/general name, SL-261/test name, sulcotrione/general name, sulfentrazone/general name, sulfometuron-methyl/general name, sulfosulfuron general name, TCBA (2,3,6-TBA)/general name, 2,3,6-TBA-salts and esters, TCTP (chlorthal-dimethyl, tetorachlorothiophene)/general name, tebutam/general name, tebuthiuron/general name, tefuryltrione/general name, tembotrione/general name, tepraloxydim/general name, terbacil/general name, terbumeton/general name, terbuthylazine/general name, terbutryn/general name, tetrapion (flupropanate)/general name, thenylchlor/general name, thiazafluron/general name, thiazopyr/general name, thidiazimin/general name, thidiazuron/general name, thiencarbazone-methyl/general name, thifensulfuron-methyl/general name, tolpyralate/general name, topramezon general name, tralkoxydim/general name, triafamone/general name, triallate/general name, triasulfuron/general name, triaziflam/general name, tribenuron-methyl/general name, triclopyr/general name, triclopyr-salts and esters, tridiphane/general name, trietazine/general name, trifludimoxadin/general name, trifloxysulfuron/general name, trifluralin/general name, triflusulfuron-methyl/general name, tritosulfuron/general name, 2,4-PA/general name, 2,4-PA-salts and esters, 2,4-DB/general name, and 2,4-DB-salts and esters. These components may be used singly or in combination of two or more of them. When these components are mixed, the mixing ratio may be freely selected.

Examples of safeners may include AD-67, benoxacor/general name, cloquintocet-mexyl/general name, cyomerinil/general name, dichlormid/general name, dicyclonone/general name, cyprosulfamide/general name, diethorate/general name, DKA-24, dymron/general name, fenclorazole-ethyl/general name, fenclorim/general name, HEXIM/general name, flurazole/general name, fluxofenim/general name, furilazole/general name, isoxadifen/general name, isoxadifen-ethyl/general name, MCPA, mecoprop/general name, mefenpyr/general name, mefenpyr-ethyl/general name, mefenpyr-diethyl/general name, mephenate/general name, MG-191, NA (Naphthalic anhydride), OM (Octamethylene-diamine), oxabetrinil/general name, PPG-1292, and R-29148. These agricultural chemical active components may be used singly or in combination of two or more of them. When these components are mixed, the mixing ratio may be freely selected.

Although the application amount of the compound of the present invention varies depending on the application situation, the application time, the application method, the cultivated crop and the like, the appropriate application amount is generally 0.005 kg/ha to 50 kg/ha as the amount of the active component.

Next, the formulation examples of the herbicide formulations when the compound of the present invention is used will be described. However, the formulation examples of the present invention are not limited to these examples. Hereinafter, the term "part" in the formulation examples means part by weight.

Water-Dispersible Agent

| Compound of the present invention | 0.1 parts to 80 parts |
| Solid carrier | 5 parts to 98.9 parts |
| Surfactant | 1 part to 10 parts |
| Others | 0 parts to 5 parts |

Examples of Others may include anti-caking agents, stabilizing agents and the like.

Emulsion Agent

| Compound of the present invention | 0.1 parts to 30 parts |
| Liquid carrier | 45 parts to 95 parts |
| Surfactant | 4.9 parts to 15 parts |
| Others | 0 parts to 10 parts |

Examples of Others may include spreading agents, stabilizing agents and the like.

Flowable Agent

| Compound of the present invention | 0.1 parts to 70 parts |
| Liquid carrier | 15 parts to 98.89 parts |
| Surfactant | 1 part to 12 parts |
| Others | 0.01 parts to 30 parts |

Examples of Others may include antifreeze agents, thickeners and the like.

Dry Flowable Agent

| Compound of the present invention | 0.1 parts to 90 parts |
| Solid carrier | 0 parts to 98.9 parts |
| Surfactant | 1 part to 20 parts |
| Others | 0 parts to 10 parts |

Examples of Others may include binders, stabilizing agents and the like.

Liquid Agent

| Compound of the present invention | 0.01 parts to 70 parts |
| Liquid carrier | 20 parts to 99.99 parts |
| Others | 0 parts to 10 parts |

Examples of Others may include antifreeze agents, spreading agents and the like.

Granule Agent

| Compound of the present invention | 0.01 parts to 80 parts |
| Solid carrier | 10 parts to 99.99 parts |
| Others | 0 parts to 10 parts |

Examples of Others may include binders, stabilizing agents and the like.

Powder Agent

| Compound of the present invention | 0.01 parts to 30 parts |
| Solid carrier | 65 parts to 99.99 parts |
| Others | 0 parts to 10 parts |

Examples of Others may include anti-drift agents, stabilizing agents and the like.

When the agents are used, the herbicide formulation is applied without any treatment or by diluting the agent to 1 to 10,000 times with water.

Herbicide Formulation Example

Next, examples of agricultural chemical formulation containing the compound of the present invention as the active component will be descried. The present invention, however, is not limited to these examples. Hereinafter, the term "part" in the formulation examples means part by weight.

[Formulation Example 1] Water-Dispersible Agent

| Compound of the present invention No. 1-001 | 20 parts |
| Pyrophyllite | 76 parts |
| Sorpol 5039 | 2 parts |
| (Anionic surfactant: manufactured by TOHO Chemical Industry Co., Ltd., trade name) | |
| CARPLEX #80 | 2 parts |
| (Synthetic hydrated silicic acid: Shionogi & Co., Ltd., trade name) | |

The above components are uniformly mixed and pulverized to give the water-dispersible agent.

[Formulation Example 2] Emulsion Agent

| Compound of the present invention No. 1-001 | 5 parts |
|---|---|
| Xylene | 75 parts |
| N-methylpyrrolidone | 15 parts |
| Sorpol 2680 | 5 parts |
| (Anionic surfactant: manufactured by TOHO Chemical Industry Co., Ltd., trade name) | |

The above components are mixed to give the emulsion agent.

[Formulation Example 3] Flowable Agent

| Compound of the present invention No. 1-001 | 25 parts |
|---|---|
| Agrisol S-710 | 10 parts |
| (Nonionic surfactant: Kao Corporation, trade name) | |
| Lunox 1000C | 0.5 parts |
| (Anionic surfactant: manufactured by TOHO Chemical Industry Co., Ltd., trade name) | |
| Xanthane gum | 0.02 parts |
| Water | 64.48 Parts |

After the above components are uniformly mixed, the mixture was wet-pulverized to give the flowable agent.

[Formulation Example 4] Dry Flowable Agent

| Compound of the present invention No. 1-001 | 75 parts |
|---|---|
| HITENOL NE-15 | 5 parts |
| (Anionic surfactant: manufactured by DKS Co. Ltd., trade name) | |
| Vanillex N | 10 parts |
| (Anionic surfactant: manufactured by NIPPON PAPER INDUSTRIES CO., LTD., trade name) | |
| CARPLEX #80 | 10 parts |
| (Synthetic hydrated silicic acid: Shionogi & Co., Ltd., trade name) | |

The above components are uniformly mixed and pulverized and then a small amount of water was added to the mixture to stir, to mix, and to knead. The resultant mixture was granulated with an extruding-type granulator. The granules are dried to form the dry flowable agent.

[Formulation Example 5] Granular Agent

| Compound of the present invention No. 1-001 | 1 part |
|---|---|
| Bentonite | 55 parts |
| Talc | 44 parts |

The above components are uniformly mixed and pulverized and then a small amount of water was added to the mixture to stir, to mix, and to knead. The resultant mixture was granulated with an extruding-type granulator. The granules are dried to give the granular agent.

EXAMPLES

Hereinafter the present invention will be further described in detail by specifically describing Synthesis Examples and Test Examples of the heterocyclic amide compounds of Formula (1) in the present invention as Examples. The present invention, however, is not limited to these Examples.

As a medium pressure preparative liquid chromatography described in Synthesis Examples and Reference Examples, Medium pressure preparative apparatus; YFLC-Wprep (flow rate: 18 ml/min, 40 μm silica gel packed column) manufactured by Yamazen Corporation was used.

The chemical shift values of proton nuclear magnetic resonance in Examples were measured at 300 MHz using $Me_4Si$ (tetramethylsilane) as a reference substance. Solvents used in measurement are described in Synthesis Examples below. The symbols of the chemical shift values of proton nuclear magnetic resonance in Examples have the following meanings.

s: singlet, d: doublet, t: triplet, m: multiplet, q: quartet, and br: broad

SYNTHESIS EXAMPLES

Synthesis Example 1

3-Isopropyl-5-methyl-N-(5-methyl-1,3,4-oxadiazol-2-yl)-[1,2,4]triazolo[4,3-a]pyridine-8-carboxamide (compound No. 1-003)

Step 1; Synthesis of methyl 2-hydrazinyl-6-methylnicotinate

To the mixed solution of 3.0 g (16.2 mmol) of methyl 2-chloro-6-methylnicotinate and 30 ml of dioxane, 1.62 g (32.3 mmol) of hydrazine monohydrate was added at room temperature. After completion of the addition, the reaction mixture was stirred at 60° C. for 4 hours and subsequently 80° C. for 6 hours. After completion of stirring, the reaction was terminated by adding water and the reaction liquid was extracted with ethyl acetate (150 ml, 2 times). The obtained organic phase was washed with a saturated sodium bicarbonate aqueous solution. Thereafter, the organic phase was dehydrated and dried with saturated sodium chloride aqueous solution and then anhydrous sodium sulfate in this order and the solvent was distilled away under reduced pressure. The precipitated solid was washed with hexane and filtered to give 1.60 g of the target product as an orange solid.

Melting point: 90° C. to 91° C.

Step 2; Synthesis of methyl 2-(2-isobutyrylhydrazinyl)-6-methylnicotinate

To the mixed solution of 1.5 g (8.28 mmol) of methyl 2-hydrazinyl-6-methylnicotinate, 838 mg (8.28 mmol) of triethylamine, and 20 ml of tetrahydrofuran, 882 mg (8.28 mmol) of isobutyryl chloride was added under cooling with ice. After completion of the addition, the reaction mixture was stirred for 30 minutes under cooling with ice. After completion of stirring, the reaction was terminated by adding water and the reaction liquid was extracted with ethyl acetate (100 ml, 1 time). The obtained organic phase was washed with water. Thereafter, the organic phase was dehydrated and dried with saturated sodium chloride aqueous solution and then anhydrous sodium sulfate in this order and the solvent was distilled away under reduced pressure. The precipitated solid was washed with hexane and diisopropyl ether and filtered to give 1.68 g of the target product as a flesh-colored solid.

Melting point: 99° C. to 101° C.

Step 3; Synthesis of methyl 3-isopropyl-5-methyl-[1,2,4]triazolo[4,3-a]pyridine-8-carboxylate To the mixed solution of 1.6 g (63.7 mmol) of methyl 2-(2-isobutyrylhydrazinyl)-6-methylnicotinate and 10 ml of toluene, 3 ml of phosphoryl chloride was added at room temperature. After completion of the addition, the reaction mixture was stirred for 5 hours under heating to reflux. After completion of stirring, the reaction mixture was added to ice-water to terminate the reaction. Thereafter, the reaction liquid was washed with ethyl acetate (50 ml, 1 time). To the obtained aqueous phase, potassium carbonate was added under cooling with ice to adjust the pH to 8 to 9. Thereafter, the reaction liquid was extracted with ethyl acetate (100 ml, 2 times). The obtained organic phase was dried over anhydrous sodium sulfate and the solvent was distilled away under reduced pressure. The precipitated solid was washed with diisopropyl ether and filtered to give 490 mg of the target product as a light yellow solid.

Melting point: 138° C. to 140° C.

Step 4; Synthesis of 3-isopropyl-5-methyl-[1,2,4]triazolo[4,3-a]pyridine-8-carboxylic acid To the mixed solution of 450 mg (1.93 mmol) of methyl 3-isopropyl-5-methyl-[1,2,4]triazolo[4,3-a]pyridine-8-carboxylate and 4 ml of methanol, 2 ml of 1 M sodium hydroxide aqueous solution was added at room temperature. After completion of the addition, the reaction mixture was stirred for 2 hours at room temperature. After completion of stirring, 1 M hydrochloric acid was added to adjust the pH to 2 to 3. After the solvent in the reaction liquid was distilled away under reduced pressure, the precipitated solid was washed with water and filtered to give 250 mg of the target product as a light yellow solid.

Melting point: 194° C. to 195° C.

Step 5; Synthesis of 3-isopropyl-5-methyl-N-(5-methyl-1,3,4-oxadiazol-2-yl)-[1,2,4]triazolo[4,3-a]pyridine-8-carboxamide To a mixed solvent of 400 mg (1.95 mmol) of 3-isopropyl-5-methyl-[1,2,4]triazolo[4,3-a]pyridine-8-carboxylic acid, 0.1 ml of N,N-dimethylformamide, and 3 ml of methylene chloride, 463 mg (3.91 mmol) of oxalyl chloride was added at room temperature. After completion of the addition, the reaction mixture was stirred for 1 hour at room temperature. After completion of stirring, the solvent in the reaction mixture was distilled away under reduced pressure to give crude 3-isopropyl-5-methyl-[1,2,4]triazolo[4,3-a]pyridine-8-carboxylic acid chloride hydrochloride. To the mixed solution of 540 mg (1.95 mmol) of the obtained crude 3-isopropyl-5-methyl-[1,2,4]triazolo[4,3-a]pyridine-8-carboxylic acid chloride hydrochloride, 180 mg (1.82 mmol) of 5-methyl-1,3,4-oxadiazol-2-amine and 5 ml of methylene chloride, 368 mg (3.91 mmol) of triethylamine was added under cooling with ice. After completion of the addition, the reaction mixture was stirred for 20 hours at room temperature. After completion of stirring, 5 ml of pyridine and 10 mg of 4-(dimethylamino)pyridine were added to reaction mixture. Thereafter, the resultant reaction mixture was stirred at 60° C. for 10 hours. After completion of stirring, the reaction was terminated by adding water and the reaction liquid was extracted with ethyl acetate (20 ml, 1 time). The obtained organic phase was washed with water. Thereafter, the organic phase was dehydrated and dried with saturated sodium chloride aqueous solution and anhydrous sodium sulfate and the solvent was distilled away under reduced pressure. The precipitated solid was washed with diisopropyl ether and ethyl acetate and filtered to give 60 mg of the target product as a brown solid.

Synthesis Example 2

3-Isopropyl-N-(5-methyl-1,3,4-oxadiazol-2-yl)-5-(trifluoromethyl)-[1,2,4]triazolo[4,3-a]pyridine-8-carboxamide (Compound No. 1-004)

To the mixed solution of 160 mg (0.59 mmol) of 3-isopropyl-5-(trifluoromethyl)-[1,2,4]triazolo[4,3-a]pyridine-8-carboxylic acid, 70 mg (0.71 mmol) of 5-methyl-1,3,4-oxadiazol-2-amine, and 5 ml of N,N-dimethylformamide, 135 mg (0.71 mmol) of 1-ethyl-3-(3-dimethylaminopropyl)carbodiimide hydrochloride and 96 mg (0.71 mmol) of 1-hydroxy-7-azabenzotriazole were added. After completion of the addition, the reaction mixture was stirred for 24 hours at room temperature. After completion of stirring, the reaction was terminated by adding water and the reaction liquid was extracted with chloroform (100 ml, 1 time). The obtained organic phase was washed with water. Thereafter, the organic phase was dried over anhydrous sodium sulfate and the solvent was distilled away under reduced pressure. The obtained residue was purified with silica gel chromatography {n-hexane:ethyl acetate=1:1 to 0:1 (volume ratio; the same applies hereafter)} to give 90 mg of the target product as a white solid.

Melting point: 176° C. to 178° C.

Synthesis Example 3

3-Isopropyl-N-(5-methyl-1,3,4-oxadiazol-2-yl)-5-(methylthio)-[1,2,4]triazolo[4,3-a]pyridine-8-carboxamide (Compound No. 1-009)

Step 1; Synthesis of methyl 2-hydrazinyl-6-chloronicotinate

To the mixed solution of 11.5 g (55.8 mmol) of methyl 2,6-dichloronicotinate and 150 ml of dioxane, 5.58 g (111 mmol) of hydrazine monohydrate was added at room temperature. After completion of the addition, the reaction mixture was stirred for 18 hours at room temperature. After completion of stirring, the reaction was terminated by adding water and the solvent in the reaction liquid was distilled away under reduced pressure. The precipitated solid was washed with water and filtered to give 10.7 g of the target product as a yellow solid.

Melting point: 82° C. to 83° C.

Step 2; Synthesis of methyl 2-(2-isobutyrylhydrazinyl)-6-chloronicotinate

To the mixed solution of 5.0 g (24.8 mmol) of methyl 2-hydrazinyl-6-chloronicotinate, 2.5 g (24.8 mmol) of triethylamine, and 20 ml of tetrahydrofuran, 2.64 g (24.8 mmol) of isobutyryl chloride was added under cooling with ice. After completion of the addition, the reaction mixture was stirred for 2 hours under cooling with ice. After completion of stirring, the reaction was terminated by adding water and the reaction liquid was extracted with ethyl acetate (150 ml, 1 time). The obtained organic phase was washed with water. Thereafter, the organic phase was dehydrated and dried with saturated sodium chloride aqueous solution and then anhydrous sodium sulfate in this order and the solvent was distilled away under reduced pressure. The precipitated solid was washed with diisopropyl ether and hexane and filtered to give 5.90 g of the target product as a white solid.
Melting point: 147° C. to 148° C.

Step 3; Synthesis of methyl 3-isopropyl-5-chloro-[1,2,4]triazolo[4,3-a]pyridine-8-carboxylate 5.9 g (21.7 mmol) of methyl 2-(2-isobutyrylhydrazinyl)-6-chloronicotinate and 20 ml of phosphoryl chloride were mixed at room temperature and thereafter the reaction mixture was stirred for 5 hours under heating to reflux. After completion of stirring, the reaction mixture was added to ice-water to terminate the reaction. Thereafter, the reaction liquid was washed with ethyl acetate (50 ml, 1 time). Potassium carbonate was added to the obtained aqueous phase under cooling with ice to adjust the pH to 8 to 9 and the reaction liquid was extracted with ethyl acetate (200 ml, 2 times). The obtained organic phase was dried over anhydrous sodium sulfate and the solvent was distilled away under reduced pressure. The precipitated solid was washed with diisopropyl ether and filtered to give 4.75 g of the target product as a brownish light yellow solid.
Melting point: 105° C. to 107° C.

Step 4; Synthesis of methyl 3-isopropyl-5-(methylthio)-[1,2,4]triazolo[4,3-a]pyridine-8-carboxylate To the mixed solution of 420 mg (1.66 mmol) of methyl 3-isopropyl-5-chloro-[1,2,4]triazolo[4,3-a]pyridine-8-carboxylate and 3 ml of N,N-dimethylformamide, 140 mg (1.99 mmol) of sodium thiomethoxide was added under cooling with ice. After completion of the addition, the reaction mixture was stirred for 45 minutes under cooling with ice. After completion of stirring, the reaction was terminated by adding water and the reaction liquid was extracted with ethyl acetate (30 ml, 3 times). The obtained organic phase was dehydrated and dried with saturated sodium chloride aqueous solution and then anhydrous sodium sulfate in this order and the solvent was distilled away under reduced pressure. The precipitated solid was washed with diisopropyl ether and filtered to give 280 mg of the target product as a brown solid.
Melting point: 142° C. to 145° C.

Step 5; Synthesis of 3-isopropyl-N-(5-methyl-1,3,4-oxadiazol-2-yl)-5-(methylthio)-[1,2,4]triazolo[4,3-a]pyridine-8-carboxamide To the mixed solution of 140 mg (0.53 mmol) of methyl 3-isopropyl-5-(methylthio)-[1,2,4]triazolo[4,3-a]pyridine-8-carboxylate, 3 ml of methanol, and 1 ml of water, 0.6 ml of 1 M sodium hydroxide aqueous solution was added at room temperature. After completion of the addition, the reaction mixture was stirred for 17 hours at room temperature. After completion of stirring, the reaction was terminated by adding 1 ml of 1 M hydrochloric acid. The solvent in the reaction liquid was distilled away under reduced pressure to give crude 3-isopropyl-5-(methylthio)-[1,2,4]triazolo[4,3-a]pyridine-8-carboxylic acid. To the mixed solution of 190 mg (0.53 mmol) of the obtained crude 3-isopropyl-5-(methylthio)-[1,2,4]triazolo[4,3-a]pyridine-8-carboxylic acid, 104 mg (1.06 mmol) of 5-methyl-1,3,4-oxadiazol-2-amine, and 3 ml of pyridine, 126 mg (1.06 mmol) of thionyl chloride was added at room temperature. After completion of the addition, the reaction mixture was stirred at 60° C. for 5 hours. After completion of stirring, the reaction was terminated by adding water and the solvent was distilled away under reduced pressure. The precipitated solid was washed with diisopropyl ether and chloroform and filtered to give 57 mg of the target product as an ocherous solid.

Synthesis Example 4

3-Chloro-N-(5-methyl-1,3,4-oxadiazol-2-yl)-5-(trifluoromethyl)-[1,2,4]triazolo[4,3-a]pyridine-8-carboxamide (Compound No. 1-013)

Step 1; Synthesis of 3-chloro-5-(trifluoromethyl)-[1,2,4]triazolo[4,3-a]pyridine-8-carboxylic acid To the mixed solution of 300 mg (1.30 mmol) of 5-(trifluoromethyl)-[1,2,4]triazolo[4,3-a]pyridine-8-carboxylic acid and 6 ml of N,N-dimethylformamide, 347 mg (2.60 mmol) of N-chlorosuccinimide was added at room temperature. After completion of the addition, the reaction mixture was stirred at 60° C. for 4 hours. After completion of stirring, the reaction was terminated by adding water and the reaction liquid was extracted with ethyl acetate (50 ml, 2 times). The obtained organic phase was dehydrated and dried with saturated sodium chloride aqueous solution and then anhydrous sodium sulfate in this order and the solvent was distilled away under reduced pressure. The precipitated solid was washed with diisopropyl ether and filtered to give 210 mg of the target product as a brown solid.

Step 2; Synthesis of 3-chloro-N-(5-methyl-1,3,4-oxadiazol-2-yl)-5-(trifluoromethyl)-[1,2,4]triazolo[4,3-a]pyridine-8-carboxamide To the mixed solution of 70 mg (0.26 mmol) of 3-chloro-5-(trifluoromethyl)-[1,2,4]triazolo[4,3-a]pyridine-8-carboxylic acid, 52 mg (0.53 mmol) of 5-methyl-1,3,4-oxadiazol-2-amine, 10 mg (0.03 mmol) of 4-(dimethylamino)pyridine, and 5 ml of pyridine, 63 mg (0.53 mmol) of thionyl chloride was added at room temperature. The reaction mixture was stirred for 1 hour at room temperature. After completion of stirring, the reaction was terminated by adding water and the reaction liquid was extracted with chloroform (15 ml, 3 times). The obtained organic phase was dehydrated and dried with saturated sodium chloride aqueous solution and then anhydrous sodium sulfate in this order and the solvent was distilled away under reduced pressure. The precipitated solid was washed with diisopropyl ether and filtered to give 52 mg of the target product as a light yellow solid.
Melting point: 238° C. to 241° C.

Synthesis Example 5

3-Isopropyl-N-(4-methyl-1,2,5-oxadiazol-3-yl)-5-(trifluoromethyl)-[1,2,4]triazolo[4,3-a]pyridine-8-carboxamide (Compound No. 3-001)

To the mixed solution of 165 mg (0.60 mmol) of 3-isopropyl-5-(trifluoromethyl)-[1,2,4]triazolo[4,3-a]pyridine-8-carboxylic acid, 0.1 ml of N,N-dimethylformamide, and 5 ml of methylene chloride, 83 mg (0.66 mmol) of oxalyl chloride was added at room temperature. After completion of the addition, the reaction mixture was stirred for 20 minutes at room temperature. After completion of stirring, the mixed solution of 119 mg (1.21 mmol) of 4-methyl-1, 2,5-oxadiazol-3-amine, 122 mg (1.21 mmol) of triethylamine, and 3 ml of methylene chloride was added. After completion of the addition, the reaction mixture was stirred for 1 hour at room temperature. After completion of stirring, the solvent was distilled away under reduced pressure. The obtained residue was purified with silica gel chromatography (n-hexane:ethyl acetate=9:1 to 2:1) to give 168 mg of the target product as a white solid.

Melting point: 185° C. to 186° C.

Synthesis Example 6

5-Chloro-3-isopropyl-N-(1-methyl-1H-tetrazol-5-yl)-[1,2,4]triazolo[4,3-a]pyridine-8-carboxamide (Compound No. 2-004)

To the mixed solution of 500 mg (1.97 mmol) of methyl 5-chloro-3-isopropyl-[1,2,4]triazolo[4,3-a]pyridine-8-carboxylate, 3 ml of methanol, and 1 ml of water, 2 ml of 1 M sodium hydroxide aqueous solution was added under cooling with ice. After completion of the addition, the reaction mixture was stirred for 1 hour at room temperature. After completion of stirring, the reaction was terminated by adding 2.5 ml of 1 M hydrochloric acid. The solvent in the reaction liquid was distilled away under reduced pressure to give crude 5-chloro-3-isopropyl-[1,2,4]triazolo[4,3-a]pyridine-8-carboxylic acid. To the mixed solution of 500 mg (1.97 mmol) of the obtained crude 5-chloro-3-isopropyl-[1,2,4]triazolo[4,3-a]pyridine-8-carboxylic acid, 390 mg (3.94 mmol) of 1-methyl-1H-tetrazol-5-amine, 24 mg (0.19 mmol) of 4-(dimethylamino)pyridine, and 5 ml of pyridine, 469 mg (3.94 mmol) of thionyl chloride was added at room temperature. After completion of the addition, the reaction mixture was stirred for 2 days at room temperature. After completion of stirring, the reaction was terminated by adding water and the reaction liquid was extracted with ethyl acetate (50 ml, 2 times). The obtained organic phase was dehydrated and dried with saturated sodium chloride aqueous solution and then anhydrous sodium sulfate in this order and the solvent was distilled away under reduced pressure. The obtained residue was purified with silica gel chromatography (n-hexane:ethyl acetate=4:1 to 1:1) to give 140 mg of the target product as a light yellow solid.

Melting point: 189° C. to 190° C.

Synthesis Example 7

3-(Methoxymethyl)-N-(1-methyl-1H-tetrazol-5-yl)-5-(trifluoromethyl)-[1,2,4]triazol o[4,3-a]pyridine-8-carboxamide (Compound No. 2-010)

Step 1; Synthesis of methyl 2-(2-(2-methoxyacetyl)hydrazinyl)-6-(trifluoromethyl)nicotinate (Compound No. A1-05a)

To the mixed solution of 1.0 g (4.25 mmol) of methyl 2-hydrazinyl-6-(trifluoromethyl)nicotinate, 473 mg (4.68 mmol) of triethylamine, and 20 ml of tetrahydrofuran, 2 ml of tetrahydrofuran solution of 508 mg (4.68 mmol) of methoxyacetyl chloride was added under cooling with ice. After completion of the addition, the reaction solution was stirred for 30 minutes under cooling with ice. After completion of the reaction, the solvent in the reaction solution was distilled away under reduced pressure. After 15 ml of water was added, the mixture was extracted with chloroform (30 ml, 1 time and 10 ml, 2 times). The obtained organic phase was dehydrated and dried with saturated sodium chloride aqueous solution and then anhydrous sodium sulfate in this order and the solvent was distilled away under reduced pressure. The precipitated solid was washed with diisopropyl ether and filtered to give 1.16 g of the target product as a white solid.

Melting point: 76° C. to 77° C.

Step 2; Synthesis of methyl 3-(methoxymethyl)-5-(trifluoromethyl)-[1,2,4]triazolo[4,3-a]pyridine-8-carboxylate (Compound No. B1-05a)

To the mixed solution of 1.16 g (3.78 mmol) of methyl 2-(2-(2-methoxyacetyl)hydrazinyl)-6-(trifluoromethyl)nicotinate and 17 ml of toluene, 1.74 g (11.3 mmol) of phosphoryl chloride was added at room temperature. After completion of the addition, the reaction solution was stirred for 5 hours under heating to reflux. After completion of the reaction, the reaction solution was poured into separately prepared 20 ml of water. A sodium hydrogen carbonate aqueous solution was added to adjust the pH to 8 to 9 and thereafter the resultant mixture was extracted with ethyl acetate (30 ml, 1 time and 15 ml, 3 times). The combined organic phase was dehydrated and dried with saturated sodium chloride aqueous solution and then anhydrous sodium sulfate in this order and the solvent was distilled away under reduced pressure. The precipitated solid was washed with diisopropyl ether and filtered to give 721 mg of the target product as a yellow solid.

Melting point: 95° C. to 97° C.

Step 3; Synthesis of 3-(methoxymethyl)-5-(trifluoromethyl)-[1,2,4]triazolo[4,3-a]pyridine-8-carboxylic acid (Compound No. C1-05)

To the mixed solution of 693 mg (2.39 mmol) of methyl 3-(methoxymethyl)-5-(trifluoromethyl)-[1,2,4]triazolo[4,3-a]pyridine-8-carboxylate and 7 ml of ethanol, 7 ml of aqueous solution of 115 mg (2.87 mmol) of sodium hydroxide was added under cooling with ice. After completion of the addition, the reaction solution was stirred for 30 minutes under cooling with ice. After completion of the reaction, 1 M hydrochloric acid was added to the reaction solution to adjust the pH to 2 to 3. Thereafter, the resultant mixture was extracted with chloroform (30 ml, 1 time and 15 ml, 3 times). The obtained organic phase was dehydrated and dried with saturated sodium chloride aqueous solution and anhydrous sodium sulfate in this order and the solvent was distilled away under reduced pressure. The precipitated solid was washed with diisopropyl ether and filtered to give 553 mg of the target product as a yellow solid.

Melting point: 111° C. to 112° C.

Step 4; Synthesis of 3-(methoxymethyl)-N-(1-methyl-1H-tetrazol-5-yl)-5-(trifluoromethyl)-[1,2,4]triazolo[4,3-a]pyridine-8-carboxamide To the mixed solution of 100 mg (0.36 mmol) of 3-(methoxymethyl)-5-(trifluoromethyl)-[1,2,4]triazolo[4,3-a]pyridine-8-carboxylic acid, 72 mg (0.73 mmol) of 1-methyl-1H-tetrazol-5-amine, 5 mg of 4-dimethylaminopyridine, and 2 ml of pyridine, 87 mg (0.73 mmol) of thionyl chloride was added at room temperature. After completion of the addition, the reaction solution was stirred at room temperature for 30 minutes. After completion of the reaction, the solvent in the reaction solution was distilled away under reduced pressure. To the obtained residue, 1 mol/L hydrochloric acid was added to adjust the pH to 2 to 3. Thereafter, the resultant mixture was extracted with chloroform (15 ml, 3 times). The obtained organic phase was dehydrated and dried with saturated sodium chloride aqueous solution and anhydrous sodium sulfate in this order and the solvent was distilled away under reduced pressure. The precipitated solid was washed with diisopropyl ether and filtered to give 76 mg of the target product as a white solid.
Melting point: 205° C. to 209° C.

Synthesis Example 8

N-(5-Methyl-1,3,4-oxadiazol-2-yl)-3-(methylthio)-5-(trifluoromethyl)-[1,2,4]triazol o[4,3-a]pyridine-8-carboxamide (Compound No. 1-018)

Step 1; Synthesis of methyl 3-thioxo-5-(trifluoromethyl)-2,3-dihydro-[1,2,4]triazolo[4,3-a]pyridine-8-carboxylate The mixed solution of 1.0 g (4.25 mmol) of methyl 2-hydrazinyl-6-(trifluoromethyl)nicotinate, 795 mg (4.46 mmol) of 1,1'-thiocarbonyldiimidazole, and 10 ml of N,N-dimethylformamide was stirred at 60° C. for 3 hours. After completion of the reaction, the solvent in the reaction solution was distilled away under reduced pressure. The precipitated solid was washed with diisopropyl ether and filtered to give 534 mg of the mixture of the target product and imidazole as a red solid.

Step 2; Synthesis of methyl 3-(methylthio)-5-(trifluoromethyl)-[1,2,4]triazolo[4,3-a]pyridine-8-carboxylate To 10 ml of N,N-dimethylformamide solution of 534 mg of methyl 3-thioxo-5-(trifluoromethyl)-2,3-dihydro-[1,2,4]triazolo[4,3-a]pyridine-8-carboxylate obtained in Step 1 containing imidazole, 402 mg of methyl iodide was added at room temperature. After completion of the addition, the reaction solution was stirred at room temperature for 1.5 hours. After completion of the reaction, the solvent in the reaction solution was distilled away under reduced pressure. 15 ml of water was added to the obtained residue and the resultant mixture was extracted with chloroform (15 ml, 3 times). The obtained organic phase was dehydrated and dried with saturated sodium chloride aqueous solution and anhydrous sodium sulfate in this order and the solvent was distilled away under reduced pressure. The precipitated solid was washed with diisopropyl ether and filtered to give 336 mg of the target product as a yellow solid.
Melting point: 163° C. to 167° C.

Step 3; Synthesis of 3-(methylthio)-5-(trifluoromethyl)-[1,2,4]triazolo[4,3-a]pyridine-8-carboxylic acid To the mixed solution of 332 mg (1.14 mmol) of methyl 3-(methylthio)-5-(trifluoromethyl)-[1,2,4]triazolo[4,3-a]pyridine-8-carboxylate and 3 ml of methanol, 2.8 ml (1.4 mmol) of 0.5 mol/L sodium hydroxide aqueous solution was added under cooling with ice. After completion of the addition, the reaction solution was stirred for 1 hour under cooling with ice. After completion of the reaction, 1 mol/L hydrochloric acid was added to the reaction solution to adjust the pH to 2 to 3. The precipitated solid was washed with 1 mol/L hydrochloric acid, water, and diisopropyl ether and filtered to give 228 mg of the target product as a yellow solid.
Melting point: 158° C. to 162° C.

Step 4; Synthesis of N-(5-methyl-1,3,4-oxadiazol-2-yl)-3-(methylthio)-5-(trifluoromethyl)-[1,2,4]triazolo[4,3-a]pyridine-8-carboxamide To the mixed solution of 100 mg (0.36 mmol) of 3-(methylthio)-5-(trifluoromethyl)-[1,2,4]triazolo[4,3-a]pyridine-8-carboxylic acid, 71 mg (0.72 mmol) of 5-methyl-1,3,4-oxadiazol-2-amine, 4 mg of 4-dimethylaminopyridine, and 2 ml of pyridine, 129 mg (1.08 mmol) of thionyl chloride was added under cooling with ice. After completion of the addition, the reaction solution was stirred at room temperature for 20 minutes. After completion of the reaction, the solvent in the reaction solution was distilled away under reduced pressure. To the obtained residue, 1 mol/L hydrochloric acid was added to adjust the pH to 2 to 3. Thereafter, the resultant mixture was extracted with chloroform (15 ml, 3 times). The obtained organic phase was dehydrated and dried with saturated sodium chloride aqueous solution and anhydrous sodium sulfate in this order and the solvent was distilled away under reduced pressure. The precipitated solid was washed with diisopropyl ether and filtered to give 100 mg of the target product as a yellow solid.
Melting point: 230° C. to 233° C.

Synthesis Example 9

3-Isopropyl-N-(1-methyl-1H-tetrazol-5-yl)-5-(trifluoromethyl)-[1,2,4]triazolo[4,3-a]pyridine-8-carbothioamide (compound No. 2-039)

The mixed solution of 100 mg (0.28 mmol) of 3-isopropyl-N-(1-methyl-1H-tetrazol-5-yl)-5-(trifluoromethyl)-[1,2,4]triazolo[4,3-a]pyridine-8-carboxamide, 114 mg (0.28 mmol) of Lawesson's reagent [2,4-bis(4-methoxyphenyl)-1,3,2,4-dithiadiphosphetane-2,4-disulfide], and 3 ml of toluene was stirred at 110° C. for 5 hours. After completion of stirring, 114 mg (0.28 mmol) of Lawesson's reagent was added to the reaction solution and the resultant solution was additionally stirred at 110° C. for 3 hours. After completion of the reaction, 5 ml of 0.1 N hydrochloric acid was added to the reaction solution and the resultant mixture was extracted with ethyl acetate (15 ml, 1 time). The obtained organic phase was dehydrated and dried with saturated sodium chloride aqueous solution and anhydrous sodium sulfate in this order and the solvent was distilled away under reduced pressure. The obtained residue was purified with the medium pressure preparative liquid chromatography eluting the residue with n-hexane-ethyl acetate (gradient from 4:1 to 3:7) to give 66 mg of the target product as a yellow solid.
Melting point: 198° C. to 200° C.

Synthesis Example 10

3-Allyl-N-(5-methyl-1,3,4-oxadiazol-2-yl)-5-(trifluoromethyl)-[1,2,4]triazolo[4,3-a]pyridine-8-carboxamide and N-(5-methyl-1,3,4-oxadiazol-2-yl)-3-(prop-1-en-1-yl)-5-(trifluoromethyl)-[1,2,4]triazolo[4,3-a]pyridine-8-carboxamide (compound No. 1-159 and compound No. 1-159*)

Step 1; Synthesis of methyl 3-allyl-5-(trifluoromethyl)-[1,2,4]triazolo[4,3-a]pyridine-8-carboxylate and methyl 3-(prop-1-en-1-yl)-5-(trifluoromethyl)-[1,2,4]triazolo[4,3-a]pyridine-8-carboxylate To the mixed solution of 1.20 g (3.96 mmol) of methyl 2-(2-(but-3-enoyl)hydrazinyl)-6-(trifluoromethyl)nicotinate synthesized in a similar method to the Step 1 in Synthesis Example 7 and 18 ml of toluene, 1.82 g (11.9 mmol) of phosphoryl chloride was added at room temperature. After completion of the addition, the reaction solution was stirred for 5 hours under heating to reflux. After completion of the reaction, the reaction solution was poured into separately prepared 20 ml of water. A sodium hydrogen carbonate aqueous solution was added to adjust the pH to 8 to 9 and thereafter the resultant mixture was extracted with ethyl acetate (30 ml, 1 time and 15 ml, 3 times). The combined organic phase was dehydrated and dried with saturated sodium chloride aqueous solution and then anhydrous sodium sulfate in this order and the solvent was distilled away under reduced pressure. The obtained residue was purified with the medium pressure preparative liquid chromatography eluting the residue with n-hexane-ethyl acetate (gradient from 7:3 to 0:1) to give 730 mg of the target product as a white solid [methyl 3-allyl-5-(trifluoromethyl)-[1,2,4]triazolo[4,3-a]pyridine-8-carboxylate/methyl 3-(prop-1-en-1-yl)-5-(trifluoromethyl)-[1,2,4]triazolo[4,3-a]pyridine-8-carboxylate=4/1].

$^1$H NMR of methyl 3-allyl-5-(trifluoromethyl)-[1,2,4]triazolo[4,3-a]pyridine-8-carboxylate (CDCl$_3$, Me$_4$Si, 300 MHz) δ 7.97 (d, 1H, J=7.2 Hz), 7.44 (d, 1H, J=7.2 Hz), 6.31-6.20 (m, 1H), 5.26-5.12 (m, 2H), 4.10 (s, 3H), 4.00 (dd, 2H, J=6.3 Hz, 1.2 Hz).

$^1$H NMR of methyl 3-(prop-1-en-1-yl)-5-(trifluoromethyl)-[1,2,4]triazolo[4,3-a]pyridine-8-carboxylate (CDCl$_3$, Me$_4$Si, 300 MHz) δ 7.94 (d, 1H, J=6.0 Hz), 7.42 (d, 1H, J=6.0 Hz), 7.00-6.90 (m, 1H), 6.66-6.58 (m, 1H), 4.10 (s, 3H), 2.04 (dd, 3H, J=6.6 Hz, 1.8 Hz).

Melting point: 121° C. to 123° C.

Step 2; Synthesis of 3-allyl-5-(trifluoromethyl)-[1,2,4]triazolo[4,3-a]pyridine-8-carboxylic acid and 3-(prop-1-en-1-yl)-5-(trifluoromethyl)-[1,2,4]triazolo[4,3-a]pyridine-8-carboxylic acid To the mixed solution of 720 mg (2.65 mmol) of the mixture of methyl 3-allyl-5-(trifluoromethyl)-[1,2,4]triazolo[4,3-a]pyridine-8-carboxylate and methyl 3-(prop-1-en-1-yl)-5-(trifluoromethyl)-[1,2,4]triazolo[4,3-a]pyridine-8-carboxylate and 10 ml of ethanol, 7.0 ml (3.5 mmol) of 0.5 mol/L sodium hydroxide aqueous solution was added under cooling with ice. After completion of the addition, the reaction solution was stirred for 30 minutes under cooling with ice. After completion of the reaction, 1 M hydrochloric acid was added to the reaction solution to adjust the pH to 2 to 3. Thereafter, the resultant mixture was extracted with ethyl acetate (15 ml, 2 times). The obtained organic phase was dehydrated and dried with saturated sodium chloride aqueous solution and anhydrous sodium sulfate in this order and the solvent was distilled away under reduced pressure to give 467 mg of the target product as a white solid [3-allyl-5-(trifluoromethyl)-[1,2,4]triazolo[4,3-a]pyridine-8-carboxylic acid/3-(prop-1-en-1-yl)-5-(trifluoromethyl)-[1,2,4]triazolo[4,3-a]pyridine-8-carboxylic acid=4/1].

$^1$H NMR of 3-allyl-5-(trifluoromethyl)-[1,2,4]triazolo[4,3-a]pyridine-8-carboxylic acid (CDCl$_3$, Me$_4$Si, 300 MHz) δ 8.25 (d, 1H, J=7.5 Hz), 7.61 (d, 1H, 7.5 Hz), 6.34-6.20 (m, 1H), 5.35-5.22 (m, 2H), 4.00 (dd, 2H, J=6.3 Hz, 1.2 Hz). (The proton peak of CO$_2$H was not observed.)

$^1$H NMR of 3-(prop-1-en-1-yl)-5-(trifluoromethyl)-[1,2,4]triazolo[4,3-a]pyridine-8-carboxylic acid (CDCl$_3$, Me$_4$Si, 300 MHz) δ 8.22 (d, 1H, J=8.1 Hz), 7.58 (d, 1H, J=8.1 Hz), 7.12-7.00 (m, 1H), 6.67-6.60 (m, 1H), 2.07 (dd, 3H, J=6.9 Hz, 1.8 Hz). (The proton peak of CO$_2$H was not observed.)

Melting point: 103° C. to 104° C.

Step 3; Synthesis of 3-allyl-N-(5-methyl-1,3,4-oxadiazol-2-yl)-5-(trifluoromethyl)[1,2,4]triazolo[4,3-a]pyridine-8-carboxamide and N-(5-methyl-1,3,4-oxadiazol-2-yl)-3-(prop-1-en-1-yl)-5-(trifluoromethyl)-[1,2,4]triazolo[4,3-a]pyridine-8-carboxamide To the mixed solution of 100 mg (0.37 mmol) of the mixture of 3-allyl-5-(trifluoromethyl)-[1,2,4]triazolo[4,3-a]pyridine-8-carboxylic acid and 3-(prop-1-en-1-yl)-5-(trifluoromethyl)-[1,2,4]triazolo[4,3-a]pyridine-8-carboxylic acid, 55 mg (0.55 mmol) of 5-methyl-1,3,4-oxadiazol-2-amine, 5 mg (0.04 mmol) of 1-hydroxy-7-azabenzotriazole and 2 ml of N,N-dimethylformamide, 106 mg (0.55 mmol) of 1-ethyl-3-(3-dimethylaminopropyl)carbodiimide hydrochloride was added at room temperature. After completion of the addition, the reaction mixture was stirred for 1 hour at room temperature. After completion of stirring, 3 ml of 1 mol/l hydrochloric acid was added and the reaction liquid was extracted with ethyl acetate (10 ml, 2 times). The obtained organic phase was washed with water. Thereafter, the organic phase was dried over anhydrous sodium sulfate and the solvent was distilled away under reduced pressure. The obtained solid was purified by recrystallization from ethyl acetate to give 67 mg of the target product as a light yellow solid. [3-allyl-N-(5-methyl-1,3,4-oxadiazol-2-yl)-5-(trifluoromethyl)-[1,2,4]triazolo[4,3-a]pyridine-8-carboxamide/N-(5-methyl-1,3,4-oxadiazol-2-yl)-3-(prop-1-en-1-yl)-5-(trifluoromethyl)-[1,2,4]triazolo[4,3-a]pyridine-8-carboxamide=4/1].

$^1$H NMR of 3-allyl-N-(5-methyl-1,3,4-oxadiazol-2-yl)-5-(trifluoromethyl)-[1,2,4]triazolo[4,3-a]pyridine-8-carboxamide (CDCl$_3$, Me$_4$Si, 300 MHz) δ 12.9 (brs, 1H), 8.42 (d, 1H, J=7.5 Hz), 7.63 (d, 1H, J=7.5 Hz), 6.38-6.24 (m, 1H), 5.36-5.23 (m, 2H), 4.03 (dd, 2H, J=6.9 Hz, 1.2 Hz), 2.59 (s, 3H).

$^1$H NMR of N-(5-methyl-1,3,4-oxadiazol-2-yl)-3-(prop-1-en-1-yl)-5-(trifluoromethyl)-[1,2,4]triazolo[4,3-a]pyridine-8-carboxamide (CDCl$_3$, Me$_4$Si, 300 MHz) δ 12.9 (brs, 1H), 8.38 (d, 1H, J=6.9 Hz), 7.60 (d, 1H, J=6.9 Hz), 7.12-7.00 (m, 1H), 6.69-6.62 (m, 1H), 2.60 (s, 3H), 2.09 (dd, 3H, J=6.6 Hz, 1.8 Hz).

Melting point: 159° C. to 161° C.

Synthesis Example 11

3-Allyl-N-(1-methyl-1H-tetrazol-5-yl)-5-(trifluoromethyl)-[1,2,4]triazolo[4,3-a]pyridine-8-carboxamide and N-(1-methyl-1H-tetrazol-5-yl)-3-(prop-1-en-1-yl)-5-(trifluoromethyl)-[1,2,4]triazolo[4,3-a]pyridine-8-carboxamide (Compound No. 2-105 and compound No. 2-105*)

To the mixed solution of 100 mg (0.37 mmol) of the mixture of 3-allyl-5-(trifluoromethyl)-[1,2,4]triazolo[4,3-a]pyridine-8-carboxylic acid and 3-(prop-1-en-1-yl)-5-(trifluoromethyl)-[1,2,4]triazolo[4,3-a]pyridine-8-carboxylic acid synthesized in Step 2 of Synthesis Example 7, 56 mg (0.57 mmol) of 1-methyl-1H-tetrazol-5-amine, and 2 ml of pyridine, 66 mg (0.55 mmol) of thionyl chloride was added at a temperature of 15° C. or lower. After completion of the addition, the temperature of the reaction solution was retained at 15° C. or lower and stirred for 1.5 hours. After completion of the reaction, the solvent in the reaction solution was distilled away under reduced pressure. To the obtained residue, 1.5 ml of acetonitrile and 2 ml of 1 mol/L hydrochloric acid were added and the resultant mixture was extracted with ethyl acetate (10 ml, 2 times). The obtained organic phase was dehydrated and dried with saturated sodium chloride aqueous solution and anhydrous sodium sulfate in this order and the solvent was distilled away under reduced pressure. The precipitated solid was washed with ethyl acetate and filtered to give 27 mg of the target product as a light brown solid. [3-allyl-N-(1-methyl-1H-tetrazol-5-yl)-5-(trifluoromethyl)-[1,2,4]triazolo[4,3-a]pyridine-8-carboxamide/N-(1-methyl-1H-tetrazol-5-yl)-3-(prop-1-en-1-yl)-5-(trifluoromethyl)-[1,2,4]triazolo[4,3-a]pyridine-8-carboxamide=3/1].

$^1$H NMR of 3-allyl-N-(1-methyl-1H-tetrazol-5-yl)-5-(trifluoromethyl)-[1,2,4]triazolo[4,3-a]pyridine-8-carboxamide (CDCl$_3$, Me$_4$Si, 300 MHz) δ 12.5 (brs, 1H), 8.40 (d, 1H, J=7.5 Hz), 7.65 (d, 1H, J=7.5 Hz), 6.37-6.24 (m, 1H), 5.37-5.24 (m, 2H), 4.13 (s, 3H), 4.06 (dd, 2H, J=6.6 Hz, 1.2 Hz).

$^1$H NMR of N-(1-methyl-1H-tetrazol-5-yl)-3-(prop-1-en-1-yl)-5-(trifluoromethyl)-[1,2,4]triazolo[4,3-a]pyridine-8-carboxamide (CDCl$_3$, Me$_4$Si, 300 MHz) δ 12.5 (brs, 1H), 8.36 (d, 1H, J=7.2 Hz), 7.62 (d, 1H, J=7.2 Hz), 7.13-7.01 (m, 1H), 6.70-6.62 (m, 1H), 4.13 (s, 3H), 2.10 (dd, 3H, J=6.6 Hz, 1.5 Hz).

Melting point: 164° C. to 167° C.

Synthesis Example 12

3-(2,2-Dichloro-1-methylcyclopropyl)-N-ethyl-N-(5-methyl-1,3,4-oxadiazol-2-yl)-5-(trifluoromethyl)-[1,2,4]triazolo[4,3-a]pyridine-8-carboxamide (compound No. 1-174)

To 1 ml of N,N-dimethylformamide solution of 67 mg of 3-(2,2-dichloro-1-methylcyclopropyl)-N-(5-methyl-1,3,4-oxadiazol-2-yl)-5-(trifluoromethyl)-[1,2,4]triazolo[4,3-a]pyridine-8-carboxamide, 31 mg of potassium carbonate and 48 mg of ethyl iodide were added at room temperature. After completion of the addition, the reaction mixture was stirred at 55° C. for 30 minutes. After completion of the reaction, 2 ml of water was added and the resultant mixture was extracted with ethyl acetate (3 ml, 2 times). The obtained organic phase was dehydrated and dried with saturated sodium chloride aqueous solution and anhydrous magnesium sulfate in this order and the solvent was distilled away under reduced pressure. The obtained residue was purified with the medium pressure preparative liquid chromatography eluting the residue with n-hexane-ethyl acetate (gradient from 2:1 to 0:1) to give 21 mg of the target product as a colorless resinous substance.

$^1$H NMR (CDCl$_3$, Me$_4$Si, 300 MHz) δ 7.72 (d, 1H, J=7.8 Hz), 7.53 (d, 1H, J=7.8 Hz), 4.15 (q, 2H, J=7.2 Hz), 2.78 (d, 1H, J=7.8 Hz), 2.38 (s, 3H), 1.83 (d, 1H, J=7.8 Hz), 1.80 (s, 3H), 1.43 (t, 3H, J=7.2 Hz).

The compound of the present invention can be synthesized in accordance with Synthesis Examples described above. Examples of the compounds of the present invention produced in similar methods to Synthesis Example 1 to Synthesis Example 9 are listed in Fourth Table to Tenth Table. The present invention, however, is not limited to these examples. In Tables, Me is methyl group. Similarly, Et is ethyl group, Pr is propyl group, Pen is pentyl group, Hex is hexyl group, Ph is phenyl group, Bn is benzyl group, i- is iso, c- is cyclo, and t- is tertiary.

The substituents of D-2, D-3a, D-4a, D-5, D-6a, D-7a, D-8a, D-9, D-9a, D-9b, D-10a, D-11, D-12, D-13a, D-14, D-15, D-16a, D-16m, D-17, D-17a, D-17b, D-18, D-19, D-20a, D-23a, and D-24f in Tables are the following structures.

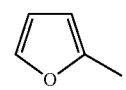
D-2

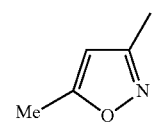
D-3a

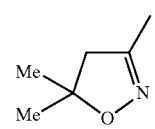
D-4a

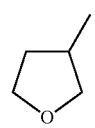
D-5

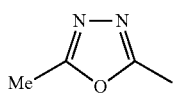
D-6a

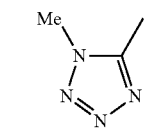
D-7a

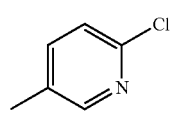
D-8a

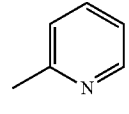
D-9

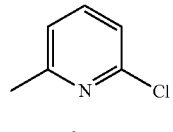
D-9a

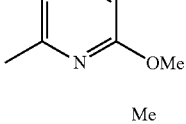
D-9b

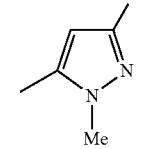
D-10a

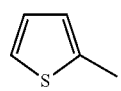
D-11

-continued

D-12 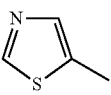

D-13a 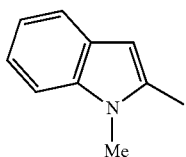

D-14 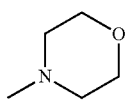

D-15 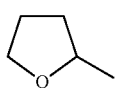

D-16a 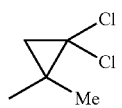

D-16m 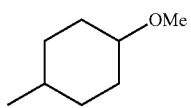

D-17 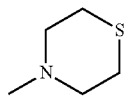

D-17a 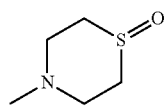

D-17b 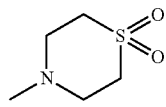

D-18 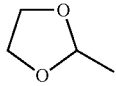

D-19 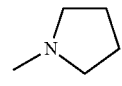

D-20a 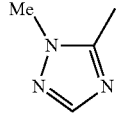

D-23a 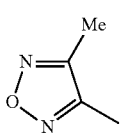

-continued

D-24f 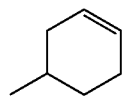

In Tables, "*1" is "Resinous". "*2" means that decomposition was observed at the time of melting point measurement. "*3" is a mixture of the compounds 1-158 and 1-158* of the present invention that are isomers having different structures and the ratio thereof 1-158/1-158* equals to 9/1. As described in Synthesis Example 10, "*4" is the mixture of the compounds 1-159 and 1-159* of the present invention that are isomers having different structures and the ratio thereof 1-159/1-159* equals to 4/1. As described in Synthesis Example 11, "*5" is the mixture of the compounds 2-105 and 2-105* of the present invention that are isomers having different structures and the ratio thereof 2-105/2-105* equals to 3/1.

FOURTH TABLE

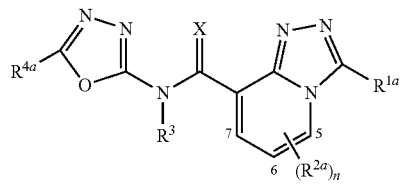

TABLE 27

| No. | $R^{1a}$ | $(R^{2a})_n$ | X | $R^3$ | $R^{4a}$ | Melting point (° C.) |
|---|---|---|---|---|---|---|
| 1-001 | H | 5-CF$_3$ | O | H | Me | 220-223 |
| 1-002 | Me | 5-CF$_3$ | O | H | Me | 242-245 |
| 1-003 | i-Pr | 5-Me | O | H | Me | *2 |
| 1-004 | i-Pr | 5-CF$_3$ | O | H | Me | 176-178 |
| 1-005 | i-Pr | 5-CF$_3$ | O | H | Et | 176-180 |
| 1-006 | i-Pr | 5-CF$_3$ | O | H | Bn | 141-150 |
| 1-007 | i-Pr | 5-CF$_3$ | O | H | Ph | 173-177 |
| 1-008 | i-Pr | 5-CF$_3$ | O | H | D-2 | 152-156 |
| 1-009 | i-Pr | 5-SMe | O | H | Me | *2 |
| 1-010 | c-Pr | 5-CF$_3$ | O | H | Me | 157-165 |
| 1-011 | 3-Pen | 5-CF$_3$ | O | H | Me | 171-174 |
| 1-012 | Ph | 5-CF$_3$ | O | H | Me | 266-270 |
| 1-013 | Cl | 5-CF$_3$ | O | H | Me | 238-241 |
| 1-014 | Br | 5-CF$_3$ | O | H | Me | 252-260 |
| 1-015 | CH$_2$OMe | 5-CF$_3$ | O | H | Me | 115-125 |
| 1-016 | 4-MeO—Ph | 5-CF$_3$ | O | H | Me | 205-208 |
| 1-017 | 4-Cl—Ph | 5-CF$_3$ | O | H | Me | 256-258 |
| 1-018 | SMe | 5-CF$_3$ | O | H | Me | 230-233 |
| 1-019 | CH$_2$O(CH$_2$)$_2$OMe | 5-CF$_3$ | O | H | Me | 90-91 |
| 1-020 | CH$_2$OCH$_2$CF$_3$ | 5-CF$_3$ | O | H | Me | 148-149 |
| 1-021 | CH(CH$_3$)CH$_2$CH$_3$ | 5-CF$_3$ | O | H | Me | 160-162 |
| 1-022 | D-3a | 5-CF$_3$ | O | H | Me | 218-221 |
| 1-023 | i-Pr | 6-CF$_3$ | O | H | Me | 160-162 |
| 1-024 | n-Pr | 5-CF$_3$ | O | H | Me | 172-176 |
| 1-025 | CH$_2$OPh | 5-CF$_3$ | O | H | Me | 188-190 |
| 1-026 | c-Pen | 5-CF$_3$ | O | H | Me | 170-171 |
| 1-027 | CH$_2$OEt | 5-CF$_3$ | O | H | Me | 141-143 |
| 1-028 | tBu | 5-CF$_3$ | O | H | Me | 161-165 |
| 1-029 | D-4a | 5-CF$_3$ | O | H | Me | 172-176 |
| 1-030 | CH$_2$SMe | 5-CF$_3$ | O | H | Me | 153-155 |
| 1-031 | CH$_2$SCH$_2$CF$_3$ | 5-CF$_3$ | O | H | Me | 162-163 |
| 1-032 | SEt | 5-CF$_3$ | O | H | Me | 182-184 |
| 1-033 | SCH(CH$_3$)$_2$ | 5-CF$_3$ | O | H | Me | 186-188 |
| 1-034 | S(O)Et | 5-CF$_3$ | O | H | Me | 192-193 |
| 1-035 | S(O)CH(CH$_3$)$_2$ | 5-CF$_3$ | O | H | Me | 153-157 |
| 1-036 | CH$_2$S(O)Me | 5-CF$_3$ | O | H | Me | 190-191 |

TABLE 27-continued

| No. | $R^{1a}$ | $(R^{2a})_n$ | X | $R^3$ | $R^{4a}$ | Melting point (° C.) |
|---|---|---|---|---|---|---|
| 1-037 | CH$_2$S(O)$_2$Me | 5-CF$_3$ | O | H | Me | *1 |
| 1-038 | CH$_2$S(O)CH$_2$CF$_3$ | 5-CF$_3$ | O | H | Me | 200-202 |
| 1-039 | CH$_2$S(O)$_2$CH$_2$CF$_3$ | 5-CF$_3$ | O | H | Me | *1 |
| 1-040 | S(O)$_2$Me | 5-CF$_3$ | O | H | Me | *1 |
| 1-041 | S(O)$_2$Et | 5-CF$_3$ | O | H | Me | *1 |
| 1-042 | CH$_2$C(O)OEt | 5-CF$_3$ | O | H | Me | 187-189 |
| 1-043 | 4-Me—Ph | 5-CF$_3$ | O | H | Me | 221-223 |
| 1-044 | 4-F—Ph | 5-CF$_3$ | O | H | Me | 203-208 |
| 1-045 | 4-CF$_3$—Ph | 5-CF$_3$ | O | H | Me | 196-198 |
| 1-046 | 3-MeO—Ph | 5-CF$_3$ | O | H | Me | 178-182 |
| 1-047 | 2-MeO—Ph | 5-CF$_3$ | O | H | Me | 180-185 |
| 1-048 | CH$_2$C(O)OH | 5-CF$_3$ | O | H | Me | 139-141 |

TABLE 28

| No. | $R^{1a}$ | $(R^{2a})_n$ | X | $R^3$ | $R^{4a}$ | Melting point (° C.) |
|---|---|---|---|---|---|---|
| 1-049 | CH$_2$C(O)OCH(CH$_3$)$_2$ | 5-CF$_3$ | O | H | Me | 157-159 |
| 1-050 | i-Pr | 5-CF$_3$ | O | H | H | 171-175 |
| 1-051 | i-Pr | 5-CF$_3$ | O | H | c-Pr | 161-162 |
| 1-052 | i-Pr | 5-CF$_3$ | O | H | (CH$_2$)$_2$OMe | 125-135 |
| 1-053 | i-Pr | 5-CF$_2$H | O | H | Me | 160-162 |
| 1-054 | D-8a | 5-CF$_3$ | O | H | Me | 240-243 |
| 1-055 | D-9a | 5-CF$_3$ | O | H | Me | 205-208 |
| 1-056 | D-10a | 5-CF$_3$ | O | H | Me | 274-275 |
| 1-057 | D-11 | 5-CF$_3$ | O | H | Me | 222-224 |
| 1-058 | D-12 | 5-CF$_3$ | O | H | Me | 213-216 |
| 1-059 | D-13a | 5-CF$_3$ | O | H | Me | 272-274 |
| 1-060 | CH$_2$C(O)O(CH$_2$)$_2$OMe | 5-CF$_3$ | O | H | Me | 152-153 |
| 1-061 | CH$_2$C(O)NHCH(CH$_3$)$_2$ | 5-CF$_3$ | O | H | Me | 222-227 |
| 1-062 | CH$_2$OC(O)Me | 5-CF$_3$ | O | H | Me | 165-167 |
| 1-063 | S(CH$_2$)$_2$OMe | 5-CF$_3$ | O | H | Me | 99-101 |
| 1-064 | SCH$_2$CH=CH$_2$ | 5-CF$_3$ | O | H | Me | 213-217 |
| 1-065 | SCH$_2$C≡CH | 5-CF$_3$ | O | H | Me | 114-117 |
| 1-066 | i-Pr | 5-CF$_2$CF$_3$ | O | H | Me | 193-195 |
| 1-067 | CH$_2$OH | 5-CF$_3$ | O | H | Me | 236-238 |
| 1-068 | CHO | 5-CF$_3$ | O | H | Me | 222-223 |
| 1-069 | CH$_2$(4-MeO—Ph) | 5-CF$_3$ | O | H | Me | 172-174 |
| 1-070 | 3,5-(MeO)$_2$—Ph | 5-CF$_3$ | O | H | Me | 228-229 |
| 1-071 | 3,5-(Cl)$_2$—Ph | 5-CF$_3$ | O | H | Me | 254-256 |
| 1-072 | CH=NOMe | 5-CF$_3$ | O | H | Me | 204-207 |
| 1-073 | S(O)(CH$_2$)$_2$OMe | 5-CF$_3$ | O | H | Me | 199-201 |
| 1-074 | S(O)CH$_2$CH=CH$_2$ | 5-CF$_3$ | O | H | Me | 134-137 |
| 1-075 | i-Pr | 5-CF$_3$-6-Me | O | H | Me | 168-169 |
| 1-076 | NMe$_2$ | 5-CF$_3$ | O | H | Me | 184-185 |
| 1-077 | S(O)CH$_2$C≡CH | 5-CF$_3$ | O | H | Me | 205-212 |
| 1-078 | CH(Me)SMe | 5-CF$_3$ | O | H | Me | 137-139 |
| 1-079 | CH(Me)S(O)Me | 5-CF$_3$ | O | H | Me | 127-129 |
| 1-080 | CH(Me)S(O)$_2$Me | 5-CF$_3$ | O | H | Me | 159-160 |
| 1-081 | i-Pr | 5-Ph | O | H | Me | 131-133 |
| 1-082 | NHPh | 5-CF$_3$ | O | H | Me | 179-182 |
| 1-083 | (CH$_2$)$_2$SMe | 5-CF$_3$ | O | H | Me | 157-159 |
| 1-084 | (CH$_2$)$_2$S(O)Me | 5-CF$_3$ | O | H | Me | 179-181 |
| 1-085 | (CH$_2$)$_2$S(O)$_2$Me | 5-CF$_3$ | O | H | Me | 191-192 |
| 1-086 | N(Me)Ph | 5-CF$_3$ | O | H | Me | 175-178 |
| 1-087 | S(CH$_2$)$_2$CH$_3$ | 5-CF$_3$ | O | H | Me | 141-142 |
| 1-088 | i-Pr | 5-[3,5-(F)$_2$—Ph} | O | H | Me | 191-193 |
| 1-089 | i-Pr | 5-CF$_3$-7-Me | O | H | Me | 120-124 |
| 1-090 | NHCH(CH$_3$)$_2$ | 5-CF$_3$ | O | H | Me | 163-164 |
| 1-091 | SCH(CH$_3$)$_2$ | 5-CF$_3$ | O | H | H | 211-213 |
| 1-092 | S(O)(CH$_2$)$_2$CH$_3$ | 5-CF$_3$ | O | H | Me | 193-195 |
| 1-093 | SCH$_2$CH(CH$_3$)$_2$ | 5-CF$_3$ | O | H | Me | 143-145 |
| 1-094 | SCH(CH$_3$)CH$_2$CH$_3$ | 5-CF$_3$ | O | H | Me | 150-153 |
| 1-095 | SC(CH$_3$)$_3$ | 5-CF$_3$ | O | H | Me | 178-180 |
| 1-096 | D-14 | 5-CF$_3$ | O | H | Me | 166-168 |

TABLE 29

| No. | $R^{1a}$ | $(R^{2a})_n$ | X | $R^3$ | $R^{4a}$ | Melting point (° C.) |
|---|---|---|---|---|---|---|
| 1-097 | i-Pr | 5-CF$_3$ | O | H | D-15 | 108-111 |
| 1-098 | i-Pr | 5-CF$_3$ | O | H | D-14 | *1 |
| 1-099 | i-Pr | 5-CF$_3$ | O | H | 4-MeO—Ph | 154-158 |
| 1-100 | i-Pr | 5-CF$_3$ | O | H | CF$_3$ | 111-116 |
| 1-101 | i-Pr | 5-CF$_3$ | O | H | D-9 | 167-169 |
| 1-102 | NH(D-9b) | 5-CF$_3$ | O | H | Me | 219-221 |

TABLE 29-continued

| No. | $R^{1a}$ | $(R^{2a})_n$ | X | $R^3$ | $R^{4a}$ | Melting point (° C.) |
|---|---|---|---|---|---|---|
| 1-103 | $NMe_2$ | 5-$CF_3$ | O | H | H | 200-205 |
| 1-104 | $CH_2$(c-Pr) | 5-$CF_3$ | O | H | Me | 160-163 |
| 1-105 | D-16a | 5-$CF_3$ | O | H | Me | 232-235 |
| 1-106 | SEt | 5-$CF_3$ | O | H | H | 189-191 |
| 1-107 | $CH_2O(CH_2)_2OMe$ | 5-$CF_3$ | O | H | H | 117-118 |
| 1-108 | $S(CH_2)_2CH_3$ | 5-$CF_3$ | O | H | H | 198-200 |
| 1-109 | $NH(CH_2)_2OMe$ | 5-$CF_3$ | O | H | Me | 150-155 |
| 1-110 | D-14 | 5-$CF_3$ | O | H | H | 180-182 |
| 1-111 | $NHS(O)_2Ph$ | 5-$CF_3$ | O | H | Me | 259-261 |
| 1-112 | OEt | 5-$CF_3$ | O | H | H | 135-145 |
| 1-113 | $SCH_2Ph$ | 5-$CF_3$ | O | H | Me | 187-190 |
| 1-114 | $SCH_2$(4-MeO—Ph) | 5-$CF_3$ | O | H | Me | 155-158 |
| 1-115 | $SCH_2$(c-Pr) | 5-$CF_3$ | O | H | Me | 135-137 |
| 1-116 | $SCH_2$(D-15) | 5-$CF_3$ | O | H | Me | 142-143 |
| 1-117 | $SCH_2CN$ | 5-$CF_3$ | O | H | Me | 179-182 |
| 1-118 | D-17 | 5-$CF_3$ | O | H | Me | *1 |
| 1-119 | D-17a | 5-$CF_3$ | O | H | Me | 250-255 |
| 1-120 | D-17b | 5-$CF_3$ | O | H | Me | 235-238 |
| 1-121 | $N(Me)(CH_2)_2OMe$ | 5-$CF_3$ | O | H | H | 131-134 |
| 1-122 | $N(Me)CH(CH_3)_2$ | 5-$CF_3$ | O | H | H | 155-157 |
| 1-123 | $N(Me)$(c-Hex) | 5-$CF_3$ | O | H | H | 64-66 |
| 1-124 | $SCH_2CF_3$ | 5-$CF_3$ | O | H | Me | 156-157 |
| 1-125 | $SCH_2C(O)CH_3$ | 5-$CF_3$ | O | H | Me | 178-182 |
| 1-126 | $SCH_2$(D-18) | 5-$CF_3$ | O | H | Me | 200-203 |
| 1-127 | $SCH_2C(O)OMe$ | 5-$CF_3$ | O | H | Me | 184-185 |
| 1-128 | $SCH_2CH=CH_2$ | 5-$CF_3$ | O | H | H | 188-190 |
| 1-129 | $N(Me)(CH_2)_2OMe$ | 5-$CF_3$ | O | H | Me | 75-80 |
| 1-130 | $NH(CH_2)_2SMe$ | 5-$CF_3$ | O | H | Me | 111-115 |
| 1-131 | $NHCH_2CF_3$ | 5-$CF_3$ | O | H | Me | 140-144 |
| 1-132 | $N(Me)CH(CH_3)_2$ | 5-$CF_3$ | O | H | Me | 164-168 |
| 1-133 | $N(Me)$(c-Hex) | 5-$CF_3$ | O | H | Me | 135-140 |
| 1-134 | $N(Me)Et$ | 5-$CF_3$ | O | H | Me | 125-128 |
| 1-135 | $N(Et)_2$ | 5-$CF_3$ | O | H | Me | 135-137 |
| 1-136 | D-19 | 5-$CF_3$ | O | H | Me | 151-152 |
| 1-137 | $N(Me)Et$ | 5-$CF_3$ | O | H | H | 141-143 |
| 1-138 | $N(Et)_2$ | 5-$CF_3$ | O | H | H | 130-131 |
| 1-139 | D-19 | 5-$CF_3$ | O | H | H | 217-218 |
| 1-140 | i-Pr | 5-$CF_3$ | O | H | D-11 | 200-201 |
| 1-141 | i-Pr | 5-$CF_3$ | O | H | $CH_2SMe$ | 114-116 |
| 1-142 | i-Pr | 5-$CF_3$ | O | H | $CH_2S(O)_2Me$ | 171-173 |
| 1-143 | i-Pr | 5-$CF_3$ | O | H | $CH_2S(O)Me$ | 149-150 |
| 1-144 | c-Pr | 5-$CF_3$ | O | H | H | 170-174 |

TABLE 30

| No. | $R^{1a}$ | $(R^{2a})_n$ | X | $R^3$ | $R^{4a}$ | Melting point (° C.) |
|---|---|---|---|---|---|---|
| 1-145 | 3-Pen | 5-$CF_3$ | O | H | H | 228-231 |
| 1-146 | $CH_2SMe$ | 5-$CF_3$ | O | H | H | 176-179 |
| 1-147 | 4-F—Ph | 5-$CF_3$ | O | H | H | 222-226 |
| 1-148 | 3,5-$(MeO)_2$-Ph | 5-$CF_3$ | O | H | H | 217-220 |
| 1-149 | 4-MeO—Ph | 5-$CF_3$ | O | H | H | 210-213 |
| 1-150 | D-8a | 5-$CF_3$ | O | H | H | 244-248 |
| 1-151 | $CH_2$(4-MeO—Ph) | 5-$CF_3$ | O | H | H | 187-190 |
| 1-152 | $N(Me)CH_2C≡CH$ | 5-$CF_3$ | O | H | Me | 161-163 |
| 1-153 | $N(Me)(CH_2)_2CN$ | 5-$CF_3$ | O | H | Me | 138-143 |
| 1-154 | S(c-Pen) | 5-$CF_3$ | O | H | Me | 153-155 |
| 1-155 | S(c-Pen) | 5-$CF_3$ | O | H | H | 214-216 |
| 1-156 | $SCH_2$(D-8a) | 5-$CF_3$ | O | H | Me | 171-172 |
| 1-157 | $SCH_2$(D-8a) | 5-$CF_3$ | O | H | H | 204-207 |
| 1-158 | $CH_2CH=CH_2$ | 5-$CF_3$ | O | H | H | 155-158(*3) |
| 1-158* | CH=CHMe | 5-$CF_3$ | O | H | H | 155-158(*3) |
| 1-159 | $CH_2CH=CH_2$ | 5-$CF_3$ | O | H | Me | 159-161(*4) |
| 1-159* | CH=CHMe | 5-$CF_3$ | O | H | Me | 159-161(*4) |
| 1-160 | C≡CMe | 5-$CF_3$ | O | H | H | *2 |
| 1-161 | C≡CMe | 5-$CF_3$ | O | H | Me | >280 |
| 1-162 | $CH_2CF_3$ | 5-$CF_3$ | O | H | Me | 199-203 |
| 1-163 | $N(Me)CH_2C≡CH$ | 5-$CF_3$ | O | H | H | 216-218 |
| 1-164 | $N(Me)(CH_2)_2CN$ | 5-$CF_3$ | O | H | H | 105-110 |
| 1-165 | $N(Me)$(4-MeO—Ph) | 5-$CF_3$ | O | H | Me | 136-139 |
| 1-166 | $N(Me)CH_2CH=CH_2$ | 5-$CF_3$ | O | H | Me | 127-129 |
| 1-167 | $N(Me)CH_2$(4-MeO—Ph) | 5-$CF_3$ | O | H | Me | 191-194 |
| 1-168 | $CH_2CN$ | 5-$CF_3$ | O | H | Me | 196-199 |
| 1-169 | D-16m | 5-$CF_3$ | O | H | Me | 146-147 |
| 1-170 | D-24f | 5-$CF_3$ | O | H | Me | 182-185 |
| 1-171 | $N(Me)$(4-MeO—Ph) | 5-$CF_3$ | O | H | H | 180-185 |
| 1-172 | $N(Me)CH_2CH=CH_2$ | 5-$CF_3$ | O | H | H | 135-137 |
| 1-173 | $(CH_2)_2OMe$ | 5-$CF_3$ | O | H | Me | 157-158 |
| 1-174 | D-16a | 5-$CF_3$ | O | Et | Me | *1 |

FIFTH TABLE

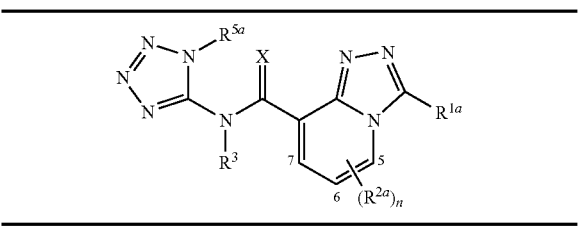

TABLE 31

| No. | $R^{1a}$ | $(R^{2a})_n$ | X | $R^3$ | $R^{5a}$ | Melting point (° C.) |
|---|---|---|---|---|---|---|
| 2-001 | H | 5-CF$_3$ | O | H | Me | 247-251 |
| 2-002 | Me | 5-CF$_3$ | O | H | Me | 215-219 |
| 2-003 | i-Pr | 5-CF$_3$ | O | H | Me | 215-220 |
| 2-004 | i-Pr | 5-Cl | O | H | Me | 189-190 |
| 2-005 | c-Pr | 5-CF$_3$ | O | H | Me | 190-195 |
| 2-006 | 3-Pen | 5-CF$_3$ | O | H | Me | 143-144 |
| 2-007 | Ph | 5-CF$_3$ | O | H | Me | 245-247 |
| 2-008 | Cl | 5-CF$_3$ | O | H | Me | 193-195 |
| 2-009 | Br | 5-CF$_3$ | O | H | Me | 186-193 |
| 2-010 | CH$_2$OMe | 5-CF$_3$ | O | H | Me | 205-209 |
| 2-011 | 4-MeO—Ph | 5-CF$_3$ | O | H | Me | 173-177 |
| 2-012 | 4-Cl—Ph | 5-CF$_3$ | O | H | Me | 256-258 |
| 2-013 | SMe | 5-CF$_3$ | O | H | Me | 210-215 |
| 2-014 | CH$_2$O(CH$_2$)$_2$OMe | 5-CF$_3$ | O | H | Me | 152-154 |
| 2-015 | CH$_2$OCH$_2$CF$_3$ | 5-CF$_3$ | O | H | Me | 170-171 |
| 2-016 | CH(CH$_3$)CH$_2$CH$_3$ | 5-CF$_3$ | O | H | Me | 181-184 |
| 2-017 | D-3a | 5-CF$_3$ | O | H | Me | 251-253 |
| 2-018 | i-Pr | 6-CF$_3$ | O | H | Me | 169-171 |
| 2-019 | n-Pr | 5-CF$_3$ | O | H | Me | 149-150 |
| 2-020 | CH$_2$OPh | 5-CF$_3$ | O | H | Me | 116-117 |
| 2-021 | c-Pen | 5-CF$_3$ | O | H | Me | 197-201 |
| 2-022 | D-5 | 5-CF$_3$ | O | H | Me | 147-149 |
| 2-023 | i-Pr | 5-CF$_3$ | O | Me | Me | 215-216 |
| 2-024 | SEt | 5-CF$_3$ | O | H | Me | 157-159 |
| 2-025 | SCH(CH$_3$)$_2$ | 5-CF$_3$ | O | H | Me | 200-204 |
| 2-026 | CH$_2$OEt | 5-CF$_3$ | O | H | Me | 183-184 |
| 2-027 | tBu | 5-CF$_3$ | O | H | Me | 217-218 |
| 2-028 | D-4a | 5-CF$_3$ | O | H | Me | 186-188 |
| 2-029 | CH$_2$SMe | 5-CF$_3$ | O | H | Me | 189-191 |
| 2-030 | CH$_2$SCH$_2$CF$_3$ | 5-CF$_3$ | O | H | Me | 155-158 |
| 2-031 | S(O)Et | 5-CF$_3$ | O | H | Me | 190-191 |
| 2-032 | S(O)CH(CH$_3$)$_2$ | 5-CF$_3$ | O | H | Me | 163-167 |
| 2-033 | CH$_2$S(O)Me | 5-CF$_3$ | O | H | Me | 204-206 |
| 2-034 | CH$_2$S(O)$_2$Me | 5-CF$_3$ | O | H | Me | 212-214 |
| 2-035 | CH$_2$S(O)CH$_2$CF$_3$ | 5-CF$_3$ | O | H | Me | 138-142 |
| 2-036 | CH$_2$S(O)$_2$CH$_2$CF$_3$ | 5-CF$_3$ | O | H | Me | 176-178 |
| 2-037 | S(O)$_2$Me | 5-CF$_3$ | O | H | Me | *1 |
| 2-038 | S(O)$_2$Et | 5-CF$_3$ | O | H | Me | *1 |
| 2-039 | i-Pr | 5-CF$_3$ | S | H | Me | 198-200 |
| 2-040 | CH$_2$C(O)OEt | 5-CF$_3$ | O | H | Me | 202-204 |
| 2-041 | i-Pr | 5-CF$_3$ | O | H | CH$_2$CH$_2$OMe | *1 |
| 2-042 | 4-Me—Ph | 5-CF$_3$ | O | H | Me | 221-225 |
| 2-043 | 4-F—Ph | 5-CF$_3$ | O | H | Me | 236-240 |
| 2-044 | 3-MeO—Ph | 5-CF$_3$ | O | H | Me | 210-212 |
| 2-045 | 2-MeO—Ph | 5-CF$_3$ | O | H | Me | 150-153 |
| 2-046 | i-Pr | 5-CF$_3$ | O | H | CH$_2$C(O)OMe | 149-154 |
| 2-047 | i-Pr | 5-CF$_2$H | O | H | Me | 172-173 |
| 2-048 | i-Pr | 5-CF$_3$ | O | H | CH$_2$CH$_2$SMe | *1 |

TABLE 32

| No. | $R^{1a}$ | $(R^{2a})_n$ | X | $R^3$ | $R^{5a}$ | Melting point (° C.) |
|---|---|---|---|---|---|---|
| 2-049 | i-Pr | 5-CF$_2$CF$_3$ | O | H | Me | 240-241 |
| 2-050 | i-Pr | 5-CF$_3$-6-Me | O | H | Me | 208-209 |
| 2-051 | NMe$_2$ | 5-CF$_3$ | O | H | Me | 222-225 |
| 2-052 | CH(Me)SMe | 5-CF$_3$ | O | H | Me | 202-204 |
| 2-053 | CH(Me)S(O)Me | 5-CF$_3$ | O | H | Me | 150-152 |
| 2-054 | CH(Me)S(O)$_2$Me | 5-CF$_3$ | O | H | Me | 117-125 |

TABLE 32-continued

| No. | $R^{1a}$ | $(R^{2a})_n$ | X | $R^3$ | $R^{5a}$ | Melting point (° C.) |
|---|---|---|---|---|---|---|
| 2-055 | i-Pr | 5-Ph | O | H | Me | 193-198 |
| 2-056 | NHPh | 5-CF$_3$ | O | H | Me | 255-260 |
| 2-057 | (CH$_2$)$_2$SMe | 5-CF$_3$ | O | H | Me | 144-146 |
| 2-058 | (CH$_2$)$_2$S(O)Me | 5-CF$_3$ | O | H | Me | 96-102 |
| 2-059 | (CH$_2$)$_2$S(O)$_2$Me | 5-CF$_3$ | O | H | Me | 173-175 |
| 2-060 | D-8a | 5-CF$_3$ | O | H | Me | 217-220 |
| 2-061 | D-11 | 5-CF$_3$ | O | H | Me | 223-224 |
| 2-062 | D-10a | 5-CF$_3$ | O | H | Me | 246-248 |
| 2-063 | 3,5-(MeO)$_2$—Ph | 5-CF$_3$ | O | H | Me | 197-199 |
| 2-064 | 3,5-(Cl)$_2$—Ph | 5-CF$_3$ | O | H | Me | 269-271 |
| 2-065 | CH$_2$(4-MeO—Ph) | 5-CF$_3$ | O | H | Me | 167-168 |
| 2-066 | NHCH(CH$_3$)$_2$ | 5-CF$_3$ | O | H | Me | 104-107 |
| 2-067 | S(O)Me | 5-CF$_3$ | O | H | Me | 228-229 |
| 2-068 | S(CH$_2$)$_2$CH$_3$ | 5-CF$_3$ | O | H | Me | 136-138 |
| 2-069 | S(O)(CH$_2$)$_2$CH$_3$ | 5-CF$_3$ | O | H | Me | 155-157 |
| 2-070 | S(O)$_2$(CH$_2$)$_2$CH$_3$ | 5-CF$_3$ | O | H | Me | 203-205 |
| 2-071 | SCH$_2$CH(CH$_3$)$_2$ | 5-CF$_3$ | O | H | Me | 159-160 |
| 2-072 | SCH(CH$_3$)CH$_2$CH$_3$ | 5-CF$_3$ | O | H | Me | 170-173 |
| 2-073 | i-Pr | 5-CF$_3$ | O | H | Ph | 133-136 |
| 2-074 | NH(CH$_2$)$_2$OMe | 5-CF$_3$ | O | H | Me | 111-115 |
| 2-075 | D-14 | 5-CF$_3$ | O | H | Me | 240-245 |
| 2-076 | SCH$_2$Ph | 5-CF$_3$ | O | H | Me | 179-181 |
| 2-077 | SCH$_2$(4-MeO—Ph) | 5-CF$_3$ | O | H | Me | 190-192 |
| 2-078 | D-17 | 5-CF$_3$ | O | H | Me | 285-290 |
| 2-079 | N(Me)(CH$_2$)$_2$OMe | 5-CF$_3$ | O | H | Me | 168-169 |
| 2-080 | NH(CH$_2$)$_2$SMe | 5-CF$_3$ | O | H | Me | *1 |
| 2-081 | NHCH$_2$CF$_3$ | 5-CF$_3$ | O | H | Me | *1 |
| 2-082 | N(Me)CH(CH$_3$)$_2$ | 5-CF$_3$ | O | H | Me | 171-172 |
| 2-083 | N(Me)(c-Hex) | 5-CF$_3$ | O | H | Me | 144-145 |
| 2-084 | SCH$_2$(c-Pr) | 5-CF$_3$ | O | H | Me | 168-169 |
| 2-085 | SCH$_2$(D-15) | 5-CF$_3$ | O | H | Me | 139-141 |
| 2-086 | SCH$_2$CN | 5-CF$_3$ | O | H | Me | 144-145 |
| 2-087 | SCH$_2$CF$_3$ | 5-CF$_3$ | O | H | Me | 160-161 |
| 2-088 | N(Me)Et | 5-CF$_3$ | O | H | Me | 110-112 |
| 2-089 | N(Et)$_2$ | 5-CF$_3$ | O | H | Me | 159-160 |
| 2-090 | i-Pr | 5-CF$_3$ | O | H | n-Pr | 111-112 |
| 2-091 | i-Pr | 5-CF$_3$ | O | H | CH$_2$CH=CH$_2$ | 118-119 |
| 2-092 | i-Pr | 5-CF$_3$ | O | H | CH$_2$C(O)OEt | 104-105 |
| 2-093 | i-Pr | 5-CF$_3$ | O | H | CH$_2$(4-Cl—Ph) | 147-148 |
| 2-094 | N(Me)CH$_2$C≡CH | 5-CF$_3$ | O | H | Me | 176-178 |
| 2-095 | N(Me)(CH$_2$)$_2$CN | 5-CF$_3$ | O | H | Me | 125-128 |
| 2-096 | S(c-Pen) | 5-CF$_3$ | O | H | Me | 192-194 |

TABLE 33

| No. | $R^{1a}$ | $(R^{2a})_n$ | X | $R^3$ | $R^{5a}$ | Melting point (° C.) |
|---|---|---|---|---|---|---|
| 2-097 | SCH$_2$(D-8a) | 5-CF$_3$ | O | H | Me | 175-178 |
| 2-098 | SEt | 5-CF$_3$ | O | H | CH$_2$CH$_2$OMe | 130-131 |
| 2-099 | N(Me)(4-MeO—Ph) | 5-CF$_3$ | O | H | Me | 141-142 |
| 2-100 | N(Me)CH$_2$CH=CH$_2$ | 5-CF$_3$ | O | H | Me | 183-184 |
| 2-101 | S(CH$_2$)$_2$OMe | 5-CF$_3$ | O | H | Me | 144-145 |
| 2-102 | SCH$_2$CH=CH$_2$ | 5-CF$_3$ | O | H | Me | 172-174 |
| 2-103 | SCH$_2$C≡CH | 5-CF$_3$ | O | H | Me | 190-191 |
| 2-104 | i-Pr | 5-CF$_3$ | O | H | H | 276-280 |
| 2-105 | CH$_2$CH=CH$_2$ | 5-CF$_3$ | O | H | Me | 164-167 (*5) |
| 2-105* | CH=CHMe | 5-CF$_3$ | O | H | Me | 164-167 (*5) |
| 2-106 | C≡CMe | 5-CF$_3$ | O | H | Me | 244-246 |
| 2-107 | CH$_2$OC(O)Me | 5-CF$_3$ | O | H | Me | 176-178 |
| 2-108 | CH$_2$OH | 5-CF$_3$ | O | H | Me | 155-158 |
| 2-109 | CHO | 5-CF$_3$ | O | H | Me | 250-252 |
| 2-110 | D-16a | 5-CF$_3$ | O | H | Me | 194-201 |

SIXTH TABLE

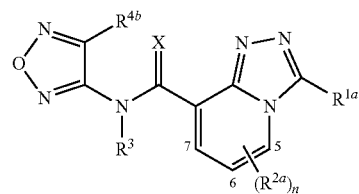

TABLE 34

| No. | $R^{1a}$ | $(R^{2a})_n$ | X | $R^3$ | $R^{4b}$ | Melting point (° C.) |
|---|---|---|---|---|---|---|
| 3-001 | i-Pr | 5-$CF_3$ | O | H | Me | 185-186 |
| 3-002 | $SCH_2CH(CH_3)_2$ | 5-$CF_3$ | O | H | Me | 136-137 |

SEVENTH TABLE

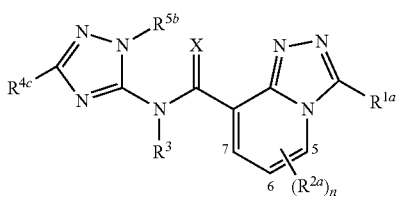

TABLE 35

| No. | $R^{1a}$ | $(R^{2a})_n$ | X | $R^3$ | $R^{4c}$ | $R^{5b}$ | Melting point (° C.) |
|---|---|---|---|---|---|---|---|
| 4-001 | i-Pr | 5-$CF_3$ | O | H | H | Me | 182-185 |
| 4-002 | i-Pr | 5-$CF_3$ | O | H | H | Et | *1 |
| 4-003 | SEt | 5-$CF_3$ | O | H | H | Me | 119-120 |
| 4-004 | i-Pr | 5-$CF_3$ | O | H | H | H | 250-255 |

EIGHTH TABLE

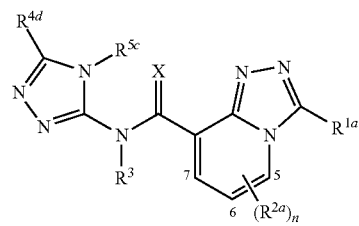

TABLE 36

| No. | $R^{1a}$ | $(R^{2a})_n$ | X | $R^3$ | $R^{4d}$ | $R^{5c}$ | Melting point (° C.) |
|---|---|---|---|---|---|---|---|
| 5-001 | i-Pr | 5-$CF_3$ | O | H | Me | Me | 215-220 |
| 5-002 | i-Pr | 5-$CF_3$ | O | H | —CH=CH—CH=CH— | | 219-223 |
| 5-003 | i-Pr | 5-$CF_3$ | O | H | —$(CH_2)_4$— | | 130-135 |

NINTH TABLE

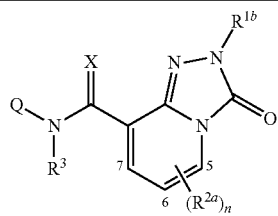

TABLE 37

| No. | Q | $R^{1b}$ | $(R^{2a})_n$ | X | $R^3$ | Melting point (° C.) |
|---|---|---|---|---|---|---|
| 6-001 | D-6a | Me | 5-$CF_3$ | O | H | 250-260 |
| 6-002 | D-7a | Me | 5-$CF_3$ | O | H | 245-246 |
| 6-003 | D-6a | Et | 5-$CF_3$ | O | H | 234-236 |
| 6-004 | D-7a | Et | 5-$CF_3$ | O | H | 176-178 |
| 6-005 | D-6a | i-Pr | 5-$CF_3$ | O | H | 184-190 |
| 6-006 | D-6a | $CH_2Ph$ | 5-$CF_3$ | O | H | 155-162 |
| 6-007 | D-20a | Et | 5-$CF_3$ | O | H | 182-185 |
| 6-008 | D-23a | Et | 5-$CF_3$ | O | H | 162-164 |

TENTH TABLE

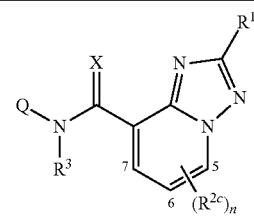

TABLE 38

| No. | Q | $R^{1c}$ | $(R^{2c})_n$ | X | $R^3$ | Melting point (° C.) |
|---|---|---|---|---|---|---|
| 7-001 | D-6a | i-Pr | 5-$CF_3$ | O | H | 252-255 |
| 7-002 | D-7a | i-Pr | 5-$CF_3$ | O | H | 168-170 |

Among the compounds of the present invention, $^1$H-NMR data of compounds that have no melting points and the isomer mixtures of "*3", "*4", and "*5" are listed in Eleventh Table.

The chemical shift values of proton nuclear magnetic resonance were measured in a deuterated chloroform solvent at 300 MHz using $Me_4Si$ (tetramethylsilane) as a reference substance. Symbols in Fourth Table have the following meanings. s: singlet, brs: broad-singlet, d: doublet, dd: double doublet, t: triplet, q: quartet, and m: multiplet.

[Eleventh Table]

TABLE 39

| No. | $^1$H-NMR (CDCl$_3$, Me$_4$Si, 300 MHz) |
|---|---|
| 1-003 | δ8.21 (d, 1H, J = 7.2 Hz), 6.77 (d, 1H, J = 7.2 Hz), 3.85-3.70 (m, 1H), 2.97 (s, 3H), 2.55 (s, 3H), 1.58 (d, 6H, J = 7. 2 Hz)○ |
| 1-009 | δ8.24 (d, 1H, J = 7.5 Hz), 6.67 (d, 1H, J = 7.5 Hz), 4.92 (brs, 1H), 4.25-4.10 (m, 1H), 2.75 (s, 3H), 2.55 (s, 3H), 1.60 (d, 6H, J = 6.9 Hz)○ |
| 1-037 | δ8.51 (d, 1H, J = 6.9 Hz), 7.72 (d, 1H, J = 6.9 Hz), 5.05 (s, 2H), 3.26 (s, 3H), 2.60 (s, 3H)○ (Proton peak of CONH was not observed.) |

TABLE 39-continued

| No. | ¹H-NMR (CDCl₃, Me₄Si, 300 MHz) |
|---|---|
| 1-039 | δ8.54 (d, 1H, J = 7.5 Hz), 7.76 (d, 1H, J = 7.5 Hz), 5.17 (s, 2H), 4.36 (q, 2H, J = 9.0 Hz), 2.60 (Proton peak of CONH was not observed.) |
| 1-040 | δ8.54 (d, 1H, J = 7.2 Hz), 7.79 (d, 1H, J = 7.2 Hz), 3.78 (s, 3H), 2.60 (s, 3H)o (Proton peak of CONH was not observed.) |
| 1-041 | δ8.53 (d, 1H, J = 7.5 Hz), 7.78 (d, 1H, J = 7.5 Hz), 4.00 (q, 2H, J = 7. 5 Hz), 2.60 (s, 3H), 1.59(t, 3H, J = 7.5 Hz)o (Proton peak of CONH was not observed.) |
| 1-098 | δ8.34 (d, 1H, J = 7.5 Hz), 7.59 (d, 1H, J = 7.5 Hz), 3.82 (t, 4H, J = 4.9 Hz), 3.79-3.68 (m, 1H), 3.54 (t, 4H, J = 4.9 Hz), 1.56(d, 6H, J = 6.5 Hz)o (Proton peak of CONH was not observed.) |
| 1-118 | δ12.68 (brs, 1H), 8.39 (d, 1H, J = 7.4 Hz), 7.59 (d, 1H, J = 7.4 Hz), 3.59-3.39 (m, 4H), 3.05-2.78 (m, 4H), 2.59 (s, 3H) |
| 1-158 | δ13.1 (brs, 1H), 8.44 (d, 1H, J = 7.5 Hz), 8.30 (s, 1H), 7.64 (d, 1H, J = 7.5 Hz), 6.38-6.25 (m, 1H), 5.38-5.24 (m, 2H), 4.04 (dd, 2H, J = 3.9 Hz, 1.2 Hz)o |
| 1-158* | δ13.0 (brs, 1H), 8.43 (d, 1H, J = 6.6 Hz), 8.30 (s, 1H), 7.62 (d, 1H, J = 6.6 Hz), 7.11-7.01 (m, 1H), 6.71-6.61(m, 1H), 2.10 (d, 3H, J = 6.6 Hz)o |
| 1-159 | δ12.9 (brs, 1H), 8.42 (d, 1H, J = 7.5 Hz), 7.63 (d, 1H, J = 7.5 Hz), 6.38-6.24 (m, 1H), 5.36-5.23 (m, 2H), 4.03 (dd, 2H, J = 6.9 Hz, 1.2 Hz), 2.59 (s, 3H)o |
| 1-159* | δ12.9 (brs, 1H), 8.38 (d, 1H, J = 6.9 Hz), 7.60 (d, 1H, J = 6.9 Hz), 7.12-7.00 (m, 1H), 6.69-6.62 (m, 1H), 2.60 (s, 3H), 2.09 (dd, 3H, J = 6.6 Hz, 1.8 Hz)o |
| 1-160 | δ12.8 (brs, 1H), 8.46 (d, 1H, J = 7.2 Hz), 8.31 (s, 1H), 7.65 (d, 1H, J = 7.2 Hz), 2.27 (s, 3H)o |
| 1-161 | δ12.6 (brs, 1H), 8.44 (d, 1H, J = 7.2 Hz), 7.64 (d, 1H, J = 7.2 Hz), 2.59 (s, 3H), 2.27 (s, 3H)o |
| 1-174 | δ7.72 (d, 1H, J = 7.8 Hz), 7.53 (d, 1H, J = 7.8 Hz), 4.15 (q, 2H, J = 7.2 Hz), 2.78 (d, 1H, J = 7.8 Hz), 2.38 (s, 3H), 1.83 (d, 1H, J = 7.8 Hz), 1.80 (s, 3H), 1.43 (t, 3H, J = 7.2 Hz)o |
| 2-037 | δ12.08 (brs, 1H), 8.62 (d, 1H, J = 7.5 Hz), 7.86 (d, 1H, J = 7.5 Hz), 4.12 (s, 3H), 3.80 (s, 3H)o |
| 2-038 | δ12.11 (brs, 1H), 8.62 (d, 1H, J = 7.2 Hz), 7.86 (d, 1H, J = 7.2 Hz), 4.12 (s, 3H), 4.01 (q, 2H, J = 7.2 Hz), 1.60 (t, 3H, J = 7.2 Hz)o |
| 2-041 | δ12.49 (brs, 1H), 8.35 (d, 1H, J = 7.5 Hz), 7.62 (d, 1H, 7.5 Hz), 4.65-4.55 (m, 2H), 3.90-3.80 (m, 2H), 3.75-3.65 (m, 1H), 3.38 (s, 3H), 1.60-1.50(m, 6H)o |

TABLE 40

| No. | ¹H-NMR (CDCl₃, Me₄Si, 300 MHz) |
|---|---|
| 2-048 | δ12.6 (brs, 1H), 8.35 (d, 1H, J = 7.5 Hz), 7.64 (d, 1H, J = 7.5 Hz), 4.60 (t, 2H, J = 7.2 Hz), 3.80-3.65 (m, 1H), 3.09 (t, 2H, J = 7.2 Hz), 2.11 (s, 3H), 1.56 (d, 6H, J = 6.9 Hz)o |
| 2-080 | δ12.4 (brs, 1H), 8.14 (d, 1H, J = 6.6 Hz), 7.40 (d, 1H, J = 6.6 Hz), 5.24 (brs, 1H), 4.11 (s, 3H), 3.88-3.80 (m, 2H), 2.99-2.91 (m, 2H), 2.16 (s, 3H)o |
| 2-081 | δ12.3 (brs, 1H), 8.23 (d, 1H, J = 7.2 Hz), 7.49 (d, 1H, J = 7.2 Hz), 4.78 (brs, 1H), 4.45-4.32 (m, 2H), 4.11 (s, 3H)o |
| 2-105 | δ12.5 (brs, 1H), 8.40 (d, 1H, J = 7.5 Hz), 7.65 (d, 1H, J = 7.5 Hz), 6.37-6.24 (m, 1H), 5.37-5.24 (m, 2H), 4.13 (s, 3H), 4.06 (dd, 2H, J = 6.6 Hz, 1.2 Hz)o |
| 2-105* | δ12.5 (brs, 1H), 8.36 (d, 1H, J = 7.2 Hz), 7.62 (d, 1H, J = 7.2 Hz), 7.13-7.01 (m, 1H), 6.70-6.62 (m, 1H), 4.13 (s, 3H), 2.10 (dd, 3H, J = 6.6 Hz, 1.5 Hz)o |
| 4-002 | δ12.3(brs, 1H), 8.37 (d, 1H, J = 7.5 Hz), 7.88(s, 1H), 7.61 (d, 1H, J = 7.5 Hz), 4.23 (q, 2H, J = 7.5 Hz), 3.80-3.60 (m, 1H), 1.60-1.50 (m, 9H)o |

REFERENCE EXAMPLE

Reference Example 1

Compounds listed in Twelfth Table were synthesized by a similar method to Step 1 of Synthesis Example 7. In Tables, Me is methyl group. Similarly, Et is ethyl group, Pr is propyl group, Pen is pentyl group, Ph is phenyl group, Bn is benzyl group, n- is normal, i- is iso, c- is cyclo, and t- is tertiary.

In Tables, substituents of D-3a, D-4a, D-5, D-8a, D-9a, D-10a, D-11, D-12, D-13a, D-14, D-16a, and D-16m are the following structures.

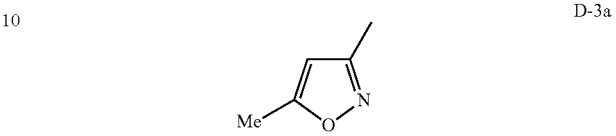
D-3a

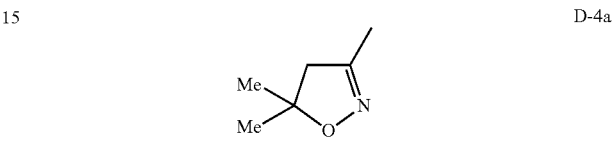
D-4a

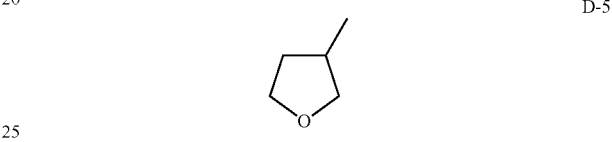
D-5

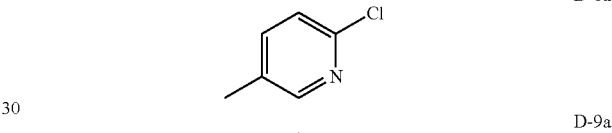
D-8a

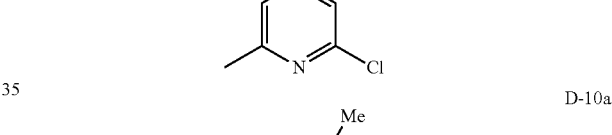
D-9a

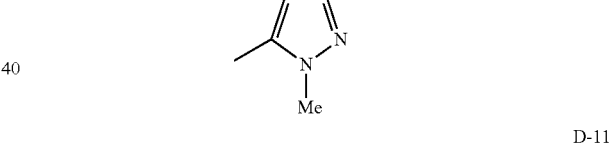
D-10a

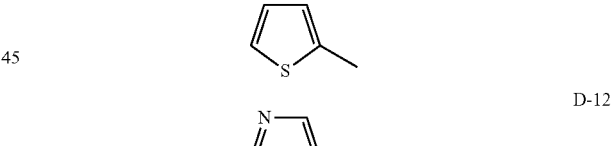
D-11

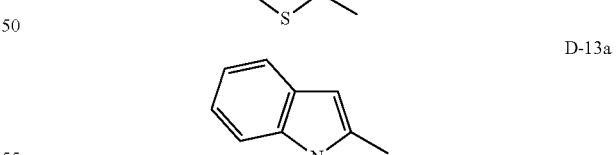
D-12

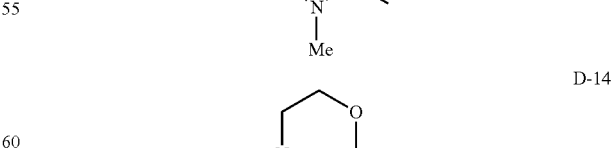
D-13a

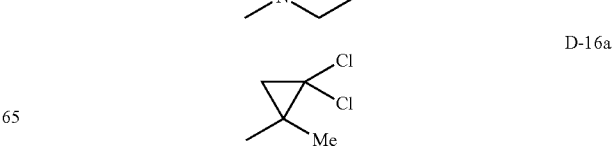
D-14

D-16a

-continued

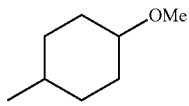

D-16m

In Tables, "*1" is "Resinous". $^1$H-NMR data of compounds that have no melting points are listed in Sixteenth Table. The chemical shift values of proton nuclear magnetic resonance in Sixteenth Table were measured in a deuterated chloroform solvent at 300 MHz using Me$_4$Si (tetramethylsilane) as a reference substance. Symbols in Sixteenth Table have the following meanings. s: singlet, brs: broad-singlet, d: doublet, dd: double doublet, t: triplet, q: quartet, and m: multiplet.

TWELFTH TABLE

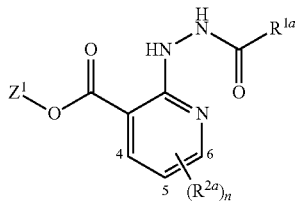

TABLE 41

| No. | $R^{1a}$ | $(R^{2a})n$ | $Z^1$ | Melting point (° C.) |
|---|---|---|---|---|
| A1-01a | H | 6-CF$_3$ | Me | *1 |
| A1-02a | c-Pr | 6-CF$_3$ | Me | 143-144 |
| A1-03a | 3-Pen | 6-CF$_3$ | Me | 125-126 |
| A1-04a | Ph | 6-CF$_3$ | Me | *1 |
| A1-05a | CH$_2$OMe | 6-CF$_3$ | Me | 76-77 |
| A1-06a | 4-MeO—Ph | 6-CF$_3$ | Me | 116-120 |
| A1-07a | 4-Cl—Ph | 6-CF$_3$ | Me | 163-165 |
| A1-08a | CH$_2$O(CH$_2$)$_2$OMe | 6-CF$_3$ | Me | *1 |
| A1-09a | CH$_2$OCH$_2$CF$_3$ | 6-CF$_3$ | Me | 82-85 |
| A1-10a | CH(CH$_3$)CH$_2$CH$_3$ | 6-CF$_3$ | Me | 148-149 |
| A1-11a | D-3a | 6-CF$_3$ | Me | 121-122 |
| A1-12a | i-Pr | 5-CF$_3$ | Me | 130-131 |
| A1-13a | n-Pr | 6-CF$_3$ | Me | 119-120 |
| A1-14a | CH$_2$OPh | 6-CF$_3$ | Me | 95-97 |
| A1-15a | c-Pen | 6-CF$_3$ | Me | 158-159 |
| A1-16a | D-5 | 6-CF$_3$ | Me | 155-156 |
| A1-17a | CH$_2$OEt | 6-CF$_3$ | Me | 55-57 |
| A1-18a | t-Bu | 6-CF$_3$ | Me | 144-146 |
| A1-19a | D-4a | 6-CF$_3$ | Me | 99-100 |
| A1-20a | CH$_2$SMe | 6-CF$_3$ | Me | 127-129 |
| A1-21a | CH$_2$SCH$_2$CF$_3$ | 6-CF$_3$ | Me | 114-116 |
| A1-22b | CH$_2$C(O)OEt | 6-CF$_3$ | Bn | 110-112 |
| A1-23a | 4-Me—Ph | 6-CF$_3$ | Me | 183-185 |
| A1-24a | 4-F—Ph | 6-CF$_3$ | Me | 117-119 |
| A1-25a | 4-CF$_3$—Ph | 6-CF$_3$ | Me | 160-162 |
| A1-26a | 3-MeO—Ph | 6-CF$_3$ | Me | 103-106 |
| A1-27a | 2-MeO—Ph | 6-CF$_3$ | Me | 160-164 |
| A1-28a | i-Pr | 6-CF$_2$H | Me | 140-141 |
| A1-29a | D-8a | 6-CF$_3$ | Me | 172-175 |
| A1-30a | D-9a | 6-CF$_3$ | Me | 160-170 |
| A1-31a | D-10a | 6-CF$_3$ | Me | 161-163 |
| A1-32a | D-11 | 6-CF$_3$ | Me | 45-50 |
| A1-33a | D-12 | 6-CF$_3$ | Me | 40-45 |
| A1-34a | D-13a | 6-CF$_3$ | Me | 183-184 |
| A1-35b | CH$_2$OC(O)Me | 6-CF$_3$ | Bn | 89-91 |
| A1-36a | CH$_2$(4-MeO—Ph) | 6-CF$_3$ | Me | 121-122 |
| A1-37c | i-Pr | 6-CF$_2$CF$_3$ | Et | 120-121 |
| A1-38a | 3,5-(MeO)$_2$—Ph | 6-CF$_3$ | Me | 106-107 |
| A1-39a | 3,5-(Cl)$_2$—Ph | 6-CF$_3$ | Me | 178-179 |
| A1-40a | i-Pr | 5-Me-6-CF$_3$ | Me | 169-174 |
| A1-41c | i-Pr | 4-Me-6-CF$_3$ | Et | 140-141 |

TABLE 41-continued

| No. | $R^{1a}$ | $(R^{2a})n$ | $Z^1$ | Melting point (° C.) |
|---|---|---|---|---|
| A1-42a | (CH$_2$)$_2$SMe | 6-CF$_3$ | Me | 90-91 |
| A1-43a | CH(Me)SMe | 6-CF$_3$ | Me | 166-167 |
| A1-44c | i-Pr | 6-Ph | Et | 144-146 |
| A1-45c | i-Pr | 6-{3,5-(F)$_2$—Ph} | Et | 144-146 |
| A1-46a | NMe$_2$ | 6-CF$_3$ | Me | 134-137 |
| A1-47c | D-14 | 6-CF$_3$ | Et | 101-105 |
| A1-48a | CH$_2$(c-Pr) | 6-CF$_3$ | Me | 119-122 |

TABLE 42

| No. | $R^{1a}$ | $(R^{2a})n$ | $Z^1$ | Melting point (° C.) |
|---|---|---|---|---|
| A1-49a | D-16a | 6-CF$_3$ | Me | 70-75 |
| A1-50a | C≡CMe | 6-CF$_3$ | Me | 151-153 |
| A1-51a | CH$_2$CF$_3$ | 6-CF$_3$ | Me | 170-172 |
| A1-52a | CH$_2$CN | 6-CF$_3$ | Me | 163-165 |
| A1-53c | D-16m | 6-CF$_3$ | Et | 120-125 |
| A1-55c | (CH$_2$)$_2$OMe | 6-CF$_3$ | Et | 96-98 |

Reference Example 2

Compounds listed in Thirteenth Table were synthesized by a similar method to Step 2 of Synthesis Example 7. In Tables, Me is methyl group. Similarly, Et is ethyl group, Pr is propyl group, Pen is pentyl group, Ph is phenyl group, Bn is benzyl group, n- is normal, i- is iso, c- is cyclo, and t- is tertiary.

In Tables, substituents of D-3a, D-4a, D-5, D-8a, D-9a, D-10a, D-11, D-12, D-13a, D-14, D-16a, D-16m and D-24f are the following structures.

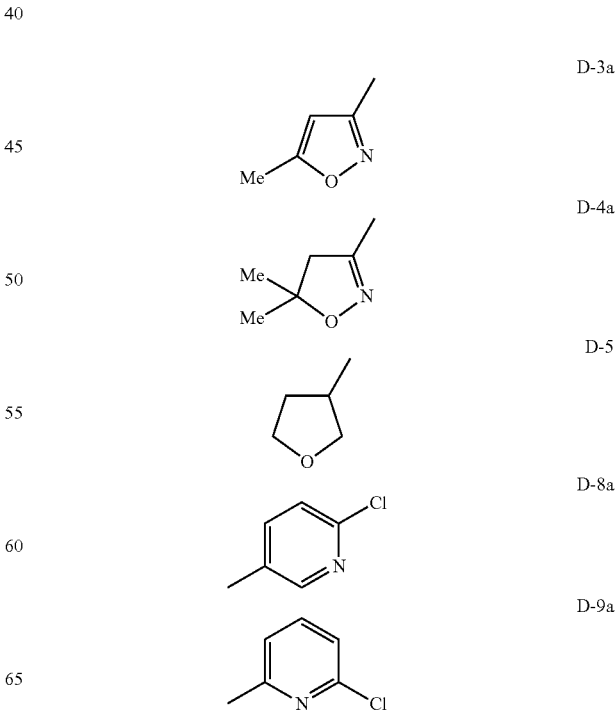

-continued

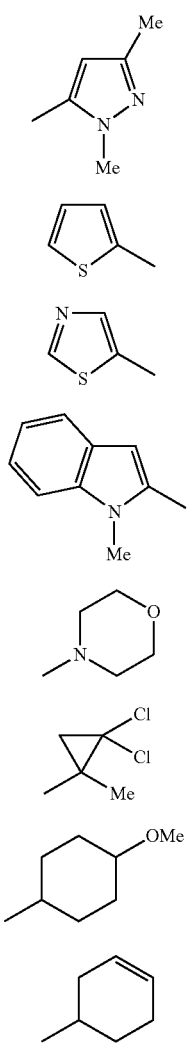

D-10a

D-11

D-12

D-13a

D-14

D-16a

D-16m

D-24f

In Tables, "*1" is "Resinous". ¹H-NMR data of compounds that have no melting points are listed in Sixteenth Table.

THIRTEENTH TABLE

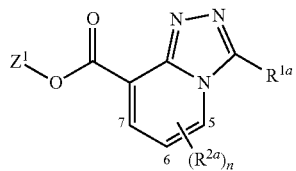

TABLE 43

| No. | R$^{1\,a}$ | (R$^{2a}$)n | Z$^1$ | Melting point (° C.) |
|---|---|---|---|---|
| B1-01a | H | 5-CF$_3$ | Me | *1 |
| B1-02a | c-Pr | 5-CF$_3$ | Me | *1 |
| B1-04a | Ph | 5-CF$_3$ | Me | *1 |
| B1-05a | CH$_2$OMe | 5-CF$_3$ | Me | 95-97 |
| B1-06a | 4-MeO—Ph | 5-CF$_3$ | Me | 160-162 |
| B1-07a | 4-Cl—Ph | 5-CF$_3$ | Me | 148-152 |
| B1-08a | CH$_2$O(CH$_2$)$_2$OMe | 5-CF$_3$ | Me | *1 |

TABLE 43-continued

| No. | R$^{1\,a}$ | (R$^{2a}$)n | Z$^1$ | Melting point (° C.) |
|---|---|---|---|---|
| B1-09a | CH$_2$OCH$_2$CF$_3$ | 5-CF$_3$ | Me | 87-89 |
| B1-10a | CH(CH$_3$)CH$_2$CH$_3$ | 5-CF$_3$ | Me | 86-94 |
| B1-11a | D-3a | 5-CF$_3$ | Me | 140-141 |
| B1-12a | i-Pr | 6-CF$_3$ | Me | 105-107 |
| B1-13a | n-Pr | 5-CF$_3$ | Me | 129-130 |
| B1-14a | CH$_2$OPh | 5-CF$_3$ | Me | 102-103 |
| B1-15a | c-Pen | 5-CF$_3$ | Me | 130-134 |
| B1-17a | CH$_2$OEt | 5-CF$_3$ | Me | 87-89 |
| B1-18a | t-Bu | 5-CF$_3$ | Me | 75-77 |
| B1-19a | D-4a | 5-CF$_3$ | Me | 137-139 |
| B1-20a | CH$_2$SMe | 5-CF$_3$ | Me | 97-99 |
| B1-21a | CH$_2$SCH$_2$CF$_3$ | 5-CF$_3$ | Me | 125-126 |
| B1-22b | CH$_2$C(O)OEt | 5-CF$_3$ | Bn | 72-73 |
| B1-23a | 4-Me—Ph | 5-CF$_3$ | Me | 142-145 |
| B1-24a | 4-F—Ph | 5-CF$_3$ | Me | 133-135 |
| B1-25a | 4-CF$_3$—Ph | 5-CF$_3$ | Me | 170-171 |
| B1-26a | 3-MeO—Ph | 5-CF$_3$ | Me | 135-142 |
| B1-27a | 2-MeO—Ph | 5-CF$_3$ | Me | *1 |
| B1-28a | i-Pr | 5-CF$_2$H | Me | 142-145 |
| B1-29a | D-8a | 5-CF$_3$ | Me | *1 |
| B1-30a | D-9a | 5-CF$_3$ | Me | 140-145 |
| B1-31a | D-10a | 5-CF$_3$ | Me | 126-129 |
| B1-32a | D-11 | 5-CF$_3$ | Me | 122-124 |
| B1-33a | D-12 | 5-CF$_3$ | Me | 171-172 |
| B1-34a | D-13a | 5-CF$_3$ | Me | *1 |
| B1-35b | CH$_2$OC(O)Me | 5-CF$_3$ | Bn | 88-89 |
| B1-36a | CH$_2$(4-MeO—Ph) | 5-CF$_3$ | Me | 92-110 |
| B1-37c | i-Pr | 5-CF$_2$CF$_3$ | Et | 57-58 |
| B1-38a | 3,5-(MeO)$_2$—Ph | 5-CF$_3$ | Me | 150-161 |
| B1-39a | 3,5-(Cl)$_2$—Ph | 5-CF$_3$ | Me | 157-164 |
| B1-40a | i-Pr | 5-CF$_3$-6-Me | Me | 58-59 |
| B1-41c | i-Pr | 5-CF$_3$-7-Me | Et | 76-77 |
| B1-42a | (CH$_2$)$_2$SMe | 5-CF$_3$ | Me | 126-127 |
| B1-43a | CH(Me)SMe | 5-CF$_3$ | Me | 103-104 |
| B1-44c | i-Pr | 5-Ph | Et | 133-134 |
| B1-45c | i-Pr | 5-{3,5-(F)$_2$—Ph} | Et | 125-127 |
| B1-46a | NMe$_2$ | 5-CF$_3$ | Me | 135-137 |
| B1-47c | D-14 | 5-CF$_3$ | Et | 138-139 |
| B1-48a | CH$_2$(c-Pr) | 5-CF$_3$ | Me | 130-135 |
| B1-49a | D-16a | 5-CF$_3$ | Me | *1 |
| B1-50a | C≡CMe | 5-CF$_3$ | Me | 163-168 |

TABLE 44

| No. | R$^{1\,a}$ | (R$^{2a}$)n | Z$^1$ | Melting point (° C.) |
|---|---|---|---|---|
| B1-51a | CH$_2$CF$_3$ | 5-CF$_3$ | Me | 150-154 |
| B1-52a | CH$_2$CN | 5-CF$_3$ | Me | 165-170 |
| B1-53c | D-16m | 5-CF$_3$ | Et | 95-102 |
| B1-54c | D-24f | 5-CF$_3$ | Et | 101-110 |
| B1-55c | (CH$_2$)$_2$OMe | 5-CF$_3$ | Et | 82-83 |

Reference Example 3

Compounds listed in Fourteenth Table were synthesized by a similar method to Step 3 of Synthesis Example 7. In Tables, Me is methyl group. Similarly, Et is ethyl group, Pr is propyl group, Pen is pentyl group, Ph is phenyl group, Bn is benzyl group, n- is normal, i- is iso, c- is cyclo, and t- is tertiary.

In Tables, substituents of D-3a, D-4a, D-5, D-8a, D-9a, D-10a, D-11, D-12, D-13a, D-14, D-16a, D-16m and D-24f are the following structures.

D-3a 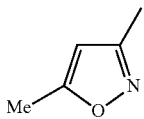

D-4a 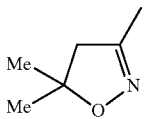

D-5 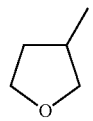

D-8a 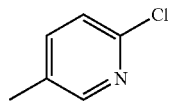

D-9a 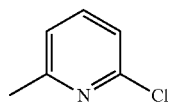

D-10a 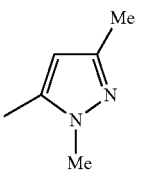

D-11 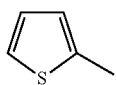

D-12 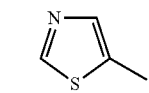

D-13a 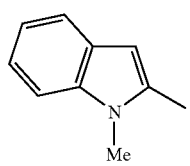

D-14 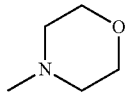

D-16a 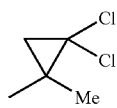

D-16m 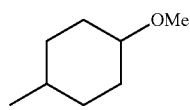

-continued

D-24f 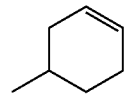

In Tables, "1" is "Resinous". $^1$H-NMR data of compounds that have no melting points are listed in Sixteenth Table.

FOURTEENTH TABLE

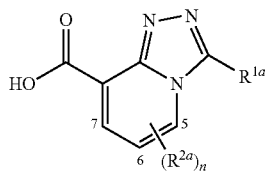

TABLE 45

| No. | $R^{1a}$ | $(R^{2a})n$ | Melting point (° C.) |
|---|---|---|---|
| C1-01 | H | 5-CF$_3$ | *1 |
| C1-02 | c-Pr | 5-CF$_3$ | *1 |
| C1-03 | 3-Pen | 5-CF$_3$ | 137-139 |
| C1-04 | Ph | 5-CF$_3$ | *1 |
| C1-05 | CH$_2$OMe | 5-CF$_3$ | 111-112 |
| C1-06 | 4-MeO—Ph | 5-CF$_3$ | 215-218 |
| C1-07 | 4-Cl—Ph | 5-CF$_3$ | 241-247 |
| C1-08 | CH$_2$O(CH$_2$)$_2$OMe | 5-CF$_3$ | 47-49 |
| C1-09 | CH$_2$OCH$_2$CF$_3$ | 5-CF$_3$ | 67-70 |
| C1-10 | CH(CH$_3$)CH$_2$CH$_3$ | 5-CF$_3$ | 137-140 |
| C1-11 | D-3a | 5-CF$_3$ | 197-201 |
| C1-12 | i-Pr | 6-CF$_3$ | 224-226 |
| C1-13 | n-Pr | 5-CF$_3$ | 134-135 |
| C1-14 | CH$_2$OPh | 5-CF$_3$ | 136-140 |
| C1-15 | c-Pen | 5-CF$_3$ | 156-158 |
| C1-16 | D-5 | 5-CF$_3$ | 195-200 |
| C1-17 | CH$_2$OEt | 5-CF$_3$ | 96-97 |
| C1-18 | t-Bu | 5-CF$_3$ | 125-131 |
| C1-19 | D-4a | 5-CF$_3$ | 184-186 |
| C1-20 | CH$_2$SMe | 5-CF$_3$ | 110-111 |
| C1-21 | CH$_2$SCH$_2$CF$_3$ | 5-CF$_3$ | 56-59 |
| C1-22 | CH$_2$C(O)OEt | 5-CF$_3$ | 124-126 |
| C1-23 | 4-Me—Ph | 5-CF$_3$ | 250-253 |
| C1-24 | 4-F—Ph | 5-CF$_3$ | 249-251 |
| C1-25 | 4-CF$_3$—Ph | 5-CF$_3$ | 199-201 |
| C1-26 | 3-MeO—Ph | 5-CF$_3$ | 179-181 |
| C1-27 | 2-MeO—Ph | 5-CF$_3$ | 85-90 |
| C1-28 | i-Pr | 5-CF$_2$H | 193-195 |
| C1-29 | D-8a | 5-CF$_3$ | 237-240 |
| C1-30 | D-9a | 5-CF$_3$ | 231-234 |
| C1-31 | D-10a | 5-CF$_3$ | 215-220 |
| C1-32 | D-11 | 5-CF$_3$ | 190-195 |
| C1-33 | D-12 | 5-CF$_3$ | 218-223 |
| C1-34 | D-13a | 5-CF$_3$ | 185-188 |
| C1-35 | CH$_2$OC(O)Me | 5-CF$_3$ | 126-128 |
| C1-36 | CH$_2$(4-MeO—Ph) | 5-CF$_3$ | 73-75 |
| C1-37 | i-Pr | 5-CF$_2$CF$_3$ | 170-175 |
| C1-38 | 3,5-(MeO)$_2$—Ph | 5-CF$_3$ | 158-160 |
| C1-39 | 3,5-(Cl)$_2$—Ph | 5-CF$_3$ | 250-252 |
| C1-40 | i-Pr | 5-CF$_3$-6-Me | 153-154 |
| C1-41 | i-Pr | 5-CF$_3$-7-Me | 190-192 |
| C1-42 | (CH$_2$)$_2$SMe | 5-CF$_3$ | 149-151 |
| C1-43 | CH(Me)SMe | 5-CF$_3$ | 145-146 |
| C1-44 | i-Pr | 5-Ph | 218-219 |
| C1-45 | i-Pr | 5-{3,5-(F)$_2$—Ph} | 210-220 |
| C1-46 | NMe$_2$ | 5-CF$_3$ | 181-183 |
| C1-47 | D-14 | 5-CF$_3$ | 210-213 |
| C1-48 | CH$_2$(c-Pr) | 5-CF$_3$ | 109-114 |

TABLE 46

| No. | R¹ ᵃ | (R²ᵃ)n | Melting point (° C.) |
|---|---|---|---|
| C1-49 | D-16a | 5-CF₃ | 159-164 |
| C1-50 | C≡CMe | 5-CF₃ | 234-238 |
| C1-51 | CH₂CF₃ | 5-CF₃ | 168-171 |
| C1-52 | CH₂CN | 5-CF₃ | 227-231 |
| C1-53 | D-16m | 5-CF₃ | 118-120 |
| C1-54 | D-24f | 5-CF₃ | 169-170 |
| C1-55 | (CH₂)₂OMe | 5-CF₃ | 104-105 |

Reference Example 4

3-(Ethylthio)-5-(trifluoromethyl)-[1,2,4]triazolo[4,3-a]pyridine-8-carboxylic acid Step 1; Synthesis of 3-(thioxo)-5-(trifluoromethyl)-2,3-dihydro-[1,2,4]triazolo[4,3-a]pyridine-8-carboxylic acid To 20 ml of methanol solution of 2.0 g of methyl 3-thioxo-5-(trifluoromethyl)-2,3-dihydro-[1,2,4]triazolo[4,3-a]pyridine-8-carboxylate synthesized by a similar method to Step 1 of Synthesis Example 8 containing imidazole, 17 ml of 0.5 mol/L sodium hydroxide aqueous solution was added under cooling with ice. After completion of the addition, the reaction solution was stirred at room temperature for 3.5 hours. After completion of the reaction, 20 ml of 1 mol/L hydrochloric acid was added to the reaction solution and the precipitated solid in the reaction solution was separated by filtration. The obtained solid was washed with 1 mol/L hydrochloric acid, water, and diisopropyl ether in this order and filtered to give 1.1 g of the target product as a yellow solid.

Melting point: 235° C. to 240° C.

Step 2; Synthesis of 3-(ethylthio)-5-(trifluoromethyl)-[1,2,4]triazolo[4,3-a]pyridine-8-carboxylic acid To 10 ml of N,N-dimethylformamide solution of 700 mg (2.66 mmol) of 3-(thioxo)-5-(trifluoromethyl)-2,3-dihydro-[1,2,4]triazolo[4,3-a]pyridine-8-carboxylic acid, 898 mg (5.76 mmol) of ethyl iodide was added at room temperature. After completion of the addition, the reaction solution was stirred at room temperature for 4 days. After completion of the reaction, the solvent in the reaction solution was distilled away under reduced pressure. To the obtained residue, 5 ml of water and 5 ml of 1 mol/l hydrochloric acid were added and the precipitated solid was separated by filtration. The obtained solid was washed with water and diisopropyl ether in this order to give 486 mg of the target product as a yellow solid.

Melting point: 113° C. to 114° C.

Reference Example 5

The following compounds were synthesized by similar methods to Step 2 and Step 3 of Synthesis Example 8 or Reference Example 4.

Methyl 3-(isopropylthio)-5-(trifluoromethyl)-[1,2,4]triazolo[4,3-a]pyridine-8-carboxylate Melting point: 120° C. to 122° C.

3-(Isopropylthio)-5-(trifluoromethyl)-[1,2,4]triazolo[4,3-a]pyridine-8-carboxylic acid Melting point: 135° C. to 136° C.

3-((2-Methoxyethyl)thio)-5-(trifluoromethyl)-[1,2,4]triazolo[4,3-a]pyridine-8-carboxylic acid Melting point: 106° C. to 111° C.

3-(Allylthio)-5-(trifluoromethyl)-[1,2,4]triazolo[4,3-a]pyridine-8-carboxylic acid Melting point: 96° C. to 99° C.

3-(Prop-2-yn-1-ylthio)-5-(trifluoromethyl)-[1,2,4]triazolo[4,3-a]pyridine-8-carboxylic acid Melting point: 179° C. to 181° C.

Methyl 3-(n-propylthio)-5-(trifluoromethyl)-[1,2,4]triazolo[4,3-a]pyridine-8-carboxylate Melting point: 87° C. to 88° C.

3-(n-Propylthio)-5-(trifluoromethyl)-[1,2,4]triazolo[4,3-a]pyridine-8-carboxylic acid Melting point: 106° C. to 108° C.

Methyl 3-(isobutylthio)-5-(trifluoromethyl)-[1,2,4]triazolo[4,3-a]pyridine-8-carboxylate Melting point: 105° C. to 106° C.

3-(Isobutylthio)-5-(trifluoromethyl)-[1,2,4]triazolo[4,3-a]pyridine-8-carboxylic acid Melting point: 110° C. to 112° C.

Methyl 3-(s-butylthio)-5-(trifluoromethyl)-[1,2,4]triazolo[4,3-a]pyridine-8-carboxylate Melting point: 88° C. to 90° C.

3-(s-Butylthio)-5-(trifluoromethyl)-[1,2,4]triazolo[4,3-a]pyridine-8-carboxylic acid Melting point: 107° C. to 109° C.

Methyl 3-(benzylthio)-5-(trifluoromethyl)-[1,2,4]triazolo[4,3-a]pyridine-8-carboxylate Melting point: 130° C. to 135° C.

3-(Benzylthio)-5-(trifluoromethyl)-[1,2,4]triazolo[4,3-a]pyridine-8-carboxylic acid Melting point: 153° C. to 156° C.

Methyl 3-((4-methoxybenzyl)thio)-5-(trifluoromethyl)-[1,2,4]triazolo[4,3-a]pyridine-8-carboxylate Melting point: 119° C. to 121° C.

3-((4-Methoxybenzyl)thio)-5-(trifluoromethyl)-[1,2,4]triazolo[4,3-a]pyridine-8-carboxylic acid Melting point: 180° C. to 182° C.

Methyl 3-((cyclopropylmethyl)thio)-5-(trifluoromethyl)-[1,2,4]triazolo[4,3-a]pyridine-8-carboxylate Melting point: 122° C. to 123° C.

3-((Cyclopropylmethyl)thio)-5-(trifluoromethyl)-[1,2,4]triazolo[4,3-a]pyridine-8-carboxylic acid Melting point: 127° C. to 129° C.

Methyl 3-(((tetrahydrofuran-2-yl)methyl)thio)-5-(trifluoromethyl)-[1,2,4]triazolo[4,3-a]pyridine-8-carboxylate $^1$H NMR (CDCl$_3$, Me$_4$Si, 300 MHz) δ 7.95 (d, 1H, J=7.2 Hz), 7.42 (d, 1H, J=7.2 Hz), 4.34-4.25 (m, 1H), 4.09 (s, 3H), 3.92-3.84 (m, 1H), 3.79-3.68 (m, 2H), 3.56-3.49 (m, 1H), 2.17-2.06 (m, 1H), 1.99-1.87 (m, 2H), 1.76-1.68 (m, 1H).

3-(((Tetrahydrofuran-2-yl)methyl)thio)-5-(trifluoromethyl)-[1,2,4]triazolo[4,3-a]pyridine-8-carboxylic acid Melting point: 108° C. to 112° C.

Methyl 3-((cyanomethyl)thio)-5-(trifluoromethyl)-[1,2,4]triazolo[4,3-a]pyridine-8-carboxylate Melting point: 146° C. to 148° C.

3-((Cyanomethyl)thio)-5-(trifluoromethyl)-[1,2,4]triazolo[4,3-a]pyridine-8-carboxylic acid Melting point: 138° C. to 140° C.

Methyl 3-((2-oxopropyl)thio)-5-(trifluoromethyl)-[1,2,4]triazolo[4,3-a]pyridine-8-carboxylate Melting point: 84° C. to 87° C.

3-((2-Oxopropyl)thio)-5-(trifluoromethyl)-[1,2,4]triazolo[4,3-a]pyridine-8-carboxylic acid Melting point: 121° C. to 124° C.

Methyl 3-(((1,3-dioxolan-2-yl)methyl)thio)-5-(trifluoromethyl)-[1,2,4]triazolo[4,3-a]pyridine-8-carboxylate Melting point: 99° C. to 102° C.

3-(((1,3-Dioxolan-2-yl)methyl)thio)-5-(trifluoromethyl)-[1,2,4]triazolo[4,3-a]pyridine-8-carboxylic acid Melting point: 110° C. to 112° C.

3-((2,2,2-Trifluoroethyl)thio)-5-(trifluoromethyl)-[1,2,4]triazolo[4,3-a]pyridine-8-carboxylic acid Melting point: 150° C. to 151° C.

3-((2-methoxy-2-oxoethyl)thio)-5-(trifluoromethyl)-[1,2,4]triazolo[4,3-a]pyridine-8-carboxylic acid Melting point: 143° C. to 144° C.

Methyl 3-(cyclopentylthio)-5-(trifluoromethyl)-[1,2,4]triazolo[4,3-a]pyridine-8-carboxylate Melting point: 92° C. to 94° C.

3-(Cyclopentylthio)-5-(trifluoromethyl)-[1,2,4]triazolo[4,3-a]pyridine-8-carboxylic acid Melting point: 143° C. to 146° C.

Methyl 3-(((6-chloropyridin-3-yl)methyl)thio)-5-(trifluoromethyl)-[1,2,4]triazolo[4,3-a]pyridine-8-carboxylate Melting point: 99° C. to 100° C.

3-(((6-Chloropyridin-3-yl)methyl)thio)-5-(trifluoromethyl)-[1,2,4]triazolo[4,3-a]pyridine-8-carboxylate Melting point: 159° C. to 160° C.

Reference Example 6

Synthesis of methyl 2-methyl-3-oxo-5-(trifluoromethyl)-2,3-dihydro-[1,2,4]triazolo[4,3-a]pyridine-8-carboxylate To the mixture of 500 mg (1.91 mmol) of methyl 3-oxo-5-(trifluoromethyl)-2,3-dihydro-[1,2,4]triazolo[4,3-a]pyridine-8-carboxylate, 525 mg (3.82 mmol) of potassium carbonate, and 10 ml of acetonitrile, 298 mg (2.10 mmol) of methyl iodide was added at room temperature. After completion of the addition, the reaction solution was stirred at room temperature for 5 hours. After completion of the reaction, 20 ml of chloroform was added to the reaction solution and the precipitated solid was separated by filtration. The solvent in the solution obtained by the filtration was distilled away under reduced pressure. The obtained residue after distilling the solvent away was purified with the medium pressure preparative liquid chromatography eluting the residue with n-hexane-ethyl acetate (gradient from 17:3 to 2:3) to give 312 mg of the target product as a yellow solid.

Melting point: 189° C. to 190° C.

The following compounds were synthesized by a similar method.

Methyl 2-ethyl-3-oxo-5-(trifluoromethyl)-2,3-dihydro-[1,2,4]triazolo[4,3-a]pyridine-8-carboxylate Melting point: 135° C. to 137° C.

Methyl 2-isopropyl-3-oxo-5-(trifluoromethyl)-2,3-dihydro-[1,2,4]triazolo[4,3-a]pyridine-8-carboxylate Melting point: 124° C. to 125° C.

Methyl 2-benzyl-3-oxo-5-(trifluoromethyl)-2,3-dihydro-[1,2,4]triazolo[4,3-a]pyridine-8-carboxylate Melting point: 99° C. to 100° C.

Reference Example 7

Synthesis of 2-methyl-3-oxo-5-(trifluoromethyl)-2,3-dihydro-[1,2,4]triazolo[4,3-a]pyridine-8-carboxylic acid To 3 ml of ethanol solution of 312 mg (1.13 mmol) of methyl 2-methyl-3-oxo-5-(trifluoromethyl)-2,3-dihydro-[1,2,4]triazolo[4,3-a]pyridine-8-carboxylate, 3 ml of aqueous solution of 50 mg (1.25 mmol) of sodium hydroxide was added under cooling with ice. After completion of the addition, the reaction solution was stirred for 1 hour at the same temperature. After completion of the reaction, 3 ml of 1 mol/L hydrochloric acid was added to the reaction solution and the resultant mixture was extracted with dichloromethane (10 ml, 3 times). The obtained organic phase was dehydrated and dried with saturated sodium chloride aqueous solution and anhydrous sodium sulfate in this order and the solvent was distilled away under reduced pressure. The precipitated solid was washed with diisopropyl ether and filtered to give 250 mg of the target product as a yellow solid.

Melting point: 155° C. to 160° C.

The following compounds were synthesized by a similar method.

2-Ethyl-3-oxo-5-(trifluoromethyl)-2,3-dihydro-[1,2,4]triazolo[4,3-a]pyridine-8-carboxylic acid Melting point: 160° C. to 163° C.

2-Isopropyl-3-oxo-5-(trifluoromethyl)-2,3-dihydro-[1,2,4]triazolo[4,3-a]pyridine-8-carboxylic acid Melting point: 160° C. to 162° C.

2-Benzyl-3-oxo-5-(trifluoromethyl)-2,3-dihydro-[1,2,4]triazolo[4,3-a]pyridine-8-carboxylic acid Melting point: 84° C. to 86° C.

Reference Example 8

Synthesis of methyl 3-thioxo-5-(trifluoromethyl)-2,3-dihydro-[1,2,4]triazolo[4,3-a]pyridine-8-carboxylate 100 mg of the mixture of methyl 3-thioxo-5-(trifluoromethyl)-2,3-dihydro-[1,2,4]triazolo[4,3-a]pyridine-8-carboxylate synthesized by the method of Step 1 of Synthesis Example 8 and imidazole was dissolved in 50 ml of ethyl acetate and the resultant mixture was washed with 20 ml of 1 mol/L hydrochloric acid. The obtained organic phase was dried over anhydrous sodium sulfate and the solvent was distilled away under reduced pressure to give 63 mg of the target product as an orange-yellow solid.

Melting point: 218° C. to 220° C.

Reference Example 9

3-(Phenylamino)-5-(trifluoromethyl)-[1,2,4]triazolo[4,3-a]pyridine-8-carboxylic acid Step 1; Synthesis of methyl 2-(2-(phenylcarbamoyl)hydrazinyl)-6-(trifluoromethyl)nicotinate To 13 ml of tetrahydrofuran solution of 500 mg (2.13 mmol) of methyl 2-hydrazinyl-6-(trifluoromethyl)nicotinate, 255 mg (2.14 mmol) of phenyl isocyanate was added under cooling with ice. After completion of the addition, the reaction solution was stirred for 14 hours at the same temperature. After completion of the reaction, the solvent in the reaction solution was distilled away under reduced pressure. The precipitated solid was washed with diisopropyl ether to give 740 mg of the target product as a white solid.

Melting point: 190° C. to 195° C.

Step 2; Synthesis of methyl 3-(phenylamino)-5-(trifluoromethyl)-[1,2,4]triazolo[4,3-a]pyridine-8-carboxylate To the mixed solution of 730 mg (2.06 mmol) of methyl 2-(2-(phenylcarbamoyl)hydrazinyl)-6-(trifluoromethyl)nicotinate and 15 ml of toluene, 940 mg (6.11 mmol) of phosphoryl chloride was added at room temperature. After completion of the addition, the reaction mixture was stirred for 3 hours under heating to reflux. After completion of stirring, the reaction mixture was cooled to room temperature and added to ice-water to terminate the reaction. Thereafter, the reaction liquid was extracted with ethyl acetate (30 ml, 2 times). The obtained organic phase was dried over anhydrous sodium sulfate and the solvent was distilled away under reduced pressure. The obtained residue was purified with the medium pressure preparative liquid chromatography eluting the residue with n-hexane-ethyl acetate-methanol (gradient from 90:10:0 to 0:100:0 to 0:90:10) to give 480 mg of the target product as a yellow solid.

Melting point: 225° C. to 230° C.

Step 3; Synthesis of 3-(phenylamino)-5-(trifluoromethyl)-[1,2,4]triazolo[4,3-a]pyridine-8-carboxylic acid To the mixed solution of 470 mg (1.40 mmol) of methyl 3-(phenylamino)-5-(trifluoromethyl)-[1,2,4]triazolo[4,3-a]pyridine-8-carboxylate and 10 ml of methanol, 8.0 ml (8.0 mmol) of 1 mol/L sodium hydroxide aqueous solution was added under cooling with ice. After completion of the addition, the reaction solution was stirred for 3 hours under cooling with ice. After completion of the reaction, the solvent in the reaction solution was distilled away under reduced pressure and thereafter 1 N hydrochloric acid was added to the reaction solution to adjust the pH to 5 to 6. The reaction mixed liquid was extracted with ethyl acetate (30 ml, 2 times) and the obtained organic phase was dried over anhydrous sodium sulfate, followed by distilling the solvent away under reduced pressure. The precipitated solid was washed with diisopropyl ether to give 250 mg of the target product as an orange solid.

Melting point: 125° C. to 130° C.

Reference Example 10

3-((2-Methoxyethyl)(methyl)amino)-5-(trifluoromethyl)-[1,2,4]triazolo[4,3-a]pyridine-8-carboxylic acid Step 1; Synthesis of ethyl 2-(2-((2-methoxyethyl)(methyl)carbamoyl)hydrazinyl)-6-(trifluoromethyl)nicotinate A mixture of 500 mg (1.82 mmol) of ethyl 3-oxo-5-(trifluoromethyl)-2,3-dihydro-[1,2,4]triazolo[4,3-a]pyridine-8-carboxylate, 320 mg (3.59 mmol) of N-(2-methoxyethyl)methylamine, and 10 ml of tetrahydrofuran was stirred for 3 hours under heating to reflux. After completion of the reaction, the solvent in the reaction solution was distilled away under reduced pressure. The obtained residue was purified with the medium pressure preparative liquid chromatography eluting the residue with n-hexane-ethyl acetate (gradient from 90:10 to 0:100) to give 610 mg of the target product as a light yellow solid.

Melting point: 65° C. to 66° C.

Step 2; Synthesis of ethyl 3-((2-methoxyethyl)(methyl)amino)-5-(trifluoromethyl)-[1,2,4]triazolo[4,3-a]pyridine-8-carboxylate To the mixed solution of 595 mg (1.63 mmol) of ethyl 2-(2-((2-methoxyethyl)(methyl)carbamoyl)hydrazinyl)-6-(trifluoromethyl)nicotinate and 10 ml of toluene, 750 mg (4.94 mmol) of phosphoryl chloride was added at room temperature. After completion of the addition, the reaction mixture was stirred for 1.5 hours under heating to reflux. After completion of stirring, the reaction mixture was cooled to room temperature and added to ice-water to terminate the reaction. Subsequently sodium hydrogen carbonate aqueous solution was added to adjust the pH to 8 to 9. Thereafter, the resultant mixture was extracted with ethyl acetate (30 ml, 2 times). The obtained organic phase was dried over anhydrous sodium sulfate and the solvent was distilled away under reduced pressure. The obtained residue was purified with the medium pressure preparative liquid chromatography eluting the residue with n-hexane-ethyl acetate (gradient from 90:10 to 0:100) to give 520 mg of the target product as an orange liquid.

$^1$H NMR (CDCl$_3$, Me$_4$Si, 300 MHz) δ 7.91 (d, 1H, J=7.2 Hz), 7.80 (d, 1H, J=7.2 Hz), 4.55 (q, 2H, J=6.9 Hz), 3.75-3.41 (m, 4H), 3.27 (s, 3H), 2.87 (s, 3H), 1.48 (t, 3H, J=6.9 Hz).

Step 3; Synthesis of 3-((2-methoxyethyl)(methyl)amino)-5-(trifluoromethyl)-[1,2,4]triazolo[4,3-a]pyridine-8-carboxylic acid To the mixed solution of 500 mg (1.44 mmol) of ethyl 3-((2-methoxyethyl)(methyl)amino)-5-(trifluoromethyl)-[1,2,4]triazolo[4,3-a]pyridine-8-carboxylate and 10 ml of ethanol, 4.5 ml (4.5 mmol) of 1 mol/L sodium hydroxide aqueous solution was added under cooling with ice. After completion of the addition, the reaction solution was stirred for 1 hour under cooling with ice. After completion of the reaction, the solvent in the reaction solution was distilled away under reduced pressure and thereafter 1 mol/L hydrochloric acid was added to the reaction solution to adjust the pH to 4. The reaction mixed liquid was extracted with ethyl acetate (30 ml, 2 times) and the obtained organic phase was dried over anhydrous sodium sulfate, followed by distilling the solvent away under reduced pressure to give 470 mg of the target product as a light yellow solid.

Melting point: 115° C. to 120° C.

Reference Example 11

Compounds listed in Fifteenth Table were synthesized by a similar method to Reference Example 9 or Reference Example 10. In Tables, Me is methyl group. Similarly, Et is ethyl group, Ph is phenyl group, and c- is cyclo.

In Tables, substituents of D-9b, D-14, D-17, and D-19 are the following structures.

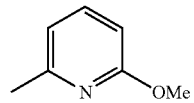

D-9b

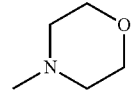

D-14

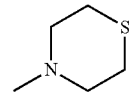

D-17

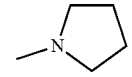

D-19

FIFTEENTH TABLE

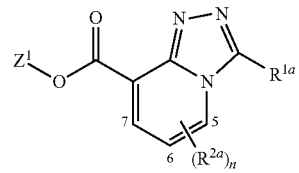

TABLE 47

| No. | $R^{1a}$ | $(R^{2a})_n$ | $Z^1$ | Melting point (° C.) |
|---|---|---|---|---|
| C2-01 | N(Me)Ph | 5-CF$_3$ | H | 160-170 |
| C2-02 | NHCH(CH$_3$)$_2$ | 5-CF$_3$ | H | 145-146 |
| C2-03 | D-14 | 5-CF$_3$ | H | 210-213 |
| C2-04 | NH(D-9b) | 5-CF$_3$ | H | 170-174 |
| C2-05 | NH(CH$_2$)$_2$OMe | 5-CF$_3$ | H | 150-155 |
| C2-06 | NHSO$_2$Ph | 5-CF$_3$ | H | >290 |
| C2-07 | D-17 | 5-CF$_3$ | H | 160-165 |
| C2-08 | NH(CH$_2$)$_2$SMe | 5-CF$_3$ | H | 173-176 |
| C2-09 | NHCH$_2$CF$_3$ | 5-CF$_3$ | H | 180-183 |
| C2-10 | N(Me)CH(CH$_3$)$_2$ | 5-CF$_3$ | H | 135-137 |
| C2-11 | N(Me)Hex-c | 5-CF$_3$ | H | 184-186 |
| C2-12 | N(Me)Et | 5-CF$_3$ | H | 140-141 |
| C2-13 | N(Et)$_2$ | 5-CF$_3$ | H | 126-127 |
| C2-14 | D-19 | 5-CF$_3$ | H | 150-151 |
| C2-15 | N(Me)CH$_2$C≡CH | 5-CF$_3$ | H | 133-134 |
| C2-16 | N(Me)(CH$_2$)$_2$CN | 5-CF$_3$ | H | 136-137 |
| C2-17 | N(Me)(4-MeO—Ph) | 5-CF$_3$ | H | 168-171 |
| C2-18 | N(Me)CH$_2$CH=CH$_2$ | 5-CF$_3$ | H | 117-118 |
| C2-19 | N(Me)CH$_2$(4-MeO—Ph) | 5-CF$_3$ | H | 105-110 |

[Sixteenth Table]

TABLE 48

| No. | $^1$H-NMR (CDCl$_3$, Me$_4$Si, 300 MHz) |
|---|---|
| A1-01a | δ10.02 (brs, 1H), 8.34 (d, 1H, J = 7.8 Hz), 8.26 (s, 1H), 8.23 (brs, 1H), 7.11 (d, 1H, J = 7.8 Hz), 3.96 (s, 3H)o |
| A1-04a | δ10.21 (d, 1H, J = 6.0 Hz), 8.84 (d, 1H, J = 5.7 Hz), 8.35 (dd, 1H, J = 7.2 Hz, 0.9 Hz), 7.88-7.85 (m, 2H), 7.56-7.46 (m, 3H), 7.08 (d, 1H, J = 7.8 Hz), 3.98 (s, 3H)o |
| A1-08a | δ9.70 (brs, 1H), 9.26 (brs, 1H), 8.32 (d, 1H, J = 7.8 Hz), 7.07 (d, 1H, J = 7.8 Hz), 4.21 (s, 2H), 3.95 (s, 3H), 3.89-3.86 (m, 2H), 3.65-3.62 (m, 2H), 3.40 (s, 3H)o |
| B1-01a | δ9.04 (d, 1H, J = 1.8 Hz), 8.14 (d, 1H, J = 6.6 Hz), 7.41 (d, 1H, J = 6.6 Hz), 4.13 (s, 3H)o |

TABLE 48-continued

| No. | $^1$H-NMR (CDCl$_3$, Me$_4$Si, 300 MHz) |
|---|---|
| B1-02a | δ7.95 (d, 1H, J = 7.5 Hz), 7.44 (d, 1H, J = 7.5 Hz), 4.09 (s, 3H), 2.32-2.25 (m, 1H), 1.38-1.33 (m, 2H), 1.22-1.16 (m, 2H)○ |
| B1-04a | δ8.04 (dd, 1H, J = 7.2 Hz, 0.6 Hz), 7.60-7.42 (m, 6H), 4.14 (s, 3H)○ |
| B1-08a | δ8.04 (d, 1H, J = 7.2 Hz), 7.49 (d, 1H, J = 7.2 Hz), 5.21 (d, 2H, J = 0.9 Hz), 4.11 (s, 3H), 3.75-3.72 (m, 2H), 3.54-3.51 (m, 2H), 3.33 (s, 3H)○ |
| B1-27a | δ8.04 (d, 1H, J = 7.5 Hz), 7.45-7.60 (m, 1H), 7.35-7.45 (m, 2H), 7.00-7.15 (m, 1H), 6.90-7.00 (m, 1H), 4.13 (s, 3H), 3.65 (s, 3H)○ |
| B1-29a | δ8.49 (s, 1H), 8.00-8.15 (m, 1H), 7.75-7.85 (m, 1H), 7.40-7.60 (m, 2H), 4.13 (s, 3H)○ |
| B1-34a | δ8.17 (d, 1H, J = 7.2 Hz), 7.70 (d, 1H, J = 8.1 Hz), 7.54 (d, 1H, J = 7.2 Hz), 7.35-7.45 (m, 2H), 7.20-7.30 (m, 2H), 4.17 (s, 3H), 3.54 (s, 3H)○ |
| B1-49a | δ8.00 (d, 1H, J = 7.5 Hz), 7.54 (d, 1H, J = 7.5 Hz), 4.10 (s, 3H), 2.91 (d, 1H, J = 7.5 Hz), 1.91 (d, 1H, J = 7.5 Hz), 1.85 (s, 3H)○ |
| C1-01 | δ9.06 (d, 1H, J = 1.5 Hz), 8.33 (d, 1H, J = 7.2 Hz), 7.57 (d, 1H, J = 6.9 Hz)○ (Proton peak of CO$_2$H was not observed.) |
| C1-02 | δ8.38 (d, 1H, J = 7.5 Hz), 7.60 (d, 1H, H = 7.5 Hz), 2.39-2.28 (m, 1H), 1.42-1.35 (m, 2H), 1.29-1.23 (m, 2H)○ (Proton peak of CO$_2$H was not observed.) |
| C1-04 | δ8.30 (d, 1H, J = 6.9 Hz), 7.60-7.49 (m, 6H)○ (Proton peak of CO$_2$H was not observed.) |

TEST EXAMPLES

Subsequently, usefulness of the compound of the present invention as a herbicide will be specifically described in the following Test Examples. The present invention, however, is not limited to these Test Examples.

[Test Example 1] Herbicidal Activity Test by Application Before Weed Generation in Submerged Conditions After alluvial soil was placed into 1/10000 are of Wagner pot, water was poured and mixed to form a submerged condition having a water depth of 4 cm. Seeds of Echinochloa oryzacola Vasing., Scirpus juncoides, and Monochoria vaginalis were sowed in a mixed manner in the above pot and thereafter 2.5 leaf stage Oryza sativa seedling was transplanted. On the day of sowing seeds, the emulsion agent containing the compound of the present invention prepared in accordance with Formulation Example 2 was diluted with water so as to be a predetermined herbicide amount and the diluted compound was applied to the surface of the water. The pot was placed in a greenhouse of 25° C. to 30° C. to grow plant. Three weeks after the herbicide application, effects on each plant were investigated in accordance with the following criteria. The results are listed in Seventeenth Table.
Criteria
5 Herbicidal ratio of 90% or more (almost completely withered)
4 Herbicidal ratio of 70% or more and less than 90%
3 Herbicidal ratio of 40% or more and less than 70%
2 Herbicidal ratio of 20% or more and less than 40%
1 Herbicidal ratio of 5% or more and less than 20%
0 Herbicidal ratio of 5% or less (almost no effect)

[Test Example 2] Herbicidal Activity Test by Application During Weed Generation in Submerged Conditions After alluvial soil was placed into 1/10000 are of Wagner pot, water was poured and mixed to form a submerged condition having a water depth of 4 cm. Seeds of Echinochloa oryzacola Vasing., Scirpus juncoides, and Monochoria vaginalis were sowed in a mixed manner in the above pot and the pot was placed in the greenhouse of 25° C. to 30° C. to grow the plants. When Echinochloa oryzacola Vasing., Scirpus juncoides, and Monochoria vaginalis were grown to one leaf stage to two leaf stage, the emulsion agent containing the compound of the present invention prepared in accordance with Formulation Example 2 was diluted with water so as to be a predetermined herbicide amount and the diluted compound was applied to the surface of the water. Three weeks after the herbicide application, effects on each plant were investigated in accordance with the criteria of Test Example 1. The results are listed in Eighteenth Table.

[Test Example 3] Herbicidal Effect Test by Application to Foliage

After alluvial soil was placed into 1/10000 are of Wagner pot, water was poured and mixed to form a condition having a water depth of 0.1 cm to 0.5 cm. Seeds of Echinochloa crus-galli var. crus-galli, Leptochloa chinensis, Cyperus difformis, and Oryza sativa were sowed and the pot was placed in the greenhouse of 25° C. to 30° C. to grow the plants. After the plants were grown for 14 days, the emulsion agent containing the compound of the present invention prepared in accordance with Formulation Example 2 was diluted with water so as to be a predetermined herbicide amount and the diluted compound was uniformly applied to a stem and leaf part with a small-size spray. Three weeks after the herbicide application, effects on each plant were investigated in accordance with the criteria of Test Example 1. The results are listed in Nineteenth Table.

[Test Example 4] Herbicidal Effect Test by Application to Foliage

Sterilized diluvial soil was placed in a plastic box having a length of 21 cm, a width of 13 cm, and a depth of 7 cm. Each of the seeds of Digitaria ciliaris, Setaria viridis, Echinochloa crus-galli var. crus-galli, Avena fatua, Alopecurus myosuroides, Lolium multiflorum Lam., Apera spica-venti., Abutilon theophrasti, Amaranthus retroflexus, Chenopodium album, Stellaria media, Galium spurium, Veronica persica, Zea mays, Glycine max, Oryza sativa, Triticum aestivum, Beta vulgaris ssp. vulgaris, and Brassica campestris L. was sowed in a spot-like manner and was covered with the soil of about 1.5 cm thick. Thereafter, the plants were grown in the greenhouse of 25° C. to 30° C. After the plants were grown for 14 days, the emulsion agent containing the compound of the present invention prepared in accordance with Formulation Example 2 was diluted with water so as to be a predetermined herbicide amount and the diluted compound was uniformly applied to a stem and leaf part with a small-size spray. Three weeks after the herbicide application, effects on each plant were investigated in accordance with the criteria of Test Example 1. The results are listed in Twentieth Table.

The symbols in Seventeenth Table to Twentieth Table have the following meanings.
A: Echinochloa oryzicola Vasing., B: Scirpus juncoides, C: Monochoria vaginalis, D: Leptochloa chinensis, E: Cyperus difformis, F: Digitaria ciliaris, G: Setaria viridis, H: Echinochloa crus-galli var. crus-galli, I: Avena fatua, J: Alopecurus myosuroides, K: Lolium multiflorum Lam., L: Apera spica-venti., M: Abutilon theophrasti, N: Amaranthus retroflexus, O: Chenopodium album, P: Stellaria media, Q:

*Galium spurium*, R: *Veronica persica*, a: transplanted *Oryza sativa*, b: directly sowed *Oryza sativa*, c: *Zea mays*, d: *Glycine max*, e: *Triticum aestivum*, f: *Beta vulgaris* ssp. *vulgaris*, and g: *Brassica campestris* L.

The application herbicide amount (g/ha) means an amount that a concentration is adjusted so that, when an application amount is converted into per hectare (1 ha), the herbicide is applied by the number of grams (g) of the described value.

[Seventeenth Table]

TABLE 49

| No. | Application herbicide amount (g/ha) | A | B | C | a |
|---|---|---|---|---|---|
| 1-001 | 320 | 3 | 2 | 2 | 0 |
| 1-002 | 320 | 2 | 1 | 0 | 0 |
| 1-004 | 320 | 5 | 4 | 4 | 1 |
| 1-005 | 320 | 5 | 4 | 4 | 0 |
| 1-010 | 320 | 5 | 3 |   | 0 |
| 1-011 | 320 | 5 | 4 | 5 | 1 |
| 1-012 | 320 | 5 | 3 | 4 | 0 |
| 1-014 | 320 | 5 | 4 | 3 | 0 |
| 1-015 | 320 | 2 | 3 | 3 | 0 |
| 1-016 | 320 | 4 | 0 | 0 | 0 |
| 1-017 | 320 | 3 | 2 | 0 | 0 |
| 1-018 | 320 | 1 | 3 | 5 | 0 |
| 1-019 | 320 | 5 | 3 | 4 | 2 |
| 1-020 | 320 | 4 | 3 | 2 | 0 |
| 1-021 | 320 | 5 | 4 | 4 | 2 |
| 1-022 | 320 | 2 | 2 | 0 | 0 |
| 1-024 | 320 | 5 | 2 | 0 | 0 |
| 1-026 | 320 | 5 | 4 | 4 | 2 |
| 1-027 | 320 | 5 | 3 | 4 | 1 |
| 1-029 | 320 | 5 | 3 | 4 | 2 |
| 1-030 | 320 | 5 | 3 | 3 | 0 |
| 1-031 | 320 | 4 | 3 | 3 | 0 |
| 1-032 | 320 | 5 | 3 | 2 | 2 |
| 1-033 | 320 | 5 | 4 | 3 | 0 |
| 1-034 | 320 | 4 | 4 | 3 | 3 |
| 1-035 | 320 | 5 | 4 | 4 | 2 |
| 1-036 | 320 | 4 | 3 | 3 | 4 |
| 1-037 | 320 | 0 | 2 | 3 | 0 |
| 1-038 | 320 | 2 | 2 | 1 | 0 |
| 1-040 | 320 | 3 | 3 | 3 | 1 |
| 1-041 | 320 | 3 | 3 | 3 | 0 |
| 1-042 | 320 | 2 | 2 | 2 | 0 |
| 1-043 | 320 | 5 | 3 | 3 | 3 |
| 1-044 | 320 | 5 | 3 | 3 | 1 |
| 1-046 | 320 | 5 | 3 | 3 | 2 |
| 1-047 | 320 | 4 | 3 | 2 | 1 |
| 1-048 | 320 | 3 | 0 | 0 | 1 |
| 1-049 | 320 | 5 | 2 | 0 | 0 |
| 1-050 | 320 | 5 | 5 | 4 | 2 |
| 1-051 | 320 | 5 | 4 | 4 | 0 |
| 1-052 | 320 | 3 | 3 | 2 | 0 |
| 1-053 | 320 | 2 | 3 | 2 | 0 |
| 1-054 | 320 | 5 | 3 | 4 | 2 |
| 1-055 | 320 | 4 | 4 | 4 | 1 |
| 1-056 | 320 | 5 | 5 | 4 | 3 |
| 1-057 | 320 | 5 | 5 | 4 | 2 |
| 1-058 | 320 | 5 | 5 | 4 | 4 |

TABLE 50

| No. | Application herbicide amount (g/ha) | A | B | C | a |
|---|---|---|---|---|---|
| 1-059 | 320 | 2 | 3 | 2 | 0 |
| 1-060 | 320 | 4 | 4 | 3 | 2 |
| 1-062 | 320 | 3 | 2 | 1 | 0 |
| 1-063 | 320 | 5 | 4 | 3 | 0 |
| 1-064 | 320 | 5 | 4 | 3 | 0 |
| 1-065 | 320 | 5 | 3 | 2 | 0 |
| 1-066 | 320 | 5 | 4 | 2 | 2 |
| 1-067 | 320 | 3 | 0 | 0 | 0 |
| 1-068 | 320 | 2 | 3 | 3 | 0 |

TABLE 50-continued

| No. | Application herbicide amount (g/ha) | A | B | C | a |
|---|---|---|---|---|---|
| 1-069 | 320 | 5 | 4 | 3 | 0 |
| 1-070 | 320 | 5 | 5 | 5 | 3 |
| 1-071 | 320 | 4 | 5 | 4 | 0 |
| 1-073 | 320 | 4 | 3 | 2 | 3 |
| 1-074 | 320 | 2 | 2 | 0 | 0 |
| 1-075 | 320 | 2 | 0 | 2 | 0 |
| 1-076 | 320 | 5 | 4 | 4 | 3 |
| 1-077 | 320 | 0 | 0 | 2 | 0 |
| 1-078 | 320 | 4 | 4 | 3 | 4 |
| 1-079 | 320 | 4 | 4 | 3 | 4 |
| 1-080 | 320 | 5 | 4 | 4 | 4 |
| 1-082 | 320 | 3 | 2 | 2 | 0 |
| 1-083 | 320 | 2 | 3 | 3 | 0 |
| 1-084 | 320 | 2 | 3 | 2 | 0 |
| 1-085 | 320 | 3 | 4 | 3 | 3 |
| 1-086 | 320 | 5 | 4 | 4 | 5 |
| 1-087 | 320 | 5 |   | 3 | 0 |
| 1-090 | 320 | 3 | 4 | 2 | 0 |
| 1-091 | 320 | 5 | 5 | 5 | 0 |
| 1-092 | 320 | 5 | 5 | 4 | 3 |
| 1-093 | 320 | 5 | 4 | 3 | 0 |
| 1-094 | 320 | 5 | 5 | 3 | 0 |
| 1-095 | 320 | 5 | 5 | 5 | 1 |
| 1-096 | 320 | 5 | 4 | 4 | 3 |
| 1-100 | 320 | 4 | 3 | 3 | 0 |
| 1-102 | 320 | 3 | 2 | 2 | 2 |
| 1-103 | 320 | 5 | 4 | 4 | 3 |
| 1-104 | 320 | 4 | 3 | 2 | 0 |
| 1-105 | 320 | 5 | 5 | 4 | 0 |
| 1-106 | 320 | 5 | 5 | 4 | 1 |
| 1-107 | 320 | 5 | 4 | 5 | 2 |
| 1-108 | 320 | 5 | 5 | 5 | 0 |
| 1-109 | 320 | 0 | 2 | 0 | 0 |
| 1-110 | 320 | 5 | 4 | 4 | 4 |
| 1-112 | 320 | 3 | 3 | 2 | 0 |
| 1-113 | 320 | 4 | 3 | 2 | 0 |
| 1-114 | 320 | 3 | 2 | 0 | 0 |
| 1-115 | 320 | 5 | 4 | 3 | 0 |

TABLE 51

| No. | Application herbicide amount (g/ha) | A | B | C | a |
|---|---|---|---|---|---|
| 1-116 | 320 | 5 | 4 | 2 | 0 |
| 1-118 | 320 | 3 | 2 | 0 | 2 |
| 1-119 | 320 | 2 | 1 | 0 | 3 |
| 1-120 | 320 | 5 | 3 | 1 | 3 |
| 1-121 | 320 | 5 | 4 | 4 | 3 |
| 1-122 | 320 | 5 | 5 | 5 | 3 |
| 1-123 | 320 | 5 | 4 | 4 | 1 |
| 1-124 | 320 | 3 | 3 | 1 | 0 |
| 1-125 | 320 | 0 | 3 | 1 | 0 |
| 1-126 | 320 | 3 | 4 | 2 | 0 |
| 1-128 | 288 | 5 | 4 | 2 | 0 |
| 1-129 | 320 | 5 | 4 | 3 | 1 |
| 1-130 | 320 | 1 | 0 | 0 | 1 |
| 1-131 | 320 | 2 | 1 | 0 | 0 |
| 1-132 | 320 | 5 | 4 | 4 | 2 |
| 1-133 | 320 | 5 | 3 | 4 | 0 |
| 1-134 | 320 | 3 | 3 | 2 | 0 |
| 1-135 | 320 | 3 | 4 | 4 | 1 |
| 1-136 | 320 | 5 | 3 | 3 | 1 |
| 1-137 | 320 | 5 | 5 | 5 | 3 |
| 1-138 | 320 | 5 | 5 | 4 | 2 |
| 1-139 | 320 | 5 | 4 | 3 | 2 |
| 1-143 | 320 | 0 | 0 | 2 | 0 |
| 1-144 | 320 | 5 | 3 | 3 | 1 |
| 1-145 | 320 | 5 | 5 | 5 | 4 |
| 1-146 | 320 | 5 | 5 | 5 | 3 |
| 1-147 | 320 | 5 | 5 | 5 | 2 |
| 1-148 | 320 | 5 | 5 | 5 | 4 |
| 1-149 | 320 | 5 | 4 | 3 | 3 |
| 1-150 | 320 | 5 | 5 | 5 | 4 |

TABLE 51-continued

| No. | Application herbicide amount (g/ha) | A | B | C | a |
|---|---|---|---|---|---|
| 1-151 | 320 | 5 | 5 | 3 | 0 |
| 1-152 | 320 | 5 | 4 | 3 | 2 |
| 1-153 | 320 | 3 | 3 | 4 | 2 |
| 1-154 | 320 |   | 3 | 2 | 0 |
| 1-155 | 320 |   | 4 | 3 | 0 |
| 1-156 | 320 |   | 2 | 0 | 0 |
| 1-157 | 320 |   | 3 | 2 | 2 |
| 1-158 | 320 |   | 4 | 0 | 0 |
| 1-159 | 320 |   | 3 | 0 | 0 |
| 1-161 | 320 |   | 2 | 0 | 0 |
| 1-162 | 320 |   | 2 | 0 | 0 |
| 1-163 | 320 |   | 4 | 4 | 2 |
| 1-164 | 320 |   | 5 | 4 | 3 |
| 1-165 | 320 | 4 | 3 | 4 | 0 |
| 1-166 | 320 |   | 3 | 2 | 0 |
| 1-167 | 320 | 4 | 2 | 0 | 0 |
| 1-169 | 320 | 5 | 4 | 4 | 0 |

TABLE 52

| No. | Application herbicide amount (g/ha) | A | B | C | a |
|---|---|---|---|---|---|
| 1-171 | 320 | 5 | 4 | 4 | 1 |
| 1-172 | 320 | 5 | 4 | 3 | 1 |
| 2-001 | 320 | 2 | 3 | 4 | 0 |
| 2-002 | 320 | 2 | 3 | 3 | 0 |
| 2-003 | 320 | 5 | 5 | 5 | 4 |
| 2-005 | 320 | 5 | 5 | 5 | 0 |
| 2-006 | 320 | 5 | 5 | 5 | 4 |
| 2-007 | 320 | 5 | 5 | 5 | 3 |
| 2-008 | 320 | 4 | 4 | 4 | 1 |
| 2-009 | 320 | 3 | 3 | 4 | 0 |
| 2-010 | 320 | 5 | 5 | 4 | 4 |
| 2-011 | 320 | 5 | 5 | 5 | 2 |
| 2-012 | 320 | 5 | 4 | 3 | 1 |
| 2-013 | 320 | 5 | 4 | 5 | 3 |
| 2-014 | 320 | 5 | 5 | 5 | 4 |
| 2-015 | 320 | 5 | 5 | 5 | 1 |
| 2-016 | 320 | 5 | 5 | 5 | 4 |
| 2-017 | 320 | 5 | 3 | 4 | 4 |
| 2-019 | 320 | 5 | 5 | 4 | 2 |
| 2-020 | 320 | 3 | 2 | 2 | 1 |
| 2-021 | 320 | 5 | 5 | 5 | 4 |
| 2-022 | 320 | 5 | 5 | 5 | 5 |
| 2-023 | 320 | 2 | 1 | 0 | 3 |
| 2-024 | 320 | 5 | 5 | 5 | 5 |
| 2-025 | 320 | 5 | 5 | 5 | 5 |
| 2-026 | 320 | 5 | 5 | 4 | 4 |
| 2-027 | 320 | 5 | 5 | 5 | 4 |
| 2-028 | 320 | 5 | 5 | 5 | 5 |
| 2-029 | 320 | 5 | 5 | 5 | 5 |
| 2-030 | 320 | 5 | 4 | 4 | 3 |
| 2-031 | 320 | 5 | 5 | 5 | 5 |
| 2-032 | 320 | 5 | 5 | 5 | 5 |
| 2-033 | 320 | 5 | 4 | 5 | 4 |
| 2-034 | 320 | 5 | 4 | 4 | 4 |
| 2-035 | 320 | 4 | 3 | 3 | 4 |
| 2-037 | 320 | 5 | 5 | 5 | 4 |
| 2-038 | 320 | 5 | 5 | 5 | 4 |
| 2-039 | 320 | 5 | 5 | 5 | 4 |
| 2-040 | 320 | 4 | 4 | 4 | 4 |
| 2-041 | 320 | 5 | 5 | 4 | 0 |
| 2-042 | 320 | 5 | 4 | 4 | 5 |
| 2-043 | 320 | 5 | 5 | 5 | 4 |
| 2-044 | 320 | 5 | 5 | 5 | 4 |
| 2-045 | 320 | 5 | 5 | 5 | 5 |
| 2-046 | 320 | 4 | 0 | 0 | 0 |
| 2-047 | 320 | 5 | 4 | 5 | 4 |
| 2-048 | 320 | 5 | 5 | 4 | 4 |

TABLE 53

| No. | Application herbicide amount (g/ha) | A | B | C | a |
|---|---|---|---|---|---|
| 2-049 | 320 | 5 | 5 | 4 | 3 |
| 2-050 | 192 | 4 | 2 | 3 | 2 |
| 2-051 | 320 | 5 | 5 | 5 | 4 |
| 2-052 | 320 | 5 | 5 | 5 | 5 |
| 2-053 | 320 | 5 | 5 | 4 | 5 |
| 2-054 | 320 | 5 | 5 | 5 | 5 |
| 2-056 | 320 | 4 | 4 | 3 | 1 |
| 2-057 | 320 | 4 | 4 | 4 | 4 |
| 2-058 | 320 | 4 | 4 | 5 | 5 |
| 2-059 | 320 | 4 | 4 | 4 | 5 |
| 2-060 | 320 | 5 | 5 | 5 | 5 |
| 2-061 | 320 | 5 | 5 | 5 | 4 |
| 2-062 | 320 | 5 | 5 | 5 | 5 |
| 2-063 | 320 | 5 |   | 5 | 4 |
| 2-064 | 320 | 5 |   | 2 | 3 |
| 2-065 | 320 | 5 | 4 | 4 | 2 |
| 2-066 | 320 | 5 | 5 | 4 | 3 |
| 2-067 | 320 | 5 | 4 | 4 | 5 |
| 2-068 | 320 | 5 | 5 | 4 | 5 |
| 2-069 | 320 | 5 | 5 | 5 | 5 |
| 2-070 | 320 | 5 | 5 | 5 | 4 |
| 2-071 | 320 | 5 | 5 | 5 | 4 |
| 2-072 | 320 | 5 | 5 | 5 | 3 |
| 2-073 | 320 | 4 | 3 | 4 | 2 |
| 2-074 | 320 | 4 | 4 | 3 | 3 |
| 2-075 | 320 | 5 | 5 | 5 | 5 |
| 2-076 | 320 | 5 | 4 | 3 | 2 |
| 2-077 | 320 | 5 | 3 | 3 | 1 |
| 2-078 | 320 | 5 | 4 | 2 | 4 |
| 2-079 | 320 | 5 | 5 | 5 | 4 |
| 2-080 | 320 | 3 | 0 | 0 | 2 |
| 2-081 | 320 | 4 | 3 | 4 | 3 |
| 2-082 | 320 | 5 | 5 | 5 | 5 |
| 2-083 | 320 | 5 | 5 | 4 | 2 |
| 2-084 | 320 | 5 | 5 | 4 | 4 |
| 2-085 | 320 | 5 | 5 | 4 | 1 |
| 2-086 | 320 | 3 | 2 | 3 | 0 |
| 2-087 | 320 | 5 | 5 | 4 | 3 |
| 2-088 | 141 | 5 | 5 | 5 | 3 |
| 2-089 | 320 | 5 | 5 | 5 | 4 |
| 2-090 | 320 | 5 | 5 | 5 | 4 |
| 2-091 | 320 | 5 | 5 | 5 | 0 |
| 2-093 | 320 | 5 | 5 | 4 | 2 |
| 2-094 | 320 | 5 | 5 | 5 | 4 |
| 2-095 | 320 | 5 | 5 | 5 | 5 |
| 2-096 | 320 |   | 5 | 4 | 3 |
| 2-097 | 320 |   | 4 | 3 | 1 |

TABLE 54

| No. | Application herbicide amount (g/ha) | A | B | C | a |
|---|---|---|---|---|---|
| 2-098 | 320 |   | 5 | 4 | 2 |
| 2-099 | 320 | 5 | 4 | 5 | 4 |
| 2-100 | 320 | 5 | 5 | 5 | 3 |
| 2-101 | 320 | 5 | 5 | 5 | 3 |
| 2-102 | 320 | 5 | 5 | 4 | 1 |
| 2-103 | 320 | 5 | 4 | 5 | 3 |
| 2-105 | 320 | 5 | 5 | 5 | 4 |
| 2-106 | 320 | 5 | 3 | 4 | 2 |
| 2-107 | 320 | 2 | 3 | 2 | 1 |
| 2-108 | 320 | 4 | 3 | 2 | 0 |
| 2-109 | 260 | 2 | 3 |   | 0 |
| 2-110 | 320 | 5 | 5 | 5 | 4 |
| 4-003 | 320 |   | 2 | 0 | 0 |
| 6-002 | 320 | 4 | 3 | 2 | 0 |
| 6-004 | 320 | 0 | 0 | 2 | 0 |
| 7-001 | 320 | 0 | 2 | 4 | 0 |
| 7-002 | 320 | 3 | 3 | 4 | 1 |

[Eighteenth Table]

TABLE 55

| No. | Application herbicide amount (g/ha) | A | B | C |
|---|---|---|---|---|
| 1-001 | 320 | 4 | 4 | 2 |
| 1-002 | 320 | 3 | 0 | 0 |
| 1-004 | 320 | 4 | 3 | 4 |
| 1-005 | 320 | 5 | 1 | 0 |
| 1-010 | 320 | 4 | 1 | 4 |
| 1-011 | 320 | 5 | 3 | 3 |
| 1-012 | 320 | 2 | 2 | 2 |
| 1-014 | 280 | 2 | 3 | 0 |
| 1-015 | 320 | 4 | 2 | 1 |
| 1-016 | 320 | 3 | 0 | 0 |
| 1-017 | 320 | 2 | 2 | 0 |
| 1-018 | 320 | 0 | 2 | 0 |
| 1-019 | 320 | 4 | 3 | 3 |
| 1-020 | 320 | 2 | 2 | 2 |
| 1-021 | 320 | 4 | 4 | 3 |
| 1-022 | 320 | 2 | 2 | 0 |
| 1-024 | 320 | 4 | 1 | 0 |
| 1-026 | 320 | 3 | 1 | 0 |
| 1-027 | 320 | 4 | 3 | 3 |
| 1-029 | 320 | 3 | 2 | 3 |
| 1-030 | 320 | 4 | 3 | 3 |
| 1-031 | 320 | 3 | 2 | 2 |
| 1-032 | 320 | 4 | 3 | 3 |
| 1-033 | 320 | 4 | 4 | 3 |
| 1-034 | 320 | 4 | 3 | 4 |
| 1-035 | 320 | 5 | 4 | 4 |
| 1-036 | 320 | 3 | 2 | 4 |
| 1-037 | 320 | 2 | 2 | |
| 1-038 | 320 | 1 | 1 | 0 |
| 1-040 | 320 | 3 | 2 | |
| 1-041 | 320 | 2 | 3 | |
| 1-042 | 320 | 1 | 2 | 3 |
| 1-043 | 320 | 3 | 3 | 3 |
| 1-044 | 320 | 2 | 3 | 2 |
| 1-046 | 320 | 4 | | |
| 1-047 | 320 | 3 | 2 | 3 |
| 1-048 | 320 | 0 | 1 | 0 |
| 1-049 | 320 | 4 | 2 | 2 |
| 1-050 | 320 | 5 | 4 | 3 |
| 1-051 | 320 | 4 | 3 | 4 |
| 1-052 | 320 | 1 | 1 | 0 |
| 1-053 | 320 | 1 | 2 | 0 |
| 1-054 | 320 | 4 | 3 | 3 |
| 1-055 | 320 | 3 | 3 | 3 |
| 1-056 | 320 | 5 | 4 | 4 |
| 1-057 | 320 | 2 | 3 | 3 |
| 1-058 | 320 | 4 | 5 | 4 |

TABLE 56

| No. | Application herbicide amount (g/ha) | A | B | C |
|---|---|---|---|---|
| 1-059 | 320 | 2 | 3 | 2 |
| 1-060 | 320 | 2 | 3 | 2 |
| 1-061 | 320 | 0 | 1 | 1 |
| 1-062 | 320 | 2 | 2 | 2 |
| 1-063 | 320 | 4 | 3 | 2 |
| 1-064 | 320 | 2 | 3 | 2 |
| 1-065 | 320 | 1 | 2 | 2 |
| 1-066 | 320 | 2 | 3 | 2 |
| 1-068 | 320 | 2 | 2 | 2 |
| 1-069 | 320 | 4 | 4 | 4 |
| 1-070 | 320 | 5 | 5 | 5 |
| 1-071 | 320 | 3 | 5 | 4 |
| 1-073 | 320 | 2 | 2 | 1 |
| 1-074 | 320 | 2 | 0 | 0 |
| 1-076 | 320 | 2 | 0 | 4 |
| 1-078 | 320 | 4 | 3 | 3 |
| 1-079 | 320 | 4 | 3 | 4 |
| 1-080 | 320 | 5 | 3 | 4 |
| 1-083 | 320 | 2 | 2 | 2 |

TABLE 56-continued

| No. | Application herbicide amount (g/ha) | A | B | C |
|---|---|---|---|---|
| 1-084 | 320 | 2 | 1 | 0 |
| 1-085 | 320 | 3 | 2 | 2 |
| 1-086 | 320 | 4 | 4 | 4 |
| 1-087 | 320 | 4 | | 3 |
| 1-090 | 320 | 2 | 1 | 3 |
| 1-091 | 320 | 5 | 5 | 5 |
| 1-092 | 320 | 4 | 4 | 3 |
| 1-093 | 320 | 3 | 3 | 3 |
| 1-094 | 320 | 4 | 3 | 3 |
| 1-095 | 320 | 4 | 5 | 4 |
| 1-096 | 320 | 4 | 3 | 4 |
| 1-100 | 320 | 4 | 3 | 4 |
| 1-102 | 320 | 1 | 1 | 1 |
| 1-103 | 320 | 4 | 5 | 4 |
| 1-104 | 320 | 4 | 3 | 3 |
| 1-105 | 320 | 3 | 4 | 3 |
| 1-106 | 320 | 5 | 5 | 4 |
| 1-107 | 320 | 5 | 4 | 4 |
| 1-108 | 320 | 4 | 4 | 3 |
| 1-109 | 320 | 0 | 1 | 0 |
| 1-110 | 320 | 4 | 3 | 4 |
| 1-112 | 320 | 1 | 2 | 0 |
| 1-113 | 320 | 2 | 0 | 0 |
| 1-114 | 320 | 0 | 1 | 0 |
| 1-115 | 320 | 3 | 3 | |
| 1-116 | 320 | 3 | 4 | 0 |
| 1-118 | 320 | 2 | 3 | 0 |
| 1-119 | 320 | 4 | 1 | 0 |

TABLE 57

| No. | Application herbicide amount (g/ha) | A | B | C |
|---|---|---|---|---|
| 1-120 | 320 | 3 | 3 | 2 |
| 1-121 | 320 | 4 | 4 | 4 |
| 1-122 | 320 | 4 | 3 | 3 |
| 1-123 | 320 | 3 | 2 | 3 |
| 1-124 | 320 | 3 | 3 | 1 |
| 1-125 | 320 | 0 | 2 | 1 |
| 1-126 | 320 | 1 | 3 | 3 |
| 1-128 | 288 | 1 | 3 | 0 |
| 1-129 | 320 | 3 | 4 | 3 |
| 1-131 | 320 | 0 | 1 | 0 |
| 1-132 | 320 | 4 | 4 | 4 |
| 1-133 | 320 | 2 | 2 | 3 |
| 1-134 | 320 | 1 | 3 | 3 |
| 1-135 | 320 | 2 | 2 | 3 |
| 1-136 | 320 | 0 | 2 | 2 |
| 1-137 | 320 | 3 | 3 | 3 |
| 1-138 | 320 | 3 | 3 | 3 |
| 1-139 | 320 | 4 | 3 | 3 |
| 1-144 | 320 | 4 | 4 | 3 |
| 1-145 | 320 | 4 | 4 | 4 |
| 1-146 | 320 | 3 | 3 | 3 |
| 1-147 | 320 | 4 | 2 | 3 |
| 1-148 | 320 | 5 | 5 | 4 |
| 1-149 | 320 | 3 | 3 | 2 |
| 1-150 | 320 | 5 | 5 | 4 |
| 1-151 | 320 | 4 | 4 | 2 |
| 1-152 | 320 | 3 | 3 | 3 |
| 1-153 | 320 | 3 | 3 | 3 |
| 1-154 | 320 | 0 | 2 | 0 |
| 1-155 | 320 | 1 | 2 | 0 |
| 1-156 | 320 | 0 | 3 | 2 |
| 1-157 | 320 | 0 | 1 | 0 |
| 1-158 | 320 | 2 | 3 | 0 |
| 1-159 | 320 | 3 | | |
| 1-162 | 320 | 3 | 1 | 0 |
| 1-163 | 320 | 4 | | |
| 1-164 | 320 | 4 | 4 | 4 |
| 1-165 | 320 | 2 | 2 | |
| 1-166 | 320 | 2 | 3 | |
| 1-168 | 320 | 2 | 2 | |

TABLE 57-continued

| No. | Application herbicide amount (g/ha) | A | B | C |
|---|---|---|---|---|
| 1-169 | 320 | 3 | 4 | 4 |
| 1-171 | 320 | 4 | | |
| 1-172 | 320 | 3 | 4 | 3 |
| 1-173 | 320 | 3 | 2 | 2 |
| 2-001 | 320 | 2 | 2 | 3 |
| 2-002 | 320 | 2 | 1 | 2 |
| 2-003 | 320 | 5 | 3 | 4 |

TABLE 58

| No. | Application herbicide amount (g/ha) | A | B | C |
|---|---|---|---|---|
| 2-005 | 320 | 5 | 3 | 4 |
| 2-006 | 320 | 5 | 5 | 5 |
| 2-007 | 320 | 4 | 4 | 4 |
| 2-008 | 320 | 3 | 2 | 3 |
| 2-009 | 320 | 3 | 2 | 3 |
| 2-010 | 320 | 5 | 4 | 4 |
| 2-011 | 320 | 4 | 3 | 4 |
| 2-012 | 320 | 4 | 5 | 5 |
| 2-013 | 320 | 5 | 3 | 2 |
| 2-014 | 320 | 5 | 5 | 5 |
| 2-015 | 320 | 4 | 5 | 4 |
| 2-016 | 320 | 5 | 5 | 5 |
| 2-017 | 320 | 5 | 4 | 4 |
| 2-019 | 320 | 4 | 3 | 4 |
| 2-020 | 320 | 2 | 2 | 0 |
| 2-021 | 320 | 5 | 4 | 4 |
| 2-022 | 320 | 5 | 5 | 4 |
| 2-023 | 320 | 0 | 1 | 1 |
| 2-024 | 320 | 5 | 4 | 4 |
| 2-025 | 320 | 5 | 4 | 5 |
| 2-026 | 320 | 5 | 5 | 4 |
| 2-027 | 320 | 5 | 4 | 4 |
| 2-028 | 320 | 5 | 4 | 4 |
| 2-029 | 320 | 5 | 4 | 4 |
| 2-030 | 320 | 4 | 3 | 4 |
| 2-031 | 320 | 5 | 4 | 4 |
| 2-032 | 320 | 5 | 5 | 5 |
| 2-033 | 320 | 4 | 3 | 4 |
| 2-034 | 320 | 5 | 4 | 4 |
| 2-035 | 320 | 2 | 2 | 3 |
| 2-037 | 320 | 5 | 5 | 5 |
| 2-038 | 320 | 5 | 4 | 5 |
| 2-039 | 320 | 5 | 5 | 5 |
| 2-040 | 320 | 4 | 3 | 4 |
| 2-041 | 320 | 5 | 4 | 3 |
| 2-042 | 320 | 4 | 3 | 4 |
| 2-043 | 320 | 5 | 4 | 4 |
| 2-044 | 320 | 5 | 4 | 4 |
| 2-045 | 320 | 5 | 3 | 4 |
| 2-047 | 320 | 3 | 5 | 4 |
| 2-048 | 320 | 3 | 4 | 3 |
| 2-049 | 320 | 5 | 5 | 4 |
| 2-050 | 192 | 1 | 0 | 2 |
| 2-051 | 320 | 5 | 5 | 5 |
| 2-052 | 320 | 5 | 4 | 4 |
| 2-053 | 320 | 5 | 4 | 4 |
| 2-054 | 320 | 5 | 4 | 5 |

TABLE 59

| No. | Application herbicide amount (g/ha) | A | B | C |
|---|---|---|---|---|
| 2-056 | 320 | 3 | 3 | 3 |
| 2-057 | 320 | 4 | 4 | 4 |
| 2-058 | 320 | 4 | 4 | 4 |
| 2-059 | 320 | 4 | 3 | 4 |
| 2-060 | 320 | 5 | 3 | 5 |
| 2-061 | 320 | 4 | 5 | 5 |
| 2-062 | 320 | 5 | 4 | 5 |
| 2-060 | 320 | 5 | 4 | 5 |
| 2-061 | 320 | 4 | 5 | 5 |
| 2-062 | 320 | 5 | 4 | 5 |
| 2-063 | 320 | 5 | 4 | 5 |
| 2-064 | 320 | 3 | 4 | 3 |
| 2-065 | 320 | 5 | 4 | 4 |
| 2-066 | 320 | 3 | | 3 |
| 2-067 | 320 | 5 | 4 | 5 |
| 2-068 | 320 | 5 | 5 | 4 |
| 2-069 | 320 | 5 | 5 | 5 |
| 2-070 | 320 | 5 | 5 | 5 |
| 2-071 | 320 | 3 | 5 | 5 |
| 2-072 | 320 | 5 | 5 | 5 |
| 2-073 | 320 | 2 | 2 | 3 |
| 2-074 | 320 | 4 | 4 | 3 |
| 2-075 | 320 | 5 | 5 | 5 |
| 2-076 | 320 | 2 | 3 | 2 |
| 2-077 | 320 | 2 | 2 | 2 |
| 2-078 | 320 | 4 | 4 | 3 |
| 2-079 | 320 | 5 | 5 | 5 |
| 2-080 | 320 | 2 | 1 | 0 |
| 2-081 | 320 | 2 | 2 | 2 |
| 2-082 | 320 | 5 | 4 | 3 |
| 2-083 | 320 | 3 | 3 | 3 |
| 2-084 | 320 | 4 | 4 | 3 |
| 2-085 | 320 | 4 | 4 | 3 |
| 2-086 | 320 | 0 | 2 | 1 |
| 2-087 | 320 | 4 | 4 | 3 |
| 2-088 | 141 | 4 | 3 | 4 |
| 2-089 | 320 | 4 | 4 | 5 |
| 2-090 | 320 | 5 | 5 | 4 |
| 2-091 | 320 | 4 | 5 | 4 |
| 2-093 | 320 | 2 | 4 | 3 |
| 2-094 | 320 | 5 | 5 | 4 |
| 2-095 | 320 | 4 | 5 | 5 |
| 2-096 | 320 | 3 | 3 | 3 |
| 2-097 | 320 | 0 | 2 | 2 |
| 2-098 | 320 | 5 | 4 | 3 |
| 2-099 | 320 | 5 | 5 | 4 |
| 2-100 | 320 | 4 | 3 | 4 |

TABLE 60

| No. | Application herbicide amount (g/ha) | A | B | C |
|---|---|---|---|---|
| 2-101 | 320 | 4 | 4 | 5 |
| 2-102 | 320 | 4 | 4 | 4 |
| 2-103 | 320 | 4 | 3 | 4 |
| 2-105 | 320 | 4 | 4 | 4 |
| 2-106 | 320 | 1 | 2 | 3 |
| 2-107 | 320 | 2 | 1 | 2 |
| 2-108 | 320 | 0 | 1 | |
| 2-109 | 260 | 1 | 1 | |
| 2-110 | 320 | 5 | 5 | 4 |
| 6-002 | 320 | 3 | 2 | 3 |
| 6-004 | 320 | 3 | 0 | 2 |
| 7-002 | 320 | 4 | 2 | 2 |

[Nineteenth Table]

TABLE 61

| No. | Application herbicide amount (g/ha) | H | D | E | b |
|---|---|---|---|---|---|
| 1-001 | 320 | 5 | 5 | 4 | 0 |
| 1-002 | 400 | 4 | 4 | | 0 |
| 1-004 | 400 | 4 | 5 | 5 | 0 |
| 1-005 | 400 | 2 | 5 | 5 | 0 |
| 1-008 | 320 | 3 | 0 | | 0 |
| 1-010 | 400 | 5 | 5 | 4 | 0 |

TABLE 61-continued

| No. | Application herbicide amount (g/ha) | H | D | E | b |
|---|---|---|---|---|---|
| 1-011 | 400 | 5 | 5 | 5 | 0 |
| 1-012 | 400 | 3 | 5 |   | 0 |
| 1-013 | 320 | 3 | 4 | 3 | 0 |
| 1-014 | 320 | 5 | 2 | 4 | 1 |
| 1-015 | 320 | 5 | 5 | 4 | 1 |
| 1-016 | 320 | 5 | 5 | 5 | 1 |
| 1-017 | 320 | 4 | 3 | 4 | 0 |
| 1-018 | 320 | 4 | 4 | 4 | 2 |
| 1-019 | 320 | 5 | 5 | 5 | 4 |
| 1-020 | 320 | 5 | 4 | 4 | 2 |
| 1-021 | 320 | 5 | 5 | 5 | 3 |
| 1-022 | 320 | 5 | 5 | 4 | 2 |
| 1-024 | 320 | 5 | 4 | 4 | 2 |
| 1-025 | 320 | 4 | 3 | 2 | 2 |
| 1-026 | 320 | 5 | 4 | 4 | 4 |
| 1-027 | 320 | 5 | 5 | 5 | 3 |
| 1-029 | 320 | 4 | 5 | 4 | 4 |
| 1-030 | 320 | 5 | 5 | 5 | 4 |
| 1-031 | 320 | 5 | 4 | 3 | 2 |
| 1-032 | 320 | 5 | 5 | 5 | 2 |
| 1-033 | 320 | 5 | 5 | 5 | 1 |
| 1-034 | 320 | 5 | 5 | 5 | 5 |
| 1-035 | 320 | 5 | 5 | 5 | 4 |
| 1-036 | 320 | 5 | 5 | 5 | 4 |
| 1-037 | 320 | 5 | 5 | 5 | 2 |
| 1-038 | 320 | 5 | 5 | 4 | 2 |
| 1-039 | 320 | 3 | 3 | 3 | 2 |
| 1-040 | 320 | 4 | 5 | 4 | 3 |
| 1-041 | 320 | 4 | 5 | 5 | 2 |
| 1-042 | 320 | 5 |   | 4 | 1 |
| 1-043 | 320 | 5 | 4 | 5 | 5 |
| 1-044 | 320 | 5 | 4 | 4 | 3 |
| 1-045 | 320 | 1 | 3 | 4 | 0 |
| 1-046 | 320 | 5 | 3 | 3 | 3 |
| 1-047 | 320 | 5 | 5 | 4 | 3 |
| 1-048 | 320 | 5 | 4 | 3 | 0 |
| 1-049 | 320 | 5 | 4 | 4 | 1 |
| 1-050 | 320 | 5 | 5 | 5 | 1 |
| 1-051 | 320 | 4 | 5 | 4 | 0 |
| 1-052 | 320 | 4 | 5 | 5 | 0 |
| 1-053 | 320 | 4 | 4 | 4 | 0 |

TABLE 62

| No. | Application herbicide amount (g/ha) | H | D | E | b |
|---|---|---|---|---|---|
| 1-054 | 320 | 5 | 5 | 5 | 3 |
| 1-055 | 320 | 5 | 4 | 5 | 2 |
| 1-056 | 320 | 5 | 5 | 5 | 4 |
| 1-057 | 320 | 5 | 5 | 5 | 3 |
| 1-058 | 320 | 5 | 5 | 5 | 4 |
| 1-059 | 320 | 0 | 3 | 3 | 0 |
| 1-060 | 320 | 5 | 4 | 3 | 2 |
| 1-061 | 320 | 5 | 4 | 3 | 1 |
| 1-062 | 320 | 5 | 4 | 4 | 2 |
| 1-063 | 320 | 5 | 5 | 5 | 2 |
| 1-064 | 320 | 5 | 4 | 4 | 2 |
| 1-065 | 320 | 3 | 1 | 3 | 0 |
| 1-066 | 320 | 1 | 4 | 3 | 0 |
| 1-067 | 320 | 5 | 5 | 5 | 2 |
| 1-068 | 320 | 5 | 5 | 5 | 1 |
| 1-069 | 320 | 5 | 5 | 5 | 1 |
| 1-070 | 320 | 4 | 5 | 5 | 0 |
| 1-071 | 320 | 0 | 3 | 5 | 0 |
| 1-072 | 320 | 2 | 1 | 0 | 0 |
| 1-073 | 320 | 5 | 5 | 5 | 4 |
| 1-074 | 320 | 5 | 4 | 3 | 0 |
| 1-075 | 320 | 5 | 4 | 4 | 1 |
| 1-076 | 320 | 5 | 4 | 5 | 3 |
| 1-077 | 320 | 5 | 4 | 3 | 0 |
| 1-078 | 320 | 5 | 5 | 5 | 5 |
| 1-079 | 320 | 5 | 5 | 5 | 5 |
| 1-080 | 320 | 5 | 5 | 5 | 5 |

TABLE 62-continued

| No. | Application herbicide amount (g/ha) | H | D | E | b |
|---|---|---|---|---|---|
| 1-081 | 320 | 2 | 0 | 0 | 0 |
| 1-082 | 320 | 4 | 4 | 4 | 0 |
| 1-083 | 320 | 5 | 5 | 5 | 2 |
| 1-084 | 320 | 5 | 5 | 5 | 2 |
| 1-085 | 320 | 5 | 5 | 5 | 3 |
| 1-086 | 320 | 5 | 5 | 5 | 0 |
| 1-087 | 320 | 5 | 5 | 5 | 1 |
| 1-089 | 224 | 3 | 3 | 2 | 0 |
| 1-090 | 320 | 5 | 5 | 5 | 0 |
| 1-091 | 320 | 5 | 5 | 5 | 0 |
| 1-092 | 320 | 5 | 5 | 5 | 4 |
| 1-093 | 320 | 4 | 5 | 4 | 1 |
| 1-094 | 320 | 5 | 4 | 4 | 1 |
| 1-095 | 320 | 4 | 4 | 4 | 1 |
| 1-096 | 320 | 5 | 5 | 4 | 4 |
| 1-100 | 320 | 5 | 5 | 4 | 0 |
| 1-101 | 320 | 1 | 0 | 0 | 0 |
| 1-102 | 320 | 4 | 5 | 4 | 2 |
| 1-103 | 320 | 5 | 5 | 5 | 4 |
| 1-104 | 320 | 5 | 5 | 4 | 0 |

TABLE 63

| No. | Application herbicide amount (g/ha) | H | D | E | b |
|---|---|---|---|---|---|
| 1-105 | 320 | 5 | 5 | 5 | 0 |
| 1-106 | 320 | 5 | 5 | 5 | 3 |
| 1-107 | 320 | 5 | 5 | 5 | 3 |
| 1-108 | 320 | 5 | 5 | 5 | 1 |
| 1-109 | 320 | 5 | 5 | 3 | 2 |
| 1-110 | 320 | 5 | 5 | 5 | 5 |
| 1-112 | 320 | 3 | 2 | 1 | 0 |
| 1-113 | 320 | 4 | 3 | 3 | 0 |
| 1-114 | 320 | 4 | 4 | 2 | 0 |
| 1-115 | 320 | 5 | 4 | 4 | 0 |
| 1-116 | 320 | 4 | 4 | 0 | 0 |
| 1-117 | 320 | 4 | 4 | 2 | 0 |
| 1-118 | 320 | 5 | 5 | 3 | 3 |
| 1-119 | 320 | 5 | 5 | 2 | 3 |
| 1-120 | 320 | 5 | 5 | 5 | 3 |
| 1-121 | 320 | 5 | 5 | 5 | 3 |
| 1-122 | 320 | 5 | 5 | 5 | 3 |
| 1-123 | 320 | 4 | 4 | 4 | 1 |
| 1-124 | 320 | 4 | 4 | 4 | 0 |
| 1-125 | 320 | 5 | 4 | 3 | 1 |
| 1-126 | 320 | 4 | 4 | 4 | 0 |
| 1-127 | 320 | 4 | 4 | 3 | 0 |
| 1-128 | 288 | 4 | 3 | 3 | 0 |
| 1-129 | 320 | 5 | 5 | 4 | 3 |
| 1-130 | 320 | 5 | 4 | 2 | 2 |
| 1-131 | 320 | 4 | 4 | 3 | 2 |
| 1-132 | 320 | 5 | 5 | 4 | 3 |
| 1-133 | 320 | 4 | 2 | 0 | 0 |
| 1-134 | 320 | 5 | 4 | 2 | 2 |
| 1-135 | 320 | 5 | 4 | 2 | 1 |
| 1-136 | 320 | 4 | 4 | 0 | 2 |
| 1-137 | 320 | 5 | 5 | 4 | 3 |
| 1-138 | 320 | 5 | 5 | 4 | 3 |
| 1-139 | 320 | 4 | 5 | 5 | 1 |
| 1-141 | 320 | 4 | 2 | 3 | 1 |
| 1-142 | 320 | 3 | 1 | 0 | 0 |
| 1-143 | 320 | 4 | 2 | 4 | 0 |
| 1-144 | 320 | 5 | 4 | 2 |   |
| 1-145 | 320 | 5 | 5 | 5 |   |
| 1-146 | 320 | 5 | 5 | 4 |   |
| 1-147 | 320 | 5 | 5 | 3 |   |
| 1-148 | 320 | 5 | 5 | 5 |   |
| 1-149 | 320 | 5 | 5 | 5 |   |
| 1-150 | 320 | 5 | 5 | 5 |   |
| 1-151 | 320 | 5 | 4 | 4 |   |
| 1-152 | 320 | 5 | 5 | 4 |   |
| 1-153 | 320 | 5 | 5 | 3 |   |

TABLE 64

| No. | Application herbicide amount (g/ha) | H | D | E | b |
|---|---|---|---|---|---|
| 1-154 | 320 | 3 | 2 | 4 | |
| 1-155 | 320 | 1 | 2 | 5 | |
| 1-156 | 320 | 3 | 2 | 2 | |
| 1-157 | 320 | 4 | 3 | 4 | |
| 1-158 | 320 | 5 | 4 | 4 | |
| 1-159 | 320 | 5 | 3 | 0 | |
| 1-162 | 320 | 4 | 4 | 2 | |
| 1-163 | 320 | 5 | 5 | 4 | |
| 1-164 | 320 | 5 | 5 | 4 | |
| 1-165 | 320 | 5 | 4 | | 0 |
| 1-166 | 320 | 4 | 3 | | 2 |
| 1-167 | 320 | 1 | 2 | | |
| 1-168 | 320 | 4 | 3 | | 3 |
| 1-169 | 320 | 5 | 4 | | 1 |
| 1-170 | 320 | 2 | 4 | | 1 |
| 1-171 | 320 | 4 | 4 | | 0 |
| 1-172 | 320 | 5 | 5 | | 3 |
| 1-173 | 320 | 5 | 4 | | 2 |
| 1-174 | 320 | 2 | 2 | | 0 |
| 2-001 | 320 | 4 | 4 | 3 | 1 |
| 2-002 | 320 | 5 | 4 | 2 | 2 |
| 2-003 | 200 | 5 | 5 | 5 | 0 |
| 2-005 | 320 | 5 | 5 | 4 | 2 |
| 2-006 | 320 | 5 | 5 | 5 | 5 |
| 2-007 | 320 | 5 | 5 | 5 | 4 |
| 2-008 | 320 | 4 | 5 | 4 | 0 |
| 2-009 | 320 | 5 | 4 | 3 | 4 |
| 2-010 | 320 | 5 | 5 | 5 | 5 |
| 2-011 | 320 | 5 | 5 | 5 | 5 |
| 2-012 | 320 | 4 | 5 | 5 | 2 |
| 2-013 | 320 | 5 | 5 | 5 | 5 |
| 2-014 | 320 | 5 | 5 | 5 | 5 |
| 2-015 | 320 | 5 | 5 | 5 | 4 |
| 2-016 | 320 | 5 | 5 | 5 | 5 |
| 2-017 | 320 | 5 | 5 | 5 | 5 |
| 2-019 | 320 | 5 | 5 | 5 | 5 |
| 2-020 | 320 | 4 | 4 | 4 | 4 |
| 2-021 | 320 | 5 | 5 | 5 | 5 |
| 2-022 | 320 | 5 | 5 | 5 | 5 |
| 2-023 | 320 | 4 | 1 | 0 | 1 |
| 2-024 | 320 | 5 | 5 | 5 | 5 |
| 2-025 | 320 | 5 | 5 | 5 | 5 |
| 2-026 | 320 | 5 | 5 | 5 | 5 |
| 2-027 | 320 | 5 | 5 | 5 | 5 |
| 2-028 | 320 | 5 | 5 | 5 | 5 |
| 2-029 | 320 | 5 | 5 | 5 | 5 |
| 2-030 | 320 | 4 | 5 | 4 | 5 |

TABLE 65

| No. | Application herbicide amount (g/ha) | H | D | E | b |
|---|---|---|---|---|---|
| 2-031 | 320 | 5 | 5 | 5 | 5 |
| 2-032 | 320 | 5 | 5 | 5 | 5 |
| 2-033 | 320 | 5 | 5 | 5 | 5 |
| 2-034 | 320 | 5 | 5 | 5 | 5 |
| 2-035 | 320 | 5 | 5 | 4 | 5 |
| 2-036 | 320 | 4 | 5 | 4 | 1 |
| 2-037 | 320 | 5 | 5 | 5 | 5 |
| 2-038 | 320 | 5 | 5 | 5 | 5 |
| 2-039 | 320 | 5 | | 5 | 4 |
| 2-040 | 320 | 4 | | 5 | 4 |
| 2-041 | 320 | 5 | 5 | 5 | 3 |
| 2-042 | 320 | 5 | 5 | 5 | 5 |
| 2-043 | 320 | 5 | 5 | 5 | 5 |
| 2-044 | 320 | 5 | 5 | 5 | 5 |
| 2-045 | 320 | 5 | 5 | 5 | 5 |
| 2-046 | 320 | 2 | 3 | 3 | 0 |
| 2-047 | 320 | 4 | 5 | 5 | 3 |
| 2-048 | 320 | 5 | 5 | 5 | 3 |
| 2-049 | 320 | 5 | 5 | 5 | 1 |
| 2-050 | 192 | 4 | 3 | 3 | 0 |
| 2-051 | 320 | 5 | 5 | 5 | 4 |
| 2-052 | 320 | 5 | 5 | 5 | 5 |
| 2-053 | 320 | 5 | 5 | 5 | 5 |
| 2-054 | 320 | 5 | 5 | 5 | 5 |
| 2-055 | 131 | 2 | 0 | 0 | 0 |
| 2-056 | 320 | 4 | 5 | 4 | 4 |
| 2-057 | 320 | 5 | 5 | 5 | 5 |
| 2-058 | 320 | 5 | 5 | 5 | 5 |
| 2-059 | 320 | 5 | 5 | 5 | 5 |
| 2-060 | 320 | 5 | 5 | 5 | 5 |
| 2-061 | 320 | 5 | 5 | 5 | 5 |
| 2-062 | 320 | 5 | 5 | 5 | 5 |
| 2-063 | 320 | 5 | 5 | 5 | 3 |
| 2-064 | 320 | 1 | 4 | 5 | 0 |
| 2-065 | 320 | 5 | 5 | 5 | 3 |
| 2-066 | 320 | 5 | 5 | 5 | 3 |
| 2-067 | 320 | 5 | 5 | 5 | 5 |
| 2-068 | 320 | 5 | 5 | 5 | 5 |
| 2-069 | 320 | 5 | 5 | 5 | 5 |
| 2-070 | 320 | 5 | 5 | 5 | 3 |
| 2-071 | 320 | 4 | 5 | 5 | 3 |
| 2-072 | 320 | 4 | 5 | 5 | 1 |
| 2-073 | 320 | 4 | 3 | 5 | 2 |
| 2-074 | 320 | 5 | 5 | 4 | 5 |
| 2-075 | 320 | 5 | 5 | 5 | 5 |
| 2-076 | 320 | 5 | 4 | 4 | 1 |
| 2-077 | 320 | 2 | 4 | 3 | 0 |

TABLE 66

| No. | Application herbicide amount (g/ha) | H | D | E | b |
|---|---|---|---|---|---|
| 2-078 | 320 | 5 | 5 | 3 | 4 |
| 2-079 | 320 | 5 | 5 | 5 | 5 |
| 2-080 | 320 | 4 | 5 | 5 | 3 |
| 2-081 | 320 | 5 | 5 | 5 | 4 |
| 2-082 | 320 | 5 | 5 | 5 | 5 |
| 2-083 | 320 | 4 | 4 | 5 | 0 |
| 2-084 | 320 | 5 | 5 | 5 | 5 |
| 2-085 | 320 | 5 | 5 | 4 | 4 |
| 2-086 | 320 | 5 | 5 | 4 | 3 |
| 2-087 | 320 | 5 | 5 | 5 | 3 |
| 2-088 | 141 | 5 | 5 | 4 | 3 |
| 2-089 | 320 | 4 | 5 | 4 | 2 |
| 2-090 | 320 | 5 | 4 | 5 | |
| 2-091 | 320 | 5 | 3 | 4 | |
| 2-092 | 320 | 2 | 3 | 2 | |
| 2-093 | 320 | 1 | 2 | 5 | |
| 2-094 | 320 | 5 | 5 | 5 | |
| 2-095 | 320 | 5 | 5 | 5 | |
| 2-096 | 320 | 0 | 0 | 5 | |
| 2-097 | 320 | 2 | 3 | 4 | |
| 2-098 | 320 | 5 | 5 | 5 | |
| 2-099 | 320 | 5 | 5 | | 4 |
| 2-100 | 320 | 5 | 5 | | 3 |
| 2-101 | 320 | 5 | 5 | | 4 |
| 2-102 | 320 | 5 | 4 | | 1 |
| 2-103 | 320 | 5 | 5 | | 1 |
| 2-105 | 320 | 5 | 4 | | 5 |
| 2-106 | 320 | 1 | 2 | | 0 |
| 2-107 | 320 | 4 | 5 | | 4 |
| 2-108 | 320 | 4 | 5 | | 4 |
| 2-109 | 260 | 3 | 5 | | 2 |
| 2-110 | 320 | 5 | 5 | | 3 |
| 3-002 | 320 | 0 | 3 | | 0 |
| 4-002 | 320 | 0 | 4 | 0 | 0 |
| 4-003 | 320 | 4 | 3 | 0 | |
| 5-001 | 320 | 1 | 0 | 0 | 0 |
| 6-002 | 320 | 5 | 5 | 4 | 0 |
| 6-003 | 320 | 1 | 5 | 0 | 0 |
| 6-004 | 320 | 4 | 5 | 2 | 3 |
| 7-001 | 320 | 1 | 2 | | |
| 7-002 | 320 | 4 | 4 | 4 | 0 |

[Twentieth Table]

TABLE 67

| No. | Application herbicide amount (g/ha) | F | G | H | I | J | K | L | M | N | O | P | Q | R | b | c | d | e | f | g |
|---|---|---|---|---|---|---|---|---|---|---|---|---|---|---|---|---|---|---|---|---|
| 1-001 | 320 | 4 | 3 | 4 | 1 | 1 | 1 | 1 | 3 | 3 | 5 | 4 | 4 | 4 | 0 | 0 | 3 | 1 | 4 | 4 |
| 1-002 | 320 | 4 | 2 | 5 | 3 | 1 | 2 | 1 | 3 | 3 | 5 | 5 | 4 |   | 0 | 0 | 3 | 1 | 5 | 4 |
| 1-004 | 320 | 5 | 4 | 5 | 2 | 2 | 2 | 3 | 4 | 4 | 5 | 5 | 1 | 4 | 0 | 4 | 4 | 2 | 4 | 3 |
| 1-005 | 320 | 3 | 3 | 4 | 1 | 0 | 0 | 0 | 4 | 3 | 5 | 1 | 0 | 3 | 0 | 1 | 0 | 0 | 0 | 0 |
| 1-008 | 320 | 3 | 1 | 5 | 0 | 0 | 0 | 0 | 0 | 2 | 3 | 0 | 0 | 0 | 0 | 0 | 0 | 0 | 0 | 0 |
| 1-010 | 320 | 3 | 3 | 4 | 3 | 2 | 1 | 2 | 5 | 5 | 5 | 5 | 1 | 5 | 0 | 1 | 4 | 1 | 5 | 3 |
| 1-011 | 320 | 5 | 4 | 5 | 1 | 1 | 1 | 2 | 5 | 5 | 5 | 5 | 2 | 5 | 0 | 3 | 4 | 0 | 5 | 3 |
| 1-012 | 320 | 3 | 4 | 4 | 0 | 0 | 1 | 1 | 3 | 3 | 5 | 4 | 2 | 4 | 0 | 1 | 2 | 0 | 3 | 4 |
| 1-013 | 320 | 3 | 1 | 4 | 0 | 1 | 1 | 0 | 3 | 3 | 5 | 4 | 1 | 3 | 0 | 0 | 0 | 1 | 3 | 0 |
| 1-014 | 320 | 3 | 3 | 4 | 1 | 1 | 1 | 0 | 4 | 5 | 5 | 5 | 3 | 4 | 1 | 0 | 3 | 1 | 5 | 2 |
| 1-015 | 320 | 4 | 3 | 5 | 3 | 1 | 1 | 3 | 5 | 5 | 5 | 5 | 3 | 5 | 0 | 1 | 4 | 2 | 5 | 4 |
| 1-016 | 320 | 4 | 2 | 5 | 1 | 1 | 1 | 0 | 5 | 5 | 5 | 5 | 2 | 4 | 0 | 0 | 0 | 0 | 5 | 3 |
| 1-017 | 320 | 3 | 0 | 5 | 0 | 0 | 0 | 0 | 5 | 5 | 5 | 4 | 0 | 4 | 0 | 0 | 3 | 0 | 5 | 3 |
| 1-018 | 320 | 0 | 2 | 1 | 0 | 0 | 0 | 0 | 3 | 4 | 5 | 4 | 0 | 4 | 0 | 0 | 0 | 0 | 1 | 0 |
| 1-019 | 320 | 5 | 4 | 5 | 3 | 2 | 2 | 4 | 4 | 5 | 5 | 5 | 4 | 4 | 2 | 2 | 4 | 3 | 5 | 4 |
| 1-020 | 320 | 4 | 3 | 5 | 1 | 1 | 1 | 1 | 2 | 4 | 5 | 4 | 3 | 3 | 0 | 1 | 0 | 1 | 5 | 3 |
| 1-021 | 320 | 4 | 3 | 4 | 1 | 1 | 1 | 1 | 5 | 5 | 5 | 5 | 3 | 4 | 1 | 0 | 3 | 1 | 5 | 3 |
| 1-022 | 320 | 4 | 3 | 5 | 1 | 1 | 1 | 1 | 5 | 5 | 5 | 4 | 2 | 4 | 0 | 2 | 3 | 1 | 4 | 2 |
| 1-024 | 320 | 4 | 3 | 4 | 1 | 0 | 0 | 1 | 4 | 5 | 5 | 4 | 3 | 4 | 0 | 2 | 4 | 0 | 4 | 4 |
| 1-025 | 320 | 3 | 2 | 4 | 0 | 0 | 0 | 0 | 5 | 3 | 5 | 4 | 3 | 3 | 0 | 0 | 3 | 0 | 5 | 2 |
| 1-026 | 320 | 3 | 3 | 3 | 1 | 1 | 1 | 2 | 3 | 4 | 5 | 5 | 2 | 5 | 0 | 0 | 3 | 1 | 5 | 3 |
| 1-027 | 320 | 5 | 4 | 5 | 2 | 2 | 1 | 3 | 5 | 5 | 5 | 5 | 3 | 5 | 0 | 1 | 5 | 2 | 5 | 4 |
| 1-029 | 320 | 5 | 4 | 5 | 1 | 1 | 1 | 1 | 5 | 5 | 5 | 5 | 0 | 5 | 3 | 1 | 3 | 1 | 5 | 1 |
| 1-030 | 320 | 5 | 5 | 5 | 4 | 3 | 3 | 4 | 5 | 5 | 5 | 5 | 4 | 4 | 3 | 2 | 5 | 3 | 5 | 4 |
| 1-031 | 320 | 4 | 4 | 5 | 2 | 1 | 1 | 1 | 5 | 4 | 5 | 4 | 3 | 4 | 0 | 1 | 3 | 1 | 3 | 3 |
| 1-032 | 320 | 5 | 5 | 5 | 2 | 1 | 1 | 2 | 5 | 5 | 5 | 5 | 2 | 4 | 0 | 0 | 4 | 1 | 5 | 4 |
| 1-033 | 320 | 5 | 5 | 5 | 2 | 1 | 1 | 2 | 5 | 5 | 5 | 5 | 3 | 5 | 0 | 2 | 3 | 1 | 5 | 4 |
| 1-034 | 320 | 5 | 5 | 5 | 3 | 1 | 3 | 3 | 5 | 5 | 5 | 5 | 3 | 5 | 5 | 1 | 4 | 2 | 5 | 4 |
| 1-035 | 320 | 5 | 5 | 5 | 2 | 2 | 2 | 3 | 5 | 5 | 5 | 5 | 2 | 5 | 4 | 3 | 4 | 2 | 5 | 3 |
| 1-036 | 320 | 5 | 5 | 5 | 4 | 3 | 3 | 4 | 5 | 5 | 5 | 5 | 4 | 5 | 3 | 3 | 4 | 3 | 5 | 5 |
| 1-037 | 320 | 5 | 4 | 4 | 3 | 2 | 2 | 3 | 5 | 5 | 5 | 4 | 4 | 5 | 0 | 1 | 3 | 3 | 5 | 4 |
| 1-038 | 320 | 5 | 5 | 5 | 3 | 1 | 1 | 2 | 5 | 5 | 5 | 5 | 3 | 5 | 0 | 0 | 4 | 1 | 5 | 4 |
| 1-039 | 320 | 2 | 0 | 4 | 0 | 0 | 0 | 0 | 0 | 1 | 4 | 0 | 0 | 0 | 0 | 0 | 0 | 0 | 2 | 0 |
| 1-040 | 320 | 5 | 4 | 4 | 3 | 3 | 3 | 4 | 5 | 5 | 5 | 5 | 3 | 5 | 0 | 0 | 1 | 3 | 5 | 1 |
| 1-041 | 320 | 5 | 4 | 5 | 3 | 1 | 2 | 4 | 5 | 5 | 5 | 5 | 3 | 4 | 0 | 0 | 2 | 3 | 5 | 0 |
| 1-042 | 320 | 4 | 3 | 5 | 2 | 0 | 0 | 2 | 4 | 4 | 5 | 4 | 3 | 4 | 0 | 1 | 3 | 0 | 5 | 3 |
| 1-043 | 320 | 4 | 3 | 5 | 2 | 1 | 1 | 1 | 5 | 5 | 5 | 4 | 3 | 4 | 4 | 2 | 2 | 0 | 5 | 3 |
| 1-044 | 320 | 4 | 4 | 5 | 1 | 1 | 2 | 4 | 5 | 5 | 5 | 4 | 3 | 5 | 0 | 0 | 3 | 0 | 5 | 4 |
| 1-045 | 320 | 3 | 1 | 2 | 0 | 0 | 0 | 0 | 4 | 4 | 5 | 2 | 2 | 3 | 0 | 0 | 1 | 0 | 3 | 3 |
| 1-046 | 320 | 5 | 5 | 5 | 1 | 0 | 0 | 1 | 5 | 5 | 5 | 4 | 2 | 4 | 1 | 2 | 3 | 0 | 5 | 4 |
| 1-047 | 320 | 4 | 4 | 5 | 1 | 0 | 0 | 1 | 5 | 5 | 5 | 4 | 2 | 4 | 0 | 1 | 3 | 0 | 5 | 4 |
| 1-048 | 320 | 5 | 3 | 5 | 2 | 1 | 1 | 2 | 5 | 4 | 5 | 4 | 3 | 4 | 0 | 0 | 4 | 1 | 5 | 4 |
| 1-049 | 320 | 5 | 4 | 5 | 0 | 2 | 2 | 3 | 5 | 5 | 5 | 4 | 3 | 4 | 0 | 4 | 3 | 1 | 5 | 4 |
| 1-050 | 320 | 5 | 4 | 5 | 3 | 2 | 3 | 3 | 5 | 5 | 5 | 5 | 2 | 5 | 1 | 3 | 4 | 3 | 5 | 5 |
| 1-051 | 320 | 3 | 3 | 4 | 1 | 0 | 1 | 1 | 5 | 3 | 5 | 3 | 2 | 3 | 0 | 0 | 1 | 1 | 3 | 1 |
| 1-052 | 320 | 3 | 1 | 2 | 0 | 1 | 1 | 3 | 4 | 4 | 5 | 2 | 1 | 3 | 0 | 0 | 2 | 0 | 3 | 3 |
| 1-053 | 320 | 3 | 2 | 3 | 1 | 0 | 0 | 0 | 4 | 4 | 5 | 2 | 2 | 4 | 0 | 0 | 3 | 0 | 3 | 1 |

TABLE 68

| No. | Application herbicide amount (g/ha) | F | G | H | I | J | K | L | M | N | O | P | Q | R | b | c | d | e | f | g |
|---|---|---|---|---|---|---|---|---|---|---|---|---|---|---|---|---|---|---|---|---|
| 1-054 | 320 | 5 | 4 | 5 | 3 | 3 | 3 | 3 | 5 | 5 | 5 | 4 | 4 | 5 | 0 | 1 | 3 | 3 | 4 | 4 |
| 1-055 | 320 | 4 | 3 | 4 | 1 | 3 | 2 | 3 | 5 | 5 | 5 | 5 | 2 | 4 | 0 | 0 | 3 | 1 | 5 | 4 |
| 1-056 | 320 | 5 | 5 | 5 | 3 | 2 | 2 | 3 | 5 | 5 | 5 | 5 | 4 | 5 | 4 | 4 | 4 | 1 | 5 | 5 |
| 1-057 | 320 | 4 | 4 | 4 | 3 | 2 | 2 | 2 | 5 | 5 | 5 | 5 | 1 | 5 | 0 | 1 | 3 | 0 | 5 | 3 |
| 1-058 | 320 | 5 | 5 | 5 | 3 | 3 | 3 | 2 | 5 | 5 | 5 | 5 | 5 | 5 | 4 | 4 | 1 | 5 | 4 |   |
| 1-059 | 320 | 0 | 0 | 2 | 0 | 0 | 0 | 0 | 4 | 2 | 5 | 2 | 0 | 2 | 0 | 0 | 0 | 0 | 0 | 0 |
| 1-060 | 320 | 5 | 3 | 5 | 3 | 2 | 2 | 1 | 4 | 4 | 5 | 4 | 3 | 5 | 3 | 0 | 4 | 3 | 5 | 4 |
| 1-061 | 320 | 3 | 3 | 4 | 3 | 1 | 1 | 1 | 5 | 5 | 5 | 4 | 4 | 5 | 1 | 1 | 4 | 0 | 4 | 4 |
| 1-062 | 320 | 5 | 3 | 5 | 3 | 1 | 0 | 1 | 5 | 4 | 5 | 4 | 4 | 4 | 3 | 0 | 3 | 2 | 4 | 4 |
| 1-063 | 320 | 5 | 5 | 5 | 2 | 2 | 2 | 3 | 4 | 4 | 5 | 4 | 3 | 5 | 0 | 3 | 4 | 2 | 5 | 3 |
| 1-064 | 320 | 5 | 4 | 5 | 1 | 1 | 1 | 1 | 3 | 4 |   |   | 3 | 3 | 0 | 0 | 3 | 0 | 4 | 3 |
| 1-065 | 320 | 4 | 1 | 1 | 1 | 0 | 0 | 0 | 3 | 3 | 5 | 4 | 0 | 3 | 0 | 0 | 3 | 0 | 4 | 2 |
| 1-066 | 320 | 3 | 1 | 4 | 1 | 0 | 0 | 0 | 3 | 1 | 5 | 4 | 1 | 4 | 0 | 0 | 3 | 0 | 4 | 0 |
| 1-067 | 320 | 5 | 4 | 5 | 1 | 0 | 0 | 0 | 4 | 1 | 5 | 4 | 3 | 4 | 2 | 0 | 3 | 0 | 4 | 4 |
| 1-068 | 320 | 5 | 4 | 5 | 1 | 1 | 1 | 1 | 3 | 3 | 5 | 4 | 3 | 4 | 2 | 0 | 3 | 1 | 4 | 4 |
| 1-069 | 320 | 5 | 5 | 5 | 2 | 2 | 2 | 4 | 3 | 3 | 5 |   | 3 |   | 0 | 1 | 3 | 1 | 5 | 3 |
| 1-070 | 320 | 4 | 4 | 5 | 1 | 0 | 0 | 0 | 4 | 4 | 5 | 5 | 3 |   | 0 | 0 | 4 | 0 | 4 | 3 |
| 1-071 | 320 | 1 | 0 | 0 | 0 | 0 | 0 | 0 | 3 | 2 | 5 |   | 1 | 3 | 0 | 0 | 0 | 0 | 2 | 0 |

TABLE 68-continued

| No. | Application herbicide amount (g/ha) | F | G | H | I | J | K | L | M | N | O | P | Q | R | b | c | d | e | f | g |
|---|---|---|---|---|---|---|---|---|---|---|---|---|---|---|---|---|---|---|---|---|
| 1-072 | 320 | 0 | 0 | 3 | 0 | 0 | 0 | 0 | 1 | 0 | 4 | 2 | 0 | 1 | 0 | 0 | 0 | 0 | 0 | 0 |
| 1-073 | 320 | 5 | 5 | 5 | 3 | 2 | 3 | 3 | 5 | 5 | 5 | 5 | 2 |   | 5 | 0 | 4 | 3 | 5 | 3 |
| 1-074 | 320 | 4 | 4 | 5 | 1 | 0 | 0 | 0 |   | 4 | 5 | 4 | 3 | 3 | 0 | 0 | 3 | 0 | 4 | 3 |
| 1-075 | 320 | 3 | 1 | 3 | 0 | 0 | 0 | 0 | 1 | 2 | 5 | 3 | 0 | 3 | 0 | 0 | 0 | 0 | 1 | 1 |
| 1-076 | 320 | 5 | 5 | 5 | 3 | 3 | 3 | 4 | 4 | 4 | 5 | 5 | 2 | 4 | 0 | 3 | 3 | 3 | 5 | 4 |
| 1-077 | 320 | 4 | 2 | 4 | 0 | 0 | 0 | 0 | 2 | 3 | 5 | 4 | 1 | 3 | 0 | 0 | 3 | 0 | 3 | 3 |
| 1-078 | 320 | 5 | 5 | 5 | 4 | 3 | 3 | 4 | 5 | 5 | 5 | 4 |   |   | 4 | 4 | 4 | 4 | 5 | 4 |
| 1-079 | 320 | 5 | 5 | 5 | 4 | 2 | 3 |   | 5 | 5 | 5 | 5 | 4 |   | 4 | 1 | 5 | 4 | 5 | 5 |
| 1-080 | 320 | 5 | 5 | 5 | 4 | 5 | 4 | 5 | 5 | 5 | 5 |   | 5 |   | 4 | 4 | 5 | 5 | 5 | 5 |
| 1-081 | 320 | 0 | 0 | 0 | 0 | 0 | 0 | 0 | 0 | 0 | 4 | 2 |   | 0 | 0 | 0 | 0 | 0 | 1 | 0 |
| 1-082 | 320 | 4 | 3 | 4 | 0 | 0 | 1 | 1 | 4 | 3 | 5 |   | 0 | 4 | 0 | 0 | 3 | 0 |   | 0 |
| 1-083 | 320 | 5 | 5 | 5 | 3 | 0 | 1 | 0 | 5 | 5 | 5 | 4 | 4 | 4 | 1 | 1 | 4 | 1 | 5 | 4 |
| 1-084 | 320 | 5 | 5 | 5 | 3 | 0 | 0 | 0 | 5 | 5 | 5 | 4 | 4 | 5 | 3 | 1 | 4 | 0 | 4 | 4 |
| 1-085 | 320 | 5 | 5 | 5 |   | 3 | 3 | 3 | 5 | 5 | 5 | 4 | 4 | 5 | 3 | 3 | 4 | 3 | 4 | 4 |
| 1-086 | 320 | 5 | 4 | 5 | 0 | 0 | 0 | 0 | 5 | 4 | 5 | 5 | 1 | 4 | 1 | 1 | 1 | 0 | 5 | 4 |
| 1-087 | 320 | 5 | 5 | 5 | 3 | 3 | 1 | 2 | 5 | 5 | 5 | 4 | 1 | 4 | 0 | 4 | 4 | 2 | 5 | 4 |
| 1-088 | 320 | 0 | 0 | 0 | 0 | 0 | 0 | 0 | 0 | 1 | 2 | 0 | 0 | 0 | 0 | 0 | 0 | 0 | 0 | 0 |
| 1-089 | 224 | 1 | 0 | 3 | 2 | 0 | 0 | 0 | 2 | 1 | 4 | 4 | 0 | 3 | 0 | 0 | 1 | 0 | 3 | 1 |
| 1-090 | 320 | 5 | 3 | 5 | 3 | 1 | 1 | 1 | 3 |   | 5 | 4 | 1 | 5 | 0 | 1 | 4 | 0 | 5 | 4 |
| 1-091 | 320 | 5 | 5 | 5 | 4 | 2 | 3 | 3 | 5 | 5 | 5 | 5 | 4 | 5 | 0 | 2 | 4 | 3 | 5 | 5 |
| 1-092 | 320 | 5 | 5 | 5 | 2 | 1 | 1 | 1 | 4 | 4 | 5 | 5 | 3 | 5 | 5 | 1 | 4 | 0 | 5 | 3 |
| 1-093 | 320 | 5 | 3 | 5 | 1 | 0 | 1 | 1 | 4 | 4 | 5 | 4 | 1 | 4 | 0 | 4 | 3 | 0 | 5 | 3 |
| 1-094 | 320 | 5 | 4 | 5 | 2 | 1 | 1 | 1 | 4 | 4 | 5 | 5 | 0 | 4 | 0 | 4 | 3 | 1 | 5 | 3 |
| 1-095 | 320 | 5 | 3 | 5 | 1 | 1 | 2 | 1 | 4 | 4 | 5 | 5 | 3 | 5 | 0 | 2 | 3 | 1 | 5 | 3 |
| 1-096 | 320 | 5 | 5 | 5 | 2 | 1 | 2 | 3 | 4 | 5 | 5 | 4 | 4 | 5 | 4 | 4 | 4 | 1 | 5 | 5 |
| 1-100 | 320 | 3 | 1 | 4 | 1 | 0 | 0 | 0 | 3 | 1 | 5 | 3 | 0 | 1 | 0 | 0 | 1 | 0 | 3 | 0 |
| 1-102 | 320 | 3 | 3 | 4 | 0 | 0 | 0 | 0 | 3 | 4 | 5 | 4 | 2 | 4 | 0 | 0 | 1 | 0 | 4 | 2 |
| 1-103 | 320 | 5 | 5 | 5 | 4 | 2 | 3 | 3 | 4 | 5 | 5 | 5 | 4 | 5 | 1 | 2 | 4 | 3 | 5 | 5 |
| 1-104 | 320 | 5 | 5 | 5 | 4 | 1 | 1 | 2 | 4 | 4 | 5 | 5 | 3 | 4 | 0 | 3 | 4 | 2 | 4 | 4 |

TABLE 69

| No. | Application herbicide amount (g/ha) | F | G | H | I | J | K | L | M | N | O | P | Q | R | b | c | d | e | f | g |
|---|---|---|---|---|---|---|---|---|---|---|---|---|---|---|---|---|---|---|---|---|
| 1-105 | 320 | 4 | 1 | 4 | 1 | 1 | 1 | 1 | 3 | 3 | 5 | 4 | 1 | 3 | 0 | 1 | 2 | 1 | 4 | 3 |
| 1-106 | 320 | 5 | 5 | 5 | 4 | 1 | 3 | 3 | 4 | 5 | 5 | 5 | 4 | 5 | 3 | 1 | 3 | 3 | 5 | 4 |
| 1-107 | 320 | 5 | 5 | 5 | 4 | 3 | 3 | 3 | 4 | 5 | 5 | 5 | 4 | 5 | 4 | 1 | 5 | 3 | 5 | 5 |
| 1-108 | 320 | 5 | 5 | 5 | 2 | 1 | 2 | 2 | 4 | 5 | 5 | 5 | 3 | 5 | 1 | 1 | 4 | 1 | 5 | 3 |
| 1-109 | 320 | 4 | 3 | 5 | 1 | 0 | 0 | 0 | 4 | 4 | 5 | 4 | 2 | 4 | 0 | 1 | 3 | 0 | 4 | 4 |
| 1-110 | 320 | 5 | 5 | 5 | 4 | 3 | 3 | 3 | 4 | 5 | 5 | 5 | 4 | 5 | 4 | 4 | 3 | 3 | 5 | 5 |
| 1-112 | 320 | 1 | 0 | 2 | 0 | 0 | 0 | 0 | 3 | 4 | 5 | 4 | 0 | 5 | 0 | 0 | 3 | 0 | 5 | 3 |
| 1-113 | 320 | 1 | 0 | 2 | 0 | 0 | 0 | 0 | 1 | 3 | 5 | 4 | 0 | 3 | 0 | 0 | 0 | 0 | 3 | 0 |
| 1-114 | 320 | 1 | 0 | 3 | 0 | 0 | 0 | 0 | 2 | 3 | 5 | 4 | 1 | 3 | 0 | 0 | 0 | 0 | 4 | 0 |
| 1-115 | 320 | 5 | 5 | 5 | 2 | 2 | 1 | 2 | 3 | 4 | 5 | 4 | 3 | 4 | 0 | 0 | 2 | 2 | 5 | 1 |
| 1-116 | 320 | 5 | 4 | 5 | 3 | 1 | 1 | 1 | 4 | 4 | 5 | 5 | 3 | 4 | 0 | 0 | 3 | 2 | 5 | 4 |
| 1-117 | 320 | 1 | 1 | 4 | 0 | 0 | 0 | 0 | 3 | 3 | 5 | 3 | 1 | 3 | 0 | 0 | 3 | 0 | 3 | 1 |
| 1-118 | 320 | 5 | 5 | 5 | 3 | 1 | 1 | 3 | 4 | 4 | 5 | 4 | 4 | 5 | 4 | 0 | 4 | 1 | 5 | 5 |
| 1-119 | 320 | 5 | 4 | 5 | 3 | 3 | 2 | 3 | 5 | 5 | 5 | 4 | 4 | 5 | 3 | 2 | 4 | 3 | 5 | 5 |
| 1-120 | 320 | 5 | 5 | 5 | 3 | 3 | 3 | 5 | 4 | 5 | 5 | 5 | 5 | 5 | 2 | 0 | 4 | 3 | 5 | 5 |
| 1-121 | 320 | 5 | 4 | 5 | 3 | 3 | 3 | 3 | 4 | 5 | 5 | 5 | 3 | 5 | 2 | 2 | 4 | 3 | 5 | 5 |
| 1-122 | 320 | 5 | 5 | 5 | 2 | 3 | 3 | 4 | 5 | 5 | 5 | 4 | 5 |   | 2 | 5 | 2 | 5 | 5 |   |
| 1-123 | 320 | 4 | 3 | 4 | 1 | 0 | 0 | 0 | 4 | 4 | 5 | 4 | 2 | 3 |   | 0 | 3 | 0 | 4 | 3 |
| 1-124 | 320 | 5 | 3 | 5 | 2 | 0 | 0 | 1 | 5 | 4 | 5 | 3 | 2 | 2 |   | 1 | 3 | 0 | 3 | 0 |
| 1-125 | 320 | 4 | 1 | 4 | 1 | 0 | 0 | 0 | 3 | 3 | 5 | 4 | 0 | 0 |   | 2 | 3 | 1 | 5 | 3 |
| 1-126 | 320 | 4 | 3 | 5 | 0 | 0 | 0 | 1 | 3 | 3 | 5 | 5 | 1 | 4 |   | 1 | 2 | 0 | 5 | 3 |
| 1-127 | 320 | 1 | 1 | 4 | 0 | 0 | 0 | 0 | 2 | 1 | 5 | 3 | 0 | 1 |   | 0 | 1 | 0 | 2 | 0 |
| 1-128 | 288 | 5 | 2 | 5 | 0 | 1 | 1 | 1 | 3 | 3 | 5 | 5 | 1 | 5 |   | 0 | 3 | 1 | 5 | 3 |
| 1-129 | 320 | 4 | 4 | 5 | 2 | 1 | 1 | 1 | 3 | 4 | 5 | 5 | 0 |   |   | 2 | 4 | 1 | 5 | 3 |
| 1-130 | 320 | 4 | 4 | 5 | 1 | 1 | 1 | 1 | 3 | 3 | 5 | 3 | 4 | 3 |   | 0 | 3 | 0 | 5 | 4 |
| 1-131 | 320 | 4 | 3 | 4 | 0 | 0 | 0 | 0 | 3 | 3 | 5 | 3 | 0 | 3 |   | 0 | 3 | 0 | 3 | 0 |
| 1-132 | 320 | 4 | 3 | 5 | 1 | 1 | 1 | 2 | 4 | 3 | 5 |   | 2 | 4 |   | 2 | 3 | 1 | 5 | 4 |
| 1-133 | 320 | 3 | 0 | 4 | 0 | 0 | 0 | 0 | 3 | 3 | 4 | 4 | 1 | 2 |   | 0 | 3 | 0 | 3 | 0 |
| 1-134 | 320 | 4 | 3 | 5 | 0 | 1 | 1 | 1 | 4 | 3 | 5 | 4 | 3 | 4 |   | 0 | 3 | 1 | 5 | 4 |
| 1-135 | 320 | 4 | 3 | 4 | 1 | 1 | 1 | 1 | 3 | 3 | 5 | 4 | 0 | 1 |   | 0 | 3 | 0 | 4 | 0 |
| 1-136 | 320 | 4 | 2 | 4 | 0 | 0 | 0 | 1 | 3 | 2 | 5 | 4 | 0 | 3 |   | 1 | 3 | 0 | 4 | 0 |
| 1-137 | 320 | 4 | 5 | 5 | 3 | 2 | 2 | 4 | 3 | 4 | 5 | 5 | 3 | 5 |   | 0 | 4 | 2 | 5 | 5 |
| 1-138 | 320 | 4 | 3 | 5 | 2 | 1 | 1 | 3 | 3 | 5 | 5 | 5 | 2 | 5 |   | 0 | 3 | 1 | 5 | 4 |
| 1-139 | 320 | 5 | 3 | 5 | 1 | 0 | 1 | 0 | 3 | 4 | 5 | 5 | 2 | 5 |   | 0 | 3 | 1 | 5 | 4 |
| 1-141 | 320 | 3 | 1 | 4 | 0 | 0 | 0 | 0 | 3 | 3 | 4 | 3 | 1 | 3 |   | 0 | 1 | 0 | 4 | 4 |
| 1-142 | 320 | 1 | 0 | 3 | 0 | 0 | 0 | 0 | 0 | 1 | 4 | 2 | 1 | 0 |   | 0 | 0 | 0 | 3 | 0 |
| 1-143 | 320 | 2 | 0 | 4 | 0 | 0 | 0 | 0 | 2 | 2 | 4 | 3 | 2 | 3 |   | 0 | 1 | 0 | 2 | 3 |
| 1-144 | 320 | 3 | 2 | 5 | 2 | 1 | 1 | 0 | 2 | 4 | 5 | 5 | 3 | 4 | 0 | 0 | 4 | 1 | 5 | 4 |

TABLE 69-continued

| No. | Application herbicide amount (g/ha) | F | G | H | I | J | K | L | M | N | O | P | Q | R | b | c | d | e | f | g |
|---|---|---|---|---|---|---|---|---|---|---|---|---|---|---|---|---|---|---|---|---|
| 1-145 | 320 | 5 | 4 | 5 | 3 | 1 | 2 | 3 | 3 | 4 | 5 | 5 | 1 | 5 | 3 | 0 | 3 | 2 | 5 | 3 |
| 1-146 | 320 | 5 | 5 | 5 | 4 | 2 | 4 | 4 | 4 | 5 | 5 | 5 | 5 | 5 | 5 | 0 | 5 | 3 | 5 | 5 |
| 1-147 | 320 | 4 | 3 | 4 | 3 | 2 | 3 | 3 | 3 | 4 | 5 | 5 | 3 | 5 | 0 | 0 | 3 | 3 | 5 | 5 |
| 1-148 | 320 | 4 | 3 | 5 | 1 | 1 | 3 | 2 | 3 | 5 | 5 | 5 | 4 | 5 | 3 | 0 | 3 | 0 | 5 | 4 |
| 1-149 | 320 | 4 | 3 | 4 | 1 | 1 | 1 | 2 | 3 | 3 | 5 | 5 | 3 | 5 | 1 | 0 | 3 | 0 | 5 | 5 |
| 1-150 | 320 | 4 | 3 | 5 | 3 | 1 | 3 | 3 | 3 | 5 | 5 | 5 | 4 | 5 | 3 | 0 | 4 | 3 | 5 | 5 |
| 1-151 | 320 | 5 | 3 | 5 | 3 | 1 | 3 | 2 | 3 | 5 | 5 | 5 | 4 | 5 | 0 | 0 | 4 | 3 | 5 | 5 |
| 1-152 | 320 | 4 | 3 | 4 | 2 | 0 | 1 | 1 | 3 | 4 | 5 | 4 | 1 | 3 | 0 | 0 | 3 | 0 | 4 | 1 |
| 1-153 | 320 | 4 | 4 | 5 | 3 | 1 | 1 | 2 | 3 | 4 | 5 | 5 | 4 | 4 | 3 | 0 | 5 | 2 | 5 | 3 |

TABLE 70

| No. | Application herbicide amount (g/ha) | F | G | H | I | J | K | L | M | N | O | P | Q | R | b | c | d | e | f | g |
|---|---|---|---|---|---|---|---|---|---|---|---|---|---|---|---|---|---|---|---|---|
| 1-154 | 320 | 3 | 2 | 3 | 0 | 0 | 0 | 0 | 2 | 2 | 5 | 4 | 0 | 0 | 0 | 0 | 2 | 0 | 4 | 0 |
| 1-155 | 320 | 3 | 1 | 3 | 0 | 0 | 0 | 0 | 3 | 3 | 5 |   | 0 | 2 | 0 | 0 | 3 | 0 | 5 | 0 |
| 1-156 | 320 | 2 | 1 | 4 | 1 | 1 | 1 | 2 | 3 | 3 | 5 | 4 | 1 | 3 | 0 | 0 | 3 | 1 | 3 | 0 |
| 1-157 | 320 | 3 | 1 | 3 | 1 | 1 | 1 | 1 | 3 | 3 | 5 |   | 1 | 2 | 0 | 0 | 3 | 1 | 4 | 2 |
| 1-158 | 320 | 5 | 4 | 5 | 3 | 1 | 2 | 3 | 4 | 4 | 5 | 5 | 3 | 4 | 0 | 0 | 4 | 2 | 5 | 3 |
| 1-159 | 320 | 4 | 4 | 5 | 2 | 1 | 2 | 2 | 3 | 3 | 5 | 5 | 2 | 3 | 0 | 0 | 3 | 1 | 4 | 1 |
| 1-160 | 320 | 1 | 0 | 2 | 0 | 0 | 0 | 0 | 3 | 1 | 4 | 3 | 0 | 1 | 0 | 0 | 2 | 0 | 2 | 0 |
| 1-161 | 320 | 3 | 0 | 3 | 0 | 0 | 0 | 0 | 1 | 0 | 4 | 0 | 0 | 1 | 0 | 0 | 1 | 0 | 1 | 0 |
| 1-162 | 320 | 3 | 1 | 4 | 1 | 1 | 1 | 0 | 3 | 4 | 4 | 3 | 2 | 3 | 0 | 0 | 3 | 0 | 3 | 1 |
| 1-163 | 320 | 4 | 3 | 5 | 2 | 1 | 1 | 1 | 4 | 4 | 5 | 4 | 3 | 2 | 0 | 0 | 4 | 1 | 4 | 3 |
| 1-164 | 320 | 5 | 5 | 5 | 3 | 1 | 1 | 3 | 4 | 5 | 5 |   | 4 |   | 4 | 0 | 5 | 3 | 5 | 4 |
| 1-165 | 320 | 3 | 1 | 4 | 0 | 0 | 0 | 2 | 3 | 4 | 5 | 4 | 2 | 4 | 0 | 0 | 1 | 0 | 5 | 4 |
| 1-166 | 320 | 5 | 4 | 5 | 1 | 0 | 1 | 1 | 3 | 4 | 5 | 4 | 1 |   | 0 | 0 | 4 | 0 | 5 | 4 |
| 1-167 | 320 | 0 | 0 | 2 | 1 | 0 | 1 | 1 | 2 | 2 | 5 | 5 | 2 | 4 | 0 | 0 | 1 | 0 | 5 | 0 |
| 1-168 | 320 | 5 | 4 | 5 | 1 | 0 | 1 | 0 | 3 | 3 | 5 | 5 | 1 | 5 | 3 | 0 | 3 | 1 | 5 | 3 |
| 1-169 | 320 | 4 | 3 | 5 | 1 | 1 | 1 | 1 | 3 |   | 5 | 5 | 1 | 4 | 0 | 1 | 5 | 1 | 5 | 0 |
| 1-170 | 320 | 4 | 3 | 4 | 1 | 0 | 1 | 1 | 3 | 3 | 5 | 4 | 2 | 4 | 0 | 0 | 2 | 0 | 5 | 3 |
| 1-171 | 320 | 3 | 3 | 5 | 0 | 0 | 0 | 1 | 4 | 4 | 5 | 5 | 2 | 3 | 0 | 0 | 3 | 0 | 5 | 3 |
| 1-172 | 320 | 5 | 4 | 5 | 2 | 1 | 1 | 1 | 5 | 5 | 5 | 5 | 4 | 4 | 3 | 0 | 4 | 1 | 5 | 4 |
| 1-173 | 320 | 4 | 3 | 5 | 2 | 1 | 1 | 1 | 5 | 5 | 5 | 4 | 4 | 4 | 3 | 0 | 4 | 1 | 5 | 4 |
| 1-174 | 320 | 0 | 0 | 0 | 0 | 0 | 0 | 0 | 0 | 4 | 5 | 3 | 3 | 3 | 0 | 0 | 0 | 0 | 4 | 0 |
| 2-001 | 320 | 3 | 0 | 4 | 1 | 0 | 1 | 0 | 5 | 5 | 5 | 5 | 4 | 5 | 0 | 0 | 2 | 0 | 5 | 4 |
| 2-002 | 320 | 4 | 3 | 5 | 3 | 1 | 1 | 1 | 5 | 5 | 5 | 5 | 4 | 5 | 2 | 0 | 3 | 1 | 5 | 4 |
| 2-003 | 320 | 5 | 5 | 5 | 3 | 3 | 3 | 5 | 5 | 5 | 5 | 5 | 4 | 5 | 4 | 1 | 4 | 3 | 5 | 5 |
| 2-005 | 320 | 5 | 4 | 5 | 3 | 3 | 2 | 4 | 5 | 5 | 5 | 5 | 4 | 5 | 0 | 1 | 3 | 3 | 5 | 5 |
| 2-006 | 320 | 5 | 5 | 5 | 3 | 2 | 1 | 4 | 5 | 5 | 5 | 5 | 3 | 5 | 5 | 1 | 4 | 3 | 5 | 4 |
| 2-007 | 320 | 5 | 4 | 5 | 3 | 2 | 2 | 4 | 5 | 5 | 5 | 5 | 1 | 5 | 2 | 0 | 3 | 2 | 5 | 4 |
| 2-008 | 320 | 3 | 2 | 4 | 3 | 1 | 2 | 1 | 5 | 5 | 5 | 5 | 3 | 4 | 1 | 0 | 3 | 2 | 5 | 3 |
| 2-009 | 320 | 4 | 3 | 5 | 3 | 1 | 2 | 1 | 5 | 5 | 5 | 5 | 4 | 4 | 2 | 1 | 4 | 1 | 5 | 4 |
| 2-010 | 320 | 4 | 3 | 5 | 4 | 3 | 3 | 2 | 5 | 5 | 5 | 5 | 4 | 5 | 5 | 3 | 4 | 3 | 5 | 5 |
| 2-011 | 320 | 5 | 3 | 5 | 3 | 3 | 2 | 3 | 5 | 5 | 5 | 5 | 3 | 5 | 5 | 1 | 4 | 1 | 5 | 1 |
| 2-012 | 320 | 4 | 1 | 4 | 3 | 2 | 2 | 2 | 5 | 5 | 5 | 5 | 4 | 4 | 5 | 3 | 4 | 4 | 5 | 4 |
| 2-013 | 320 | 5 | 5 | 5 | 4 | 3 | 3 | 4 | 5 | 5 | 5 | 5 | 4 | 5 | 5 | 3 | 4 | 4 | 5 | 4 |
| 2-014 | 320 | 5 | 5 | 5 | 4 | 4 | 4 | 4 | 5 | 5 | 5 | 5 | 4 | 5 | 5 | 3 | 4 | 4 | 5 | 4 |
| 2-015 | 320 | 5 | 4 | 5 | 2 | 2 | 2 | 2 | 5 | 5 | 5 | 4 | 3 | 3 | 4 | 2 | 2 | 2 | 4 | 3 |
| 2-016 | 320 | 5 | 5 | 5 | 4 | 4 | 4 | 4 | 5 | 5 | 5 | 5 | 3 | 5 | 5 | 1 | 4 | 4 | 5 | 4 |
| 2-017 | 320 | 5 | 5 | 5 | 4 | 3 | 2 | 4 | 5 | 5 | 5 | 5 | 1 | 5 | 5 | 1 | 4 | 3 | 5 | 4 |
| 2-018 | 320 | 2 | 1 | 1 | 0 | 0 | 0 | 0 | 3 | 3 | 3 | 0 | 1 | 2 | 0 | 0 | 0 | 0 | 1 | 0 |
| 2-019 | 320 | 5 | 5 | 5 | 3 | 2 | 2 | 4 | 5 | 5 | 5 | 5 | 3 | 5 | 4 | 0 | 4 | 3 | 5 | 4 |
| 2-020 | 320 | 3 | 3 | 3 | 1 | 0 | 1 | 1 | 5 | 4 | 5 | 4 | 2 | 4 | 2 | 0 | 3 | 1 | 5 | 3 |
| 2-021 | 320 | 5 | 5 | 5 | 3 | 3 | 3 | 4 | 5 | 5 | 5 | 5 | 4 | 5 | 4 | 0 | 4 | 3 | 5 | 4 |
| 2-022 | 320 | 4 | 5 | 5 | 4 | 3 | 3 | 5 | 5 | 5 | 5 | 5 | 4 | 5 | 5 | 1 | 5 | 3 | 5 | 5 |
| 2-023 | 320 | 1 | 1 | 4 | 0 | 0 | 0 | 0 | 3 | 5 | 4 | 3 |   | 4 | 0 | 0 | 1 | 0 | 4 | 1 |
| 2-024 | 320 | 5 | 5 | 5 | 4 | 3 | 4 | 5 | 5 | 5 | 5 | 5 | 4 | 5 | 5 | 5 | 5 | 4 | 5 | 5 |
| 2-025 | 320 | 5 | 5 | 5 | 4 | 3 | 3 | 4 | 5 | 5 | 5 | 5 | 4 | 5 | 5 | 1 | 4 | 3 | 5 | 4 |
| 2-026 | 320 | 5 | 4 | 5 | 3 | 4 | 3 | 3 | 5 | 5 | 5 | 5 | 4 | 5 | 5 | 2 | 5 | 3 | 5 | 5 |
| 2-027 | 320 | 5 | 5 | 5 | 3 | 4 | 3 | 4 | 5 | 5 | 5 | 5 | 4 | 5 | 4 | 0 | 1 | 3 | 5 | 4 |

TABLE 71

| No. | Application herbicide amount (g/ha) | F | G | H | I | J | K | L | M | N | O | P | Q | R | b | c | d | e | f | g |
|---|---|---|---|---|---|---|---|---|---|---|---|---|---|---|---|---|---|---|---|---|
| 2-028 | 320 | 5 | 5 | 5 | 4 | 4 | 4 | 5 | 5 | 5 | 5 | 5 | 4 | 5 | 5 | 3 | 4 | 4 | 5 | 5 |
| 2-029 | 320 | 5 | 5 | 5 | 5 | 5 | 5 | 5 | 5 | 5 | 5 | 5 | 4 | 5 | 5 | 4 | 5 | 5 | 5 | 5 |

TABLE 71-continued

| No. | Application herbicide amount (g/ha) | F | G | H | I | J | K | L | M | N | O | P | Q | R | b | c | d | e | f | g |
|---|---|---|---|---|---|---|---|---|---|---|---|---|---|---|---|---|---|---|---|---|
| 2-030 | 320 | 5 | 5 | 5 | 4 | 3 | 3 | 5 | 5 | 5 | 5 | 5 | 3 | 5 | 5 | 0 | 4 | 3 | 5 | 5 |
| 2-031 | 320 | 5 | 5 | 5 | 5 | 4 | 5 | 5 | 5 | 5 | 5 | 5 | 5 | 5 | 5 | 5 | 5 | 5 | 5 | 5 |
| 2-032 | 320 | 5 | 5 | 5 | 5 | 3 | 4 | 5 | 5 | 5 | 5 | 5 | 5 | 5 | 5 | 5 | 5 | 5 | 5 | 5 |
| 2-033 | 320 | 5 | 5 | 5 | 5 | 4 | 4 | 5 | 5 | 5 | 5 | 5 | 5 | 5 | 5 | 4 | 5 | 4 | 5 | 5 |
| 2-034 | 320 | 5 | 5 | 5 | 5 | 5 | 5 | 5 | 5 | 5 | 5 | 5 | 5 | 5 | 5 | 3 | 5 | 5 | 5 | 5 |
| 2-035 | 320 | 5 | 5 | 5 | 4 | 3 | 4 | 4 | 5 | 5 | 5 | 5 | 2 | 5 | 5 | 2 | 4 | 4 | 5 | 5 |
| 2-036 | 320 | 5 | 4 | 5 | 1 | 0 | 0 | 3 | 5 | 5 | 5 | 5 | 4 | 4 | 0 | 0 | 2 | 0 | 5 | 3 |
| 2-037 | 320 | 5 | 5 | 5 | 5 | 5 | 5 | 5 | 5 | 5 | 5 | 5 | 5 | 5 | 5 | 5 | 4 | 5 | 5 | 5 |
| 2-038 | 320 | 5 | 5 | 5 | 5 | 5 | 5 | 5 | 5 | 5 | 5 | 5 | 5 | 5 | 5 | 5 | 5 | 5 | 5 | 5 |
| 2-039 | 320 | 5 | 5 | 5 | 4 | 3 | 3 | 4 | 5 | 5 | 5 | 5 | 4 | 5 | 4 | 3 | 4 | 3 | 5 | 5 |
| 2-040 | 320 | 5 | 3 | 5 | 3 | 1 | 1 | 3 | 5 | 5 | 5 | 5 | 4 | 5 | 4 | 1 | 4 | 2 | 5 | 3 |
| 2-041 | 320 | 4 | 3 | 5 | 3 | 3 | 3 | 4 | 5 | 4 | 5 | 5 | 4 | 4 | 2 | 0 | 4 | 3 | 5 | 4 |
| 2-042 | 320 | 5 | 5 | 5 | 2 | 2 | 1 | 0 | 5 | 5 | 5 | 3 | 1 | 5 | 4 | 0 | 3 | 0 | 4 | 2 |
| 2-043 | 320 | 5 | 4 | 5 | 4 | 3 | 2 | 4 | 5 | 5 | 5 | 5 | 5 | 5 | 5 | 3 | 1 | 4 | 3 | 5 | 4 |
| 2-044 | 320 | 5 | 4 | 5 | 2 | 2 | 2 | 3 | 5 | 5 | 5 | 4 | 3 | 5 | 3 | 2 | 4 | 1 | 5 | 3 |
| 2-045 | 320 | 5 | 4 | 5 | 2 | 1 | 1 | 3 | 5 | 5 | 5 | 5 | 3 | 5 | 4 | 3 | 4 | 1 | 5 | 5 |
| 2-046 | 320 | 0 | 1 | 3 | 0 | 0 | 0 | 0 | 4 | 4 | 4 | 2 | 1 | 1 | 0 | 0 | 0 | 0 | 2 | 0 |
| 2-047 | 320 | 5 | 3 | 5 | 3 | 1 | 1 | 3 | 5 | 5 | 5 | 4 | 3 | 5 | 3 | 0 | 3 | 3 | 5 | 3 |
| 2-048 | 320 | 5 | 5 | 5 | 4 | 3 | 4 | 5 | 5 | 5 | 5 | 4 | 4 |  | 4 | 4 | 5 | 4 | 5 | 5 |
| 2-049 | 320 | 5 | 5 | 5 | 3 | 1 | 3 | 4 | 4 | 3 | 5 |  | 3 | 4 | 2 | 1 | 4 | 0 | 4 | 3 |
| 2-050 | 192 | 3 | 1 | 3 | 2 | 0 | 0 | 0 | 3 | 2 | 5 | 3 | 0 | 3 | 0 | 0 | 3 | 0 | 3 | 0 |
| 2-051 | 320 | 5 | 5 | 5 | 5 | 4 | 4 | 5 | 5 | 5 | 5 | 5 | 5 | 5 | 4 | 2 | 4 | 4 | 5 | 4 |
| 2-052 | 320 | 5 | 5 | 5 | 5 | 5 | 5 | 5 | 5 | 5 | 5 | 5 |  |  | 5 | 4 | 5 | 5 | 5 | 5 |
| 2-053 | 320 | 5 | 5 | 5 | 5 | 5 | 4 | 5 | 5 | 5 | 5 | 5 | 5 |  | 5 | 4 | 5 | 5 | 5 | 5 |
| 2-054 | 320 | 5 | 5 | 5 | 5 | 4 | 5 | 5 | 5 | 5 | 5 | 5 | 4 |  | 5 | 5 | 5 | 5 | 5 | 5 |
| 2-055 | 131 | 0 | 0 | 0 | 0 | 0 | 0 | 0 | 4 | 3 | 5 | 4 | 0 |  | 0 | 0 | 1 | 0 | 1 | 0 |
| 2-056 | 320 | 5 | 3 | 4 | 1 | 1 | 1 | 1 | 4 | 4 | 5 | 5 | 4 |  | 0 | 1 | 3 | 1 | 5 | 3 |
| 2-057 | 320 | 5 | 5 | 5 | 4 | 4 | 4 | 4 | 5 | 5 | 5 | 5 | 4 | 5 | 4 | 2 | 5 | 4 | 5 | 5 |
| 2-058 | 320 | 5 | 5 | 5 | 5 | 4 | 4 | 4 | 5 | 5 | 5 | 5 | 5 | 5 | 5 | 3 | 5 | 5 | 5 | 5 |
| 2-059 | 320 | 5 | 5 | 5 | 4 | 4 | 4 | 5 | 5 | 5 | 5 | 5 | 5 | 5 | 5 | 3 | 5 | 4 | 5 | 5 |
| 2-060 | 320 | 5 | 5 | 5 | 4 | 3 | 3 | 5 | 5 | 5 | 5 | 4 | 5 | 5 | 5 | 2 | 4 | 4 | 5 | 5 |
| 2-061 | 320 | 5 | 5 | 5 | 4 | 3 | 4 | 3 | 4 | 5 | 5 | 5 | 3 | 5 | 5 | 3 | 4 | 3 | 5 | 4 |
| 2-062 | 320 | 5 | 5 | 5 | 5 | 4 | 5 | 5 | 5 | 5 | 5 | 5 | 5 | 5 | 5 | 5 | 5 | 4 | 5 | 5 |
| 2-063 | 320 | 5 | 5 | 5 | 4 | 3 | 3 | 3 | 5 | 5 | 5 | 5 | 4 | 5 | 4 | 3 | 4 | 3 | 5 | 4 |
| 2-064 | 320 | 3 | 2 | 3 | 0 | 0 | 0 | 0 | 5 | 5 | 5 | 5 | 1 | 5 | 0 | 0 | 3 | 0 | 4 | 3 |
| 2-065 | 320 | 5 | 5 | 5 | 4 | 3 | 3 | 4 | 5 | 5 | 5 | 5 | 3 | 5 | 3 | 4 | 4 | 3 | 5 | 4 |
| 2-066 | 320 | 5 | 5 | 5 | 2 | 3 | 3 | 3 | 4 | 5 | 5 | 5 | 3 | 5 | 4 | 1 | 4 | 3 | 5 | 4 |
| 2-067 | 320 | 5 | 5 | 5 | 5 | 4 | 4 | 3 | 5 | 5 | 5 | 5 | 4 | 5 | 5 | 4 | 5 | 4 | 5 | 5 |
| 2-068 | 320 | 5 | 5 | 5 | 3 | 2 | 2 | 3 | 5 | 5 | 5 | 5 | 4 | 5 | 5 | 3 | 4 | 2 | 5 | 4 |
| 2-069 | 320 | 5 | 5 | 5 | 5 | 3 | 3 | 4 | 5 | 5 | 5 | 5 | 4 | 5 | 5 | 4 | 4 | 3 | 5 | 5 |
| 2-070 | 320 | 5 | 5 | 5 | 5 | 4 | 4 | 4 | 5 | 5 | 5 | 4 | 5 | 3 | 4 | 3 | 4 | 5 | 5 | |
| 2-071 | 320 | 5 | 4 | 5 | 2 | 1 | 1 | 1 | 4 | 5 | 5 | 5 | 3 | 5 | 1 | 2 | 3 | 1 | 5 | 4 |
| 2-072 | 320 | 5 | 5 | 5 | 1 | 1 | 1 | 3 | 5 | 5 | 5 | 5 | 5 | 5 | 1 | 3 | 4 | 1 | 5 | 4 |
| 2-073 | 320 | 1 | 1 | 4 | 1 | 0 | 1 | 0 | 3 | 3 | 5 | 4 | 0 | 2 | 0 | 0 | 2 | 0 | 3 | 0 |
| 2-074 | 320 | 5 | 4 | 5 | 4 | 3 | 3 | 3 | 4 | 5 | 5 | 4 | 3 | 5 | 5 | 3 | 4 | 3 | 5 | 4 |

TABLE 72

| No. | Application herbicide amount (g/ha) | F | G | H | I | J | K | L | M | N | O | P | Q | R | b | c | d | e | f | g |
|---|---|---|---|---|---|---|---|---|---|---|---|---|---|---|---|---|---|---|---|---|
| 2-075 | 320 | 5 | 5 | 5 | 5 | 4 | 4 | 4 | 5 | 5 | 5 | 5 | 4 | 5 | 5 | 3 | 5 | 4 | 5 | 5 |
| 2-076 | 320 | 3 | 3 | 5 | 1 | 1 | 1 | 2 | 4 | 5 | 5 | 5 | 3 | 5 | 1 | 0 | 1 | 0 | 5 | 4 |
| 2-077 | 320 | 4 | 2 | 4 | 0 | 0 | 0 | 0 | 4 | 5 | 5 | 4 | 3 | 3 | 0 | 0 | 2 | 0 | 5 | 2 |
| 2-078 | 320 | 5 | 5 | 5 | 3 | 4 | 4 | 5 | 5 | 5 | 5 | 5 | 4 | 5 | 4 | 1 | 4 | 2 | 5 | 5 |
| 2-079 | 320 | 5 | 5 | 5 | 3 | 4 | 2 | 5 | 5 | 5 | 5 | 5 | 5 | 5 | 5 | 2 | 4 | 2 | 5 | 5 |
| 2-080 | 320 | 5 | 3 | 5 | 1 | 1 | 0 | 3 | 5 | 5 | 5 | 4 | 4 | 5 | 3 | 0 | 4 | 0 | 5 | 5 |
| 2-081 | 320 | 4 | 3 | 5 | 3 | 1 | 1 | 1 | 4 | 5 | 5 | 5 | 3 | 4 |  | 0 | 3 | 2 | 5 | 4 |
| 2-082 | 320 | 5 | 5 | 5 | 2 | 4 | 4 | 4 | 5 | 5 | 5 | 5 | 4 | 4 |  | 1 | 5 | 4 | 5 | 5 |
| 2-083 | 320 | 5 | 4 | 5 | 2 | 1 | 1 | 1 | 5 | 5 | 5 | 4 | 3 | 4 |  | 0 | 4 | 0 | 5 | 1 |
| 2-084 | 320 | 5 | 5 | 5 | 4 | 3 | 3 | 4 | 5 | 5 | 5 | 5 | 4 | 3 |  | 1 | 3 | 3 | 5 | 3 |
| 2-085 | 320 | 5 | 5 | 5 | 4 | 3 | 3 | 4 | 5 | 5 | 5 | 5 | 4 | 4 |  | 2 | 5 | 3 | 5 | 4 |
| 2-086 | 320 | 5 | 5 | 5 | 3 | 1 | 2 | 4 | 5 | 5 | 5 | 4 | 4 | 5 |  | 0 | 4 | 2 | 5 | 3 |
| 2-087 | 320 | 5 | 4 | 5 | 4 | 3 | 3 | 4 | 5 | 5 | 4 | 5 | 3 |  |  | 0 | 3 | 2 | 5 | 3 |
| 2-088 | 141 | 5 | 5 | 5 | 4 | 3 | 3 | 4 | 5 | 5 | 5 | 5 | 3 | 4 |  | 0 | 4 | 0 | 5 | 5 |
| 2-089 | 320 | 4 | 4 | 4 | 1 | 2 | 1 | 4 | 4 | 4 | 5 | 5 | 3 | 5 |  | 0 | 4 | 0 | 5 | 4 |
| 2-090 | 320 | 5 | 4 | 5 | 4 | 3 | 4 | 4 | 3 | 4 |  | 5 | 4 | 3 | 3 | 1 | 3 | 3 | 5 | 4 |
| 2-091 | 320 | 5 | 5 | 5 | 3 | 2 | 3 | 3 | 4 | 4 | 5 | 5 | 4 | 4 | 2 | 0 | 3 | 3 | 5 | 5 |
| 2-092 | 320 | 0 | 0 | 2 | 1 | 0 | 0 | 0 | 1 | 1 | 3 | 3 | 1 | 1 | 0 | 0 | 1 | 0 | 3 | 0 |
| 2-093 | 320 | 1 | 0 | 1 | 1 | 1 | 1 | 1 | 3 | 2 | 5 | 5 | 2 | 2 | 0 | 0 | 3 | 1 | 2 | 1 |
| 2-094 | 320 | 4 | 4 | 5 | 2 | 1 | 1 | 3 | 5 | 4 | 5 | 5 | 3 | 4 | 3 | 1 | 4 | 1 | 5 | 4 |
| 2-095 | 320 | 5 | 5 | 5 | 4 | 4 | 3 | 5 | 5 | 5 | 5 | 5 | 4 | 4 | 5 | 1 | 5 | 3 | 5 | 5 |
| 2-096 | 320 | 5 | 4 | 5 | 1 | 0 | 0 | 0 | 5 | 5 | 5 | 4 | 3 | 3 | 0 | 0 | 3 | 0 | 5 | 0 |

TABLE 72-continued

| No. | Application herbicide amount (g/ha) | F | G | H | I | J | K | L | M | N | O | P | Q | R | b | c | d | e | f | g |
|---|---|---|---|---|---|---|---|---|---|---|---|---|---|---|---|---|---|---|---|---|
| 2-097 | 320 | 4 | 3 | 5 | 2 | 1 | 1 | 2 | 3 | 3 | 5 | 4 | 3 | 4 | 0 | 0 | 3 | 0 | 4 | 1 |
| 2-098 | 320 | 5 | 5 | 5 | 4 | 2 | 3 | 4 | 4 | 5 | 5 | 5 | 4 | 4 | 1 | 4 | 3 | 5 | 4 |
| 2-099 | 320 | 5 | 4 | 5 | 2 | 0 | 1 | 1 | 4 | 4 | 5 | 5 | 4 | 5 | 3 | 0 | 4 | 0 | 5 | 4 |
| 2-100 | 320 | 5 | 4 | 5 | 3 | 2 | 3 | 4 | 5 | 5 | 5 | 5 | 5 | 5 | 5 | 0 | 4 | 0 | 5 | 5 |
| 2-101 | 320 | 5 | 5 | 5 | 3 | 3 | 3 | 4 | 5 | 5 | 5 | 5 | 4 | 5 | 4 | 2 | 5 | 3 | 5 | 5 |
| 2-102 | 320 | 5 | 4 | 5 | 1 | 0 | 1 | 3 | 5 | 5 | 5 | 5 | 3 | 5 | 1 | 0 | 4 | 1 | 5 | 3 |
| 2-103 | 320 | 4 | 3 | 5 | 1 | 0 | 1 | 2 | 4 | 5 | 5 | 5 | 4 | 4 | 2 | 0 | 4 | 0 | 5 | 3 |
| 2-105 | 320 | 5 | 4 | 5 | 4 | 3 | 3 | 4 | 5 | 5 | 5 | 5 | 3 | 5 | 4 | 0 | 4 | 3 | 5 | 5 |
| 2-106 | 320 | 3 | 1 | 3 | 1 | 0 | 0 | 0 | 5 | 4 | 5 | 4 | 3 | 3 | 0 | 0 | 4 | 0 | 5 | 3 |
| 2-107 | 320 | 5 | 3 | 5 | 1 | 0 | 0 | 0 | 5 | 5 | 5 | 5 | 4 | 5 | 3 | 0 | 5 | 0 | 5 | 4 |
| 2-108 | 320 | 4 | 3 | 5 | 1 | 0 | 0 | 0 | 5 | 5 | 5 | 5 | 4 | 5 | 4 | 0 | 4 | 1 | 5 | 5 |
| 2-109 | 256 | 3 | 2 | 4 | 1 | 0 | 1 | 0 | 5 | 5 | 5 | 5 | 3 | 5 | 1 | 0 | 4 | 1 | 5 | 4 |
| 2-110 | 320 | 5 | 4 | 5 | 3 | 2 | 3 | 3 | 5 | 5 | 5 | 5 | 5 | 5 | 4 | 0 | 4 | 3 | 5 | 4 |
| 3-002 | 320 | 0 | 0 | 0 | 0 | 0 | 0 | 0 | 1 | 3 | 4 | 1 | 0 | 0 | 0 | 0 | 0 | 0 | 0 | 0 |
| 4-001 | 320 | 1 | 2 | 3 | 1 | 0 | 0 | 0 | 5 | 5 | 5 | 3 | 3 | 3 | 0 | 0 | 2 | 0 | 2 | 0 |
| 4-002 | 320 | 1 | 1 | 2 | 1 | 0 | 0 | 0 | 5 | 4 | 4 | 3 | 1 | 1 | 0 | 0 | 1 | 0 | 0 | 0 |
| 4-003 | 320 | 2 | 1 | 4 | 0 | 0 | 0 | 1 | 4 | 2 | 5 | 4 | 1 | 2 | 0 | 0 | 4 | 0 | 4 | 1 |
| 4-004 | 320 | 0 | 0 | 0 | 0 | 0 | 0 | 0 | 0 | 0 | 4 | 0 | 0 | 0 | 0 | 0 | 0 | 0 | 0 | 0 |
| 6-001 | 320 | 1 | 2 | 1 | 0 | 0 | 0 | 0 | 3 | 3 | 4 | 4 | 2 | 2 | 0 | 0 | 0 | 0 | 3 | 0 |
| 6-002 | 320 | 4 | 3 | 5 | 1 | 0 | 0 | 0 | 5 | 5 | 5 | 5 | 3 | 4 | 0 | 0 | 3 | 0 | 3 | 3 |
| 6-003 | 320 | 4 | 3 | 3 | 0 | 0 | 0 | 0 | 4 | 2 | 3 | 4 | 1 | 1 | 0 | 0 | 0 | 0 | 1 | 0 |
| 6-004 | 320 | 5 | 4 | 5 | 3 | 1 | 2 | 1 | 5 | 5 | 5 | 4 | 4 | 3 | 0 | 0 | 4 | 1 | 2 | 3 |
| 6-005 | 320 | 3 | 1 | 3 | 0 | 1 | 1 | 1 | 4 | 3 | 3 | 1 | 1 | 1 | 0 | 0 | 0 | 0 | 1 | 0 |
| 6-006 | 320 | 0 | 0 | 0 | 0 | 0 | 0 | 0 | 1 | 0 | 3 | 1 | 0 | 1 | 0 | 0 | 0 | 0 | 0 | 0 |
| 6-007 | 320 | 0 | 0 | 0 | 0 | 0 | 0 | 0 | 2 | 3 | 3 | 0 | 0 | 0 | 0 | 0 | 2 | 0 | 3 | 0 |

TABLE 73

| No. | Application herbicide amount (g/ha) | F | G | H | I | J | K | L | M | N | O | P | Q | R | b | c | d | e | f | g |
|---|---|---|---|---|---|---|---|---|---|---|---|---|---|---|---|---|---|---|---|---|
| 6-008 | 320 | 0 | 0 | 0 | 0 | 0 | 0 | 0 | 1 | 0 | 3 | 1 | 0 | 0 | 0 | 0 | 1 | 0 | 1 | 0 |
| 7-001 | 320 | 0 | 0 | 1 | 0 | 0 | 0 | 0 | 1 | 0 | 2 | 1 | 0 | 0 | 0 | 0 | 0 | 0 | 0 | 0 |
| 7-002 | 320 | 3 | 2 | 4 | 1 | 0 | 0 | 0 | 3 | 4 | 5 | 4 | 3 | 3 | 0 | 0 | 2 | 0 | 4 | 3 |

INDUSTRIAL APPLICABILITY

The heterocyclic amide compound of the present invention is a novel compound and is useful as selective herbicides for *Oryza sative*, *Zea mays*, *Glycine max*, *Triticum aestivum*, *Beta vulgaris* ssp. *vulgaris*, and *Brassica campestris* L.

The invention claimed is:

1. A heterocyclic amide compound of Formula (1):

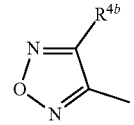

(1)

where Q is an aromatic heterocycle of any one of Q-1 to Q-5;

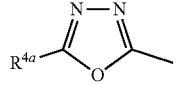

Q-1

Q-2

Q-3

Q-4

-continued

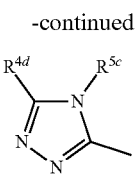
Q-5

W is an aromatic heterocycle of W-1, W-2, or W-3;

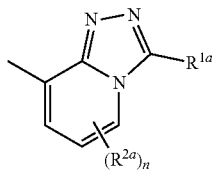
W-1

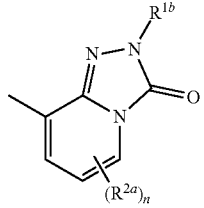
W-2

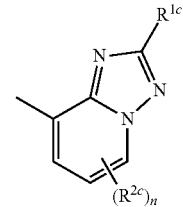
W-3

X is an oxygen atom or a sulfur atom;

$R^{1a}$ is a hydrogen atom, a halogen atom, $C_{1-6}$ alkyl, $(C_{1-6})$ alkyl substituted with $R^6$, $C_{3-6}$ cycloalkyl, $(C_{3-6})$ cycloalkyl substituted with $R^6$, $C_{2-6}$ alkenyl, $C_{2-6}$ alkynyl, $C_{3-6}$ cycloalkenyl, —C(O)R$^8$, —C(O)OR$^{16}$, cyano, —OR$^9$, —S(O)$_{m1}$R$^{10}$, —N(R$^{11}$)R$^{12}$, —C(=NR$^{12b}$)R$^{8b}$, phenyl, phenyl substituted with $(R^7)_p$, naphthyl, or any one group of U-1 to U-25;

$R^{1b}$ is a hydrogen atom, $C_{1-6}$ alkyl, $(C_{1-6})$ alkyl substituted with $R^6$, $C_{3-6}$ cycloalkyl, $(C_{1-6})$ cycloalkyl substituted with $R^6$, $C_{2-6}$ alkenyl, $C_{2-6}$ alkynyl, phenyl, phenyl substituted with $(R^7)_p$, naphthyl, 5-6-membered heteroaryl, 5-6-membered heteroaryl substituted with $R^{28}$ and $R^{28a}$, 3-7-membered heterocyclyl, or 3-7-membered heterocyclyl substituted with $R^{28}$ and $R^{28a}$;

$R^{1c}$ is $C_{1-6}$ alkyl;

$R^{2a}$ is a halogen atom, $C_{1-6}$ alkyl, $C_{1-6}$ haloalkyl, —C(O)R$^{18}$, —C(O)OR$^{24}$, cyano, nitro, —OR$^{19}$, —S(O)$_{m3}$R$^{20}$, —N(R$^{21}$)R$^{22}$, phenyl, or phenyl substituted with $(R^7)_p$; when n is an integer of 2 or more, $R^{2a}$ are optionally the same as or different from each other, and when two $R^{2a}$ are adjacent, the two adjacent $R^{2a}$ optionally form a 6-membered ring together with carbon atoms bonded to each $R^{2a}$ by forming —CH=CH—CH=CH—;

$R^{2c}$ is $C_{1-6}$ haloalkyl;

$R^3$ is a hydrogen atom, $C_{1-6}$ alkyl, $(C_{1-6})$ alkyl optionally substituted with $R^{27}$, $C_{3-6}$ cycloalkyl, $C_{3-6}$ halocycloalkyl, $C_{2-6}$ alkenyl, $C_{2-6}$ haloalkenyl, $C_{2-6}$ alkynyl, $C_{2-6}$ haloalkynyl, —C(O)R$^{25}$, or —C(O)OR$^{26}$;

$R^{4a}$ is a hydrogen atom, a halogen atom, $C_{1-6}$ alkyl, $(C_{1-6})$ alkyl substituted with $R^{27}$, $C_{3-6}$ cycloalkyl, $(C_{3-6})$ cycloalkyl substituted with $R^{27}$, $C_{2-6}$ alkenyl, $C_{2-6}$ haloalkenyl, $C_{2-6}$ alkynyl, $C_{2-6}$ haloalkynyl, $C_{3-6}$ cycloalkenyl, —NH$_2$, $C_{1-6}$ alkylamino, di($C_{1-6}$ alkyl)amino, —NHC(O)R$^8$, phenyl, phenyl substituted with $(R^{28})_r$, 5-6-membered heteroaryl, 5-6-membered heteroaryl substituted with $R^{28}$ and $R^{28a}$, 3-7-membered heterocyclyl, or 3-7-membered heterocyclyl substituted with $R^{28}$ and $R^{28a}$;

$R^{4b}$ is a hydrogen atom, a halogen atom, cyano, nitro, $C_{1-6}$ alkyl, $(C_{1-6})$ alkyl substituted with $R^{27}$, $C_{3-6}$ cycloalkyl, $(C_{3-6})$ cycloalkyl substituted with $R^{27}$, $C_{2-6}$ alkenyl, $C_{2-6}$ haloalkenyl, $C_{2-6}$ alkynyl, $C_{2-6}$ haloalkynyl, $C_{3-6}$ cycloalkenyl, —C(O)OR$^{16}$, —OR$^{38}$, —S(O)$_{m3}$R$^{20}$, —NH$_2$, $C_{1-6}$ alkylamino, di($C_{1-6}$ alkyl)amino, —NHC(O)R$^8$, phenyl, phenyl substituted with $(R^{28})_r$, 5-6-membered heteroaryl, 5-6-membered heteroaryl substituted with $R^{28}$ and $R^{28a}$, 3-7-membered heterocyclyl, or 3-7-membered heterocyclyl substituted with $R^{28}$ and $R^{28a}$;

$R^{4c}$ is a hydrogen atom, a halogen atom, $C_{1-6}$ alkyl, $(C_{1-6})$ alkyl substituted with $R^{27}$, $C_{3-6}$ cycloalkyl, $(C_{3-6})$ cycloalkyl substituted with $R^{27}$, phenyl, phenyl substituted with $(R^{28})_r$, 5-6-membered heteroaryl, 5-6-membered heteroaryl substituted with $R^{28}$ and $R^{28a}$, 3-7-membered heterocyclyl, or 3-7-membered heterocyclyl substituted with $R^{28}$ and $R^{28a}$;

$R^{4d}$ is a hydrogen atom, $C_{1-6}$ alkyl, or $(C_{1-6})$ alkyl substituted with $R^{35}$;

U-1 to U-5, U-5a, U-6, U-6a, U-7 to U-10, U-10a, U-11, U-11a, U-12, U-12a, U-13, U-13a, U-14 to U-22, U-22a, U-23, U-24, U-25, and U-26 are respective heterocycles of the following structures;

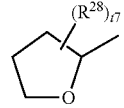
U-1

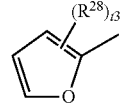
U-2

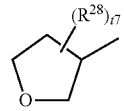
U-3

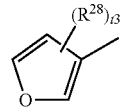
U-4

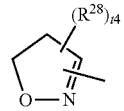
U-5

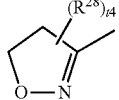
U-5a

-continued
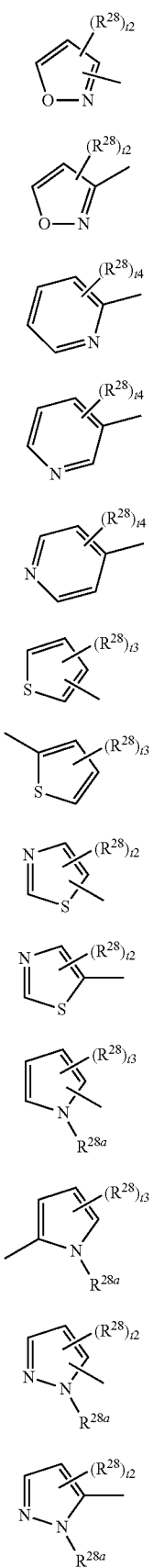
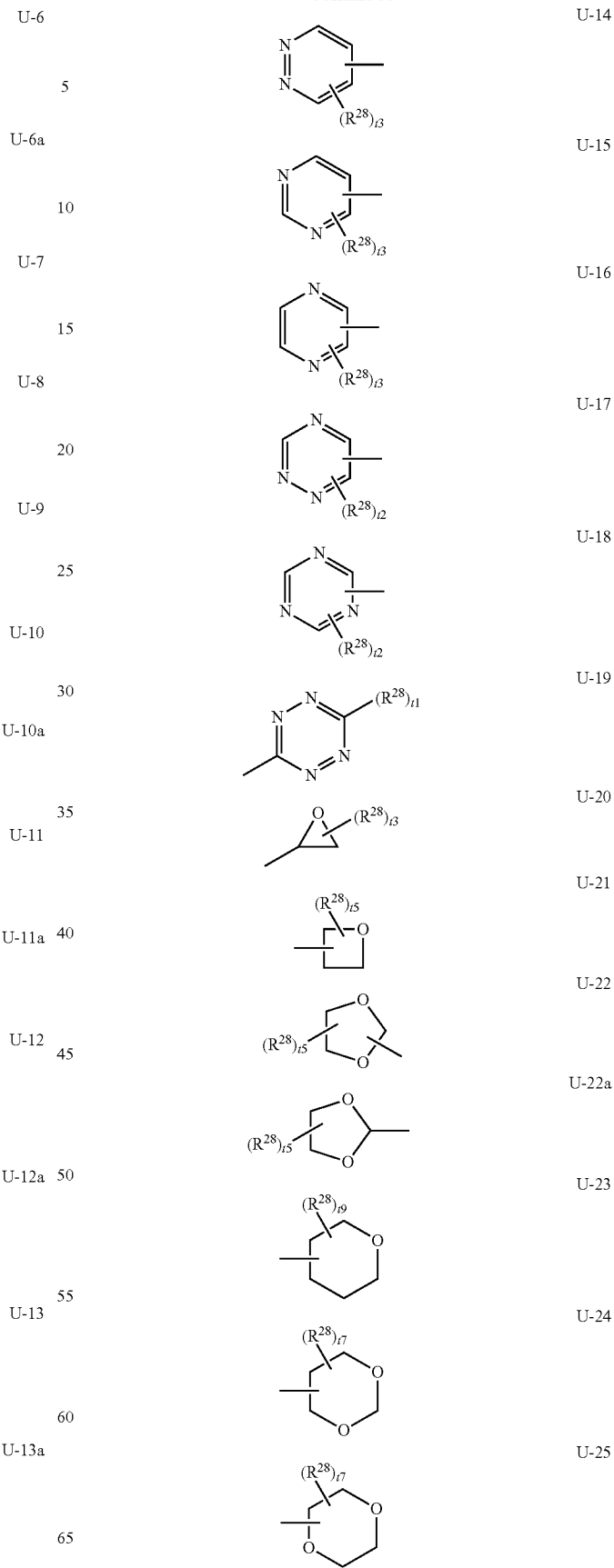

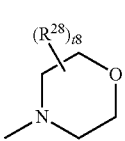

U-26

$R^{5a}$ and $R^{5b}$ are each independently a hydrogen atom, $C_{1-6}$ alkyl, $(C_{1-6})$ alkyl substituted with $R^{27}$, $C_{3-6}$ cycloalkyl, $C_{3-6}$ halocycloalkyl, $C_{2-6}$ alkenyl, $C_{2-6}$ haloalkenyl, $C_{2-6}$ alkynyl, $C_{2-6}$ haloalkynyl, $C_{3-6}$ cycloalkenyl, phenyl, or phenyl substituted with $(R^{28})_r$;

$R^{5c}$ is a hydrogen atom, $C_{1-6}$ alkyl, or $(C_{1-6})$ alkyl substituted with $R^{36}$, or $R^{5c}$ optionally forms a 6-membered ring together with a nitrogen atom to which $R^{5c}$ is bonded and a carbon atom to which $R^{4d}$ is bonded by forming $-(CH_2)_4-$ or $-CH=CH-CH=CH-$ with $R^{4d}$;

$R^6$ is a halogen atom, cyano, $C_{3-6}$ cycloalkyl, $-C(O)R^8$, $-C(O)OR^{16}$, $-OR^{13}$, $-S(O)_{m2}R^{14}$, phenyl, or phenyl substituted with $(R^7)_p$;

$R^7$ is a halogen atom, cyano, nitro, $C_{1-6}$ alkyl, $(C_{1-6})$ alkyl substituted with $R^{27}$, $C_{3-6}$ cycloalkyl, $C_{3-6}$ halocycloalkyl, $C_{2-6}$ alkenyl, $C_{2-6}$ haloalkenyl, $C_{2-6}$ alkynyl, $C_{2-6}$ haloalkynyl, $C_{3-6}$ cycloalkenyl, $C_{1-6}$ alkylcarbonyl, $C_{3-6}$ cycloalkylcarbonyl, $C_{1-6}$ haloalkylcarbonyl, $C_{3-6}$ halocycloalkylcarbonyl, $C_{1-6}$ alkoxycarbonyl, $C_{1-6}$ haloalkoxycarbonyl, $C_{1-6}$ alkylaminocarbonyl, $C_{1-6}$ haloalkylaminocarbonyl, di($C_{1-6}$ alkylamino)carbonyl, $-OR^{15}$, $-S(O)_{m3}R^{20}$, $C_{1-6}$ alkylaminosulfonyl, di($C_{1-6}$ alkyl)aminosulfonyl, $-NH_2$, $C_{1-6}$ alkylamino, di($C_{1-6}$ alkyl)amino, 5-6-membered heteroaryl, 5-6-membered heteroaryl substituted with $R^{28}$ and $R^{28a}$, 3-7-membered heterocyclyl, or 3-7-membered heterocyclyl substituted with $R^{28}$ and $R^{28a}$;

$R^8$ is a hydrogen atom, $C_{1-6}$ alkyl, or $-N(R^{11a})R^{12a}$;

$R^{8b}$ is a hydrogen atom or $C_{1-6}$ alkyl;

$R^9$ is a hydrogen atom, $C_{1-6}$ alkyl, or phenyl;

$R^{10}$ is a hydrogen atom, $C_{1-6}$ alkyl, $(C_{1-6})$ alkyl substituted with $R^{34}$, $C_{3-6}$ cycloalkyl, $C_{3-6}$ halocycloalkyl, $C_{2-6}$ alkenyl, $C_{2-6}$ haloalkenyl, $C_{2-6}$ alkynyl, or $C_{2-6}$ haloalkynyl;

$R^{11}$ and $R^{12}$ are each independently a hydrogen atom, $C_{1-6}$ alkyl, $(C_{1-6})$ alkyl substituted with $R^{34}$, $C_{3-6}$ cycloalkyl, $C_{2-6}$ alkenyl, $C_{2-6}$ haloalkenyl, $C_{2-6}$ alkynyl, $C_{2-6}$ haloalkynyl, phenylsulfonyl, phenyl, phenyl substituted with $(R^7)_p$, U-7, U-8, U-9, or U-14 to U-19, or $R^{11}$ optionally forms a 3-7-membered ring together with a nitrogen atom to which $R^{11}$ and $R^{12}$ are bonded by forming a $C_{2-6}$ alkylene chain together with $R^{12}$, and in this case, the alkylene chain optionally contains one O, S, S(O), S(O)$_2$, or N($R^{33}$) and is optionally substituted with an oxo group or a thioxo group;

$R^{11a}$ and $R^{12a}$ are each independently a hydrogen atom, $C_{1-6}$ alkyl, or phenyl, or $R^{11a}$ optionally forms a 3-7-membered ring together with a nitrogen atom to which $R^{11a}$ and $R^{12a}$ are bonded by forming a $C_{2-6}$ alkylene chain together with $R^{12a}$, and in this case, the alkylene chain optionally contains one O, S, S(O), S(O)$_2$, or N($R^{33}$) and is optionally substituted with an oxo group or a thioxo group;

$R^{12b}$ is $-OR^{19b}$;

$R^{13}$ is a hydrogen atom, $C_{1-6}$ alkyl, $(C_{1-6})$ alkyl substituted with $R^{34}$, $C_{2-6}$ alkenyl, $C_{2-6}$ haloalkenyl, $C_{2-6}$ alkynyl, $C_{2-6}$ haloalkynyl, $-C(O)R^8$, or phenyl;

$R^{14}$ is a hydrogen atom, $C_{1-6}$ alkyl, $(C_{1-6})$ alkyl substituted with $R^{34}$, $C_{2-6}$ alkenyl, $C_{2-6}$ haloalkenyl, $C_{2-6}$ alkynyl, $C_{2-6}$ haloalkynyl, or phenyl;

$R^{15}$ is a hydrogen atom, $C_{1-6}$ alkyl, $(C_{1-6})$ alkyl substituted with $R^{27}$, $C_{3-6}$ cycloalkyl, $C_{3-6}$ halocycloalkyl, $C_{2-6}$ alkenyl, $C_{2-6}$ haloalkenyl, $C_{2-6}$ alkynyl, $C_{2-6}$ haloalkynyl, or $C_{1-6}$ cycloalkenyl;

$R^{16}$ is a hydrogen atom, $C_{1-6}$ alkyl, or $(C_{1-6})$ alkyl substituted with $R^{37}$;

$R^{18}$ is a hydrogen atom or $C_{1-6}$ alkyl;

$R^{19}$ is a hydrogen atom, $C_{1-6}$ alkyl, or phenyl;

$R^{19b}$ is a hydrogen atom or $C_{1-6}$ alkyl;

$R^{20}$ is $C_{1-6}$ alkyl, $C_{1-6}$ haloalkyl, $C_{3-6}$ cycloalkyl, $C_{2-6}$ alkenyl, $C_{2-6}$ haloalkenyl, $C_{2-6}$ alkynyl, $C_{2-6}$ haloalkynyl, or $C_{3-6}$ cycloalkenyl;

$R^{21}$ and $R^{22}$ are each independently a hydrogen atom, $C_{1-6}$ alkyl, or phenyl, or $R^{21}$ optionally forms a 3-7-membered ring together with a nitrogen atom to which $R^{21}$ and $R^{22}$ are bonded by forming a $C_{2-6}$ alkylene chain together with $R^{22}$, and in this case, the alkylene chain optionally contains one O, S, S(O), S(O)$_2$, or N($R^{39}$) and is optionally substituted with an oxo group or a thioxo group;

$R^{24}$ is a hydrogen atom or $C_{1-6}$ alkyl;

$R^{25}$ and $R^{26}$ are each independently a hydrogen atom, $C_{1-6}$ alkyl, $C_{1-6}$ haloalkyl, $C_{3-6}$ cycloalkyl, $C_{3-6}$ halocycloalkyl, $C_{2-6}$ alkenyl, $C_{2-6}$ haloalkenyl, $C_{2-6}$ alkynyl, $C_{2-6}$ haloalkynyl, $C_{3-6}$ cycloalkenyl, or phenyl;

$R^{27}$ is a halogen atom, cyano, nitro, phenyl, phenyl substituted with $(R^{28})_r$, $-C(O)OR^{16}$, $-OR^{29}$, $-S(O)_{m4}R^{30}$, 5-6-membered heteroaryl, 5-6-membered heteroaryl substituted with $R^{28}$ and $R^{28a}$, 3-7-membered heterocyclyl, or 3-7-membered heterocyclyl substituted with $R^{28}$ and $R^{28a}$;

$R^{28}$ is a halogen atom, cyano, nitro, $C_{1-6}$ alkyl, $C_{1-6}$ haloalkyl, $C_{3-6}$ cycloalkyl, $C_{3-6}$ halocycloalkyl, $C_{2-6}$ alkenyl, $C_{2-6}$ haloalkenyl, $C_{2-6}$ alkynyl, $C_{2-6}$ haloalkynyl, $(C_{1-6}$ alkoxy) $C_{1-6}$ alkyl, $-OR^{31}$, or $-S(O)_{m4}R^{30}$; when t2, t3, t4, t5, t7, t8, or t9 is an integer of 2 or more, $R^{28}$ are optionally the same as or different from each other; further when two $R^{28}$ are adjacent, the two adjacent $R^{28}$ optionally form a 6-membered ring together with carbon atoms to which each $R^{28}$ is bonded by forming $-CH=CH-CH=CH-$;

$R^{28a}$ is $C_{1-6}$ alkyl, $C_{1-6}$ haloalkyl, $(C_{1-6}$ alkoxy) $C_{1-6}$ alkyl, or $(C_{1-6}$ alkylthio) $C_{1-6}$ alkyl;

$R^{29}$, $R^{30}$, and $R^{31}$ are each independently a hydrogen atom, $C_{1-6}$ alkyl, $C_{1-6}$ haloalkyl, $C_{3-6}$ cycloalkyl, $C_{3-6}$ halocycloalkyl, $C_{2-6}$ alkenyl, $C_{2-6}$ haloalkenyl, $C_{2-6}$ alkynyl, $C_{2-6}$ haloalkynyl, $C_{3-6}$ cycloalkenyl, or phenyl;

$R^{33}$ is a hydrogen atom or $C_{1-6}$ alkyl;

$R^{34}$ is a halogen atom, cyano, $C_{3-6}$ cycloalkyl, $-C(O)R^8$, $-C(O)OR^{16}$, $-OR^{33}$, $-S(O)_{m6}R^{33}$, phenyl, phenyl substituted with $(R^7)_p$, U-1, U-3, U-7, U-8, U-9, or U-14 to U-25;

$R^{35}$ is a halogen atom or $C_{1-6}$ alkoxy;

$R^{36}$ is a halogen atom or $C_{1-6}$ alkoxy;

$R^{37}$ is $C_{1-6}$ alkoxy, $R^{38}$ is $C_{1-6}$ alkyl, $(C_{1-6})$ alkyl substituted with $R^{34}$, $C_{3-6}$ cycloalkyl, $C_{3-6}$ halocycloalkyl, $C_{2-6}$ alkenyl, $C_{2-6}$ haloalkenyl, $C_{2-6}$ alkynyl, $C_{2-6}$ haloalkynyl, $C_{3-6}$ cycloalkenyl, or phenyl;

$R^{39}$ is a hydrogen atom or $C_{1-6}$ alkyl;

t1 is an integer of 0 or 1;

m1, m2, m3, m4, m6, and t2 are each independently an integer of 0, 1, or 2;

n and t3 are each independently an integer of 0, 1, 2, or 3;

p and r are each independently an integer of 1, 2, 3, 4, or 5;

t4 is an integer of 0, 1, 2, 3, or 4;

t5 is an integer of 0, 1, 2, 3, 4, or 5;

t7 is an integer of 0, 1, 2, 3, 4, 5, 6, or 7;

t8 is an integer of 0, 1, 2, 3, 4, 5, 6, 7, or 8; and t9 is an integer of 0, 1, 2, 3, 4, 5, 6, 7, 8, or 9, or a salt thereof.

2. The heterocyclic amide compound or the salt thereof according to claim 1, wherein W is an aromatic heterocycle of W-1 or W-2; and $R^{2a}$ is a halogen atom, $C_{1-6}$ alkyl, $C_{1-6}$ haloalkyl, —C(O)$R^{18}$, —C(O)O$R^{24}$, cyano, nitro, —O$R^{19}$, or —S(O)$_{m3}R^{20}$, and when n is an integer of 2 or more, $R^{2a}$ are optionally the same as or different from each other.

3. The heterocyclic amide compound or the salt thereof according to claim 2, wherein $R^{1b}$ is a hydrogen atom, $C_{1-6}$ alkyl, $(C_{1-6})$ alkyl substituted with $R^6$, $C_{3-6}$ cycloalkyl, $(C_3-6)$ cycloalkyl substituted with $R^6$, $C_{2-6}$ alkenyl, $C_{2-6}$ alkynyl, phenyl, phenyl substituted with $(R^7)_p$, naphthyl, or any one group of U-1 to U-25;

$R^{4a}$ is a hydrogen atom, a halogen atom, $C_{1-6}$ alkyl, $(C_{1-6})$ alkyl substituted with $R^{27}$, $C_{3-6}$ cycloalkyl, $(C_{3-6})$ cycloalkyl substituted with $R^{27}$, $C_{2-6}$ alkenyl, $C_{2-6}$ haloalkenyl, $C_{2-6}$ alkynyl, $C_{2-6}$ haloalkynyl, $C_{3-6}$ cycloalkenyl, —NH$_2$, $C_{1-6}$ alkylamino, di($C_{1-6}$ alkyl)amino, —NHC(O)$R^8$, phenyl, phenyl substituted with $(R^{28})_r$, or any one group of U-1 to U-26;

$R^7$ is a halogen atom, cyano, nitro, $C_{1-6}$ alkyl, $(C_{1-6})$ alkyl substituted with $R^{27}$, $C_{3-6}$ cycloalkyl, $C_{3-6}$ halocycloalkyl, $C_{2-6}$ alkenyl, $C_{2-6}$ haloalkenyl, $C_{2-6}$ alkynyl, $C_{2-6}$ haloalkynyl, $C_{3-6}$ cycloalkenyl, $C_{1-6}$ alkylcarbonyl, $C_{3-6}$ cycloalkylcarbonyl, $C_{1-6}$ haloalkylcarbonyl, $C_{3-6}$ halocycloalkylcarbonyl, $C_{1-6}$ alkoxycarbonyl, $C_{1-6}$ haloalkoxycarbonyl, $C_{1-6}$ alkylaminocarbonyl, $C_{1-6}$ haloalkylaminocarbonyl, di($C_{1-6}$ alkyl amino)carbonyl, —O$R^{15}$, —S(O)$_{m3}R^{20}$, $C_{1-6}$ alkylaminosulfonyl, di($C_{1-6}$ alkyl)aminosulfonyl, —NH$_2$, $C_{1-6}$ alkylamino, di($C_{1-6}$ alkyl)amino, or any one group of U-1 to U-26; and $R^{27}$ is a halogen atom, cyano, nitro, phenyl, phenyl substituted with $(R^{28})_r$, —C(O)O$R^{16}$, —O$R^{29}$, —S(O)$_{m4}R^{30}$, or any one group of U-1 to U-26.

4. The heterocyclic amide compound or the salt thereof according to claim 3, wherein $R^{1a}$ is a hydrogen atom, a halogen atom, $C_{1-6}$ alkyl, $(C_{1-6})$ alkyl substituted with $R^6$, $C_{3-6}$ cycloalkyl, $(C_{3-6})$ cycloalkyl substituted with $R^6$, $C_{2-6}$ alkenyl, $C_{2-6}$ alkynyl, $C_{3-6}$ cycloalkenyl, —C(O)$R^8$, —O$R^9$, —S(O)$_{m1}R^{10}$, —N($R^{11}$)$R^{12}$, —C(=N$R^{12b}$)$R^{8b}$, phenyl, phenyl substituted with $(R^7)_p$, U-3, U-5a, U-6a, U-7, U-8, U-10a, U-11a, U-12a, or U-13a;

$R^{1b}$ is $C_{1-6}$ alkyl or $(C_{1-6})$ alkyl substituted with $R^6$;

$R^{2a}$ is a halogen atom, $C_{1-6}$ alkyl, $C_{1-6}$ haloalkyl, or —S(O)$_{m3}R^{20}$, and when n is an integer of 2 or more, $R^{2a}$ are optionally the same as or different from each other;

$R^3$ is a hydrogen atom or $C_{1-6}$ alkyl;

$R^{4a}$ is a hydrogen atom, $C_{1-6}$ alkyl, $(C_{1-6})$ alkyl substituted with $R^{27}$, $C_{3-6}$ cycloalkyl, phenyl, phenyl substituted with $(R^{28})_r$, or a heterocycle of U-1, U-2, U-7, U-10a, or U-26;

$R^{4b}$ is $C_{1-6}$ alkyl;

$R^{4c}$ is a hydrogen atom;

$R^{4d}$ is $C_{1-6}$ alkyl;

$R^{5a}$ is a hydrogen atom, $C_{1-6}$ alkyl, $(C_{1-6})$ alkyl substituted with $R_{27}$, $C_{2-6}$ alkenyl, or phenyl;

$R^{5b}$ is a hydrogen atom or $C_{1-6}$ alkyl;

$R^{5c}$ is $C_{1-6}$ alkyl, or $R^{5c}$ optionally forms a 6-membered ring together with a nitrogen atom to which $R^{5c}$ is bonded and a carbon atom to which $R^{4d}$ is bonded by forming —(CH$_2$)$_4$— or —CH=CH—CH=CH— with $R^{4d}$;

$R^7$ is a halogen atom, $C_{1-6}$ alkyl, $(C_{1-6})$ alkyl substituted with $R^{27}$, or —O$R^{15}$;

$R^{8b}$ is a hydrogen atom;

$R^9$ is $C_{1-6}$ alkyl;

$R^{10}$ is $C_{1-6}$ alkyl, $(C_{1-6})$ alkyl substituted with $R^{34}$, $C_{3-6}$ cycloalkyl, $C_{2-6}$ alkenyl, or $C_{2-6}$ alkynyl;

$R^{11}$ is $C_{1-6}$ alkyl, $(C_{1-6})$ alkyl substituted with $R^{34}$, $C_{3-6}$ cycloalkyl, $C_{2-6}$ alkenyl, $C_{2-6}$ alkynyl, phenylsulfonyl, phenyl, phenyl substituted with $(R^7)_p$, or U-7;

$R^{12}$ is a hydrogen atom or $C_{1-6}$ alkyl;

$R^{11}$ optionally forms a 5-6-membered ring together with a nitrogen atom to which $R^{11}$ and $R^{12}$ are bonded by forming a $C_{4-5}$ alkylene chain together with $R^{12}$, and in this case, the alkylene chain optionally contains one O, S, S(O), or S(O)$_2$;

$R^{11a}$ is $C_{1-6}$ alkyl;

$R^{12a}$ is a hydrogen atom;

$R^{13}$ is a hydrogen atom, $C_{1-6}$ alkyl, $(C_{1-6})$ alkyl substituted with $R^{34}$, —C(O)$R^8$, or phenyl;

$R^{14}$ is $C_{1-6}$ alkyl or $(C_{1-6})$ alkyl substituted with $R^{34}$;

$R^{15}$ is $C_{1-6}$ alkyl;

$R^{19b}$ is $C_{1-6}$ alkyl;

$R^{20}$ is $C_{1-6}$ alkyl;

$R^{27}$ is a halogen atom, phenyl, phenyl substituted with $(R^{28})_r$, —O$R^{29}$, —C(O)O$R^{16}$, or —S(O)$_{m4}R^{30}$;

$R^{28}$ is a halogen atom, $C_{1-6}$ alkyl, or —O$R^{31}$; when t2, t3, t4, t5, or t7 is an integer of 2 or more, $R^{28}$ are optionally the same as or different from each other; and further when two $R^{28}$ are adjacent, the two adjacent $R^{28}$ optionally form a 6-membered ring together with carbon atoms to which each $R^{28}$ is bonded by forming —CH=CH—CH=CH—;

$R^{29}$ is $C_{1-6}$ alkyl;

$R^{30}$ is $C_{1-6}$ alkyl;

$R^{31}$ is $C_{1-6}$ alkyl;

$R^{33}$ is $C_{1-6}$ alkyl; and $R^{34}$ is a halogen atom, cyano, $C_{3-6}$ cycloalkyl, —C(O)$R^8$, —C(O)O$R^{16}$, —O$R^{33}$, —S(O)$_{m6}R^{33}$, phenyl, phenyl substituted with $(R^7)_p$, U-1, U-8, or U-22a.

5. The heterocyclic amide compound or the salt thereof according to claim 4, wherein Q is an aromatic heterocycle of Q-1; and W is an aromatic heterocycle of W-1.

6. The heterocyclic amide compound or the salt thereof according to claim 5, wherein X is an oxygen atom;

$R^{1a}$ a hydrogen atom, a halogen atom, $C_{1-6}$ alkyl, $(C_{1-6})$ alkyl substituted with $R^6$, $C_{3-6}$ cycloalkyl, $(C_{3-6})$ cycloalkyl substituted with $R^6$, $C_{2-6}$ alkenyl, $C_{2-6}$ alkynyl, $C_{3-6}$ cycloalkenyl, —C(O)$R^8$, —O$R^9$, —S(O)$_{m1}R^{10}$, —N($R^{11}$)$R^{12}$, —C(=N$R^{12b}$)$R^{8b}$, phenyl, phenyl substituted with $(R^7)_p$, U-5a, U-6a, U-7, U-8, U-10a, U-11a, U-12a, or U-13a;

$R^{2a}$ is a $C_{1-6}$ alkyl, $C_{1-6}$ haloalkyl, or —S(O)$_{m3}R^{20}$, and when n is an integer of 2 or more, $R^{2a}$ are optionally the same as or different from each other;

$R^6$ is a halogen atom, cyano, $C_{3-6}$ cycloalkyl, —C(O)$R^8$, —C(O)O$R^{16}$, —O$R^{13}$, —S(O)$_{m2}R^{14}$, or phenyl substituted with $(R^7)_p$; and $R^{27}$ is a halogen atom, phenyl, —O$R^{29}$, or —S(O)$_{m4}R^{30}$.

7. The heterocyclic amide compound or the salt thereof according to claim 6, wherein $R^{4a}$ is a hydrogen atom, $C_{1-6}$ alkyl, $(C_{1-6})$ alkyl substituted with $R^{27}$, or $C_{3-6}$ cycloalkyl; and $R^{27}$ is a halogen atom or —$OR^{29}$.

8. The heterocyclic amide compound or the salt thereof according to claim 4, wherein Q is an aromatic heterocycle of Q-3; and W is an aromatic heterocycle of W-1.

9. The heterocyclic amide compound or the salt thereof according to claim 8, wherein $R^{1a}$ is a hydrogen atom, a halogen atom, $C_{1-6}$ alkyl, $(C_{1-6})$ alkyl substituted with $R^6$, $C_{3-6}$ cycloalkyl, $(C_{3-6})$ cycloalkyl substituted with $R^6$, $C_{2-6}$ alkenyl, $C_{2-6}$ alkynyl, —$C(O)R^8$, —$S(O)_{m1}R^{10}$, —$N(R^{11})R^{12}$, phenyl, phenyl substituted with $(R^7)_p$, U-3, U-5a, U-6a, U-8, U-10a, or U-13a;

$R^{2a}$ is a halogen atom, $C_{1-6}$ alkyl, or $C_{1-6}$ haloalkyl, and when n is an integer of 2 or more, $R^{2a}$ are optionally the same as or different from each other;

$R^6$ is a halogen atom, —$C(O)OR^{16}$, —$OR^{13}$, —$S(O)_{m2}R^{14}$, or phenyl substituted with $(R^7)_p$;

$R^7$ is a halogen atom, $C_{1-6}$ alkyl, or —$OR^{15}$;

$R^8$ is a hydrogen atom or $C_{1-6}$ alkyl;

$R^{11}$ is $C_{1-6}$ alkyl, $(C_{1-6})$ alkyl substituted with $R^{34}$, $C_{3-6}$ cycloalkyl, $C_{2-6}$ alkenyl, $C_{2-6}$ alkynyl, phenyl, or phenyl substituted with $(R^7)_p$;

$R^{11}$ optionally forms a 6-membered ring together with a nitrogen atom to which $R^{11}$ and $R^{12}$ are bonded by forming a $C_5$ alkylene chain together with $R^{12}$, and in this case, the alkylene chain optionally contains one O, S, S(O), or $S(O)_2$;

$R^{16}$ is a hydrogen atom or $C_{1-6}$ alkyl;

$R^{27}$ is phenyl substituted with $(R^{28})_r$, —$OR^{29}$, —$C(O)OR^{16}$, or —$S(O)_{m4}R^{30}$;

$R^{28}$ is a halogen atom or $C_{1-6}$ alkyl; and $R^{34}$ is a halogen atom, cyano, $C_{3-6}$ cycloalkyl, —$OR^{33}$, —$S(O)_{m6}R^{33}$, phenyl, phenyl substituted with $(R^7)_p$, U-1, or U-8.

10. The heterocyclic amide compound or the salt thereof according to claim 9, wherein $R^{5a}$ is $C_{1-6}$ alkyl, $(C_{1-6})$ alkyl substituted with $R^{27}$, or $C_{2-6}$ alkenyl; and $R^{27}$ is —$OR^{29}$ or —$S(O)_{m4}R^{30}$.

11. An agricultural chemical formulation comprising one or two or more of compounds selected from the heterocyclic amide compound and the salt thereof as claimed in claim 1 as an active component.

12. A herbicide formulation comprising one or two or more of compounds selected from the heterocyclic amide compound and the salt thereof as claimed in claim 1 as an active component.

* * * * *